United States Patent
Watanabe et al.

(10) Patent No.: US 9,766,250 B2
(45) Date of Patent: Sep. 19, 2017

(54) METHOD FOR DETECTING PROTEIN-PROTEIN INTERACTION

(71) Applicant: MEDICAL & BIOLOGICAL LABORATORIES CO., LTD., Nagoya-shi, Aichi (JP)

(72) Inventors: Taku Watanabe, Ina (JP); Tatsuya Seki, Ina (JP); Aki Fujioka, Ina (JP)

(73) Assignee: MEDICAL & BIOLOGICAL LABORATORIES CO., LTD., Aichi (JP)

( * ) Notice: Subject to any disclaimer, the term of this patent is extended or adjusted under 35 U.S.C. 154(b) by 0 days.

(21) Appl. No.: 15/273,815

(22) Filed: Sep. 23, 2016

(65) Prior Publication Data

US 2017/0010277 A1    Jan. 12, 2017

Related U.S. Application Data

(62) Division of application No. 14/363,201, filed as application No. PCT/JP2012/081539 on Dec. 5, 2012, now Pat. No. 9,494,595.

(30) Foreign Application Priority Data

Dec. 5, 2011  (JP) ................................. 2011-266103

(51) Int. Cl.
*G01N 33/542* (2006.01)
*G01N 33/68* (2006.01)
*C12N 15/85* (2006.01)
*G01N 33/58* (2006.01)

(52) U.S. Cl.
CPC ......... *G01N 33/6845* (2013.01); *C12N 15/85* (2013.01); *G01N 33/542* (2013.01); *G01N 33/582* (2013.01); *G01N 2500/02* (2013.01)

(58) Field of Classification Search
CPC .. G01N 33/566; C12N 15/85; C12N 15/1138; C12N 15/62; C12N 2310/14; C12N 2310/531; C12N 2320/30
See application file for complete search history.

(56) References Cited

U.S. PATENT DOCUMENTS

| | | | |
|---|---|---|---|
| 7,118,921 B1 | 10/2006 | Brennan et al. | |
| 7,282,347 B2 | 10/2007 | Bjorn et al. | |
| 2006/0094101 A1 | 5/2006 | Yannoni et al. | |
| 2007/0031912 A1 | 2/2007 | Miyawaki et al. | |
| 2008/0153111 A1 | 6/2008 | Nibert et al. | |

FOREIGN PATENT DOCUMENTS

| | | |
|---|---|---|
| JP | 2003503423 | 1/2003 |
| JP | 2006515159 | 5/2006 |
| JP | 2006308568 | 11/2006 |
| JP | 2011211983 | 10/2011 |
| WO | 0017221 | 3/2000 |
| WO | 2006099486 | 9/2006 |

OTHER PUBLICATIONS

Communication dated Apr. 24, 2015, from the European Patent Office in counterpart European Application No. 12856145.3.
Carette et al., "Connexin 33 Impairs Gap Junction Functionality by Accelerating Connexin 43 Gap Junction Plaque Endocytosis", Traffic, 10(9,1):1272-1285 (2009).
Hashimoto et al., "Novel In Vitro Protein Fragment Complementation Assay Applicable to High-Throughput Screening in a 1536-Well Format", Journal of Biomolecular Screening, 14(8): 970-979 (2009).
Ishikawa et al., "Visualization of radiation-induced cell cycle-associated events in tumor cells expressing the fusion protein of Azami Green and the destruction box of human Geminin", Biochemical and Biophysical Research Communications, 389(3): 426-430 (2009).
Izumikawa et al., "JBIR-22, An Inhibitor for Protein-Protein Interaction of the Homodimer of Proteasome Assembly Factor 3", Journal of Natural Products, 73(4)628-631 (2010).
Sakaue-Sawano et al., "Visualizing Spatiotemporal Dynamics of Multicellular Cell-Cycle Progression", Cell 132:487-498 (2008).
Karasawa et al., "Seimei Gensho wa Dokomade Shikakuka Dekiruka –6 Atarashii Keiko Tanpakushitsu no Kaihatsu", Kagaku to Seibutsu, 45(12):863-868 (2007).
Ueyama et al., "Sequential Binding of Cytosolic Phox Complex to Phagosomes through Regulated Adaptor Proteins: Evaluation Using the Novel Monomeric Kusabira-Green System and Live Imaging of Phagocytosis", The Journal of Immunology, 181(1): 629-640 (2008).
Yoshikawa et al., "Listeria monocytogenes ActA-mediated escape from autophagic recognition", Nature Cell Biology, 11(10): 1233-1240 (2009).

*Primary Examiner* — Shafiqul Haq
*Assistant Examiner* — Carmencita M Belei
(74) *Attorney, Agent, or Firm* — Sughrue Mion, PLLC

(57) ABSTRACT

A method for detecting an interaction between a first protein and a second protein comprises the steps of:
expressing in a cell a first fusion protein comprising the first protein and an association-inducing protein, and a second fusion protein comprising the second protein and a fluorescent protein having a multimerization ability;
detecting a fluorescent focus formed by an association between the first fusion protein and the second fusion protein in the cell; and
determining an interaction between the first protein and the second protein according to the detection of the fluorescent focus.

1 Claim, 42 Drawing Sheets
(7 of 42 Drawing Sheet(s) Filed in Color)

```
                       SEQUENCE LISTING

<160> NUMBER OF SEQ ID NOS: 172

<210> SEQ ID NO 1
<211> LENGTH: 678
<212> TYPE: DNA
<213> ORGANISM: Artificial Sequence
<220> FEATURE:
<223> OTHER INFORMATION: Synthetic humanized codon Azami Green
<220> FEATURE:
<221> NAME/KEY: CDS
<222> LOCATION: (1)..(678)
<223> OTHER INFORMATION: hAG

<400> SEQUENCE: 1 atg gtg agc gtg atc aag ccc gag atg aag atc aag ctg tgc atg agg      48
Met Val Ser Val Ile Lys Pro Glu Met Lys Ile Lys Leu Cys Met Arg
1               5                   10                  15 ggc acc gtg aac ggc cac aac ttc gtg atc gag ggc gag ggc aag ggc      96
Gly Thr Val Asn Gly His Asn Phe Val Ile Glu Gly Glu Gly Lys Gly
                20                  25                  30 aac ccc tac gag ggc acc cag atc ctg gac ctg aac gtg acc gag ggc     144
Asn Pro Tyr Glu Gly Thr Gln Ile Leu Asp Leu Asn Val Thr Glu Gly
            35                  40                  45
```

```
gcc ccc ctg ccc ttc gcc tac gac atc ctg acc acc gtg ttc cag tac    192
Ala Pro Leu Pro Phe Ala Tyr Asp Ile Leu Thr Thr Val Phe Gln Tyr
 50                  55                  60 ggc aac agg gcc ttc acc aag tac ccc gcc gac atc cag gac tac ttc    240
Gly Asn Arg Ala Phe Thr Lys Tyr Pro Ala Asp Ile Gln Asp Tyr Phe
 65                  70                  75                  80 aag cag acc ttc ccc gag ggc tac cac tgg gag agg agc atg acc tac    288
Lys Gln Thr Phe Pro Glu Gly Tyr His Trp Glu Arg Ser Met Thr Tyr
                 85                  90                  95 gag gac cag ggc atc tgc acc gcc acc agc aac atc agc atg agg ggc    336
Glu Asp Gln Gly Ile Cys Thr Ala Thr Ser Asn Ile Ser Met Arg Gly
            100                 105                 110 gac tgc ttc ttc tac gac atc agg ttc gac ggc gtg aac ttc ccc ccc    384
Asp Cys Phe Phe Tyr Asp Ile Arg Phe Asp Gly Val Asn Phe Pro Pro
        115                 120                 125 aac ggc ccc gtg atg cag aag aag acc ctg aag tgg gag ccc agc acc    432
Asn Gly Pro Val Met Gln Lys Lys Thr Leu Lys Trp Glu Pro Ser Thr
    130                 135                 140 gag aag atg tac gtg agg gac ggc gtg ctg aag ggc gac gtg aac atg    480
Glu Lys Met Tyr Val Arg Asp Gly Val Leu Lys Gly Asp Val Asn Met
145                 150                 155                 160 gcc ctg ctg ctg gag ggc ggc ggc cac tac agg tgc gac ttc aag acc    528
Ala Leu Leu Leu Glu Gly Gly Gly His Tyr Arg Cys Asp Phe Lys Thr
                165                 170                 175 acc tac aag gcc aag aag gac gtg agg ctg ccc gac tac cac ttc gtg    576
Thr Tyr Lys Ala Lys Lys Asp Val Arg Leu Pro Asp Tyr His Phe Val
            180                 185                 190 gac cac agg atc gag atc ctg aag cac gac aag gac tac aac aag gtg    624
Asp His Arg Ile Glu Ile Leu Lys His Asp Lys Asp Tyr Asn Lys Val
        195                 200                 205 aag ctg tac gag aac gcc gtg gcc agg tac agc atg ctg ccc agc cag    672
Lys Leu Tyr Glu Asn Ala Val Ala Arg Tyr Ser Met Leu Pro Ser Gln
    210                 215                 220 gcc aag                                                            678
Ala Lys
225

<210> SEQ ID NO 2
<211> LENGTH: 226
<212> TYPE: PRT
<213> ORGANISM: Artificial Sequence
<220> FEATURE:
<223> OTHER INFORMATION: Synthetic humanized codon Azami Green

<400> SEQUENCE: 2

Met Val Ser Val Ile Lys Pro Glu Met Lys Ile Lys Leu Cys Met Arg
1               5                   10                  15

Gly Thr Val Asn Gly His Asn Phe Val Ile Glu Gly Glu Gly Lys Gly
            20                  25                  30

Asn Pro Tyr Glu Gly Thr Gln Ile Leu Asp Leu Asn Val Thr Glu Gly
        35                  40                  45

Ala Pro Leu Pro Phe Ala Tyr Asp Ile Leu Thr Thr Val Phe Gln Tyr
    50                  55                  60

Gly Asn Arg Ala Phe Thr Lys Tyr Pro Ala Asp Ile Gln Asp Tyr Phe
65                  70                  75                  80

Lys Gln Thr Phe Pro Glu Gly Tyr His Trp Glu Arg Ser Met Thr Tyr
                85                  90                  95

Glu Asp Gln Gly Ile Cys Thr Ala Thr Ser Asn Ile Ser Met Arg Gly
            100                 105                 110
```

```
Asp Cys Phe Phe Tyr Asp Ile Arg Phe Asp Gly Val Asn Phe Pro Pro
            115                 120                 125

Asn Gly Pro Val Met Gln Lys Lys Thr Leu Lys Trp Glu Pro Ser Thr
        130                 135                 140

Glu Lys Met Tyr Val Arg Asp Gly Val Leu Lys Gly Asp Val Asn Met
145                 150                 155                 160

Ala Leu Leu Leu Glu Gly Gly His Tyr Arg Cys Asp Phe Lys Thr
                165                 170                 175

Thr Tyr Lys Ala Lys Lys Asp Val Arg Leu Pro Asp Tyr His Phe Val
            180                 185                 190

Asp His Arg Ile Glu Ile Leu Lys His Asp Lys Asp Tyr Asn Lys Val
        195                 200                 205

Lys Leu Tyr Glu Asn Ala Val Ala Arg Tyr Ser Met Leu Pro Ser Gln
210                 215                 220

Ala Lys
225

<210> SEQ ID NO 3
<211> LENGTH: 306
<212> TYPE: DNA
<213> ORGANISM: Homo sapiens
<220> FEATURE:
<221> NAME/KEY: CDS
<222> LOCATION: (1)..(306)
<223> OTHER INFORMATION: p62(PB1)

<400> SEQUENCE: 3 atg gcg tcg ctc acc gtg aag gcc tac ctt ctg ggc aag gag gac gcg      48
Met Ala Ser Leu Thr Val Lys Ala Tyr Leu Leu Gly Lys Glu Asp Ala
1               5                   10                  15 gcg cgc gag att cgc cgc ttc agc ttc tgc tgc agc ccc gag cct gag      96
Ala Arg Glu Ile Arg Arg Phe Ser Phe Cys Cys Ser Pro Glu Pro Glu
            20                  25                  30 gcg gaa gcc gag gct gcg gcg ggt ccg gga ccc tgc gag cgg ctg ctg     144
Ala Glu Ala Glu Ala Ala Ala Gly Pro Gly Pro Cys Glu Arg Leu Leu
        35                  40                  45 agc cgg gtg gcc gcc ctg ttc ccc gcg ctg cgg cct ggc ggc ttc cag     192
Ser Arg Val Ala Ala Leu Phe Pro Ala Leu Arg Pro Gly Gly Phe Gln
50                  55                  60 gcg cac tac cgc gat gag gac ggg gac ttg gtt gcc ttt tca agt gac     240
Ala His Tyr Arg Asp Glu Asp Gly Asp Leu Val Ala Phe Ser Ser Asp
65                  70                  75                  80 gag gaa ttg aca atg gcc atg tcc tac gtg aag gat gac atc ttc cga     288
Glu Glu Leu Thr Met Ala Met Ser Tyr Val Lys Asp Asp Ile Phe Arg
                85                  90                  95 atc tac att aaa gag aaa                                              306
Ile Tyr Ile Lys Glu Lys
            100

<210> SEQ ID NO 4
<211> LENGTH: 102
<212> TYPE: PRT
<213> ORGANISM: Homo sapiens
<223> OTHER INFORMATION: p62(PB1)

<400> SEQUENCE: 4

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30
```

```
Ala Glu Ala Glu Ala Ala Ala Gly Pro Gly Pro Cys Glu Arg Leu Leu
            35                  40                  45

Ser Arg Val Ala Ala Leu Phe Pro Ala Leu Arg Pro Gly Gly Phe Gln
 50                  55                  60

Ala His Tyr Arg Asp Glu Asp Gly Asp Leu Val Ala Phe Ser Ser Asp
 65                  70                  75                  80

Glu Glu Leu Thr Met Ala Met Ser Tyr Val Lys Asp Asp Ile Phe Arg
                 85                  90                  95

Ile Tyr Ile Lys Glu Lys
                100
```

<210> SEQ ID NO 5
<211> LENGTH: 282
<212> TYPE: DNA
<213> ORGANISM: Homo sapiens
<220> FEATURE:
<221> NAME/KEY: CDS
<222> LOCATION: (1)..(282)
<223> OTHER INFORMATION: MEK5(PB1)

<400> SEQUENCE: 5

```
gtg ctg gta att cgc atc aag atc cca aat agt ggc gcg gtg gac tgg      48
Val Leu Val Ile Arg Ile Lys Ile Pro Asn Ser Gly Ala Val Asp Trp
 1               5                  10                  15 aca gtg cac tcc ggg ccg cag tta ctc ttc agg gat gtg ctg gat gtg      96
Thr Val His Ser Gly Pro Gln Leu Leu Phe Arg Asp Val Leu Asp Val
             20                  25                  30 ata ggc cag gtt ctg cct gaa gca aca act aca gca ttt gaa tat gaa     144
Ile Gly Gln Val Leu Pro Glu Ala Thr Thr Thr Ala Phe Glu Tyr Glu
         35                  40                  45 gat gaa gat ggt gat cga att aca gtg aga agt gat gag gaa atg aag     192
Asp Glu Asp Gly Asp Arg Ile Thr Val Arg Ser Asp Glu Glu Met Lys
     50                  55                  60 gca atg ctg tca tat tat tat tcc aca gta atg gaa cag caa gta aat     240
Ala Met Leu Ser Tyr Tyr Tyr Ser Thr Val Met Glu Gln Gln Val Asn
 65                  70                  75                  80 gga cag tta ata gag cct ctg cag ata ttt cca aga gcc tgc             282
Gly Gln Leu Ile Glu Pro Leu Gln Ile Phe Pro Arg Ala Cys
                 85                  90
```

<210> SEQ ID NO 6
<211> LENGTH: 94
<212> TYPE: PRT
<213> ORGANISM: Homo sapiens
<223> OTHER INFORMATION: MEK5(PB1)

<400> SEQUENCE: 6

```
Val Leu Val Ile Arg Ile Lys Ile Pro Asn Ser Gly Ala Val Asp Trp
 1               5                  10                  15

Thr Val His Ser Gly Pro Gln Leu Leu Phe Arg Asp Val Leu Asp Val
             20                  25                  30

Ile Gly Gln Val Leu Pro Glu Ala Thr Thr Thr Ala Phe Glu Tyr Glu
         35                  40                  45

Asp Glu Asp Gly Asp Arg Ile Thr Val Arg Ser Asp Glu Glu Met Lys
     50                  55                  60

Ala Met Leu Ser Tyr Tyr Tyr Ser Thr Val Met Glu Gln Gln Val Asn
 65                  70                  75                  80

Gly Gln Leu Ile Glu Pro Leu Gln Ile Phe Pro Arg Ala Cys
                 85                  90
```

```
<210> SEQ ID NO 7
<211> LENGTH: 246
<212> TYPE: DNA
<213> ORGANISM: Homo sapiens
<220> FEATURE:
<221> NAME/KEY: CDS
<222> LOCATION: (1)..(246)
<223> OTHER INFORMATION: Nbr1(PB1)

<400> SEQUENCE: 7 cag gtt act cta aat gtg act ttt aaa aat gaa att caa agc ttt ctg        48
Gln Val Thr Leu Asn Val Thr Phe Lys Asn Glu Ile Gln Ser Phe Leu
1               5                   10                  15 gtt tct gat cca gaa aat aca act tgg gct gat atc gaa gct atg gta        96
Val Ser Asp Pro Glu Asn Thr Thr Trp Ala Asp Ile Glu Ala Met Val
            20                  25                  30 aaa gtt tca ttt gat ctg aat act att caa ata aaa tac ctg gat gag       144
Lys Val Ser Phe Asp Leu Asn Thr Ile Gln Ile Lys Tyr Leu Asp Glu
        35                  40                  45 gaa aat gaa gag gta tcc atc aac agt caa gga gaa tat gaa gaa gcg       192
Glu Asn Glu Glu Val Ser Ile Asn Ser Gln Gly Glu Tyr Glu Glu Ala
    50                  55                  60 ctt aag atg gca gtt aaa cag gga aac caa ctg cag atg caa gtc cac       240
Leu Lys Met Ala Val Lys Gln Gly Asn Gln Leu Gln Met Gln Val His
65                  70                  75                  80 gaa ggg                                                                246
Glu Gly <210> SEQ ID NO 8
<211> LENGTH: 82
<212> TYPE: PRT
<213> ORGANISM: Homo sapiens
<223> OTHER INFORMATION: Nbr1(PB1)

<400> SEQUENCE: 8

Gln Val Thr Leu Asn Val Thr Phe Lys Asn Glu Ile Gln Ser Phe Leu
1               5                   10                  15

Val Ser Asp Pro Glu Asn Thr Thr Trp Ala Asp Ile Glu Ala Met Val
            20                  25                  30

Lys Val Ser Phe Asp Leu Asn Thr Ile Gln Ile Lys Tyr Leu Asp Glu
        35                  40                  45

Glu Asn Glu Glu Val Ser Ile Asn Ser Gln Gly Glu Tyr Glu Glu Ala
    50                  55                  60

Leu Lys Met Ala Val Lys Gln Gly Asn Gln Leu Gln Met Gln Val His
65                  70                  75                  80

Glu Gly

<210> SEQ ID NO 9
<211> LENGTH: 252
<212> TYPE: DNA
<213> ORGANISM: Homo sapiens
<220> FEATURE:
<221> NAME/KEY: CDS
<222> LOCATION: (1)..(252)
<223> OTHER INFORMATION: PKCiota(PB1)

<400> SEQUENCE: 9 cag gtc cgg gtg aaa gcc tac tac cgc ggg gat atc atg ata aca cat        48
Gln Val Arg Val Lys Ala Tyr Tyr Arg Gly Asp Ile Met Ile Thr His
1               5                   10                  15 ttt gaa cct tcc atc tcc ttt gag ggc ctt tgc aat gag gtt cga gac        96
Phe Glu Pro Ser Ile Ser Phe Glu Gly Leu Cys Asn Glu Val Arg Asp
```

```
                    20                  25                  30
atg tgt tct ttt gac aac gaa cag ctc ttc acc atg aaa tgg ata gat        144
Met Cys Ser Phe Asp Asn Glu Gln Leu Phe Thr Met Lys Trp Ile Asp
         35                  40                  45 gag gaa gga gac ccg tgt aca gta tca tct cag ttg gag tta gaa gaa        192
Glu Glu Gly Asp Pro Cys Thr Val Ser Ser Gln Leu Glu Leu Glu Glu
 50                  55                  60 gcc ttt aga ctt tat gag cta aac aag gat tct gaa ctc ttg att cat        240
Ala Phe Arg Leu Tyr Glu Leu Asn Lys Asp Ser Glu Leu Leu Ile His
 65                  70                  75                  80 gtg ttc cct tgt                                                        252
Val Phe Pro Cys <210> SEQ ID NO 10
<211> LENGTH: 84
<212> TYPE: PRT
<213> ORGANISM: Homo sapiens
<223> OTHER INFORMATION: PKCiota(PB1)

<400> SEQUENCE: 10

Gln Val Arg Val Lys Ala Tyr Tyr Arg Gly Asp Ile Met Ile Thr His
 1               5                   10                  15

Phe Glu Pro Ser Ile Ser Phe Glu Gly Leu Cys Asn Glu Val Arg Asp
                 20                  25                  30

Met Cys Ser Phe Asp Asn Glu Gln Leu Phe Thr Met Lys Trp Ile Asp
         35                  40                  45

Glu Glu Gly Asp Pro Cys Thr Val Ser Ser Gln Leu Glu Leu Glu Glu
 50                  55                  60

Ala Phe Arg Leu Tyr Glu Leu Asn Lys Asp Ser Glu Leu Leu Ile His
 65                  70                  75                  80

Val Phe Pro Cys

<210> SEQ ID NO 11
<211> LENGTH: 246
<212> TYPE: DNA
<213> ORGANISM: Homo sapiens
<220> FEATURE:
<221> NAME/KEY: CDS
<222> LOCATION: (1)..(246)
<223> OTHER INFORMATION: TFG(PB1)

<400> SEQUENCE: 11 aag cta atc atc aaa gct caa ctt ggg gag gat att cgg cga att cct         48
Lys Leu Ile Ile Lys Ala Gln Leu Gly Glu Asp Ile Arg Arg Ile Pro
 1               5                   10                  15 att cat aat gaa gat att act tat gat gaa tta gtg cta atg atg caa         96
Ile His Asn Glu Asp Ile Thr Tyr Asp Glu Leu Val Leu Met Met Gln
                 20                  25                  30 cga gtt ttc aga gga aaa ctt ctg agt aat gat gaa gta aca ata aag        144
Arg Val Phe Arg Gly Lys Leu Leu Ser Asn Asp Glu Val Thr Ile Lys
         35                  40                  45 tat aaa gat gaa gat gga gat ctt ata aca att ttt gat agt tct gac        192
Tyr Lys Asp Glu Asp Gly Asp Leu Ile Thr Ile Phe Asp Ser Ser Asp
 50                  55                  60 ctt tcc ttt gca att cag tgc agt agg ata ctg aaa ctg aca tta ttt        240
Leu Ser Phe Ala Ile Gln Cys Ser Arg Ile Leu Lys Leu Thr Leu Phe
 65                  70                  75                  80 gtt aat                                                                246
Val Asn
```

```
<210> SEQ ID NO 12
<211> LENGTH: 82
<212> TYPE: PRT
<213> ORGANISM: Homo sapiens
<223> OTHER INFORMATION: TFG(PB1)

<400> SEQUENCE: 12

Lys Leu Ile Ile Lys Ala Gln Leu Gly Glu Asp Ile Arg Arg Ile Pro
1               5                   10                  15

Ile His Asn Glu Asp Ile Thr Tyr Asp Glu Leu Val Leu Met Met Gln
            20                  25                  30

Arg Val Phe Arg Gly Lys Leu Leu Ser Asn Asp Glu Val Thr Ile Lys
        35                  40                  45

Tyr Lys Asp Glu Asp Gly Asp Leu Ile Thr Ile Phe Asp Ser Ser Asp
50                  55                  60

Leu Ser Phe Ala Ile Gln Cys Ser Arg Ile Leu Lys Leu Thr Leu Phe
65                  70                  75                  80

Val Asn

<210> SEQ ID NO 13
<211> LENGTH: 261
<212> TYPE: DNA
<213> ORGANISM: Homo sapiens
<220> FEATURE:
<221> NAME/KEY: CDS
<222> LOCATION: (1)..(261)
<223> OTHER INFORMATION: TEL(SAM)

<400> SEQUENCE: 13 cct cga gcg ctc agg atg gag gaa gac tcg atc cgc ctg cct gcg cac      48
Pro Arg Ala Leu Arg Met Glu Glu Asp Ser Ile Arg Leu Pro Ala His
1               5                   10                  15 ctg cgc ttg cag cca att tac tgg agc agg gat gac gta gcc cag tgg      96
Leu Arg Leu Gln Pro Ile Tyr Trp Ser Arg Asp Asp Val Ala Gln Trp
            20                  25                  30 ctc aag tgg gct gaa aat gag ttt tct tta agg cca att gac agc aac     144
Leu Lys Trp Ala Glu Asn Glu Phe Ser Leu Arg Pro Ile Asp Ser Asn
        35                  40                  45 acg ttt gaa atg aat ggc aaa gct ctc ctg ctg ctg acc aaa gag gac     192
Thr Phe Glu Met Asn Gly Lys Ala Leu Leu Leu Leu Thr Lys Glu Asp
50                  55                  60 ttt cgc tat cga tct cct cat tca ggt gat gtg ctc tat gaa ctc ctt     240
Phe Arg Tyr Arg Ser Pro His Ser Gly Asp Val Leu Tyr Glu Leu Leu
65                  70                  75                  80 cag cat att ctg aag cag agg                                         261
Gln His Ile Leu Lys Gln Arg
                85

<210> SEQ ID NO 14
<211> LENGTH: 87
<212> TYPE: PRT
<213> ORGANISM: Homo sapiens
<223> OTHER INFORMATION: TEL(SAM)

<400> SEQUENCE: 14

Pro Arg Ala Leu Arg Met Glu Glu Asp Ser Ile Arg Leu Pro Ala His
1               5                   10                  15

Leu Arg Leu Gln Pro Ile Tyr Trp Ser Arg Asp Asp Val Ala Gln Trp
            20                  25                  30

Leu Lys Trp Ala Glu Asn Glu Phe Ser Leu Arg Pro Ile Asp Ser Asn
        35                  40                  45
```

```
Thr Phe Glu Met Asn Gly Lys Ala Leu Leu Leu Thr Lys Glu Asp
    50                  55                  60

Phe Arg Tyr Arg Ser Pro His Ser Gly Asp Val Leu Tyr Glu Leu Leu
 65              70                  75                  80

Gln His Ile Leu Lys Gln Arg
                85
```

<210> SEQ ID NO 15
<211> LENGTH: 231
<212> TYPE: DNA
<213> ORGANISM: Homo sapiens
<220> FEATURE:
<221> NAME/KEY: CDS
<222> LOCATION: (1)..(231)
<223> OTHER INFORMATION: EphB2(SAM)

<400> SEQUENCE: 15

```
ctg gac cgc acg atc ccc gac tac acc agc ttt aac acg gtg gac gag      48
Leu Asp Arg Thr Ile Pro Asp Tyr Thr Ser Phe Asn Thr Val Asp Glu
 1               5                  10                  15 tgg ctg gag gcc atc aag atg ggg cag tac aag gag agc ttc gcc aat      96
Trp Leu Glu Ala Ile Lys Met Gly Gln Tyr Lys Glu Ser Phe Ala Asn
                20                  25                  30 gcc ggc ttc acc tcc ttt gac gtc gtg tct cag atg atg atg gag gac     144
Ala Gly Phe Thr Ser Phe Asp Val Val Ser Gln Met Met Met Glu Asp
            35                  40                  45 att ctc cgg gtt ggg gtc act ttg gct ggc cac cag aaa aaa atc ctg     192
Ile Leu Arg Val Gly Val Thr Leu Ala Gly His Gln Lys Lys Ile Leu
        50                  55                  60 aac agt atc cag gtg atg cgg gcg cag atg aac cag att                 231
Asn Ser Ile Gln Val Met Arg Ala Gln Met Asn Gln Ile
 65                  70                  75
```

<210> SEQ ID NO 16
<211> LENGTH: 77
<212> TYPE: PRT
<213> ORGANISM: Homo sapiens
<223> OTHER INFORMATION: EphB2(SAM)

<400> SEQUENCE: 16

```
Leu Asp Arg Thr Ile Pro Asp Tyr Thr Ser Phe Asn Thr Val Asp Glu
 1               5                  10                  15

Trp Leu Glu Ala Ile Lys Met Gly Gln Tyr Lys Glu Ser Phe Ala Asn
                20                  25                  30

Ala Gly Phe Thr Ser Phe Asp Val Val Ser Gln Met Met Met Glu Asp
            35                  40                  45

Ile Leu Arg Val Gly Val Thr Leu Ala Gly His Gln Lys Lys Ile Leu
        50                  55                  60

Asn Ser Ile Gln Val Met Arg Ala Gln Met Asn Gln Ile
 65                  70                  75
```

<210> SEQ ID NO 17
<211> LENGTH: 204
<212> TYPE: DNA
<213> ORGANISM: Homo sapiens
<220> FEATURE:
<221> NAME/KEY: CDS
<222> LOCATION: (1)..(204)
<223> OTHER INFORMATION: DGKdelta(SAM)

<400> SEQUENCE: 17

```
ccg gtt cac ctc tgg ggg aca gag gag gtt gct gcc tgg ctg gag cac      48
Pro Val His Leu Trp Gly Thr Glu Glu Val Ala Ala Trp Leu Glu His
```

```
                1               5                      10                     15
ctc agt ctc tgt gag tat aag gac atc ttc aca cgg cac gac atc cgg     96
Leu Ser Leu Cys Glu Tyr Lys Asp Ile Phe Thr Arg His Asp Ile Arg
             20                  25                  30 ggc tct gag ctc ctg cac ctg gag cgg agg gac ctc aag gac ctg ggc    144
Gly Ser Glu Leu Leu His Leu Glu Arg Arg Asp Leu Lys Asp Leu Gly
             35                  40                  45 gtg acc aag gtg ggc cac atg aag agg atc ctg tgt ggc atc aag gag    192
Val Thr Lys Val Gly His Met Lys Arg Ile Leu Cys Gly Ile Lys Glu
 50                  55                  60 ctg agc cgc agc                                                    204
Leu Ser Arg Ser
65

<210> SEQ ID NO 18
<211> LENGTH: 68
<212> TYPE: PRT
<213> ORGANISM: Homo sapiens
<223> OTHER INFORMATION: DGKdelta(SAM)

<400> SEQUENCE: 18

Pro Val His Leu Trp Gly Thr Glu Val Ala Ala Trp Leu Glu His
1               5                   10                  15

Leu Ser Leu Cys Glu Tyr Lys Asp Ile Phe Thr Arg His Asp Ile Arg
             20                  25                  30

Gly Ser Glu Leu Leu His Leu Glu Arg Arg Asp Leu Lys Asp Leu Gly
             35                  40                  45

Val Thr Lys Val Gly His Met Lys Arg Ile Leu Cys Gly Ile Lys Glu
 50                  55                  60

Leu Ser Arg Ser
65

<210> SEQ ID NO 19
<211> LENGTH: 597
<212> TYPE: DNA
<213> ORGANISM: Homo sapiens
<220> FEATURE:
<221> NAME/KEY: CDS
<222> LOCATION: (1)..(597)
<223> OTHER INFORMATION: Tankyrase(SAM)

<400> SEQUENCE: 19 ctg ata gat gcc atg ccc cca gag gcc tta cct acc tgt ttt aaa cct     48
Leu Ile Asp Ala Met Pro Pro Glu Ala Leu Pro Thr Cys Phe Lys Pro
1               5                   10                  15 cag gct act gta gtg agt gcc tct ctg atc tca cca gca tcc acc ccc    96
Gln Ala Thr Val Val Ser Ala Ser Leu Ile Ser Pro Ala Ser Thr Pro
             20                  25                  30 tcc tgc ctc tcg gct gcc agc agc ata gac aac ctc act ggc cct tta   144
Ser Cys Leu Ser Ala Ala Ser Ser Ile Asp Asn Leu Thr Gly Pro Leu
             35                  40                  45 gca gag ttg gcc gta gga gga gcc tcc aat gca ggg gat ggc gcc gcg   192
Ala Glu Leu Ala Val Gly Gly Ala Ser Asn Ala Gly Asp Gly Ala Ala
 50                  55                  60 gga aca gaa agg aag gaa gga gaa gtt gct ggt ctt gac atg aat atc   240
Gly Thr Glu Arg Lys Glu Gly Glu Val Ala Gly Leu Asp Met Asn Ile
65                  70                  75                  80 agc caa ttt cta aaa agc ctt ggc ctt gaa cac ctt cgg gat atc ttt   288
Ser Gln Phe Leu Lys Ser Leu Gly Leu Glu His Leu Arg Asp Ile Phe
                 85                  90                  95 gaa aca gaa cag att aca cta gat gtg ttg gct gat atg ggt cat gaa   336
```

```
                Glu Thr Glu Gln Ile Thr Leu Asp Val Leu Ala Asp Met Gly His Glu
                                100                 105                 110 gag ttg aaa gaa ata ggc atc aat gca tat ggg cac cgc cac aaa tta            384
Glu Leu Lys Glu Ile Gly Ile Asn Ala Tyr Gly His Arg His Lys Leu
            115                 120                 125 atc aaa gga gta gaa aga ctc tta ggt gga caa caa ggc acc aat cct            432
Ile Lys Gly Val Glu Arg Leu Leu Gly Gly Gln Gln Gly Thr Asn Pro
130                 135                 140 tat ttg act ttt cac tgt gtt aat cag gga acg att ttg ctg gat ctt            480
Tyr Leu Thr Phe His Cys Val Asn Gln Gly Thr Ile Leu Leu Asp Leu
145                 150                 155                 160 gct cca gaa gat aaa gaa tat cag tca gtg gaa gaa gag atg caa agt            528
Ala Pro Glu Asp Lys Glu Tyr Gln Ser Val Glu Glu Glu Met Gln Ser
                165                 170                 175 act att cga gaa cac aga gat ggt ggt aat gct ggc ggc atc ttc aac            576
Thr Ile Arg Glu His Arg Asp Gly Gly Asn Ala Gly Gly Ile Phe Asn
            180                 185                 190 aga tac aat gtc att cga att                                                597
Arg Tyr Asn Val Ile Arg Ile
            195
```

<210> SEQ ID NO 20
<211> LENGTH: 199
<212> TYPE: PRT
<213> ORGANISM: Homo sapiens
<223> OTHER INFORMATION: Tankyrase(SAM)

<400> SEQUENCE: 20

```
Leu Ile Asp Ala Met Pro Pro Glu Ala Leu Pro Thr Cys Phe Lys Pro
1               5                   10                  15

Gln Ala Thr Val Val Ser Ala Ser Leu Ile Ser Pro Ala Ser Thr Pro
            20                  25                  30

Ser Cys Leu Ser Ala Ala Ser Ser Ile Asp Asn Leu Thr Gly Pro Leu
        35                  40                  45

Ala Glu Leu Ala Val Gly Gly Ala Ser Asn Ala Gly Asp Gly Ala Ala
    50                  55                  60

Gly Thr Glu Arg Lys Glu Gly Glu Val Ala Gly Leu Asp Met Asn Ile
65                  70                  75                  80

Ser Gln Phe Leu Lys Ser Leu Gly Leu Glu His Leu Arg Asp Ile Phe
                85                  90                  95

Glu Thr Glu Gln Ile Thr Leu Asp Val Leu Ala Asp Met Gly His Glu
            100                 105                 110

Glu Leu Lys Glu Ile Gly Ile Asn Ala Tyr Gly His Arg His Lys Leu
        115                 120                 125

Ile Lys Gly Val Glu Arg Leu Leu Gly Gly Gln Gln Gly Thr Asn Pro
    130                 135                 140

Tyr Leu Thr Phe His Cys Val Asn Gln Gly Thr Ile Leu Leu Asp Leu
145                 150                 155                 160

Ala Pro Glu Asp Lys Glu Tyr Gln Ser Val Glu Glu Glu Met Gln Ser
                165                 170                 175

Thr Ile Arg Glu His Arg Asp Gly Gly Asn Ala Gly Gly Ile Phe Asn
            180                 185                 190

Arg Tyr Asn Val Ile Arg Ile
        195
```

<210> SEQ ID NO 21
<211> LENGTH: 270
<212> TYPE: DNA

```
<213> ORGANISM: Homo sapiens
<220> FEATURE:
<221> NAME/KEY: CDS
<222> LOCATION: (1)..(270)
<223> OTHER INFORMATION: mTOR(FRB)

<400> SEQUENCE: 21 gag atg tgg cat gaa ggc ctg gaa gag gca tct cgt ttg tac ttt ggg      48
Glu Met Trp His Glu Gly Leu Glu Glu Ala Ser Arg Leu Tyr Phe Gly
1               5                   10                  15 gaa agg aac gtg aaa ggc atg ttt gag gtg ctg gag ccc ttg cat gct      96
Glu Arg Asn Val Lys Gly Met Phe Glu Val Leu Glu Pro Leu His Ala
                20                  25                  30 atg atg gaa cgg ggc ccc cag act ctg aag gaa aca tcc ttt aat cag     144
Met Met Glu Arg Gly Pro Gln Thr Leu Lys Glu Thr Ser Phe Asn Gln
            35                  40                  45 gcc tat ggt cga gat tta atg gag gcc caa gag tgg tgc agg aag tac     192
Ala Tyr Gly Arg Asp Leu Met Glu Ala Gln Glu Trp Cys Arg Lys Tyr
        50                  55                  60 atg aaa tca ggg aat gtc aag gac ctc acc caa gcc tgg gac ctc tat     240
Met Lys Ser Gly Asn Val Lys Asp Leu Thr Gln Ala Trp Asp Leu Tyr
65                  70                  75                  80 tat cat gtg ttc cga cga atc tca aag cag                             270
Tyr His Val Phe Arg Arg Ile Ser Lys Gln
                85                  90

<210> SEQ ID NO 22
<211> LENGTH: 90
<212> TYPE: PRT
<213> ORGANISM: Homo sapiens
<223> OTHER INFORMATION: mTOR(FRB)

<400> SEQUENCE: 22

Glu Met Trp His Glu Gly Leu Glu Glu Ala Ser Arg Leu Tyr Phe Gly
1               5                   10                  15

Glu Arg Asn Val Lys Gly Met Phe Glu Val Leu Glu Pro Leu His Ala
                20                  25                  30

Met Met Glu Arg Gly Pro Gln Thr Leu Lys Glu Thr Ser Phe Asn Gln
            35                  40                  45

Ala Tyr Gly Arg Asp Leu Met Glu Ala Gln Glu Trp Cys Arg Lys Tyr
        50                  55                  60

Met Lys Ser Gly Asn Val Lys Asp Leu Thr Gln Ala Trp Asp Leu Tyr
65                  70                  75                  80

Tyr His Val Phe Arg Arg Ile Ser Lys Gln
                85                  90

<210> SEQ ID NO 23
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: FKBP12

<400> SEQUENCE: 23 atg gga gtg cag gtg gaa acc atc tcc cca gga gac ggg cgc acc ttc      48
Met Gly Val Gln Val Glu Thr Ile Ser Pro Gly Asp Gly Arg Thr Phe
1               5                   10                  15 ccc aag cgc ggc cag acc tgc gtg gtg cac tac acc ggg atg ctt gaa      96
Pro Lys Arg Gly Gln Thr Cys Val Val His Tyr Thr Gly Met Leu Glu
                20                  25                  30
```

| | | | | | | | | | | | | | | | |
|---|---|---|---|---|---|---|---|---|---|---|---|---|---|---|---|
| gat | gga | aag | aaa | ttt | gat | tcc | tcc | cgg | gac | aga | aac | aag | ccc | ttt | aag | 144 |
| Asp | Gly | Lys | Lys | Phe | Asp | Ser | Ser | Arg | Asp | Arg | Asn | Lys | Pro | Phe | Lys |
|  |  | 35 |  |  |  | 40 |  |  |  |  | 45 |  |  |  |  |

| ttt | atg | cta | ggc | aag | cag | gag | gtg | atc | cga | ggc | tgg | gaa | gaa | ggg | gtt | 192 |
|---|---|---|---|---|---|---|---|---|---|---|---|---|---|---|---|---|
| Phe | Met | Leu | Gly | Lys | Gln | Glu | Val | Ile | Arg | Gly | Trp | Glu | Glu | Gly | Val |
| 50 |  |  |  |  | 55 |  |  |  |  | 60 |  |  |  |  |  |

| gcc | cag | atg | agt | gtg | ggt | cag | aga | gcc | aaa | ctg | act | ata | tct | cca | gat | 240 |
|---|---|---|---|---|---|---|---|---|---|---|---|---|---|---|---|---|
| Ala | Gln | Met | Ser | Val | Gly | Gln | Arg | Ala | Lys | Leu | Thr | Ile | Ser | Pro | Asp |
| 65 |  |  |  |  | 70 |  |  |  |  | 75 |  |  |  |  | 80 |

| tat | gcc | tat | ggt | gcc | act | ggg | cac | cca | ggc | atc | atc | cca | cca | cat | gcc | 288 |
|---|---|---|---|---|---|---|---|---|---|---|---|---|---|---|---|---|
| Tyr | Ala | Tyr | Gly | Ala | Thr | Gly | His | Pro | Gly | Ile | Ile | Pro | Pro | His | Ala |
|  |  |  |  | 85 |  |  |  |  | 90 |  |  |  |  | 95 |  |

| act | ctc | gtc | ttc | gat | gtg | gag | ctt | cta | aaa | ctg | gaa | | | | | 324 |
|---|---|---|---|---|---|---|---|---|---|---|---|---|---|---|---|---|
| Thr | Leu | Val | Phe | Asp | Val | Glu | Leu | Leu | Lys | Leu | Glu |
|  |  |  |  | 100 |  |  |  |  | 105 |  |  |

<210> SEQ ID NO 24
<211> LENGTH: 108
<212> TYPE: PRT
<213> ORGANISM: Homo sapiens
<223> OTHER INFORMATION: FKBP12

<400> SEQUENCE: 24

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 25
<211> LENGTH: 210
<212> TYPE: DNA
<213> ORGANISM: Homo sapiens
<220> FEATURE:
<221> NAME/KEY: CDS
<222> LOCATION: (1)..(210)
<223> OTHER INFORMATION: p53

<400> SEQUENCE: 25

| atg | gag | gag | ccg | cag | tca | gat | cct | agc | gtc | gag | ccc | cct | ctg | agt | cag | 48 |
|---|---|---|---|---|---|---|---|---|---|---|---|---|---|---|---|---|
| Met | Glu | Glu | Pro | Gln | Ser | Asp | Pro | Ser | Val | Glu | Pro | Pro | Leu | Ser | Gln |
| 1 |  |  |  | 5 |  |  |  |  | 10 |  |  |  |  | 15 |  |

| gaa | aca | ttt | tca | gac | cta | tgg | aaa | cta | ctt | cct | gaa | aac | aac | gtt | ctg | 96 |
|---|---|---|---|---|---|---|---|---|---|---|---|---|---|---|---|---|
| Glu | Thr | Phe | Ser | Asp | Leu | Trp | Lys | Leu | Leu | Pro | Glu | Asn | Asn | Val | Leu |
|  |  |  | 20 |  |  |  |  | 25 |  |  |  |  | 30 |  |  |

| tcc | ccc | ttg | ccg | tcc | caa | gca | atg | gat | gat | ttg | atg | ctg | tcc | ccg | gac | 144 |
|---|---|---|---|---|---|---|---|---|---|---|---|---|---|---|---|---|
| Ser | Pro | Leu | Pro | Ser | Gln | Ala | Met | Asp | Asp | Leu | Met | Leu | Ser | Pro | Asp |
|  | 35 |  |  |  |  | 40 |  |  |  |  | 45 |  |  |  |  |

| gat | att | gaa | caa | tgg | ttc | act | gaa | gac | cca | ggt | cca | gat | gaa | gct | ccc | 192 |
|---|---|---|---|---|---|---|---|---|---|---|---|---|---|---|---|---|
| Asp | Ile | Glu | Gln | Trp | Phe | Thr | Glu | Asp | Pro | Gly | Pro | Asp | Glu | Ala | Pro |
| 50 |  |  |  |  | 55 |  |  |  |  | 60 |  |  |  |  |  |

| aga | atg | cca | gag | gct | gct | | | | | | | | | | | 210 |
|---|---|---|---|---|---|---|---|---|---|---|---|---|---|---|---|---|

```
Arg Met Pro Glu Ala Ala
65              70

<210> SEQ ID NO 26
<211> LENGTH: 70
<212> TYPE: PRT
<213> ORGANISM: Homo sapiens
<223> OTHER INFORMATION: p53

<400> SEQUENCE: 26

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala
65              70

<210> SEQ ID NO 27
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: MDM2

<400> SEQUENCE: 27 atg tgc aat acc aac atg tct gta cct act gat ggt gct gta acc acc      48
Met Cys Asn Thr Asn Met Ser Val Pro Thr Asp Gly Ala Val Thr Thr
1               5                   10                  15 tca cag att cca gct tcg gaa caa gag acc ctg gtt aga cca aag cca      96
Ser Gln Ile Pro Ala Ser Glu Gln Glu Thr Leu Val Arg Pro Lys Pro
            20                  25                  30 ttg ctt ttg aag tta tta aag tct gtt ggt gca caa aaa gac act tat     144
Leu Leu Leu Lys Leu Leu Lys Ser Val Gly Ala Gln Lys Asp Thr Tyr
        35                  40                  45 act atg aaa gag gtt ctt ttt tat ctt ggc cag tat att atg act aaa     192
Thr Met Lys Glu Val Leu Phe Tyr Leu Gly Gln Tyr Ile Met Thr Lys
    50                  55                  60 cga tta tat gat gag aag caa caa cat att gta tat tgt tca aat gat     240
Arg Leu Tyr Asp Glu Lys Gln Gln His Ile Val Tyr Cys Ser Asn Asp
65                  70                  75                  80 ctt cta gga gat ttg ttt ggc gtg cca agc ttc tct gtg aaa gag cac     288
Leu Leu Gly Asp Leu Phe Gly Val Pro Ser Phe Ser Val Lys Glu His
                85                  90                  95 agg aaa ata tat acc atg atc tac agg aac ttg gta gta gtc aat cag     336
Arg Lys Ile Tyr Thr Met Ile Tyr Arg Asn Leu Val Val Val Asn Gln
            100                 105                 110 cag gaa tca tcg gac tca ggt                                         357
Gln Glu Ser Ser Asp Ser Gly
        115

<210> SEQ ID NO 28
<211> LENGTH: 119
<212> TYPE: PRT
<213> ORGANISM: Homo sapiens
<223> OTHER INFORMATION: MDM2

<400> SEQUENCE: 28
```

```
Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
                20                  25                  30

Leu Leu Leu Lys Leu Leu Lys Ser Val Gly Ala Gln Lys Asp Thr Tyr
            35                  40                  45

Thr Met Lys Glu Val Leu Phe Tyr Leu Gly Gln Tyr Ile Met Thr Lys
        50                  55                  60

Arg Leu Tyr Asp Glu Lys Gln Gln His Ile Val Tyr Cys Ser Asn Asp
65                  70                  75                  80

Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val Asn Gln
            100                 105                 110

Gln Glu Ser Ser Asp Ser Gly
        115

<210> SEQ ID NO 29
<211> LENGTH: 297
<212> TYPE: DNA
<213> ORGANISM: Homo sapiens
<220> FEATURE:
<221> NAME/KEY: CDS
<222> LOCATION: (1)..(297)
<223> OTHER INFORMATION: Sec5

<400> SEQUENCE: 29 atg tct cga tca cga caa ccc ccc ctt gtg acc ggc atc tct cca aat        48
Met Ser Arg Ser Arg Gln Pro Pro Leu Val Thr Gly Ile Ser Pro Asn
1               5                   10                  15 gaa ggg ata cca tgg acg aag gtc aca atc agg gga gaa aat ctg ggg        96
Glu Gly Ile Pro Trp Thr Lys Val Thr Ile Arg Gly Glu Asn Leu Gly
                20                  25                  30 act ggc ccc acc gac ctc ata ggc ttg acc att tgt gga cat aat tgc       144
Thr Gly Pro Thr Asp Leu Ile Gly Leu Thr Ile Cys Gly His Asn Cys
            35                  40                  45 ctc ctg acg gca gaa tgg atg tct gca agt aaa ata gta tgt cga gtg       192
Leu Leu Thr Ala Glu Trp Met Ser Ala Ser Lys Ile Val Cys Arg Val
50                  55                  60 gga caa gcc aaa aat gac aaa gga gac att att gtc acc act aag tca       240
Gly Gln Ala Lys Asn Asp Lys Gly Asp Ile Ile Val Thr Thr Lys Ser
65                  70                  75                  80 ggt ggc aga gga acc tca aca gtc tct ttc aag cta ctc aaa cct gag       288
Gly Gly Arg Gly Thr Ser Thr Val Ser Phe Lys Leu Leu Lys Pro Glu
                85                  90                  95 aaa ata ggc                                                            297
Lys Ile Gly <210> SEQ ID NO 30
<211> LENGTH: 99
<212> TYPE: PRT
<213> ORGANISM: Homo sapiens
<223> OTHER INFORMATION: Sec5

<400> SEQUENCE: 30

Met Ser Arg Ser Arg Gln Pro Pro Leu Val Thr Gly Ile Ser Pro Asn
1               5                   10                  15

Glu Gly Ile Pro Trp Thr Lys Val Thr Ile Arg Gly Glu Asn Leu Gly
                20                  25                  30
```

```
Thr Gly Pro Thr Asp Leu Ile Gly Leu Thr Ile Cys Gly His Asn Cys
         35                  40                  45
Leu Leu Thr Ala Glu Trp Met Ser Ala Ser Lys Ile Val Cys Arg Val
 50                  55                  60
Gly Gln Ala Lys Asn Asp Lys Gly Asp Ile Ile Val Thr Thr Lys Ser
 65                  70                  75                  80
Gly Gly Arg Gly Thr Ser Thr Val Ser Phe Lys Leu Leu Lys Pro Glu
                 85                  90                  95
Lys Ile Gly

<210> SEQ ID NO 31
<211> LENGTH: 621
<212> TYPE: DNA
<213> ORGANISM: Homo sapiens
<220> FEATURE:
<221> NAME/KEY: CDS
<222> LOCATION: (1)..(621)
<223> OTHER INFORMATION: RalB

<400> SEQUENCE: 31
```

| | | | | | | | | | | | | | | | | |
|---|---|---|---|---|---|---|---|---|---|---|---|---|---|---|---|---|
| atg | gct | gcc | aac | aag | agt | aag | ggc | cag | agc | tcc | ttg | gcc | ctc | cac | aag | 48 |
| Met | Ala | Ala | Asn | Lys | Ser | Lys | Gly | Gln | Ser | Ser | Leu | Ala | Leu | His | Lys | |
| 1 | | | | 5 | | | | | 10 | | | | | 15 | | |
| gtg | atc | atg | gtt | ggc | agc | gga | ggc | gtt | ggc | aag | tca | gcc | ctg | acg | ctt | 96 |
| Val | Ile | Met | Val | Gly | Ser | Gly | Gly | Val | Gly | Lys | Ser | Ala | Leu | Thr | Leu | |
| | | | 20 | | | | | 25 | | | | | 30 | | | |
| cag | ttc | atg | tat | gac | gag | ttt | gta | gaa | gac | tat | gaa | cct | acc | aaa | gct | 144 |
| Gln | Phe | Met | Tyr | Asp | Glu | Phe | Val | Glu | Asp | Tyr | Glu | Pro | Thr | Lys | Ala | |
| | | 35 | | | | | 40 | | | | | 45 | | | | |
| gac | agt | tat | aga | aag | aaa | gtg | gtt | ctt | gat | ggg | gaa | gaa | gtt | cag | ata | 192 |
| Asp | Ser | Tyr | Arg | Lys | Lys | Val | Val | Leu | Asp | Gly | Glu | Glu | Val | Gln | Ile | |
| | 50 | | | | | 55 | | | | | 60 | | | | | |
| gat | att | ctg | gac | acc | gct | ggg | caa | gag | gac | tac | gca | gcc | att | cga | gat | 240 |
| Asp | Ile | Leu | Asp | Thr | Ala | Gly | Gln | Glu | Asp | Tyr | Ala | Ala | Ile | Arg | Asp | |
| 65 | | | | 70 | | | | | 75 | | | | | 80 | | |
| aac | tac | ttt | cgg | agt | ggg | gaa | ggg | ttt | ctt | ctt | gtg | ttc | tca | atc | aca | 288 |
| Asn | Tyr | Phe | Arg | Ser | Gly | Glu | Gly | Phe | Leu | Leu | Val | Phe | Ser | Ile | Thr | |
| | | | 85 | | | | | 90 | | | | | 95 | | | |
| gaa | cat | gaa | tcc | ttt | aca | gca | act | gcc | gaa | ttc | agg | gaa | cag | att | ctc | 336 |
| Glu | His | Glu | Ser | Phe | Thr | Ala | Thr | Ala | Glu | Phe | Arg | Glu | Gln | Ile | Leu | |
| | | 100 | | | | | 105 | | | | | 110 | | | | |
| cgt | gtg | aag | gct | gaa | gaa | gat | aaa | att | cca | ctg | ctc | gtc | gtg | gga | aac | 384 |
| Arg | Val | Lys | Ala | Glu | Glu | Asp | Lys | Ile | Pro | Leu | Leu | Val | Val | Gly | Asn | |
| | 115 | | | | | 120 | | | | | 125 | | | | | |
| aag | tct | gac | cta | gag | gag | cgg | agg | cag | gtg | cct | gtg | gag | gag | gcc | agg | 432 |
| Lys | Ser | Asp | Leu | Glu | Glu | Arg | Arg | Gln | Val | Pro | Val | Glu | Glu | Ala | Arg | |
| 130 | | | | | 135 | | | | | 140 | | | | | | |
| agt | aaa | gcc | gaa | gag | tgg | ggc | gtg | cag | tac | gtg | gag | acg | tca | gcg | aag | 480 |
| Ser | Lys | Ala | Glu | Glu | Trp | Gly | Val | Gln | Tyr | Val | Glu | Thr | Ser | Ala | Lys | |
| 145 | | | | 150 | | | | | 155 | | | | | 160 | | |
| acc | cgg | gcc | aac | gtg | gac | aag | gtg | ttc | ttt | gac | cta | atg | aga | gaa | atc | 528 |
| Thr | Arg | Ala | Asn | Val | Asp | Lys | Val | Phe | Phe | Asp | Leu | Met | Arg | Glu | Ile | |
| | | | 165 | | | | | 170 | | | | | 175 | | | |
| aga | aca | aag | aag | atg | tca | gaa | aac | aaa | gac | aag | aat | ggc | aag | aaa | agc | 576 |
| Arg | Thr | Lys | Lys | Met | Ser | Glu | Asn | Lys | Asp | Lys | Asn | Gly | Lys | Lys | Ser | |
| | | 180 | | | | | 185 | | | | | 190 | | | | |
| agc | aag | aac | aag | aaa | agt | ttt | aaa | gaa | aga | tgt | tgc | tta | cta | tga | | 621 |
| Ser | Lys | Asn | Lys | Lys | Ser | Phe | Lys | Glu | Arg | Cys | Cys | Leu | Leu | | | |
| | 195 | | | | | 200 | | | | | 205 | | | | | |

-continued

```
<210> SEQ ID NO 32
<211> LENGTH: 206
<212> TYPE: PRT
<213> ORGANISM: Homo sapiens
<223> OTHER INFORMATION: RalB

<400> SEQUENCE: 32

Met Ala Ala Asn Lys Ser Lys Gly Gln Ser Ser Leu Ala Leu His Lys
1               5                   10                  15

Val Ile Met Val Gly Ser Gly Gly Val Gly Lys Ser Ala Leu Thr Leu
            20                  25                  30

Gln Phe Met Tyr Asp Glu Phe Val Glu Asp Tyr Glu Pro Thr Lys Ala
        35                  40                  45

Asp Ser Tyr Arg Lys Lys Val Val Leu Asp Gly Glu Glu Val Gln Ile
    50                  55                  60

Asp Ile Leu Asp Thr Ala Gly Gln Glu Asp Tyr Ala Ala Ile Arg Asp
65                  70                  75                  80

Asn Tyr Phe Arg Ser Gly Glu Gly Phe Leu Leu Val Phe Ser Ile Thr
                85                  90                  95

Glu His Glu Ser Phe Thr Ala Thr Ala Glu Phe Arg Glu Gln Ile Leu
            100                 105                 110

Arg Val Lys Ala Glu Glu Asp Lys Ile Pro Leu Leu Val Val Gly Asn
        115                 120                 125

Lys Ser Asp Leu Glu Glu Arg Arg Gln Val Pro Val Glu Glu Ala Arg
    130                 135                 140

Ser Lys Ala Glu Glu Trp Gly Val Gln Tyr Val Glu Thr Ser Ala Lys
145                 150                 155                 160

Thr Arg Ala Asn Val Asp Lys Val Phe Phe Asp Leu Met Arg Glu Ile
                165                 170                 175

Arg Thr Lys Lys Met Ser Glu Asn Lys Asp Lys Asn Gly Lys Lys Ser
            180                 185                 190

Ser Lys Asn Lys Lys Ser Phe Lys Glu Arg Cys Cys Leu Leu
        195                 200                 205

<210> SEQ ID NO 33
<211> LENGTH: 621
<212> TYPE: DNA
<213> ORGANISM: Artificial Sequence
<220> FEATURE:
<223> OTHER INFORMATION: Synthetic RalB Protein Q72L mutant
<220> FEATURE:
<221> NAME/KEY: CDS
<222> LOCATION: (1)..(621)
<223> OTHER INFORMATION: RalB(Q72L)

<400> SEQUENCE: 33 atg gct gcc aac aag agt aag ggc cag agc tcc ttg gcc ctc cac aag      48
Met Ala Ala Asn Lys Ser Lys Gly Gln Ser Ser Leu Ala Leu His Lys
1               5                   10                  15 gtg atc atg gtt ggc agc gga ggc gtt ggc aag tca gcc ctg acg ctt      96
Val Ile Met Val Gly Ser Gly Gly Val Gly Lys Ser Ala Leu Thr Leu
            20                  25                  30 cag ttc atg tat gac gag ttt gta gaa gac tat gaa cct acc aaa gct     144
Gln Phe Met Tyr Asp Glu Phe Val Glu Asp Tyr Glu Pro Thr Lys Ala
        35                  40                  45 gac agt tat aga aag aaa gtg gtt ctt gat ggg gaa gaa gtt cag ata     192
Asp Ser Tyr Arg Lys Lys Val Val Leu Asp Gly Glu Glu Val Gln Ile
    50                  55                  60 gat att ctg gac acc gct ggg cta gag gac tac gca gcc att cga gat     240
Asp Ile Leu Asp Thr Ala Gly Leu Glu Asp Tyr Ala Ala Ile Arg Asp
```

```
                65                  70                  75                  80
aac tac ttt cgg agt ggg gaa ggg ttt ctt ctt gtg ttc tca atc aca        288
Asn Tyr Phe Arg Ser Gly Glu Gly Phe Leu Leu Val Phe Ser Ile Thr
                85                  90                  95 gaa cat gaa tcc ttt aca gca act gcc gaa ttc agg gaa cag att ctc        336
Glu His Glu Ser Phe Thr Ala Thr Ala Glu Phe Arg Glu Gln Ile Leu
            100                 105                 110 cgt gtg aag gct gaa gaa gat aaa att cca ctg ctc gtc gtg gga aac        384
Arg Val Lys Ala Glu Glu Asp Lys Ile Pro Leu Leu Val Val Gly Asn
        115                 120                 125 aag tct gac cta gag gag cgg agg cag gtg cct gtg gag gag gcc agg        432
Lys Ser Asp Leu Glu Glu Arg Arg Gln Val Pro Val Glu Glu Ala Arg
    130                 135                 140 agt aaa gcc gaa gag tgg ggc gtg cag tac gtg gag acg tca gcg aag        480
Ser Lys Ala Glu Glu Trp Gly Val Gln Tyr Val Glu Thr Ser Ala Lys
145                 150                 155                 160 acc cgg gcc aac gtg gac aag gtg ttc ttt gac cta atg aga gaa atc        528
Thr Arg Ala Asn Val Asp Lys Val Phe Phe Asp Leu Met Arg Glu Ile
                165                 170                 175 aga aca aag aag atg tca gaa aac aaa gac aag aat ggc aag aaa agc        576
Arg Thr Lys Lys Met Ser Glu Asn Lys Asp Lys Asn Gly Lys Lys Ser
            180                 185                 190 agc aag aac aag aaa agt ttt aaa gaa aga tgt tgc tta cta tga            621
Ser Lys Asn Lys Lys Ser Phe Lys Glu Arg Cys Cys Leu Leu
        195                 200                 205
```

<210> SEQ ID NO 34
<211> LENGTH: 206
<212> TYPE: PRT
<213> ORGANISM: Artificial Sequence
<220> FEATURE:
<223> OTHER INFORMATION: Synthetic RalB Protein Q72L mutant

<400> SEQUENCE: 34

```
Met Ala Ala Asn Lys Ser Lys Gly Gln Ser Ser Leu Ala Leu His Lys
1               5                   10                  15

Val Ile Met Val Gly Ser Gly Gly Val Gly Lys Ser Ala Leu Thr Leu
            20                  25                  30

Gln Phe Met Tyr Asp Glu Phe Val Glu Asp Tyr Glu Pro Thr Lys Ala
        35                  40                  45

Asp Ser Tyr Arg Lys Lys Val Val Leu Asp Gly Glu Glu Val Gln Ile
    50                  55                  60

Asp Ile Leu Asp Thr Ala Gly Leu Glu Asp Tyr Ala Ala Ile Arg Asp
65                  70                  75                  80

Asn Tyr Phe Arg Ser Gly Glu Gly Phe Leu Leu Val Phe Ser Ile Thr
                85                  90                  95

Glu His Glu Ser Phe Thr Ala Thr Ala Glu Phe Arg Glu Gln Ile Leu
            100                 105                 110

Arg Val Lys Ala Glu Glu Asp Lys Ile Pro Leu Leu Val Val Gly Asn
        115                 120                 125

Lys Ser Asp Leu Glu Glu Arg Arg Gln Val Pro Val Glu Glu Ala Arg
    130                 135                 140

Ser Lys Ala Glu Glu Trp Gly Val Gln Tyr Val Glu Thr Ser Ala Lys
145                 150                 155                 160

Thr Arg Ala Asn Val Asp Lys Val Phe Phe Asp Leu Met Arg Glu Ile
                165                 170                 175

Arg Thr Lys Lys Met Ser Glu Asn Lys Asp Lys Asn Gly Lys Lys Ser
            180                 185                 190
```

```
Ser Lys Asn Lys Lys Ser Phe Lys Glu Arg Cys Cys Leu Leu
        195                 200                 205

<210> SEQ ID NO 35
<211> LENGTH: 621
<212> TYPE: DNA
<213> ORGANISM: Artificial Sequence
<220> FEATURE:
<223> OTHER INFORMATION: Synthetic RalB Protein S28N mutant
<220> FEATURE:
<221> NAME/KEY: CDS
<222> LOCATION: (1)..(621)
<223> OTHER INFORMATION: RalB(S28N)

<400> SEQUENCE: 35 atg gct gcc aac aag agt aag ggc cag agc tcc ttg gcc ctc cac aag      48
Met Ala Ala Asn Lys Ser Lys Gly Gln Ser Ser Leu Ala Leu His Lys
1               5                   10                  15 gtg atc atg gtt ggc agc gga ggc gtt ggc aag aac gcc ctg acg ctt      96
Val Ile Met Val Gly Ser Gly Gly Val Gly Lys Asn Ala Leu Thr Leu
            20                  25                  30 cag ttc atg tat gac gag ttt gta gaa gac tat gaa cct acc aaa gct     144
Gln Phe Met Tyr Asp Glu Phe Val Glu Asp Tyr Glu Pro Thr Lys Ala
        35                  40                  45 gac agt tat aga aag aaa gtg gtt ctt gat ggg gaa gaa gtt cag ata     192
Asp Ser Tyr Arg Lys Lys Val Val Leu Asp Gly Glu Glu Val Gln Ile
    50                  55                  60 gat att ctg gac acc gct ggg caa gag gac tac gca gcc att cga gat     240
Asp Ile Leu Asp Thr Ala Gly Gln Glu Asp Tyr Ala Ala Ile Arg Asp
65                  70                  75                  80 aac tac ttt cgg agt ggg gaa ggg ttt ctt ctt gtg ttc tca atc aca     288
Asn Tyr Phe Arg Ser Gly Glu Gly Phe Leu Leu Val Phe Ser Ile Thr
                85                  90                  95 gaa cat gaa tcc ttt aca gca act gcc gaa ttc agg gaa cag att ctc     336
Glu His Glu Ser Phe Thr Ala Thr Ala Glu Phe Arg Glu Gln Ile Leu
            100                 105                 110 cgt gtg aag gct gaa gaa gat aaa att cca ctg ctc gtc gtg gga aac     384
Arg Val Lys Ala Glu Glu Asp Lys Ile Pro Leu Leu Val Val Gly Asn
        115                 120                 125 aag tct gac cta gag gag cgg agg cag gtg cct gtg gag gag gcc agg     432
Lys Ser Asp Leu Glu Glu Arg Arg Gln Val Pro Val Glu Glu Ala Arg
    130                 135                 140 agt aaa gcc gaa gag tgg ggc gtg cag tac gtg gag acg tca gcg aag     480
Ser Lys Ala Glu Glu Trp Gly Val Gln Tyr Val Glu Thr Ser Ala Lys
145                 150                 155                 160 acc cgg gcc aac gtg gac aag gtg ttc ttt gac cta atg aga gaa atc     528
Thr Arg Ala Asn Val Asp Lys Val Phe Phe Asp Leu Met Arg Glu Ile
                165                 170                 175 aga aca aag aag atg tca gaa aac aaa gac aag aat ggc aag aaa agc     576
Arg Thr Lys Lys Met Ser Glu Asn Lys Asp Lys Asn Gly Lys Lys Ser
            180                 185                 190 agc aag aac aag aaa agt ttt aaa gaa aga tgt tgc tta cta tga         621
Ser Lys Asn Lys Lys Ser Phe Lys Glu Arg Cys Cys Leu Leu
        195                 200                 205

<210> SEQ ID NO 36
<211> LENGTH: 206
<212> TYPE: PRT
<213> ORGANISM: Artificial Sequence
<220> FEATURE:
<223> OTHER INFORMATION: Synthetic RalB Protein S28N mutant

<400> SEQUENCE: 36
```

```
Met Ala Ala Asn Lys Ser Lys Gly Gln Ser Ser Leu Ala Leu His Lys
1               5                   10                  15

Val Ile Met Val Gly Ser Gly Val Gly Lys Asn Ala Leu Thr Leu
            20                  25                  30

Gln Phe Met Tyr Asp Glu Phe Val Glu Asp Tyr Glu Pro Thr Lys Ala
        35                  40                  45

Asp Ser Tyr Arg Lys Lys Val Val Leu Asp Gly Glu Glu Val Gln Ile
    50                  55                  60

Asp Ile Leu Asp Thr Ala Gly Gln Glu Asp Tyr Ala Ala Ile Arg Asp
65                  70                  75                  80

Asn Tyr Phe Arg Ser Gly Glu Gly Phe Leu Leu Val Phe Ser Ile Thr
                85                  90                  95

Glu His Glu Ser Phe Thr Ala Thr Ala Glu Phe Arg Glu Gln Ile Leu
                100                 105                 110

Arg Val Lys Ala Glu Glu Asp Lys Ile Pro Leu Leu Val Val Gly Asn
        115                 120                 125

Lys Ser Asp Leu Glu Glu Arg Arg Gln Val Pro Val Glu Glu Ala Arg
    130                 135                 140

Ser Lys Ala Glu Glu Trp Gly Val Gln Tyr Val Glu Thr Ser Ala Lys
145                 150                 155                 160

Thr Arg Ala Asn Val Asp Lys Val Phe Phe Asp Leu Met Arg Glu Ile
                165                 170                 175

Arg Thr Lys Lys Met Ser Glu Asn Lys Asp Lys Asn Gly Lys Lys Ser
            180                 185                 190

Ser Lys Asn Lys Lys Ser Phe Lys Glu Arg Cys Cys Leu Leu
            195                 200                 205

<210> SEQ ID NO 37
<211> LENGTH: 441
<212> TYPE: DNA
<213> ORGANISM: Homo sapiens
<220> FEATURE:
<221> NAME/KEY: CDS
<222> LOCATION: (1)..(441)
<223> OTHER INFORMATION: Calmodulin

<400> SEQUENCE: 37 gac caa ctg aca gaa gag cag att gca gag ttc aaa gaa gcc ttc tca    48
Asp Gln Leu Thr Glu Glu Gln Ile Ala Glu Phe Lys Glu Ala Phe Ser
1               5                   10                  15 tta ttc gac aag gat ggg gac ggc acc atc acc aca aag gaa ctt ggc    96
Leu Phe Asp Lys Asp Gly Asp Gly Thr Ile Thr Thr Lys Glu Leu Gly
            20                  25                  30 acc gtt atg agg tcg ctt gga caa aac cca acg gaa gca gaa ttg cag   144
Thr Val Met Arg Ser Leu Gly Gln Asn Pro Thr Glu Ala Glu Leu Gln
        35                  40                  45 gat atg atc aat gaa gtc gat gct gat ggc aat gga acg att tac ttt   192
Asp Met Ile Asn Glu Val Asp Ala Asp Gly Asn Gly Thr Ile Tyr Phe
    50                  55                  60 cct gaa ttt ctt act atg atg gct aga aaa atg aag gac aca gac agc   240
Pro Glu Phe Leu Thr Met Met Ala Arg Lys Met Lys Asp Thr Asp Ser
65                  70                  75                  80 gaa gag gaa atc cga gaa gca ttc cgt gtt ttt gac aag gat ggg aac   288
Glu Glu Glu Ile Arg Glu Ala Phe Arg Val Phe Asp Lys Asp Gly Asn
                85                  90                  95 ggc tac atc agc gct gct gaa tta cgt cac gtc atg aca aac ctc ggg   336
Gly Tyr Ile Ser Ala Ala Glu Leu Arg His Val Met Thr Asn Leu Gly
                100                 105                 110
```

```
gag aag tta aca gat gaa gaa gtt gat gaa atg ata agg gaa gca gat    384
Glu Lys Leu Thr Asp Glu Glu Val Asp Glu Met Ile Arg Glu Ala Asp
        115                 120                 125 atc gat ggt gat ggc caa gta aac tat gaa gag ttt gta caa atg atg    432
Ile Asp Gly Asp Gly Gln Val Asn Tyr Glu Glu Phe Val Gln Met Met
130                 135                 140 aca gca aag                                                        441
Thr Ala Lys
145

<210> SEQ ID NO 38
<211> LENGTH: 147
<212> TYPE: PRT
<213> ORGANISM: Homo sapiens
<223> OTHER INFORMATION: Calmodulin

<400> SEQUENCE: 38

Asp Gln Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
            20                  25                  30

Thr Val Met Arg Ser Leu Gly Gln Asn Pro Thr Glu Ala Glu Leu Gln
        35                  40                  45

Asp Met Ile Asn Glu Val Asp Ala Asp Gly Asn Gly Thr Ile Tyr Phe
    50                  55                  60

Pro Glu Phe Leu Thr Met Met Ala Arg Lys Met Lys Asp Thr Asp Ser
65                  70                  75                  80

Glu Glu Glu Ile Arg Glu Ala Phe Arg Val Phe Asp Lys Asp Gly Asn
                85                  90                  95

Gly Tyr Ile Ser Ala Ala Glu Leu Arg His Val Met Thr Asn Leu Gly
            100                 105                 110

Glu Lys Leu Thr Asp Glu Glu Val Asp Glu Met Ile Arg Glu Ala Asp
        115                 120                 125

Ile Asp Gly Asp Gly Gln Val Asn Tyr Glu Glu Phe Val Gln Met Met
    130                 135                 140

Thr Ala Lys
145

<210> SEQ ID NO 39
<211> LENGTH: 78
<212> TYPE: DNA
<213> ORGANISM: Homo sapiens
<220> FEATURE:
<221> NAME/KEY: CDS
<222> LOCATION: (1)..(78)
<223> OTHER INFORMATION: M13 peptide

<400> SEQUENCE: 39 aag agg cgc tgg aag aaa aac ttc att gcc gtc agc gct gcc aac cgg    48
Lys Arg Arg Trp Lys Lys Asn Phe Ile Ala Val Ser Ala Ala Asn Arg
1               5                   10                  15 ttc aag aag atc tcc agc tcc ggg gca ctg                            78
Phe Lys Lys Ile Ser Ser Ser Gly Ala Leu
            20                  25

<210> SEQ ID NO 40
<211> LENGTH: 26
<212> TYPE: PRT
<213> ORGANISM: Homo sapiens
<223> OTHER INFORMATION: M13 peptide
```

<400> SEQUENCE: 40

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 41
<211> LENGTH: 594
<212> TYPE: DNA
<213> ORGANISM: Homo sapiens
<220> FEATURE:
<221> NAME/KEY: CDS
<222> LOCATION: (1)..(594)
<223> OTHER INFORMATION: HRas

<400> SEQUENCE: 41

| | |
|---|---|
| atg acg gaa tat aag ctg gtg gtg gtg ggc gcc gtc ggt gtg ggc aag<br>Met Thr Glu Tyr Lys Leu Val Val Val Gly Ala Val Gly Val Gly Lys<br>1               5                   10                  15 | 48 |
| agt gcg ctg acc atc cag ctg atc cag aac cat ttt gtg gac gaa tac<br>Ser Ala Leu Thr Ile Gln Leu Ile Gln Asn His Phe Val Asp Glu Tyr<br>            20                  25                  30 | 96 |
| gac ccc act ata gag gat tcc tac cgg aag cag gtg gtc att gat ggg<br>Asp Pro Thr Ile Glu Asp Ser Tyr Arg Lys Gln Val Val Ile Asp Gly<br>        35                  40                  45 | 144 |
| gag acg tgc ctg ttg gac atc ctg gat acc gcc ggc cag gag gag tac<br>Glu Thr Cys Leu Leu Asp Ile Leu Asp Thr Ala Gly Gln Glu Glu Tyr<br>    50                  55                  60 | 192 |
| agc gcc atg cgg gac cag tac atg cgc acc ggg gag ggc ttc ctg tgt<br>Ser Ala Met Arg Asp Gln Tyr Met Arg Thr Gly Glu Gly Phe Leu Cys<br>65                  70                  75                  80 | 240 |
| gtg ttt gcc atc aac aac acc aag tct ttt gag gac atc cac cag tac<br>Val Phe Ala Ile Asn Asn Thr Lys Ser Phe Glu Asp Ile His Gln Tyr<br>                85                  90                  95 | 288 |
| agg gag cag atc aaa cgg gtg aag gac tcg gat gac gtg ccc atg gtg<br>Arg Glu Gln Ile Lys Arg Val Lys Asp Ser Asp Asp Val Pro Met Val<br>            100                 105                 110 | 336 |
| ctg gtg ggg aac aag tgt gac ctg gct gca cgc act gtg gaa tct cgg<br>Leu Val Gly Asn Lys Cys Asp Leu Ala Ala Arg Thr Val Glu Ser Arg<br>        115                 120                 125 | 384 |
| cag gct cag gac ctc gcc cga agc tac ggc atc ccc tac atc gag acc<br>Gln Ala Gln Asp Leu Ala Arg Ser Tyr Gly Ile Pro Tyr Ile Glu Thr<br>    130                 135                 140 | 432 |
| tcg gcc aag acc cgg cag gga gtg gag gat gcc ttc tac acg ttg gtg<br>Ser Ala Lys Thr Arg Gln Gly Val Glu Asp Ala Phe Tyr Thr Leu Val<br>145                 150                 155                 160 | 480 |
| cgt gag atc cgg cag cac aag ctg cgg aag ctg aac gtc tcc gga ggt<br>Arg Glu Ile Arg Gln His Lys Leu Arg Lys Leu Asn Val Ser Gly Gly<br>                165                 170                 175 | 528 |
| ctc gag aag atg agc aaa gat ggt aaa aag aaa aag aag tca aag<br>Leu Glu Lys Met Ser Lys Asp Gly Lys Lys Lys Lys Lys Ser Lys<br>            180                 185                 190 | 576 |
| aca aag tgt gta att atg<br>Thr Lys Cys Val Ile Met<br>        195 | 594 |

<210> SEQ ID NO 42
<211> LENGTH: 198
<212> TYPE: PRT
<213> ORGANISM: Homo sapiens
<223> OTHER INFORMATION: HRas

<400> SEQUENCE: 42

```
Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Ile Asp Gly
        35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Val Ser Gly Gly
                165                 170                 175

Leu Glu Lys Met Ser Lys Asp Gly Lys Lys Lys Lys Lys Ser Lys
            180                 185                 190

Thr Lys Cys Val Ile Met
        195
```

<210> SEQ ID NO 43
<211> LENGTH: 243
<212> TYPE: DNA
<213> ORGANISM: Homo sapiens
<220> FEATURE:
<221> NAME/KEY: CDS
<222> LOCATION: (1)..(243)
<223> OTHER INFORMATION: cRaf

<400> SEQUENCE: 43

```
cct tct aag aca agc aac act atc cgt gtt ttc ttg ccg aac aag caa        48
Pro Ser Lys Thr Ser Asn Thr Ile Arg Val Phe Leu Pro Asn Lys Gln
1               5                   10                  15 aga aca gtg gtc aat gtg cga aat gga atg agc ttg cat gac tgc ctt        96
Arg Thr Val Val Asn Val Arg Asn Gly Met Ser Leu His Asp Cys Leu
            20                  25                  30 atg aaa gca ctc aag gtg agg ggc ctg caa cca gag tgc tgt gca gtg       144
Met Lys Ala Leu Lys Val Arg Gly Leu Gln Pro Glu Cys Cys Ala Val
        35                  40                  45 ttc aga ctt ctc cac gaa cac aaa ggt aaa aaa gca cgc tta gat tgg       192
Phe Arg Leu Leu His Glu His Lys Gly Lys Lys Ala Arg Leu Asp Trp
50                  55                  60 aat act gat gct gcg tct ttg att gga gaa gaa ctt caa gta gat ttc       240
Asn Thr Asp Ala Ala Ser Leu Ile Gly Glu Glu Leu Gln Val Asp Phe
65                  70                  75                  80 ctg                                                                   243
Leu
```

<210> SEQ ID NO 44
<211> LENGTH: 81

```
<212> TYPE: PRT
<213> ORGANISM: Homo sapiens
<223> OTHER INFORMATION: cRaf

<400> SEQUENCE: 44

Pro Ser Lys Thr Ser Asn Thr Ile Arg Val Phe Leu Pro Asn Lys Gln
1               5                   10                  15

Arg Thr Val Val Asn Val Arg Asn Gly Met Ser Leu His Asp Cys Leu
            20                  25                  30

Met Lys Ala Leu Lys Val Arg Gly Leu Gln Pro Glu Cys Cys Ala Val
        35                  40                  45

Phe Arg Leu Leu His Glu His Lys Gly Lys Lys Ala Arg Leu Asp Trp
    50                  55                  60

Asn Thr Asp Ala Ala Ser Leu Ile Gly Glu Glu Leu Gln Val Asp Phe
65                  70                  75                  80

Leu

<210> SEQ ID NO 45
<211> LENGTH: 30
<212> TYPE: DNA
<213> ORGANISM: Homo sapiens
<220> FEATURE:
<221> NAME/KEY: CDS
<222> LOCATION: (1)..(30)
<223> OTHER INFORMATION: Smac

<400> SEQUENCE: 45 atg gcc gtg ccc atc gcc cag aaa tca gag                           30
Met Ala Val Pro Ile Ala Gln Lys Ser Glu
1               5                   10

<210> SEQ ID NO 46
<211> LENGTH: 10
<212> TYPE: PRT
<213> ORGANISM: Homo sapiens
<223> OTHER INFORMATION: Smac

<400> SEQUENCE: 46

Met Ala Val Pro Ile Ala Gln Lys Ser Glu
1               5                   10

<210> SEQ ID NO 47
<211> LENGTH: 342
<212> TYPE: DNA
<213> ORGANISM: Homo sapiens
<220> FEATURE:
<221> NAME/KEY: CDS
<222> LOCATION: (1)..(342)
<223> OTHER INFORMATION: XIAP

<400> SEQUENCE: 47 gct gtg agt tct gat agg aat ttc cca aat tca aca aat ctt cca aga    48
Ala Val Ser Ser Asp Arg Asn Phe Pro Asn Ser Thr Asn Leu Pro Arg
1               5                   10                  15 aat cca tcc atg gca gat tat gaa gca cgg atc ttt act ttt gga aca    96
Asn Pro Ser Met Ala Asp Tyr Glu Ala Arg Ile Phe Thr Phe Gly Thr
            20                  25                  30 tgg ata tac tca gtt aac aag gag cag ctt gca aga gct gga ttt tat   144
Trp Ile Tyr Ser Val Asn Lys Glu Gln Leu Ala Arg Ala Gly Phe Tyr
        35                  40                  45 gct tta ggt gaa ggt gat aaa gta aag tgc ttt cac tgt gga gga ggg   192
Ala Leu Gly Glu Gly Asp Lys Val Lys Cys Phe His Cys Gly Gly Gly
    50                  55                  60
```

-continued

```
cta act gat tgg aag ccc agt gaa gac cct tgg gaa caa cat gct aaa      240
Leu Thr Asp Trp Lys Pro Ser Glu Asp Pro Trp Glu Gln His Ala Lys
 65                  70                  75                  80 tgg tat cca ggg tgc aaa tat ctg tta gaa cag aag gga caa gaa tat      288
Trp Tyr Pro Gly Cys Lys Tyr Leu Leu Glu Gln Lys Gly Gln Glu Tyr
                 85                  90                  95 ata aac aat att cat tta act cat tca ctt gag gag tgt ctg gta aga      336
Ile Asn Asn Ile His Leu Thr His Ser Leu Glu Glu Cys Leu Val Arg
            100                 105                 110 act act                                                              342
Thr Thr <210> SEQ ID NO 48
<211> LENGTH: 114
<212> TYPE: PRT
<213> ORGANISM: Homo sapiens
<223> OTHER INFORMATION: XIAP

<400> SEQUENCE: 48

Ala Val Ser Ser Asp Arg Asn Phe Pro Asn Ser Thr Asn Leu Pro Arg
 1               5                  10                  15

Asn Pro Ser Met Ala Asp Tyr Glu Ala Arg Ile Phe Thr Phe Gly Thr
                20                  25                  30

Trp Ile Tyr Ser Val Asn Lys Glu Gln Leu Ala Arg Ala Gly Phe Tyr
            35                  40                  45

Ala Leu Gly Glu Gly Asp Lys Val Lys Cys Phe His Cys Gly Gly Gly
        50                  55                  60

Leu Thr Asp Trp Lys Pro Ser Glu Asp Pro Trp Glu Gln His Ala Lys
 65                  70                  75                  80

Trp Tyr Pro Gly Cys Lys Tyr Leu Leu Glu Gln Lys Gly Gln Glu Tyr
                 85                  90                  95

Ile Asn Asn Ile His Leu Thr His Ser Leu Glu Glu Cys Leu Val Arg
            100                 105                 110

Thr Thr

<210> SEQ ID NO 49
<211> LENGTH: 627
<212> TYPE: DNA
<213> ORGANISM: Homo sapiens
<220> FEATURE:
<221> NAME/KEY: CDS
<222> LOCATION: (1)..(627)
<223> OTHER INFORMATION: BclX(L)

<400> SEQUENCE: 49 atg tct cag agc aac cgg gag ctg gtg gtt gac ttt ctc tcc tac aag       48
Met Ser Gln Ser Asn Arg Glu Leu Val Val Asp Phe Leu Ser Tyr Lys
 1               5                  10                  15 ctt tcc cag aaa gga tac agc tgg agt cag ttt agt gat gtg gaa gag       96
Leu Ser Gln Lys Gly Tyr Ser Trp Ser Gln Phe Ser Asp Val Glu Glu
                20                  25                  30 aac agg act gag gcc cca gaa ggg act gaa tcg gag atg gag acc ccc      144
Asn Arg Thr Glu Ala Pro Glu Gly Thr Glu Ser Glu Met Glu Thr Pro
            35                  40                  45 agt gcc atc aat ggc aac cca tcc tgg cac ctg gca gac agc ccc gcg      192
Ser Ala Ile Asn Gly Asn Pro Ser Trp His Leu Ala Asp Ser Pro Ala
        50                  55                  60 gtg aat gga gcc act ggc cac agc agc agt ttg gat gcc cgg gag gtg      240
Val Asn Gly Ala Thr Gly His Ser Ser Ser Leu Asp Ala Arg Glu Val
 65                  70                  75                  80
```

| | | | | | | | | | | | | | |
|---|---|---|---|---|---|---|---|---|---|---|---|---|---|
| atc | ccc | atg | gca | gca | gta | aag | caa | gcg | ctg | agg | gag | gca | ggc | gac | gag | 288 |
| Ile | Pro | Met | Ala | Ala | Val | Lys | Gln | Ala | Leu | Arg | Glu | Ala | Gly | Asp | Glu |
| | | | 85 | | | | | 90 | | | | | 95 | | |
| ttt | gaa | ctg | cgg | tac | cgg | cgg | gca | ttc | agt | gac | ctg | aca | tcc | cag | ctc | 336 |
| Phe | Glu | Leu | Arg | Tyr | Arg | Arg | Ala | Phe | Ser | Asp | Leu | Thr | Ser | Gln | Leu |
| | | | 100 | | | | | 105 | | | | | 110 | | |
| cac | atc | acc | cca | ggg | aca | gca | tat | cag | agc | ttt | gaa | cag | gta | gtg | aat | 384 |
| His | Ile | Thr | Pro | Gly | Thr | Ala | Tyr | Gln | Ser | Phe | Glu | Gln | Val | Val | Asn |
| | | | 115 | | | | | 120 | | | | | 125 | | |
| gaa | ctc | ttc | cgg | gat | ggg | gta | aac | tgg | ggt | cgc | att | gtg | gcc | ttt | ttc | 432 |
| Glu | Leu | Phe | Arg | Asp | Gly | Val | Asn | Trp | Gly | Arg | Ile | Val | Ala | Phe | Phe |
| | | | 130 | | | | | 135 | | | | | 140 | | |
| tcc | ttc | ggc | ggg | gca | ctg | tgc | gtg | gaa | agc | gta | gac | aag | gag | atg | cag | 480 |
| Ser | Phe | Gly | Gly | Ala | Leu | Cys | Val | Glu | Ser | Val | Asp | Lys | Glu | Met | Gln |
| 145 | | | | | 150 | | | | | 155 | | | | | 160 |
| gta | ttg | gtg | agt | cgg | atc | gca | gct | tgg | atg | gcc | act | tac | ctg | aat | gac | 528 |
| Val | Leu | Val | Ser | Arg | Ile | Ala | Ala | Trp | Met | Ala | Thr | Tyr | Leu | Asn | Asp |
| | | | | 165 | | | | | 170 | | | | | 175 | |
| cac | cta | gag | cct | tgg | atc | cag | gag | aac | ggc | ggc | tgg | gat | act | ttt | gtg | 576 |
| His | Leu | Glu | Pro | Trp | Ile | Gln | Glu | Asn | Gly | Gly | Trp | Asp | Thr | Phe | Val |
| | | | 180 | | | | | 185 | | | | | 190 | | |
| gaa | ctc | tat | ggg | aac | aat | gca | gca | gcc | gag | agc | cga | aag | ggc | cag | gaa | 624 |
| Glu | Leu | Tyr | Gly | Asn | Asn | Ala | Ala | Ala | Glu | Ser | Arg | Lys | Gly | Gln | Glu |
| | | | 195 | | | | | 200 | | | | | 205 | | |
| cgc | | | | | | | | | | | | | | | | 627 |
| Arg | | | | | | | | | | | | | | | | |

<210> SEQ ID NO 50
<211> LENGTH: 209
<212> TYPE: PRT
<213> ORGANISM: Homo sapiens
<223> OTHER INFORMATION: BclX(L)

<400> SEQUENCE: 50

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
                20                  25                  30

Asn Arg Thr Glu Ala Pro Glu Gly Thr Glu Ser Glu Met Glu Thr Pro
            35                  40                  45

Ser Ala Ile Asn Gly Asn Pro Ser Trp His Leu Ala Asp Ser Pro Ala
        50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
                100                 105                 110

His Ile Thr Pro Gly Thr Ala Tyr Gln Ser Phe Glu Gln Val Val Asn
            115                 120                 125

Glu Leu Phe Arg Asp Gly Val Asn Trp Gly Arg Ile Val Ala Phe Phe
        130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

-continued

```
Glu Leu Tyr Gly Asn Asn Ala Ala Ala Glu Ser Arg Lys Gly Gln Glu
        195                 200                 205
Arg

<210> SEQ ID NO 51
<211> LENGTH: 75
<212> TYPE: DNA
<213> ORGANISM: Homo sapiens
<220> FEATURE:
<221> NAME/KEY: CDS
<222> LOCATION: (1)..(75)
<223> OTHER INFORMATION: BAD

<400> SEQUENCE: 51 aac ctc tgg gca gca cag cgc tat ggc cgc gag ctc cgg agg atg agt      48
Asn Leu Trp Ala Ala Gln Arg Tyr Gly Arg Glu Leu Arg Arg Met Ser
1               5                   10                  15 gac gag ttt gtg gac tcc ttt aag aag                                  75
Asp Glu Phe Val Asp Ser Phe Lys Lys
            20                  25

<210> SEQ ID NO 52
<211> LENGTH: 25
<212> TYPE: PRT
<213> ORGANISM: Homo sapiens
<223> OTHER INFORMATION: BAD

<400> SEQUENCE: 52

Asn Leu Trp Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 53
<211> LENGTH: 579
<212> TYPE: DNA
<213> ORGANISM: Homo sapiens
<220> FEATURE:
<221> NAME/KEY: CDS
<222> LOCATION: (1)..(579)
<223> OTHER INFORMATION: Rac1

<400> SEQUENCE: 53 atg cag gcc atc aag tgt gtg gtg gtg gga gac gga gct gta ggt aaa      48
Met Gln Ala Ile Lys Cys Val Val Val Gly Asp Gly Ala Val Gly Lys
1               5                   10                  15 act tgc cta ctg atc agt tac aca acc aat gca ttt cct gga gaa tat      96
Thr Cys Leu Leu Ile Ser Tyr Thr Thr Asn Ala Phe Pro Gly Glu Tyr
            20                  25                  30 atc cct act gtc ttt gac aat tat tct gcc aat gtt atg gta gat gga     144
Ile Pro Thr Val Phe Asp Asn Tyr Ser Ala Asn Val Met Val Asp Gly
        35                  40                  45 aaa ccg gtg aat ctg ggc tta tgg gat aca gct gga caa gaa gat tat     192
Lys Pro Val Asn Leu Gly Leu Trp Asp Thr Ala Gly Gln Glu Asp Tyr
    50                  55                  60 gac aga tta cgc ccc cta tcc tat ccg caa aca gat gtg ttc tta att     240
Asp Arg Leu Arg Pro Leu Ser Tyr Pro Gln Thr Asp Val Phe Leu Ile
65                  70                  75                  80 tgc ttt tcc ctt gtg agt cct gca tca ttt gaa aat gtc cgt gca aag     288
Cys Phe Ser Leu Val Ser Pro Ala Ser Phe Glu Asn Val Arg Ala Lys
                85                  90                  95 tgg tat cct gag gtg cgg cac cac tgt ccc aac act ccc atc atc cta     336
Trp Tyr Pro Glu Val Arg His His Cys Pro Asn Thr Pro Ile Ile Leu
```

|  |  |  |  |  |  |  |  |  |  |  |  |  |  |  |  |
|---|---|---|---|---|---|---|---|---|---|---|---|---|---|---|---|
|  |  |  |  |  | 100 |  |  |  | 105 |  |  |  | 110 |  |  |
| gtg | gga | act | aaa | ctt | gat | ctt | agg | gat | gat | aaa | gac | acg | atc | gag | aaa | 384
| Val | Gly | Thr | Lys | Leu | Asp | Leu | Arg | Asp | Asp | Lys | Asp | Thr | Ile | Glu | Lys |
|  |  | 115 |  |  |  | 120 |  |  |  | 125 |  |  |  |  |  |
| ctg | aag | gag | aag | aag | ctg | act | ccc | atc | acc | tat | ccg | cag | ggt | cta | gcc | 432
| Leu | Lys | Glu | Lys | Lys | Leu | Thr | Pro | Ile | Thr | Tyr | Pro | Gln | Gly | Leu | Ala |
|  | 130 |  |  |  |  | 135 |  |  |  |  | 140 |  |  |  |  |
| atg | gct | aag | gag | att | ggt | gct | gta | aaa | tac | ctg | gag | tgc | tcg | gcg | ctc | 480
| Met | Ala | Lys | Glu | Ile | Gly | Ala | Val | Lys | Tyr | Leu | Glu | Cys | Ser | Ala | Leu |
| 145 |  |  |  |  | 150 |  |  |  |  | 155 |  |  |  |  | 160 |
| aca | cag | cga | ggc | ctc | aag | aca | gtg | ttt | gac | gaa | gcg | atc | cga | gca | gtc | 528
| Thr | Gln | Arg | Gly | Leu | Lys | Thr | Val | Phe | Asp | Glu | Ala | Ile | Arg | Ala | Val |
|  |  |  |  | 165 |  |  |  |  | 170 |  |  |  |  | 175 |  |
| ctc | tgc | ccg | cct | ccc | gtg | aag | aag | agg | aag | aga | aaa | tgc | ctg | ctg | ttg | 576
| Leu | Cys | Pro | Pro | Pro | Val | Lys | Lys | Arg | Lys | Arg | Lys | Cys | Leu | Leu | Leu |
|  |  |  | 180 |  |  |  |  | 185 |  |  |  |  | 190 |  |  |
| taa |  |  |  |  |  |  |  |  |  |  |  |  |  |  |  | 579

<210> SEQ ID NO 54
<211> LENGTH: 192
<212> TYPE: PRT
<213> ORGANISM: Homo sapiens
<223> OTHER INFORMATION: Rac1

<400> SEQUENCE: 54

Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
            35                  40                  45

Lys Pro Val Asn Leu Gly Leu Trp Asp Thr Ala Gly Gln Glu Asp Tyr
        50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
            100                 105                 110

Val Gly Thr Lys Leu Asp Leu Arg Asp Asp Lys Asp Thr Ile Glu Lys
            115                 120                 125

Leu Lys Glu Lys Lys Leu Thr Pro Ile Thr Tyr Pro Gln Gly Leu Ala
        130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu
            180                 185                 190

<210> SEQ ID NO 55
<211> LENGTH: 252
<212> TYPE: DNA
<213> ORGANISM: Homo sapiens
<220> FEATURE:
<221> NAME/KEY: CDS
<222> LOCATION: (1)..(252)
<223> OTHER INFORMATION: PBD

<400> SEQUENCE: 55

```
aag aaa gag aaa gag cgg cca gag att tct ctc cct tca gat ttt gaa      48
Lys Lys Glu Lys Glu Arg Pro Glu Ile Ser Leu Pro Ser Asp Phe Glu
1               5                   10                  15 cac aca att cat gtc ggt ttt gat gct gtc aca ggg gag ttt acg gga      96
His Thr Ile His Val Gly Phe Asp Ala Val Thr Gly Glu Phe Thr Gly
            20                  25                  30 atg cca gag cag tgg gcc cgc ttg ctt cag aca tca aat atc act aag     144
Met Pro Glu Gln Trp Ala Arg Leu Leu Gln Thr Ser Asn Ile Thr Lys
        35                  40                  45 tcg gag cag aag aaa aac ccg cag gct gtt ctg gat gtg ttg gag ttt     192
Ser Glu Gln Lys Lys Asn Pro Gln Ala Val Leu Asp Val Leu Glu Phe
    50                  55                  60 tac aac tcg aag aag aca tcc aac agc cag aaa tac atg agc ttt aca     240
Tyr Asn Ser Lys Lys Thr Ser Asn Ser Gln Lys Tyr Met Ser Phe Thr
65                  70                  75                  80 gat aag tca gct                                                     252
Asp Lys Ser Ala
```

<210> SEQ ID NO 56
<211> LENGTH: 84
<212> TYPE: PRT
<213> ORGANISM: Homo sapiens
<223> OTHER INFORMATION: PBD

<400> SEQUENCE: 56

```
Lys Lys Glu Lys Glu Arg Pro Glu Ile Ser Leu Pro Ser Asp Phe Glu
1               5                   10                  15

His Thr Ile His Val Gly Phe Asp Ala Val Thr Gly Glu Phe Thr Gly
            20                  25                  30

Met Pro Glu Gln Trp Ala Arg Leu Leu Gln Thr Ser Asn Ile Thr Lys
        35                  40                  45

Ser Glu Gln Lys Lys Asn Pro Gln Ala Val Leu Asp Val Leu Glu Phe
    50                  55                  60

Tyr Asn Ser Lys Lys Thr Ser Asn Ser Gln Lys Tyr Met Ser Phe Thr
65                  70                  75                  80

Asp Lys Ser Ala
```

<210> SEQ ID NO 57
<211> LENGTH: 42
<212> TYPE: DNA
<213> ORGANISM: Artificial Sequence
<220> FEATURE:
<223> OTHER INFORMATION: Artificially synthesized hAG forward primer 1 sequence

<400> SEQUENCE: 57
ctagctagca ttgccaccat ggtgagcgtg atcaagcccg ag     42

<210> SEQ ID NO 58
<211> LENGTH: 38
<212> TYPE: DNA
<213> ORGANISM: Artificial Sequence
<220> FEATURE:
<223> OTHER INFORMATION: Artificially synthesized hAG reverse primer 1 sequence

<400> SEQUENCE: 58
actaccggtc ttggcctggc tgggcagcat gctgtacc       38

<210> SEQ ID NO 59

```
<211> LENGTH: 45
<212> TYPE: DNA
<213> ORGANISM: Artificial Sequence
<220> FEATURE:
<223> OTHER INFORMATION: Artificially synthesized p62(PB1) forward
      primer 1 sequence

<400> SEQUENCE: 59
aagaattcga tggcgtcgct caccgtgaag gcctaccttc tgggc            45

<210> SEQ ID NO 60
<211> LENGTH: 46
<212> TYPE: DNA
<213> ORGANISM: Artificial Sequence
<220> FEATURE:
<223> OTHER INFORMATION: Artificially synthesized p62(PB1) reverse
      primer 1 sequence

<400> SEQUENCE: 60
aattggcggc cgcttatttc tctttaatgt agattcggaa gatgtc           46

<210> SEQ ID NO 61
<211> LENGTH: 32
<212> TYPE: DNA
<213> ORGANISM: Artificial Sequence
<220> FEATURE:
<223> OTHER INFORMATION: Artificially synthesized hAG forward primer 2
      sequence

<400> SEQUENCE: 61
ggaccggtat ggtgagcgtg atcaagcccg ag                          32

<210> SEQ ID NO 62
<211> LENGTH: 34
<212> TYPE: DNA
<213> ORGANISM: Artificial Sequence
<220> FEATURE:
<223> OTHER INFORMATION: Artificially synthesized hAG reverse primer 2
      sequence

<400> SEQUENCE: 62
tttctagatc acttggcctg gctgggcagc atgc                        34

<210> SEQ ID NO 63
<211> LENGTH: 40
<212> TYPE: DNA
<213> ORGANISM: Artificial Sequence
<220> FEATURE:
<223> OTHER INFORMATION: Artificially synthesized p62(PB1) forward
      primer 2 sequence

<400> SEQUENCE: 63
gggaccggta tggcgtcgct caccgtgaag gcctaccttc                  40

<210> SEQ ID NO 64
<211> LENGTH: 40
<212> TYPE: DNA
<213> ORGANISM: Artificial Sequence
<220> FEATURE:
<223> OTHER INFORMATION: Artificially synthesized p62(PB1) reverse
      primer 2 sequence

<400> SEQUENCE: 64
acctctagat tatttctctt taatgtagat tcggaagatg                  40

<210> SEQ ID NO 65
<211> LENGTH: 50
```

```
<212> TYPE: DNA
<213> ORGANISM: Artificial Sequence
<220> FEATURE:
<223> OTHER INFORMATION: Artificially synthesized p62(PB1) forward
      primer 3 sequence

<400> SEQUENCE: 65
tagcgctagc attgccacca tggcgtcgct caccgtgaag gcctaccttc                 50

<210> SEQ ID NO 66
<211> LENGTH: 37
<212> TYPE: DNA
<213> ORGANISM: Artificial Sequence
<220> FEATURE:
<223> OTHER INFORMATION: Artificially synthesized p62(PB1) reverse
      primer 3 sequence

<400> SEQUENCE: 66
aaaaccggtt ttctctttaa tgtagattcg gaagatg                              37

<210> SEQ ID NO 67
<211> LENGTH: 54
<212> TYPE: DNA
<213> ORGANISM: Artificial Sequence
<220> FEATURE:
<223> OTHER INFORMATION: Artificially synthesized mTOR(FRB) forward
      primer sequence

<400> SEQUENCE: 67
gccgaattcg gccaccatgg agatgtggca tgaaggcctg gaagaggcat ctcg           54

<210> SEQ ID NO 68
<211> LENGTH: 52
<212> TYPE: DNA
<213> ORGANISM: Artificial Sequence
<220> FEATURE:
<223> OTHER INFORMATION: Artificially synthesized mTOR(FRB) reverse
      primer sequence

<400> SEQUENCE: 68
gggctcgagc cctgctttga gattcgtcgg aacacatgat aatagaggtc cc             52

<210> SEQ ID NO 69
<211> LENGTH: 31
<212> TYPE: DNA
<213> ORGANISM: Artificial Sequence
<220> FEATURE:
<223> OTHER INFORMATION: Artificially synthesized FKBP12 forward primer
      sequence

<400> SEQUENCE: 69
gccgaattcg atgggagtgc aggtggaaac c                                    31

<210> SEQ ID NO 70
<211> LENGTH: 32
<212> TYPE: DNA
<213> ORGANISM: Artificial Sequence
<220> FEATURE:
<223> OTHER INFORMATION: Artificially synthesized FKBP12 reverse primer
      sequence

<400> SEQUENCE: 70
gggctcgagt tattccagtt ttagaagctc ca                                   32

<210> SEQ ID NO 71
<211> LENGTH: 38
<212> TYPE: DNA
```

```
<213> ORGANISM: Artificial Sequence
<220> FEATURE:
<223> OTHER INFORMATION: Artificially synthesized MEK(PB1) forward
      primer sequence

<400> SEQUENCE: 71
ccgaattcgg tgctggtaat tcgcatcaag atcccaaa                                38

<210> SEQ ID NO 72
<211> LENGTH: 35
<212> TYPE: DNA
<213> ORGANISM: Artificial Sequence
<220> FEATURE:
<223> OTHER INFORMATION: Artificially synthesized MEK(PB1) reverse
      primer sequence

<400> SEQUENCE: 72
ttctcgagtt agcaggctct tggaaatatc tgcag                                   35

<210> SEQ ID NO 73
<211> LENGTH: 37
<212> TYPE: DNA
<213> ORGANISM: Artificial Sequence
<220> FEATURE:
<223> OTHER INFORMATION: Artificially synthesized Nbr1 (PB1) forward
      primer sequence

<400> SEQUENCE: 73
aagaattcgg caggttactc taaatgtgac ttttaaa                                 37

<210> SEQ ID NO 74
<211> LENGTH: 37
<212> TYPE: DNA
<213> ORGANISM: Artificial Sequence
<220> FEATURE:
<223> OTHER INFORMATION: Artificially synthesized Nbr1 (PB1) reverse
      primer sequence

<400> SEQUENCE: 74
ttctcgagtt acccttcgtg gacttgcatc tgcagtt                                 37

<210> SEQ ID NO 75
<211> LENGTH: 37
<212> TYPE: DNA
<213> ORGANISM: Artificial Sequence
<220> FEATURE:
<223> OTHER INFORMATION: Artificially synthesized PKCiota(PB1) forward
      primer sequence

<400> SEQUENCE: 75
aagaattcgc aggtccgggt gaaagcctac taccgcg                                 37

<210> SEQ ID NO 76
<211> LENGTH: 40
<212> TYPE: DNA
<213> ORGANISM: Artificial Sequence
<220> FEATURE:
<223> OTHER INFORMATION: Artificially synthesized PKCiota(PB1) reverse
      primer sequence

<400> SEQUENCE: 76
ttctcgagtt aacaagggaa cacatgaatc aagagttcag                              40

<210> SEQ ID NO 77
<211> LENGTH: 39
<212> TYPE: DNA
<213> ORGANISM: Artificial Sequence
```

```
<220> FEATURE:
<223> OTHER INFORMATION: Artificially synthesized TFG(PB1) forward
      primer 1 sequence

<400> SEQUENCE: 77
aactgcagca aagctaatca tcaaagctca acttgggga                           39

<210> SEQ ID NO 78
<211> LENGTH: 38
<212> TYPE: DNA
<213> ORGANISM: Artificial Sequence
<220> FEATURE:
<223> OTHER INFORMATION: Artificially synthesized TFG(PB1) reverse
      primer 1 sequence

<400> SEQUENCE: 78
ttaagctttt aattaacaaa taatgtcagt ttcagtat                            38

<210> SEQ ID NO 79
<211> LENGTH: 43
<212> TYPE: DNA
<213> ORGANISM: Artificial Sequence
<220> FEATURE:
<223> OTHER INFORMATION: Artificially synthesized TEL(SAM) forward
      primer sequence

<400> SEQUENCE: 79
aaaaggatcc gccaccatgc ctcgagcgct caggatggag gaa                      43

<210> SEQ ID NO 80
<211> LENGTH: 42
<212> TYPE: DNA
<213> ORGANISM: Artificial Sequence
<220> FEATURE:
<223> OTHER INFORMATION: Artificially synthesized TEL(SAM) reverse
      primer sequence

<400> SEQUENCE: 80
aaaaaagctt ttacctctgc ttcagaatat gctgaaggag tt                       42

<210> SEQ ID NO 81
<211> LENGTH: 39
<212> TYPE: DNA
<213> ORGANISM: Artificial Sequence
<220> FEATURE:
<223> OTHER INFORMATION: Artificially synthesized EphB2 (SAM) forward
      primer sequence

<400> SEQUENCE: 81
aaaaggatcc gccaccatgc tggaccgcac gatcccga                            39

<210> SEQ ID NO 82
<211> LENGTH: 34
<212> TYPE: DNA
<213> ORGANISM: Artificial Sequence
<220> FEATURE:
<223> OTHER INFORMATION: Artificially synthesized EphB2 (SAM) reverse
      primer sequence

<400> SEQUENCE: 82
aaaaaagctt ttaaatctgg ttcatctgcg cccg                                34

<210> SEQ ID NO 83
<211> LENGTH: 40
<212> TYPE: DNA
<213> ORGANISM: Artificial Sequence
<220> FEATURE:
```

```
<223> OTHER INFORMATION: Artificially synthesized DGKdelta(SAM) forward
      primer sequence

<400> SEQUENCE: 83
aaaaggtacc gccaccatgc cggttcacct ctgggggaca                               40

<210> SEQ ID NO 84
<211> LENGTH: 34
<212> TYPE: DNA
<213> ORGANISM: Artificial Sequence
<220> FEATURE:
<223> OTHER INFORMATION: Artificially synthesized DGKdelta(SAM) reverse
      primer sequence

<400> SEQUENCE: 84
aaaaaagctt ttagctgcgg ctcagctcct tgat                                    34

<210> SEQ ID NO 85
<211> LENGTH: 42
<212> TYPE: DNA
<213> ORGANISM: Artificial Sequence
<220> FEATURE:
<223> OTHER INFORMATION: Artificially synthesized Tankyrase(SAM) forward
      primer sequence

<400> SEQUENCE: 85
aaaaggatcc gccaccatgc tgatagatgc catgccccca ga                           42

<210> SEQ ID NO 86
<211> LENGTH: 42
<212> TYPE: DNA
<213> ORGANISM: Artificial Sequence
<220> FEATURE:
<223> OTHER INFORMATION: Artificially synthesized Tankyrase(SAM) reverse
      primer sequence

<400> SEQUENCE: 86
aaaaaagctt ttaaattcga atgacattgt atctgttgaa ga                           42

<210> SEQ ID NO 87
<211> LENGTH: 32
<212> TYPE: DNA
<213> ORGANISM: Artificial Sequence
<220> FEATURE:
<223> OTHER INFORMATION: Artificially synthesized TFG (PB1) forward
      primer 2 sequence

<400> SEQUENCE: 87
aaaccggtaa gctaatcatc aaagctcaac tt                                      32

<210> SEQ ID NO 88
<211> LENGTH: 38
<212> TYPE: DNA
<213> ORGANISM: Artificial Sequence
<220> FEATURE:
<223> OTHER INFORMATION: Artificially synthesized TFG (PB1) reverse
      primer 2 sequence

<400> SEQUENCE: 88
tttctagatt aattaacaaa taatgtcagt ttcagtat                                38

<210> SEQ ID NO 89
<211> LENGTH: 34
<212> TYPE: DNA
<213> ORGANISM: Artificial Sequence
<220> FEATURE:
<223> OTHER INFORMATION: Artificially synthesized TEL (SAM) forwarad
``` primer 2 sequence

<400> SEQUENCE: 89
aaaaaccggt cctcgagcgc tcaggatgga ggaa    34

<210> SEQ ID NO 90
<211> LENGTH: 42
<212> TYPE: DNA
<213> ORGANISM: Artificial Sequence
<220> FEATURE:
<223> OTHER INFORMATION: Artificially synthesized TEL (SAM) reverse
      primer 2 sequence

<400> SEQUENCE: 90
aaaatctaga ttacctctgc ttcagaatat gctgaaggag tt    42

<210> SEQ ID NO 91
<211> LENGTH: 33
<212> TYPE: DNA
<213> ORGANISM: Artificial Sequence
<220> FEATURE:
<223> OTHER INFORMATION: Artificially synthesized DGKdelta(SAM) forward
      primer 2 sequence

<400> SEQUENCE: 91
aaaaaccggt ccggttcacc tctggggac aga    33

<210> SEQ ID NO 92
<211> LENGTH: 34
<212> TYPE: DNA
<213> ORGANISM: Artificial Sequence
<220> FEATURE:
<223> OTHER INFORMATION: Artificially synthesized DGKdelta(SAM) reverse
      primer 2 sequence

<400> SEQUENCE: 92
aaaatctaga ttagctgcgg ctcagctcct tgat    34

<210> SEQ ID NO 93
<211> LENGTH: 33
<212> TYPE: DNA
<213> ORGANISM: Artificial Sequence
<220> FEATURE:
<223> OTHER INFORMATION: Artificially synthesized Tankyrase (SAM)
      forward primer 2 sequence

<400> SEQUENCE: 93
aaaaaccggt ctgatagatg ccatgccccc aga    33

<210> SEQ ID NO 94
<211> LENGTH: 42
<212> TYPE: DNA
<213> ORGANISM: Artificial Sequence
<220> FEATURE:
<223> OTHER INFORMATION: Artificially synthesized Tankyrase (SAM)
      reverse primer 2 sequence

<400> SEQUENCE: 94
aaaatctaga ttaaattcga atgacattgt atctgttgaa ga    42

<210> SEQ ID NO 95
<211> LENGTH: 34
<212> TYPE: DNA
<213> ORGANISM: Artificial Sequence
<220> FEATURE:
<223> OTHER INFORMATION: Artificially synthesized hKO1 forward primer
      sequence

<400> SEQUENCE: 95
aaaaaccggt atggtgagcg tgatcaagcc cgag                34

<210> SEQ ID NO 96
<211> LENGTH: 35
<212> TYPE: DNA
<213> ORGANISM: Artificial Sequence
<220> FEATURE:
<223> OTHER INFORMATION: Artificially synthesized hKO1 reverse primer
      sequence

<400> SEQUENCE: 96
aaaatctaga ttagcagtgg gccacggcgt cctcc               35

<210> SEQ ID NO 97
<211> LENGTH: 39
<212> TYPE: DNA
<213> ORGANISM: Artificial Sequence
<220> FEATURE:
<223> OTHER INFORMATION: Artificially synthesized p53 forward primer
      sequence

<400> SEQUENCE: 97
aaggatccat ggaggagccg cagtcagatc ctagcgtcg           39

<210> SEQ ID NO 98
<211> LENGTH: 43
<212> TYPE: DNA
<213> ORGANISM: Artificial Sequence
<220> FEATURE:
<223> OTHER INFORMATION: Artificially synthesized p53 reverse primer
      sequence

<400> SEQUENCE: 98
ttgcggccgc ttaagcagcc tctggcattc tgggagcttc atc      43

<210> SEQ ID NO 99
<211> LENGTH: 46
<212> TYPE: DNA
<213> ORGANISM: Artificial Sequence
<220> FEATURE:
<223> OTHER INFORMATION: Artificially synthesized MDM2 forward primer
      sequence

<400> SEQUENCE: 99
aaggatccat gtgcaatacc aacatgtctg tacctactga tggtgc   46

<210> SEQ ID NO 100
<211> LENGTH: 39
<212> TYPE: DNA
<213> ORGANISM: Artificial Sequence
<220> FEATURE:
<223> OTHER INFORMATION: Artificially synthesized MDM2 reverse primer
      sequence

<400> SEQUENCE: 100
ttctcgagtt aacctgagtc cgatgattcc tgctgattg           39

<210> SEQ ID NO 101
<211> LENGTH: 30
<212> TYPE: DNA
<213> ORGANISM: Artificial Sequence
<220> FEATURE:
<223> OTHER INFORMATION: Artificially synthesized Sec5 forward primer
      sequence -continued

<400> SEQUENCE: 101
cccggatcca tgtctcgatc acgacaaccc                              30

<210> SEQ ID NO 102
<211> LENGTH: 38
<212> TYPE: DNA
<213> ORGANISM: Artificial Sequence
<220> FEATURE:
<223> OTHER INFORMATION: Artificially synthesized Sec5 reverse primer
      sequence

<400> SEQUENCE: 102
gggaagcttt tattagccta ttttctcagg tttgagta                     38

<210> SEQ ID NO 103
<211> LENGTH: 30
<212> TYPE: DNA
<213> ORGANISM: Artificial Sequence
<220> FEATURE:
<223> OTHER INFORMATION: Artificially synthesized RalB forward primer
      sequence

<400> SEQUENCE: 103
cccggatcca tggctgccaa caagagtaag                              30

<210> SEQ ID NO 104
<211> LENGTH: 33
<212> TYPE: DNA
<213> ORGANISM: Artificial Sequence
<220> FEATURE:
<223> OTHER INFORMATION: Artificially synthesized RalB reverse primer
      sequence

<400> SEQUENCE: 104
gggaagcttt tatcatagta agcaacatct ttc                          33

<210> SEQ ID NO 105
<211> LENGTH: 34
<212> TYPE: DNA
<213> ORGANISM: Artificial Sequence
<220> FEATURE:
<223> OTHER INFORMATION: Artificially synthesized RalB(Q72L) mutant
      primer sequence

<400> SEQUENCE: 105
ctggacaccg ctgggctaga ggactacgca gcca                         34

<210> SEQ ID NO 106
<211> LENGTH: 41
<212> TYPE: DNA
<213> ORGANISM: Artificial Sequence
<220> FEATURE:
<223> OTHER INFORMATION: Artificially synthesized RalB(S28N) mutant
      primer sequence

<400> SEQUENCE: 106
cagcggaggc gttggcaaga acgccctgac gcttcagttc a                 41

<210> SEQ ID NO 107
<211> LENGTH: 43
<212> TYPE: DNA
<213> ORGANISM: Artificial Sequence
<220> FEATURE:
<223> OTHER INFORMATION: Artificially synthesized Calmodulin forward
      primer sequence

<400> SEQUENCE: 107
ttggatccgc caccatggac caactgacag aagagcagat tgc                43

<210> SEQ ID NO 108
<211> LENGTH: 40
<212> TYPE: DNA
<213> ORGANISM: Artificial Sequence
<220> FEATURE:
<223> OTHER INFORMATION: Artificially synthesized Calmodulin reverse
      primer sequence

<400> SEQUENCE: 108
aagaattccc ctttgctgtc atcatttgta caaactcttc                    40

<210> SEQ ID NO 109
<211> LENGTH: 46
<212> TYPE: DNA
<213> ORGANISM: Artificial Sequence
<220> FEATURE:
<223> OTHER INFORMATION: Artificially synthesized M13 peptide forward
      primer sequence

<400> SEQUENCE: 109
ttggatccgc caccatgaag aggcgctgga agaaaaactt cattgc             46

<210> SEQ ID NO 110
<211> LENGTH: 38
<212> TYPE: DNA
<213> ORGANISM: Artificial Sequence
<220> FEATURE:
<223> OTHER INFORMATION: Artificially synthesized M13 peptide reverse
      primer sequence

<400> SEQUENCE: 110
ccgaattccc cagtgccccg gagctggaga tcttcttg                      38

<210> SEQ ID NO 111
<211> LENGTH: 32
<212> TYPE: DNA
<213> ORGANISM: Artificial Sequence
<220> FEATURE:
<223> OTHER INFORMATION: Artificially synthesized AGNLS forward primer
      sequence

<400> SEQUENCE: 111
aaaccggtat ggtgagtgtg attaaaccag ag                            32

<210> SEQ ID NO 112
<211> LENGTH: 50
<212> TYPE: DNA
<213> ORGANISM: Artificial Sequence
<220> FEATURE:
<223> OTHER INFORMATION: Artificially synthesized AGNLS reverse primer
      sequence

<400> SEQUENCE: 112
aatctagatt atttatcctt ttcctttttta ctcttcttct tagctacttc        50

<210> SEQ ID NO 113
<211> LENGTH: 62
<212> TYPE: DNA
<213> ORGANISM: Artificial Sequence
<220> FEATURE:
<223> OTHER INFORMATION: Artificially synthesized HRas forward primer
      sequence

<400> SEQUENCE: 113

```
aagaattcga tgacggaata taagctggtg gtggtgggcg ccgtcggtgt gggcaagagt    60
gc                                                                  62
```

<210> SEQ ID NO 114
<211> LENGTH: 63
<212> TYPE: DNA
<213> ORGANISM: Artificial Sequence
<220> FEATURE:
<223> OTHER INFORMATION: Artificially synthesized HRas reverse primer
      sequence

<400> SEQUENCE: 114

```
ttctcgagac ctccggagac gttcagcttc cgcagcttgt gctgccggat ctcacgcacc    60
aac                                                                 63
```

<210> SEQ ID NO 115
<211> LENGTH: 60
<212> TYPE: DNA
<213> ORGANISM: Artificial Sequence
<220> FEATURE:
<223> OTHER INFORMATION: Artificially synthesized KRas forward primer
      sequence

<400> SEQUENCE: 115

```
aactcgagaa gatgagcaaa gatggtaaaa agaagaaaaa gaagtcaaag acaaagtgtg    60
```

<210> SEQ ID NO 116
<211> LENGTH: 60
<212> TYPE: DNA
<213> ORGANISM: Artificial Sequence
<220> FEATURE:
<223> OTHER INFORMATION: Artificially synthesized KRas reverse primer
      sequence

<400> SEQUENCE: 116

```
ttgcggccgc ttacataatt acacactttg tctttgactt cttttcttc tttttaccat     60
```

<210> SEQ ID NO 117
<211> LENGTH: 41
<212> TYPE: DNA
<213> ORGANISM: Artificial Sequence
<220> FEATURE:
<223> OTHER INFORMATION: Artificially synthesized HRas mutant primer
      sequence

<400> SEQUENCE: 117

```
gctggtggtg gtgggcgccg tcggtgtggg caagagtgcg c                        41
```

<210> SEQ ID NO 118
<211> LENGTH: 60
<212> TYPE: DNA
<213> ORGANISM: Artificial Sequence
<220> FEATURE:
<223> OTHER INFORMATION: Artificially synthesized cRaf forward primer
      sequence

<400> SEQUENCE: 118

```
aaggtacccc ttctaagaca agcaacacta tccgtgtttt cttgccgaac aagcaaagaa    60
```

<210> SEQ ID NO 119
<211> LENGTH: 52
<212> TYPE: DNA
<213> ORGANISM: Artificial Sequence
<220> FEATURE:
<223> OTHER INFORMATION: Artificially synthesized cRaf reverse primer
      sequence

<400> SEQUENCE: 119
ttaagctttt acaggaaatc tacttgaagt tcttctccaa tcaaagacgc ag    52

<210> SEQ ID NO 120
<211> LENGTH: 50
<212> TYPE: DNA
<213> ORGANISM: Artificial Sequence
<220> FEATURE:
<223> OTHER INFORMATION: Artificially synthesized Smac forward primer
      sequence

<400> SEQUENCE: 120
aggatccgcc accatggccg tgcccatcgc ccagaaatca gagaattcgg    50

<210> SEQ ID NO 121
<211> LENGTH: 49
<212> TYPE: DNA
<213> ORGANISM: Artificial Sequence
<220> FEATURE:
<223> OTHER INFORMATION: Artificially synthesized XIAP forward primer
      sequence

<400> SEQUENCE: 121
ttggatccgc caccatggct gtgagttctg ataggaattt cccaaattc    49

<210> SEQ ID NO 122
<211> LENGTH: 45
<212> TYPE: DNA
<213> ORGANISM: Artificial Sequence
<220> FEATURE:
<223> OTHER INFORMATION: Artificially synthesized XIAP reverse primer
      sequence

<400> SEQUENCE: 122
ttgaattctc agtagttctt accagacact cctcaagtga atgag    45

<210> SEQ ID NO 123
<211> LENGTH: 42
<212> TYPE: DNA
<213> ORGANISM: Artificial Sequence
<220> FEATURE:
<223> OTHER INFORMATION: Artificially synthesized BclX(L) forward primer
      sequence

<400> SEQUENCE: 123
ttctcgagga tgtctcagag caaccgggag ctggtggttg ac    42

<210> SEQ ID NO 124
<211> LENGTH: 44
<212> TYPE: DNA
<213> ORGANISM: Artificial Sequence
<220> FEATURE:
<223> OTHER INFORMATION: Artificially synthesized BclX(L) reverse primer
      sequence

<400> SEQUENCE: 124
ctaagcggcc gcttagcgtt cctggccctt tcggctctcg gctg    44

<210> SEQ ID NO 125
<211> LENGTH: 50
<212> TYPE: DNA
<213> ORGANISM: Artificial Sequence
<220> FEATURE:
<223> OTHER INFORMATION: Artificially synthesized BAD forward primer 1
      sequence

<400> SEQUENCE: 125
gcagcacagc gctatggccg cgagctccgg aggatgagtg acgagtttgt    50

<210> SEQ ID NO 126
<211> LENGTH: 50
<212> TYPE: DNA
<213> ORGANISM: Artificial Sequence
<220> FEATURE:
<223> OTHER INFORMATION: Artificially synthesized BAD forward primer 2
      sequence

<400> SEQUENCE: 126
ttggatccaa cctctgggca gcacagcgct atggccgcga gctccggagg    50

<210> SEQ ID NO 127
<211> LENGTH: 50
<212> TYPE: DNA
<213> ORGANISM: Artificial Sequence
<220> FEATURE:
<223> OTHER INFORMATION: Artificially synthesized BAD reverse primer
      sequence

<400> SEQUENCE: 127
ttgaattctt acttcttaaa ggagtccaca aactcgtcac tcatcctccg    50

<210> SEQ ID NO 128
<211> LENGTH: 34
<212> TYPE: DNA
<213> ORGANISM: Artificial Sequence
<220> FEATURE:
<223> OTHER INFORMATION: Artificially synthesized Rac1 forward primer
      sequence

<400> SEQUENCE: 128
gagaattcga tgcaggccat caagtgtgtg gtgg    34

<210> SEQ ID NO 129
<211> LENGTH: 34
<212> TYPE: DNA
<213> ORGANISM: Artificial Sequence
<220> FEATURE:
<223> OTHER INFORMATION: Artificially synthesized Rac1 reverse primer
      sequence

<400> SEQUENCE: 129
ggctcgagtt acaacagcag gcattttctc ttcc    34

<210> SEQ ID NO 130
<211> LENGTH: 43
<212> TYPE: DNA
<213> ORGANISM: Artificial Sequence
<220> FEATURE:
<223> OTHER INFORMATION: Artificially synthesized PBD forward primer
      sequence

<400> SEQUENCE: 130
ttggatccaa gaaagagaaa gagcggccag agatttctct ccc    43

<210> SEQ ID NO 131
<211> LENGTH: 46
<212> TYPE: DNA
<213> ORGANISM: Artificial Sequence
<220> FEATURE:
<223> OTHER INFORMATION: Artificially synthesized PBD reverse primer
      sequence

<400> SEQUENCE: 131
ccgaattctt acgctgactt atctgtaaag ctcatgtatt tctggc    46

<210> SEQ ID NO 132
<211> LENGTH: 654
<212> TYPE: DNA
<213> ORGANISM: Artificial Sequence
<220> FEATURE:
<223> OTHER INFORMATION: Synthetic sequence of monomeric version pf
      KO(Kusabira-Orange)
<220> FEATURE:
<221> NAME/KEY: CDS
<222> LOCATION: (1)..(654)

<400> SEQUENCE: 132

| atg | gtg | agc | gtg | atc | aag | ccc | gag | atg | aag | atg | agg | tac | tac | atg | gac | 48 |
| Met | Val | Ser | Val | Ile | Lys | Pro | Glu | Met | Lys | Met | Arg | Tyr | Tyr | Met | Asp | |
| 1 | | | | 5 | | | | | 10 | | | | | 15 | | |

| ggc | tcc | gtc | aat | ggg | cat | gag | ttc | aca | atc | gag | ggt | gag | ggc | aca | ggc | 96 |
| Gly | Ser | Val | Asn | Gly | His | Glu | Phe | Thr | Ile | Glu | Gly | Glu | Gly | Thr | Gly | |
| | | | 20 | | | | | 25 | | | | | 30 | | | |

| aga | cct | tac | gag | gga | cat | cag | gag | atg | aca | ctg | cgc | gtc | aca | atg | gcc | 144 |
| Arg | Pro | Tyr | Glu | Gly | His | Gln | Glu | Met | Thr | Leu | Arg | Val | Thr | Met | Ala | |
| | | | 35 | | | | | 40 | | | | | 45 | | | |

| gag | ggc | ggg | cca | atg | cct | ttc | gcc | ttc | gac | ctg | gtg | tcc | cac | gtg | ttc | 192 |
| Glu | Gly | Gly | Pro | Met | Pro | Phe | Ala | Phe | Asp | Leu | Val | Ser | His | Val | Phe | |
| 50 | | | | | 55 | | | | | 60 | | | | | | |

| tgt | tac | ggc | cac | aga | gtt | ttt | acc | aag | tac | cca | gaa | gag | atc | cca | gac | 240 |
| Cys | Tyr | Gly | His | Arg | Val | Phe | Thr | Lys | Tyr | Pro | Glu | Glu | Ile | Pro | Asp | |
| 65 | | | | | 70 | | | | | 75 | | | | | 80 | |

| tat | ttc | aag | cag | gcc | ttt | cct | gag | ggc | ctg | tcc | tgg | gag | agg | tcc | ctg | 288 |
| Tyr | Phe | Lys | Gln | Ala | Phe | Pro | Glu | Gly | Leu | Ser | Trp | Glu | Arg | Ser | Leu | |
| | | | | 85 | | | | | 90 | | | | | 95 | | |

| gag | ttc | gag | gac | ggc | ggc | tcc | gcc | tcc | gtg | agc | gcc | cac | atc | agc | ctg | 336 |
| Glu | Phe | Glu | Asp | Gly | Gly | Ser | Ala | Ser | Val | Ser | Ala | His | Ile | Ser | Leu | |
| | | | | 100 | | | | | 105 | | | | | 110 | | |

| agg | ggc | aac | acc | ttc | tac | cac | aag | tcc | aag | ttc | acc | ggc | gtg | aac | ttc | 384 |
| Arg | Gly | Asn | Thr | Phe | Tyr | His | Lys | Ser | Lys | Phe | Thr | Gly | Val | Asn | Phe | |
| | | | 115 | | | | | 120 | | | | | 125 | | | |

| ccc | gcc | gac | ggc | ccc | atc | atg | cag | aac | cag | agc | gtg | gac | tgg | gag | ccc | 432 |
| Pro | Ala | Asp | Gly | Pro | Ile | Met | Gln | Asn | Gln | Ser | Val | Asp | Trp | Glu | Pro | |
| | | 130 | | | | | 135 | | | | | 140 | | | | |

| tcc | acc | gag | aag | atc | acc | gcc | agc | gac | ggc | gtg | ctg | aag | ggc | gac | gtg | 480 |
| Ser | Thr | Glu | Lys | Ile | Thr | Ala | Ser | Asp | Gly | Val | Leu | Lys | Gly | Asp | Val | |
| 145 | | | | | 150 | | | | | 155 | | | | | 160 | |

| acc | atg | tac | ctg | aag | ctg | gag | ggc | ggc | ggc | aac | cac | aag | tgc | cag | atg | 528 |
| Thr | Met | Tyr | Leu | Lys | Leu | Glu | Gly | Gly | Gly | Asn | His | Lys | Cys | Gln | Met | |
| | | | | 165 | | | | | 170 | | | | | 175 | | |

| aag | acc | acc | tac | aag | gcc | gcc | aag | gag | atc | ctg | gag | atg | ccc | ggc | gac | 576 |
| Lys | Thr | Thr | Tyr | Lys | Ala | Ala | Lys | Glu | Ile | Leu | Glu | Met | Pro | Gly | Asp | |
| | | | 180 | | | | | 185 | | | | | 190 | | | |

| cac | tac | atc | ggc | cac | agg | ctg | gtg | agg | aag | acc | gag | ggc | aac | atc | acc | 624 |
| His | Tyr | Ile | Gly | His | Arg | Leu | Val | Arg | Lys | Thr | Glu | Gly | Asn | Ile | Thr | |
| | | 195 | | | | | 200 | | | | | 205 | | | | |

| gag | cag | gtg | gag | gac | gcc | gtg | gcc | cac | tcc | | | | | | | 654 |
| Glu | Gln | Val | Glu | Asp | Ala | Val | Ala | His | Ser | | | | | | | |
| 210 | | | | | 215 | | | | | | | | | | | |

<210> SEQ ID NO 133
<211> LENGTH: 218
<212> TYPE: PRT
<213> ORGANISM: Artificial Sequence
<220> FEATURE:

-continued

<223> OTHER INFORMATION: Synethetic sequence of monomeric version pf
      KO(Kusabira-Orange)

<400> SEQUENCE: 133

Met Val Ser Val Ile Lys Pro Glu Met Lys Met Arg Tyr Tyr Met Asp
1               5                  10                   15

Gly Ser Val Asn Gly His Glu Phe Thr Ile Glu Gly Glu Gly Thr Gly
                20                  25                  30

Arg Pro Tyr Glu Gly His Gln Glu Met Thr Leu Arg Val Thr Met Ala
            35                  40                  45

Glu Gly Gly Pro Met Pro Phe Ala Phe Asp Leu Val Ser His Val Phe
    50                  55                  60

Cys Tyr Gly His Arg Val Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Met
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Gln Val Glu Asp Ala Val Ala His Ser
    210                 215

<210> SEQ ID NO 134
<211> LENGTH: 678
<212> TYPE: DNA
<213> ORGANISM: Artificial Sequence
<220> FEATURE:
<223> OTHER INFORMATION: Synthetic sequence humanized mAG1
<220> FEATURE:
<221> NAME/KEY: CDS
<222> LOCATION: (1)..(678)

<400> SEQUENCE: 134 atg gtg agc gtg atc aag ccc gag atg aag atc aag ctg tgc atg agg        48
Met Val Ser Val Ile Lys Pro Glu Met Lys Ile Lys Leu Cys Met Arg
1               5                  10                  15 ggc acc gtg aac ggc cac aac ttc gtg atc gag ggc gag ggc aag ggc        96
Gly Thr Val Asn Gly His Asn Phe Val Ile Glu Gly Glu Gly Lys Gly
                20                  25                  30 aac ccc tac gag ggc acc cag atc ctg gac ctg aac gtg acc gag ggc       144
Asn Pro Tyr Glu Gly Thr Gln Ile Leu Asp Leu Asn Val Thr Glu Gly
            35                  40                  45 gcc ccc ctg ccc ttc gcc tac gac atc ctg acc acc gtg ttc cag tac       192
Ala Pro Leu Pro Phe Ala Tyr Asp Ile Leu Thr Thr Val Phe Gln Tyr
    50                  55                  60 ggc aac agg gcc ttc acc aag tac ccc gcc gac atc cag gac tac ttc       240
Gly Asn Arg Ala Phe Thr Lys Tyr Pro Ala Asp Ile Gln Asp Tyr Phe
65                  70                  75                  80

```
aag cag acc ttc ccc gag ggc tac cac tgg gag agg agc atg acc tac      288
Lys Gln Thr Phe Pro Glu Gly Tyr His Trp Glu Arg Ser Met Thr Tyr
             85                  90                  95 gag gac cag ggc atc tgc acc gcc acc agc aac atc agc atg agg ggc      336
Glu Asp Gln Gly Ile Cys Thr Ala Thr Ser Asn Ile Ser Met Arg Gly
            100                 105                 110 gac tgc ttc ttc tac gac atc agg ttc gac ggc acc aac ttc ccc ccc      384
Asp Cys Phe Phe Tyr Asp Ile Arg Phe Asp Gly Thr Asn Phe Pro Pro
            115                 120                 125 aac ggc ccc gtg atg cag aag aag acc ctg aag tgg gag ccc agc acc      432
Asn Gly Pro Val Met Gln Lys Lys Thr Leu Lys Trp Glu Pro Ser Thr
        130                 135                 140 gag aag atg tac gtg gag gac ggc gtg ctg aag ggc gac gtg aac atg      480
Glu Lys Met Tyr Val Glu Asp Gly Val Leu Lys Gly Asp Val Asn Met
145                 150                 155                 160 agg ctg ctg ctg gag ggc ggc ggc cac tac agg tgc gac ttc aag acc      528
Arg Leu Leu Leu Glu Gly Gly Gly His Tyr Arg Cys Asp Phe Lys Thr
                165                 170                 175 acc tac aag gcc aag aag gag gtg agg ctg ccc gac gcc cac aag atc      576
Thr Tyr Lys Ala Lys Lys Glu Val Arg Leu Pro Asp Ala His Lys Ile
            180                 185                 190 gac cac agg atc gag atc ctg aag cac gac aag gac tac aac aag gtg      624
Asp His Arg Ile Glu Ile Leu Lys His Asp Lys Asp Tyr Asn Lys Val
            195                 200                 205 aag ctg tac gag aac gcc gtg gcc agg tac tcc atg ctg ccc agc cag      672
Lys Leu Tyr Glu Asn Ala Val Ala Arg Tyr Ser Met Leu Pro Ser Gln
            210                 215                 220 gcc aag                                                              678
Ala Lys
225

<210> SEQ ID NO 135
<211> LENGTH: 226
<212> TYPE: PRT
<213> ORGANISM: Artificial Sequence
<220> FEATURE:
<223> OTHER INFORMATION: Synthetic sequence humanized mAG1

<400> SEQUENCE: 135

Met Val Ser Val Ile Lys Pro Glu Met Lys Ile Lys Leu Cys Met Arg
1               5                   10                  15

Gly Thr Val Asn Gly His Asn Phe Val Ile Glu Gly Glu Gly Lys Gly
            20                  25                  30

Asn Pro Tyr Glu Gly Thr Gln Ile Leu Asp Leu Asn Val Thr Glu Gly
        35                  40                  45

Ala Pro Leu Pro Phe Ala Tyr Asp Ile Leu Thr Thr Val Phe Gln Tyr
    50                  55                  60

Gly Asn Arg Ala Phe Thr Lys Tyr Pro Ala Asp Ile Gln Asp Tyr Phe
65                  70                  75                  80

Lys Gln Thr Phe Pro Glu Gly Tyr His Trp Glu Arg Ser Met Thr Tyr
                85                  90                  95

Glu Asp Gln Gly Ile Cys Thr Ala Thr Ser Asn Ile Ser Met Arg Gly
            100                 105                 110

Asp Cys Phe Phe Tyr Asp Ile Arg Phe Asp Gly Thr Asn Phe Pro Pro
        115                 120                 125

Asn Gly Pro Val Met Gln Lys Lys Thr Leu Lys Trp Glu Pro Ser Thr
    130                 135                 140

Glu Lys Met Tyr Val Glu Asp Gly Val Leu Lys Gly Asp Val Asn Met
```

```
Arg Leu Leu Leu Glu Gly Gly His Tyr Arg Cys Asp Phe Lys Thr
            165                 170                 175

Thr Tyr Lys Ala Lys Lys Glu Val Arg Leu Pro Asp Ala His Lys Ile
        180                 185                 190

Asp His Arg Ile Glu Ile Leu Lys His Asp Lys Asp Tyr Asn Lys Val
            195                 200                 205

Lys Leu Tyr Glu Asn Ala Val Ala Arg Tyr Ser Met Leu Pro Ser Gln
        210                 215                 220

Ala Lys
225

<210> SEQ ID NO 136
<211> LENGTH: 696
<212> TYPE: DNA
<213> ORGANISM: Artificial Sequence
<220> FEATURE:
<223> OTHER INFORMATION: Synthetic sequence mMiCy1
<220> FEATURE:
<221> NAME/KEY: CDS
<222> LOCATION: (1)..(696)

<400> SEQUENCE: 136 atg gtg tcc tac tcc aag cag ggc atc gcc cag gag atg cgc acc aag        48
Met Val Ser Tyr Ser Lys Gln Gly Ile Ala Gln Glu Met Arg Thr Lys
1               5                   10                  15 tac cgc atg gag ggc agc gtg aac ggc cac gag ttc acc atc gag ggc        96
Tyr Arg Met Glu Gly Ser Val Asn Gly His Glu Phe Thr Ile Glu Gly
                20                  25                  30 gtg ggc acc ggc aac ccc tac gag ggc aag cag acc tcc gag ctg gtg       144
Val Gly Thr Gly Asn Pro Tyr Glu Gly Lys Gln Thr Ser Glu Leu Val
            35                  40                  45 atc atc aag ccc aag ggc aag ccc ctg ccc ttc tcc ttc gac atc ctg       192
Ile Ile Lys Pro Lys Gly Lys Pro Leu Pro Phe Ser Phe Asp Ile Leu
        50                  55                  60 tcc acc gtg ttc cag tac ggc aac agg tgc ttc acc aag tac ccc gcc       240
Ser Thr Val Phe Gln Tyr Gly Asn Arg Cys Phe Thr Lys Tyr Pro Ala
65                  70                  75                  80 gac atg ccc gac tac ttc aag cag gcc ttc ccc gac ggc atg tcc tac       288
Asp Met Pro Asp Tyr Phe Lys Gln Ala Phe Pro Asp Gly Met Ser Tyr
                85                  90                  95 gag agg tcc ttc ctg ttc gag gac ggc ggc gtg gcc acc gcc agc tgg       336
Glu Arg Ser Phe Leu Phe Glu Asp Gly Gly Val Ala Thr Ala Ser Trp
            100                 105                 110 agc atc cgc ctg gag ggc aac tgc ttc atc cac aac tcc atc tac cac       384
Ser Ile Arg Leu Glu Gly Asn Cys Phe Ile His Asn Ser Ile Tyr His
        115                 120                 125 ggc acc aac ttc ccc gcc gac ggc ccc gtg atg aag aag cag acc atc       432
Gly Thr Asn Phe Pro Ala Asp Gly Pro Val Met Lys Lys Gln Thr Ile
    130                 135                 140 ggc tgg gac aag tcc tcc gag aag atg agc gtg gcc aag gag gtg ctg       480
Gly Trp Asp Lys Ser Ser Glu Lys Met Ser Val Ala Lys Glu Val Leu
145                 150                 155                 160 agg ggc gac gtg acc cag ttc ctg ctg ctg gag ggc ggc ggc tac cag       528
Arg Gly Asp Val Thr Gln Phe Leu Leu Leu Glu Gly Gly Gly Tyr Gln
                165                 170                 175 agg tgc cag ctg cac tcc acc tac aag acc gag aag ccc gtg gcc atg       576
Arg Cys Gln Leu His Ser Thr Tyr Lys Thr Glu Lys Pro Val Ala Met
            180                 185                 190 ccc ccc agc cac gtg gtg gag cac cag atc gtg agg acc gac ctg ggc       624
Pro Pro Ser His Val Val Glu His Gln Ile Val Arg Thr Asp Leu Gly
```

```
Pro Pro Ser His Val Val Glu His Gln Ile Val Arg Thr Asp Leu Gly
        195                 200                 205 cag acc gcc aag ggc ttc aag gtg aag ctg gag gag cac gcc gag gcc    672
Gln Thr Ala Lys Gly Phe Lys Val Lys Leu Glu Glu His Ala Glu Ala
    210                 215                 220 cac gtg aac ccc ctg aag gtg aag                                     696
His Val Asn Pro Leu Lys Val Lys
225                 230

<210> SEQ ID NO 137
<211> LENGTH: 232
<212> TYPE: PRT
<213> ORGANISM: Artificial Sequence
<220> FEATURE:
<223> OTHER INFORMATION: Synthetic sequence mMiCy1

<400> SEQUENCE: 137

Met Val Ser Tyr Ser Lys Gln Gly Ile Ala Gln Glu Met Arg Thr Lys
1               5                   10                  15

Tyr Arg Met Glu Gly Ser Val Asn Gly His Glu Phe Thr Ile Glu Gly
            20                  25                  30

Val Gly Thr Gly Asn Pro Tyr Glu Gly Lys Gln Thr Ser Glu Leu Val
        35                  40                  45

Ile Ile Lys Pro Lys Gly Lys Pro Leu Pro Phe Ser Phe Asp Ile Leu
    50                  55                  60

Ser Thr Val Phe Gln Tyr Gly Asn Arg Cys Phe Thr Lys Tyr Pro Ala
65                  70                  75                  80

Asp Met Pro Asp Tyr Phe Lys Gln Ala Phe Pro Asp Gly Met Ser Tyr
                85                  90                  95

Glu Arg Ser Phe Leu Phe Glu Asp Gly Gly Val Ala Thr Ala Ser Trp
            100                 105                 110

Ser Ile Arg Leu Glu Gly Asn Cys Phe Ile His Asn Ser Ile Tyr His
        115                 120                 125

Gly Thr Asn Phe Pro Ala Asp Gly Pro Val Met Lys Lys Gln Thr Ile
    130                 135                 140

Gly Trp Asp Lys Ser Ser Glu Lys Met Ser Val Ala Lys Glu Val Leu
145                 150                 155                 160

Arg Gly Asp Val Thr Gln Phe Leu Leu Leu Glu Gly Gly Tyr Gln
                165                 170                 175

Arg Cys Gln Leu His Ser Thr Tyr Lys Thr Glu Lys Pro Val Ala Met
            180                 185                 190

Pro Pro Ser His Val Val Glu His Gln Ile Val Arg Thr Asp Leu Gly
        195                 200                 205

Gln Thr Ala Lys Gly Phe Lys Val Lys Leu Glu Glu His Ala Glu Ala
    210                 215                 220

His Val Asn Pro Leu Lys Val Lys
225                 230

<210> SEQ ID NO 138
<211> LENGTH: 702
<212> TYPE: DNA
<213> ORGANISM: Artificial Sequence
<220> FEATURE:
<223> OTHER INFORMATION: Synthetic sequence mKikGR1
<220> FEATURE:
<221> NAME/KEY: CDS
<222> LOCATION: (1)..(702)

<400> SEQUENCE: 138
```

```
atg gtg agt gtg att aca tca gaa atg aag atc gag ctg cgt atg gaa      48
Met Val Ser Val Ile Thr Ser Glu Met Lys Ile Glu Leu Arg Met Glu
1               5                   10                  15 ggc tct gta aac ggg cac aag ttc gtg att aca ggg aaa gga agt ggc      96
Gly Ser Val Asn Gly His Lys Phe Val Ile Thr Gly Lys Gly Ser Gly
            20                  25                  30 aga cct tac gag gga aca cag act gtg gac ctg aca gtc ata gag ggc     144
Arg Pro Tyr Glu Gly Thr Gln Thr Val Asp Leu Thr Val Ile Glu Gly
        35                  40                  45 gga cct ctt cct ttt gct ttc gat atc ctg aca aca gca ttc cat tac     192
Gly Pro Leu Pro Phe Ala Phe Asp Ile Leu Thr Thr Ala Phe His Tyr
    50                  55                  60 ggc aac cgg gta ttt gtc gaa tac cca gaa gaa ata gta gac tac ttc     240
Gly Asn Arg Val Phe Val Glu Tyr Pro Glu Glu Ile Val Asp Tyr Phe
65                  70                  75                  80 aag cag tcg ttt cct gag ggt tat tct tgg gaa cga agc atg agt tac     288
Lys Gln Ser Phe Pro Glu Gly Tyr Ser Trp Glu Arg Ser Met Ser Tyr
                85                  90                  95 gaa gac ggg gga att tgc ctc gcc aca aac aat ata acg atg aag aaa     336
Glu Asp Gly Gly Ile Cys Leu Ala Thr Asn Asn Ile Thr Met Lys Lys
            100                 105                 110 gac ggc agc aac act ttt gtc aat gaa att cga ttt gat ggt aca aac     384
Asp Gly Ser Asn Thr Phe Val Asn Glu Ile Arg Phe Asp Gly Thr Asn
        115                 120                 125 ttt cct gcc aat ggt cca gtt atg cag agg aag acc gtc aaa tgg gag     432
Phe Pro Ala Asn Gly Pro Val Met Gln Arg Lys Thr Val Lys Trp Glu
    130                 135                 140 cca tcc act gag aaa atg tat gtg cgt gat gga gtg ctg aag ggt gat     480
Pro Ser Thr Glu Lys Met Tyr Val Arg Asp Gly Val Leu Lys Gly Asp
145                 150                 155                 160 gtt gaa atg gct ctg ttg ctt gaa gga ggt ggc cat tac cga tgt gac     528
Val Glu Met Ala Leu Leu Leu Glu Gly Gly Gly His Tyr Arg Cys Asp
                165                 170                 175 ttc aga act act tac aaa gca aag aag gtt gtc cag ttg cca gac tat     576
Phe Arg Thr Thr Tyr Lys Ala Lys Lys Val Val Gln Leu Pro Asp Tyr
            180                 185                 190 cac tac gtg gat cat caa atg gag ata aca agc cat gac aag gat tac     624
His Tyr Val Asp His Gln Met Glu Ile Thr Ser His Asp Lys Asp Tyr
        195                 200                 205 aac aag gtt aag gcg tat gaa cat gct aag gct tat tcc ggg acc tac     672
Asn Lys Val Lys Ala Tyr Glu His Ala Lys Ala Tyr Ser Gly Thr Tyr
    210                 215                 220 agg ggc gcc aag tat gaa ttt gaa gcc taa                             702
Arg Gly Ala Lys Tyr Glu Phe Glu Ala
225                 230

<210> SEQ ID NO 139
<211> LENGTH: 233
<212> TYPE: PRT
<213> ORGANISM: Artificial Sequence
<220> FEATURE:
<223> OTHER INFORMATION: Synthetic sequence mKikGR1

<400> SEQUENCE: 139

Met Val Ser Val Ile Thr Ser Glu Met Lys Ile Glu Leu Arg Met Glu
1               5                   10                  15

Gly Ser Val Asn Gly His Lys Phe Val Ile Thr Gly Lys Gly Ser Gly
            20                  25                  30

Arg Pro Tyr Glu Gly Thr Gln Thr Val Asp Leu Thr Val Ile Glu Gly
        35                  40                  45
```

```
Gly Pro Leu Pro Phe Ala Phe Asp Ile Leu Thr Thr Ala Phe His Tyr
        50                  55                  60

Gly Asn Arg Val Phe Val Glu Tyr Pro Glu Glu Ile Val Asp Tyr Phe
65                  70                  75                  80

Lys Gln Ser Phe Pro Glu Gly Tyr Ser Trp Glu Arg Ser Met Ser Tyr
                85                  90                  95

Glu Asp Gly Gly Ile Cys Leu Ala Thr Asn Asn Ile Thr Met Lys Lys
            100                 105                 110

Asp Gly Ser Asn Thr Phe Val Asn Glu Ile Arg Phe Asp Gly Thr Asn
            115                 120                 125

Phe Pro Ala Asn Gly Pro Val Met Gln Arg Lys Thr Val Lys Trp Glu
        130                 135                 140

Pro Ser Thr Glu Lys Met Tyr Val Arg Asp Gly Val Leu Lys Gly Asp
145                 150                 155                 160

Val Glu Met Ala Leu Leu Leu Glu Gly Gly His Tyr Arg Cys Asp
                165                 170                 175

Phe Arg Thr Thr Tyr Lys Ala Lys Lys Val Val Gln Leu Pro Asp Tyr
            180                 185                 190

His Tyr Val Asp His Gln Met Glu Ile Thr Ser His Asp Lys Asp Tyr
            195                 200                 205

Asn Lys Val Lys Ala Tyr Glu His Ala Lys Ala Tyr Ser Gly Thr Tyr
        210                 215                 220

Arg Gly Ala Lys Tyr Glu Phe Glu Ala
225                 230
```

<210> SEQ ID NO 140
<211> LENGTH: 663
<212> TYPE: DNA
<213> ORGANISM: Artificial Sequence
<220> FEATURE:
<223> OTHER INFORMATION: Synthetic sequence KCy1
<220> FEATURE:
<221> NAME/KEY: CDS
<222> LOCATION: (1)..(663)

<400> SEQUENCE: 140

```
atg gtg agt gtg att aaa cca gag atg aag atg agg tac tac atg gac     48
Met Val Ser Val Ile Lys Pro Glu Met Lys Met Arg Tyr Tyr Met Asp
1               5                   10                  15 ggc tcc gtc aat ggg cat gag ttc aca gtt gaa ggt gaa ggc aca ggc     96
Gly Ser Val Asn Gly His Glu Phe Thr Val Glu Gly Glu Gly Thr Gly
            20                  25                  30 aga cct tac gag gga aag cac aaa ata aca ctt gac gtc acc aag ggt    144
Arg Pro Tyr Glu Gly Lys His Lys Ile Thr Leu Asp Val Thr Lys Gly
        35                  40                  45 ggg cca ctg cct ttt gcg ttt gac ttg ttg tct aca gtg ttc tct tat    192
Gly Pro Leu Pro Phe Ala Phe Asp Leu Leu Ser Thr Val Phe Ser Tyr
    50                  55                  60 ggc aac aga gcc ctt act aaa tat cct gac gat atc ccc gac tat ttc    240
Gly Asn Arg Ala Leu Thr Lys Tyr Pro Asp Asp Ile Pro Asp Tyr Phe
65                  70                  75                  80 aaa caa tgc ttt cct gga ggc tat tca tgg gaa aga aag ttt gag ttc    288
Lys Gln Cys Phe Pro Gly Gly Tyr Ser Trp Glu Arg Lys Phe Glu Phe
                85                  90                  95 gaa gat ggc ggg ttg gcg ata gcc aaa gcg gaa ata agc ctt aaa gga    336
Glu Asp Gly Gly Leu Ala Ile Ala Lys Ala Glu Ile Ser Leu Lys Gly
            100                 105                 110 aac tgc ttc gaa cac aaa tcc acc att gaa ggc act ttt ccc gat agc    384
Asn Cys Phe Glu His Lys Ser Thr Ile Glu Gly Thr Phe Pro Asp Ser
```

```
                115                 120                 125
agt cct att atg caa aac aag acg cta gga tgg gaa cca tcc acc gag    432
Ser Pro Ile Met Gln Asn Lys Thr Leu Gly Trp Glu Pro Ser Thr Glu
    130                 135                 140 aag atg acc gtc cgc gac gga tca atg aag ggt gat gat gcg gcc tac    480
Lys Met Thr Val Arg Asp Gly Ser Met Lys Gly Asp Asp Ala Ala Tyr
145                 150                 155                 160 ctc aaa ttg gtg gga ggc ggc aat cac aaa tgc tac ttt aca act acc    528
Leu Lys Leu Val Gly Gly Gly Asn His Lys Cys Tyr Phe Thr Thr Thr
                165                 170                 175 tac aca gcg aag aaa aag att cct aac ctg cca gga agc cat ttc att    576
Tyr Thr Ala Lys Lys Lys Ile Pro Asn Leu Pro Gly Ser His Phe Ile
            180                 185                 190 ggc cat cgc atc tcc agt gtc gtc gag ggc act aaa att aaa gtg atg    624
Gly His Arg Ile Ser Ser Val Val Glu Gly Thr Lys Ile Lys Val Met
        195                 200                 205 gaa gat gca att gct cat ctt tac cct ttt aat ggc agc                663
Glu Asp Ala Ile Ala His Leu Tyr Pro Phe Asn Gly Ser
    210                 215                 220
```

<210> SEQ ID NO 141
<211> LENGTH: 221
<212> TYPE: PRT
<213> ORGANISM: Artificial Sequence
<220> FEATURE:
<223> OTHER INFORMATION: Synthetic sequence KCy1

<400> SEQUENCE: 141

```
Met Val Ser Val Ile Lys Pro Glu Met Lys Met Arg Tyr Tyr Met Asp
1               5                   10                  15

Gly Ser Val Asn Gly His Glu Phe Thr Val Glu Gly Glu Gly Thr Gly
            20                  25                  30

Arg Pro Tyr Glu Gly Lys His Lys Ile Thr Leu Asp Val Thr Lys Gly
        35                  40                  45

Gly Pro Leu Pro Phe Ala Phe Asp Leu Leu Ser Thr Val Phe Ser Tyr
    50                  55                  60

Gly Asn Arg Ala Leu Thr Lys Tyr Pro Asp Asp Ile Pro Asp Tyr Phe
65                  70                  75                  80

Lys Gln Cys Phe Pro Gly Gly Tyr Ser Trp Glu Arg Lys Phe Glu Phe
                85                  90                  95

Glu Asp Gly Gly Leu Ala Ile Ala Lys Ala Glu Ile Ser Leu Lys Gly
            100                 105                 110

Asn Cys Phe Glu His Lys Ser Thr Ile Glu Gly Thr Phe Pro Asp Ser
        115                 120                 125

Ser Pro Ile Met Gln Asn Lys Thr Leu Gly Trp Glu Pro Ser Thr Glu
    130                 135                 140

Lys Met Thr Val Arg Asp Gly Ser Met Lys Gly Asp Asp Ala Ala Tyr
145                 150                 155                 160

Leu Lys Leu Val Gly Gly Gly Asn His Lys Cys Tyr Phe Thr Thr Thr
                165                 170                 175

Tyr Thr Ala Lys Lys Lys Ile Pro Asn Leu Pro Gly Ser His Phe Ile
            180                 185                 190

Gly His Arg Ile Ser Ser Val Val Glu Gly Thr Lys Ile Lys Val Met
        195                 200                 205

Glu Asp Ala Ile Ala His Leu Tyr Pro Phe Asn Gly Ser
    210                 215                 220
```

<210> SEQ ID NO 142
<211> LENGTH: 678
<212> TYPE: DNA
<213> ORGANISM: Artificial Sequence
<220> FEATURE:
<223> OTHER INFORMATION: Synthetic sequence dAG(AB)
<220> FEATURE:
<221> NAME/KEY: CDS
<222> LOCATION: (1)..(678)

<400> SEQUENCE: 142

```
atg gtg agt gtg att aaa cca gag atg aag atc aag ctg tgt atg aga      48
Met Val Ser Val Ile Lys Pro Glu Met Lys Ile Lys Leu Cys Met Arg
1               5                  10                  15 ggc act gta aac ggg cat aat ttc gtg att gaa gga gaa gga aaa gga      96
Gly Thr Val Asn Gly His Asn Phe Val Ile Glu Gly Glu Gly Lys Gly
            20                  25                  30 aat cct tac gag gga acg cag att tta gac ctg aac gtc act gaa ggc     144
Asn Pro Tyr Glu Gly Thr Gln Ile Leu Asp Leu Asn Val Thr Glu Gly
        35                  40                  45 gca cct ctg cct ttc gct tac gat atc ttg aca aca gtg ttc cag tac     192
Ala Pro Leu Pro Phe Ala Tyr Asp Ile Leu Thr Thr Val Phe Gln Tyr
    50                  55                  60 ggc aac agg gca ttc acc aag tac cca gca gat att cag gac tat ttc     240
Gly Asn Arg Ala Phe Thr Lys Tyr Pro Ala Asp Ile Gln Asp Tyr Phe
65                  70                  75                  80 aag cag act ttt cct gag ggg tat cac tgg gaa aga agc atg act tat     288
Lys Gln Thr Phe Pro Glu Gly Tyr His Trp Glu Arg Ser Met Thr Tyr
                85                  90                  95 gaa gac cag ggc att tgc acc gcc aca agc aac ata agc atg cgt ggc     336
Glu Asp Gln Gly Ile Cys Thr Ala Thr Ser Asn Ile Ser Met Arg Gly
            100                 105                 110 gac tgt ttt ttc tat gac att cgt ttt gat ggt gtg aac ttt cct ccc     384
Asp Cys Phe Phe Tyr Asp Ile Arg Phe Asp Gly Val Asn Phe Pro Pro
        115                 120                 125 aat ggt ccg gtt atg cag aag aag act ctt aaa tgg gag cca tcc act     432
Asn Gly Pro Val Met Gln Lys Lys Thr Leu Lys Trp Glu Pro Ser Thr
    130                 135                 140 gag aaa atg tac gta cgt gat gga gtg ctg aag ggt gat gtt aac atg     480
Glu Lys Met Tyr Val Arg Asp Gly Val Leu Lys Gly Asp Val Asn Met
145                 150                 155                 160 gct ctg ttg ctt gaa gga ggt ggc cat tat cga tgt gat ttc aaa act     528
Ala Leu Leu Leu Glu Gly Gly Gly His Tyr Arg Cys Asp Phe Lys Thr
                165                 170                 175 act tac aaa gca aag aag gat gtc cgt ttg cca gac gcg cac aaa gtg     576
Thr Tyr Lys Ala Lys Lys Asp Val Arg Leu Pro Asp Ala His Lys Val
            180                 185                 190 gac cac cgc att gag att ttg aag cat gac aaa gat tac aac aag gtc     624
Asp His Arg Ile Glu Ile Leu Lys His Asp Lys Asp Tyr Asn Lys Val
        195                 200                 205 aag ctc tat gag aat gcc gtt gct cgc tat tct atg ctg ccg agt cag     672
Lys Leu Tyr Glu Asn Ala Val Ala Arg Tyr Ser Met Leu Pro Ser Gln
    210                 215                 220 gcc aag                                                             678
Ala Lys
225
```

<210> SEQ ID NO 143
<211> LENGTH: 226
<212> TYPE: PRT
<213> ORGANISM: Artificial Sequence
<220> FEATURE:
<223> OTHER INFORMATION: Synthetic sequence dAG(AB)

<400> SEQUENCE: 143

| Met | Val | Ser | Val | Ile | Lys | Pro | Glu | Met | Lys | Ile | Lys | Leu | Cys | Met | Arg |
|---|---|---|---|---|---|---|---|---|---|---|---|---|---|---|---|
| 1 | | | | 5 | | | | | 10 | | | | | 15 | |

| Gly | Thr | Val | Asn | Gly | His | Asn | Phe | Val | Ile | Glu | Gly | Glu | Gly | Lys | Gly |
|---|---|---|---|---|---|---|---|---|---|---|---|---|---|---|---|
| | | | 20 | | | | | 25 | | | | | 30 | | |

| Asn | Pro | Tyr | Glu | Gly | Thr | Gln | Ile | Leu | Asp | Leu | Asn | Val | Thr | Glu | Gly |
|---|---|---|---|---|---|---|---|---|---|---|---|---|---|---|---|
| | | | 35 | | | | | 40 | | | | | 45 | | |

| Ala | Pro | Leu | Pro | Phe | Ala | Tyr | Asp | Ile | Leu | Thr | Thr | Val | Phe | Gln | Tyr |
|---|---|---|---|---|---|---|---|---|---|---|---|---|---|---|---|
| | 50 | | | | | 55 | | | | | 60 | | | | |

| Gly | Asn | Arg | Ala | Phe | Thr | Lys | Tyr | Pro | Ala | Asp | Ile | Gln | Asp | Tyr | Phe |
|---|---|---|---|---|---|---|---|---|---|---|---|---|---|---|---|
| 65 | | | | | 70 | | | | | 75 | | | | | 80 |

| Lys | Gln | Thr | Phe | Pro | Glu | Gly | Tyr | His | Trp | Glu | Arg | Ser | Met | Thr | Tyr |
|---|---|---|---|---|---|---|---|---|---|---|---|---|---|---|---|
| | | | | 85 | | | | | 90 | | | | | 95 | |

| Glu | Asp | Gln | Gly | Ile | Cys | Thr | Ala | Thr | Ser | Asn | Ile | Ser | Met | Arg | Gly |
|---|---|---|---|---|---|---|---|---|---|---|---|---|---|---|---|
| | | | 100 | | | | | 105 | | | | | 110 | | |

| Asp | Cys | Phe | Phe | Tyr | Asp | Ile | Arg | Phe | Asp | Gly | Val | Asn | Phe | Pro | Pro |
|---|---|---|---|---|---|---|---|---|---|---|---|---|---|---|---|
| | | | 115 | | | | | 120 | | | | | 125 | | |

| Asn | Gly | Pro | Val | Met | Gln | Lys | Lys | Thr | Leu | Lys | Trp | Glu | Pro | Ser | Thr |
|---|---|---|---|---|---|---|---|---|---|---|---|---|---|---|---|
| | 130 | | | | | 135 | | | | | 140 | | | | |

| Glu | Lys | Met | Tyr | Val | Arg | Asp | Gly | Val | Leu | Lys | Gly | Asp | Val | Asn | Met |
|---|---|---|---|---|---|---|---|---|---|---|---|---|---|---|---|
| 145 | | | | | 150 | | | | | 155 | | | | | 160 |

| Ala | Leu | Leu | Leu | Glu | Gly | Gly | His | Tyr | Arg | Cys | Asp | Phe | Lys | Thr |
|---|---|---|---|---|---|---|---|---|---|---|---|---|---|---|
| | | | | 165 | | | | | 170 | | | | | 175 |

| Thr | Tyr | Lys | Ala | Lys | Lys | Asp | Val | Arg | Leu | Pro | Asp | Ala | His | Lys | Val |
|---|---|---|---|---|---|---|---|---|---|---|---|---|---|---|---|
| | | | 180 | | | | | 185 | | | | | 190 | | |

| Asp | His | Arg | Ile | Glu | Ile | Leu | Lys | His | Asp | Lys | Asp | Tyr | Asn | Lys | Val |
|---|---|---|---|---|---|---|---|---|---|---|---|---|---|---|---|
| | | 195 | | | | | 200 | | | | | 205 | | | |

| Lys | Leu | Tyr | Glu | Asn | Ala | Val | Ala | Arg | Tyr | Ser | Met | Leu | Pro | Ser | Gln |
|---|---|---|---|---|---|---|---|---|---|---|---|---|---|---|---|
| | 210 | | | | | 215 | | | | | 220 | | | | |

| Ala | Lys |
|---|---|
| 225 | |

<210> SEQ ID NO 144
<211> LENGTH: 678
<212> TYPE: DNA
<213> ORGANISM: Artificial Sequence
<220> FEATURE:
<223> OTHER INFORMATION: Synthetic sequence dAG(AC)
<220> FEATURE:
<221> NAME/KEY: CDS
<222> LOCATION: (1)..(678)

<400> SEQUENCE: 144

| atg | gtg | agt | gtg | att | aaa | cca | gag | atg | aag | atc | aag | ctg | tgt | atg | aga | | 48 |
|---|---|---|---|---|---|---|---|---|---|---|---|---|---|---|---|---|---|
| Met | Val | Ser | Val | Ile | Lys | Pro | Glu | Met | Lys | Ile | Lys | Leu | Cys | Met | Arg | | |
| 1 | | | | 5 | | | | | 10 | | | | | 15 | | | |

| ggc | act | gta | aac | ggg | cat | aat | ttc | gtg | att | gaa | gga | gaa | gga | aaa | gga | | 96 |
|---|---|---|---|---|---|---|---|---|---|---|---|---|---|---|---|---|---|
| Gly | Thr | Val | Asn | Gly | His | Asn | Phe | Val | Ile | Glu | Gly | Glu | Gly | Lys | Gly | | |
| | | | 20 | | | | | 25 | | | | | 30 | | | | |

| aat | cct | tac | gag | gga | acg | cag | att | tta | gac | ctg | aac | gtc | act | gaa | ggc | | 144 |
|---|---|---|---|---|---|---|---|---|---|---|---|---|---|---|---|---|---|
| Asn | Pro | Tyr | Glu | Gly | Thr | Gln | Ile | Leu | Asp | Leu | Asn | Val | Thr | Glu | Gly | | |
| | | | 35 | | | | | 40 | | | | | 45 | | | | |

| gca | cct | ctg | cct | ttc | gct | tac | gat | atc | ttg | aca | aca | gtg | ttc | cag | tac | | 192 |
|---|---|---|---|---|---|---|---|---|---|---|---|---|---|---|---|---|---|
| Ala | Pro | Leu | Pro | Phe | Ala | Tyr | Asp | Ile | Leu | Thr | Thr | Val | Phe | Gln | Tyr | | |
| | 50 | | | | | 55 | | | | | 60 | | | | | | |

| ggc | aac | agg | gca | ttc | acc | aag | tac | cca | gca | gat | att | cag | gac | tat | ttc | | 240 |
|---|---|---|---|---|---|---|---|---|---|---|---|---|---|---|---|---|---|
| Gly | Asn | Arg | Ala | Phe | Thr | Lys | Tyr | Pro | Ala | Asp | Ile | Gln | Asp | Tyr | Phe | | |

```
              65                  70                  75                  80
aag cag act ttt cct gag ggg tat cac tgg gaa aga agc atg act tat         288
Lys Gln Thr Phe Pro Glu Gly Tyr His Trp Glu Arg Ser Met Thr Tyr
                85                  90                  95 gaa gac cag ggc att tgc acc gcc aca agc aac ata agc atg cgt ggc         336
Glu Asp Gln Gly Ile Cys Thr Ala Thr Ser Asn Ile Ser Met Arg Gly
            100                 105                 110 gac tgt ttt ttc tat gac att cgt ttt gat ggt acc aac ttt cct ccc         384
Asp Cys Phe Phe Tyr Asp Ile Arg Phe Asp Gly Thr Asn Phe Pro Pro
            115                 120                 125 aat ggt ccg gtt atg cag aag aag act ctt aaa tgg gag cca tcc act         432
Asn Gly Pro Val Met Gln Lys Lys Thr Leu Lys Trp Glu Pro Ser Thr
130                 135                 140 gag aaa atg tac gta cgt gat gga gtg ctg aag ggt gat gtt aac atg         480
Glu Lys Met Tyr Val Arg Asp Gly Val Leu Lys Gly Asp Val Asn Met
145                 150                 155                 160 gct ctg ttg ctt gaa gga ggt ggc cat tat cga tgt gat ttc aaa act         528
Ala Leu Leu Leu Glu Gly Gly Gly His Tyr Arg Cys Asp Phe Lys Thr
                165                 170                 175 act tac aaa gca aag aag gat gtc cgt ttg cca gac tat cac ttt gtg         576
Thr Tyr Lys Ala Lys Lys Asp Val Arg Leu Pro Asp Tyr His Phe Val
            180                 185                 190 gac cac cgc att gag att ttg aag cat gac aaa gat tac aac aag gtc         624
Asp His Arg Ile Glu Ile Leu Lys His Asp Lys Asp Tyr Asn Lys Val
            195                 200                 205 aag ctc tat gag aat gcc gtt gct cgc tat tct atg ctg ccg agt cag         672
Lys Leu Tyr Glu Asn Ala Val Ala Arg Tyr Ser Met Leu Pro Ser Gln
210                 215                 220 gcc aag                                                                 678
Ala Lys
225

<210> SEQ ID NO 145
<211> LENGTH: 226
<212> TYPE: PRT
<213> ORGANISM: Artificial Sequence
<220> FEATURE:
<223> OTHER INFORMATION: Synthetic sequence dAG(AC)

<400> SEQUENCE: 145

Met Val Ser Val Ile Lys Pro Glu Met Lys Ile Lys Leu Cys Met Arg
1               5                   10                  15

Gly Thr Val Asn Gly His Asn Phe Val Ile Glu Gly Glu Gly Lys Gly
            20                  25                  30

Asn Pro Tyr Glu Gly Thr Gln Ile Leu Asp Leu Asn Val Thr Glu Gly
        35                  40                  45

Ala Pro Leu Pro Phe Ala Tyr Asp Ile Leu Thr Thr Val Phe Gln Tyr
    50                  55                  60

Gly Asn Arg Ala Phe Thr Lys Tyr Pro Ala Asp Ile Gln Asp Tyr Phe
65                  70                  75                  80

Lys Gln Thr Phe Pro Glu Gly Tyr His Trp Glu Arg Ser Met Thr Tyr
                85                  90                  95

Glu Asp Gln Gly Ile Cys Thr Ala Thr Ser Asn Ile Ser Met Arg Gly
            100                 105                 110

Asp Cys Phe Phe Tyr Asp Ile Arg Phe Asp Gly Thr Asn Phe Pro Pro
            115                 120                 125

Asn Gly Pro Val Met Gln Lys Lys Thr Leu Lys Trp Glu Pro Ser Thr
130                 135                 140
```

```
Glu Lys Met Tyr Val Arg Asp Gly Val Leu Lys Gly Asp Val Asn Met
145                 150                 155                 160

Ala Leu Leu Leu Glu Gly Gly His Tyr Arg Cys Asp Phe Lys Thr
                165                 170                 175

Thr Tyr Lys Ala Lys Lys Asp Val Arg Leu Pro Asp Tyr His Phe Val
            180                 185                 190

Asp His Arg Ile Glu Ile Leu Lys His Asp Lys Asp Tyr Asn Lys Val
            195                 200                 205

Lys Leu Tyr Glu Asn Ala Val Ala Arg Tyr Ser Met Leu Pro Ser Gln
            210                 215                 220

Ala Lys
225
```

<210> SEQ ID NO 146
<211> LENGTH: 672
<212> TYPE: DNA
<213> ORGANISM: Artificial Sequence
<220> FEATURE:
<223> OTHER INFORMATION: Synthetic sequence TGuv
<220> FEATURE:
<221> NAME/KEY: CDS
<222> LOCATION: (1)..(672)

<400> SEQUENCE: 146

```
atg gtg agt gtt att gga aaa gac atg ata atg aaa ttg cat gtg gaa      48
Met Val Ser Val Ile Gly Lys Asp Met Ile Met Lys Leu His Val Glu
1               5                   10                  15 gga tgt gtc aac ggc cac tcc ttc aag att gag ggt gac ggc aaa ggc      96
Gly Cys Val Asn Gly His Ser Phe Lys Ile Glu Gly Asp Gly Lys Gly
                20                  25                  30 aaa ccg tac gag gga gac caa act gtg aag ctg cgt gtt act gaa gga     144
Lys Pro Tyr Glu Gly Asp Gln Thr Val Lys Leu Arg Val Thr Glu Gly
            35                  40                  45 ggg ccc tta cca ttc gca ttt gac atc ttg tca gcc tca atg tgt tat     192
Gly Pro Leu Pro Phe Ala Phe Asp Ile Leu Ser Ala Ser Met Cys Tyr
        50                  55                  60 gga aac agg tgt ttt acc aaa tat ccg gca gag att ccc gac att ttc     240
Gly Asn Arg Cys Phe Thr Lys Tyr Pro Ala Glu Ile Pro Asp Ile Phe
65                  70                  75                  80 aag cag aca ttt cct gaa ggc tac tca tgg gaa aga gcc ttg aca ttt     288
Lys Gln Thr Phe Pro Glu Gly Tyr Ser Trp Glu Arg Ala Leu Thr Phe
                85                  90                  95 gaa gat gga ggg ttt gct tca tca agc tcg cac atc agt gtc cgt ggc     336
Glu Asp Gly Gly Phe Ala Ser Ser Ser Ser His Ile Ser Val Arg Gly
            100                 105                 110 aac tgc ttc ttc tac gac gtc aaa tat cat ggc gta aac ttc cct tcc     384
Asn Cys Phe Phe Tyr Asp Val Lys Tyr His Gly Val Asn Phe Pro Ser
        115                 120                 125 aat gga cca att atg caa aga aag aca atc ggc tgg caa cca tcc aca     432
Asn Gly Pro Ile Met Gln Arg Lys Thr Ile Gly Trp Gln Pro Ser Thr
130                 135                 140 gag aaa ttg tac atc gga gag gga acg ctg aag ggt gat gat acg atg     480
Glu Lys Leu Tyr Ile Gly Glu Gly Thr Leu Lys Gly Asp Asp Thr Met
145                 150                 155                 160 ttc ctc aag ctc gaa gga ggg gga act cat aaa tgc cac gtc cta acc     528
Phe Leu Lys Leu Glu Gly Gly Gly Thr His Lys Cys His Val Leu Thr
                165                 170                 175 act tac aaa acg aag aaa gat gtc cag atg cca gac agc cac ttc att     576
Thr Tyr Lys Thr Lys Lys Asp Val Gln Met Pro Asp Ser His Phe Ile
            180                 185                 190
```

```
gac cat cgt ctc ctg acc agc cac ctt gat aag gaa tgc aac aac gtg     624
Asp His Arg Leu Leu Thr Ser His Leu Asp Lys Glu Cys Asn Asn Val
        195                 200                 205 gaa ttg cgc gag cac gca gtt gcg cgt aac tca agt ctg cct tcc cgt     672
Glu Leu Arg Glu His Ala Val Ala Arg Asn Ser Ser Leu Pro Ser Arg
    210                 215                 220
```

<210> SEQ ID NO 147
<211> LENGTH: 224
<212> TYPE: PRT
<213> ORGANISM: Artificial Sequence
<220> FEATURE:
<223> OTHER INFORMATION: Synthetic sequence TGuv

<400> SEQUENCE: 147

```
Met Val Ser Val Ile Gly Lys Asp Met Ile Met Lys Leu His Val Glu
1               5                   10                  15

Gly Cys Val Asn Gly His Ser Phe Lys Ile Glu Gly Asp Gly Lys Gly
            20                  25                  30

Lys Pro Tyr Glu Gly Asp Gln Thr Val Lys Leu Arg Val Thr Glu Gly
        35                  40                  45

Gly Pro Leu Pro Phe Ala Phe Asp Ile Leu Ser Ala Ser Met Cys Tyr
    50                  55                  60

Gly Asn Arg Cys Phe Thr Lys Tyr Pro Ala Glu Ile Pro Asp Ile Phe
65                  70                  75                  80

Lys Gln Thr Phe Pro Glu Gly Tyr Ser Trp Glu Arg Ala Leu Thr Phe
                85                  90                  95

Glu Asp Gly Gly Phe Ala Ser Ser Ser His Ile Ser Val Arg Gly
            100                 105                 110

Asn Cys Phe Phe Tyr Asp Val Lys Tyr His Gly Val Asn Phe Pro Ser
        115                 120                 125

Asn Gly Pro Ile Met Gln Arg Lys Thr Ile Gly Trp Gln Pro Ser Thr
    130                 135                 140

Glu Lys Leu Tyr Ile Gly Glu Gly Thr Leu Lys Gly Asp Asp Thr Met
145                 150                 155                 160

Phe Leu Lys Leu Glu Gly Gly Thr His Lys Cys His Val Leu Thr
                165                 170                 175

Thr Tyr Lys Thr Lys Lys Asp Val Gln Met Pro Asp Ser His Phe Ile
            180                 185                 190

Asp His Arg Leu Leu Thr Ser His Leu Asp Lys Glu Cys Asn Asn Val
        195                 200                 205

Glu Leu Arg Glu His Ala Val Ala Arg Asn Ser Ser Leu Pro Ser Arg
    210                 215                 220
```

<210> SEQ ID NO 148
<211> LENGTH: 687
<212> TYPE: DNA
<213> ORGANISM: Artificial Sequence
<220> FEATURE:
<223> OTHER INFORMATION: Synthetic sequence Momiji
<220> FEATURE:
<221> NAME/KEY: CDS
<222> LOCATION: (1)..(687)

<400> SEQUENCE: 148

```
atg gtg agc gtg atc aag gac gag atg aag gtg aac ctg cgc atg gag      48
Met Val Ser Val Ile Lys Asp Glu Met Lys Val Asn Leu Arg Met Glu
1               5                   10                  15 ggc agc gtg aac ggc cac gac ttc gtg atc gac ggc ctg ggc tcc ggc      96
Gly Ser Val Asn Gly His Asp Phe Val Ile Asp Gly Leu Gly Ser Gly
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     | 20  |     |     |     |     | 25  |     |     |     |     | 30  |     |     |     |
| aag | ccc | aag | gag | ggc | acc | cag | acc | atc | gag | ctg | aag | gtg | gtg | aag | ggc | 144 |
| Lys | Pro | Lys | Glu | Gly | Thr | Gln | Thr | Ile | Glu | Leu | Lys | Val | Val | Lys | Gly |     |
|     |     |     | 35  |     |     |     |     | 40  |     |     |     |     | 45  |     |     |     |
| ggc | ccc | ctg | ccc | ttc | gcc | tac | gac | atc | ctg | acc | acc | gcc | ttc | cac | tac | 192 |
| Gly | Pro | Leu | Pro | Phe | Ala | Tyr | Asp | Ile | Leu | Thr | Thr | Ala | Phe | His | Tyr |     |
|     | 50  |     |     |     |     | 55  |     |     |     |     | 60  |     |     |     |     |     |
| ggc | aac | agg | gtg | ttc | gcc | aag | tac | ccc | aag | gac | atc | ccc | aac | tac | ttc | 240 |
| Gly | Asn | Arg | Val | Phe | Ala | Lys | Tyr | Pro | Lys | Asp | Ile | Pro | Asn | Tyr | Phe |     |
| 65  |     |     |     |     | 70  |     |     |     |     | 75  |     |     |     |     | 80  |     |
| gag | cag | tcc | ttc | ccc | gag | ggc | tac | tcc | tgg | gag | agg | agc | atg | atc | ttc | 288 |
| Glu | Gln | Ser | Phe | Pro | Glu | Gly | Tyr | Ser | Trp | Glu | Arg | Ser | Met | Ile | Phe |     |
|     |     |     |     | 85  |     |     |     |     | 90  |     |     |     |     | 95  |     |     |
| gag | gac | ggc | ggc | atc | tgc | atc | gcc | agg | aac | gac | atc | act | atg | gac | ggc | 336 |
| Glu | Asp | Gly | Gly | Ile | Cys | Ile | Ala | Arg | Asn | Asp | Ile | Thr | Met | Asp | Gly |     |
|     |     |     | 100 |     |     |     |     | 105 |     |     |     |     | 110 |     |     |     |
| ggc | acc | ttc | tac | aac | aag | gtg | agg | ttc | tac | ggc | gtg | aac | ttc | ccc | ccc | 384 |
| Gly | Thr | Phe | Tyr | Asn | Lys | Val | Arg | Phe | Tyr | Gly | Val | Asn | Phe | Pro | Pro |     |
|     |     |     | 115 |     |     |     |     | 120 |     |     |     |     | 125 |     |     |     |
| aac | ggc | ccc | gtg | atg | cag | aag | aag | acc | cag | aag | tgg | gag | cag | tcc | acc | 432 |
| Asn | Gly | Pro | Val | Met | Gln | Lys | Lys | Thr | Gln | Lys | Trp | Glu | Gln | Ser | Thr |     |
|     | 130 |     |     |     |     | 135 |     |     |     |     | 140 |     |     |     |     |     |
| gag | aag | atg | tac | gcc | agg | gac | ggc | gtg | ctg | acc | ggc | gac | atc | aac | atg | 480 |
| Glu | Lys | Met | Tyr | Ala | Arg | Asp | Gly | Val | Leu | Thr | Gly | Asp | Ile | Asn | Met |     |
| 145 |     |     |     |     | 150 |     |     |     |     | 155 |     |     |     |     | 160 |     |
| gcc | ctg | ctg | ctg | aag | ggc | ggc | ggc | cac | tac | agg | tgc | gac | ttc | agg | acc | 528 |
| Ala | Leu | Leu | Leu | Lys | Gly | Gly | Gly | His | Tyr | Arg | Cys | Asp | Phe | Arg | Thr |     |
|     |     |     |     | 165 |     |     |     |     | 170 |     |     |     |     | 175 |     |     |
| acc | tac | aag | gcc | aag | gag | aag | ggc | gtc | aag | ctg | ccc | ggc | tac | cac | ttc | 576 |
| Thr | Tyr | Lys | Ala | Lys | Glu | Lys | Gly | Val | Lys | Leu | Pro | Gly | Tyr | His | Phe |     |
|     |     |     | 180 |     |     |     |     | 185 |     |     |     |     | 190 |     |     |     |
| atc | gac | cac | tgc | atc | gag | atc | ctg | agc | cac | agg | aac | gac | tac | aac | aac | 624 |
| Ile | Asp | His | Cys | Ile | Glu | Ile | Leu | Ser | His | Arg | Asn | Asp | Tyr | Asn | Asn |     |
|     |     |     | 195 |     |     |     |     | 200 |     |     |     |     | 205 |     |     |     |
| gtg | acc | ctg | ttc | gag | cac | gcc | gtg | gcc | agg | tcc | ggc | ctg | caa | gac | aag | 672 |
| Val | Thr | Leu | Phe | Glu | His | Ala | Val | Ala | Arg | Ser | Gly | Leu | Gln | Asp | Lys |     |
|     | 210 |     |     |     |     | 215 |     |     |     |     | 220 |     |     |     |     |     |
| gag | aag | cag | cag | cag |     |     |     |     |     |     |     |     |     |     |     | 687 |
| Glu | Lys | Gln | Gln | Gln |     |     |     |     |     |     |     |     |     |     |     |     |
| 225 |     |     |     |     |     |     |     |     |     |     |     |     |     |     |     |     |

<210> SEQ ID NO 149
<211> LENGTH: 229
<212> TYPE: PRT
<213> ORGANISM: Artificial Sequence
<220> FEATURE:
<223> OTHER INFORMATION: Synthetic sequence Momiji

<400> SEQUENCE: 149

Met Val Ser Val Ile Lys Asp Glu Met Lys Val Asn Leu Arg Met Glu
1               5                   10                  15

Gly Ser Val Asn Gly His Asp Phe Val Ile Asp Gly Leu Gly Ser Gly
                20                  25                  30

Lys Pro Lys Glu Gly Thr Gln Thr Ile Glu Leu Lys Val Val Lys Gly
                35                  40                  45

Gly Pro Leu Pro Phe Ala Tyr Asp Ile Leu Thr Thr Ala Phe His Tyr
        50                  55                  60

Gly Asn Arg Val Phe Ala Lys Tyr Pro Lys Asp Ile Pro Asn Tyr Phe
65                  70                  75                  80

-continued

```
Glu Gln Ser Phe Pro Glu Gly Tyr Ser Trp Glu Arg Ser Met Ile Phe
                 85                  90                  95
Glu Asp Gly Gly Ile Cys Ile Ala Arg Asn Asp Ile Thr Met Asp Gly
            100                 105                 110
Gly Thr Phe Tyr Asn Lys Val Arg Phe Tyr Gly Val Asn Phe Pro Pro
        115                 120                 125
Asn Gly Pro Val Met Gln Lys Thr Gln Lys Trp Glu Gln Ser Thr
    130                 135                 140
Glu Lys Met Tyr Ala Arg Asp Gly Val Leu Thr Gly Asp Ile Asn Met
145                 150                 155                 160
Ala Leu Leu Lys Gly Gly His Tyr Arg Cys Asp Phe Arg Thr
                165                 170                 175
Thr Tyr Lys Ala Lys Glu Lys Gly Val Lys Leu Pro Gly Tyr His Phe
                180                 185                 190
Ile Asp His Cys Ile Glu Ile Leu Ser His Arg Asn Asp Tyr Asn Asn
            195                 200                 205
Val Thr Leu Phe Glu His Ala Val Ala Arg Ser Gly Leu Gln Asp Lys
    210                 215                 220
Glu Lys Gln Gln Gln
225
```

<210> SEQ ID NO 150
<211> LENGTH: 696
<212> TYPE: DNA
<213> ORGANISM: Artificial Sequence
<220> FEATURE:
<223> OTHER INFORMATION: Synthetic sequence COR3.01
<220> FEATURE:
<221> NAME/KEY: CDS
<222> LOCATION: (1)..(696)

<400> SEQUENCE: 150

```
atg gcc ctg agc aag cac ggc ctg acc aag aac atg acc acc aag tac      48
Met Ala Leu Ser Lys His Gly Leu Thr Lys Asn Met Thr Thr Lys Tyr
1               5                  10                  15 agg atg gag ggc tgc gtg gac ggc cac aag ttc gtg atc acc ggc gac      96
Arg Met Glu Gly Cys Val Asp Gly His Lys Phe Val Ile Thr Gly Asp
            20                  25                  30 ggc atc ggc gac ccc ttc gag ggc aag cag acc agc atc gac ctg tgc     144
Gly Ile Gly Asp Pro Phe Glu Gly Lys Gln Thr Ser Ile Asp Leu Cys
        35                  40                  45 gtg gtg gag ggc ggc ccc ctg ccc ttc agc gag gac atc ctg agc acc     192
Val Val Glu Gly Gly Pro Leu Pro Phe Ser Glu Asp Ile Leu Ser Thr
    50                  55                  60 gtg ttc gac tac ggc aac agg gtg ttc acc aag tac ccc cag gac ctg     240
Val Phe Asp Tyr Gly Asn Arg Val Phe Thr Lys Tyr Pro Gln Asp Leu
65                  70                  75                  80 gtg gac tac ttc aag aac agc tgc ccc gcc ggc tac acc tgg cag agg     288
Val Asp Tyr Phe Lys Asn Ser Cys Pro Ala Gly Tyr Thr Trp Gln Arg
                85                  90                  95 agc ttc ctg ttc gag gac ggc gcc gtg tgc acc gcc agc gcc gac atc     336
Ser Phe Leu Phe Glu Asp Gly Ala Val Cys Thr Ala Ser Ala Asp Ile
            100                 105                 110 agg gtg agc gtg gag gag aac tgc ttc tac cac gag agc aag ttc cac     384
Arg Val Ser Val Glu Glu Asn Cys Phe Tyr His Glu Ser Lys Phe His
        115                 120                 125 ggc gtg aac ttc ccc gcc gac ggc ccc gtg atg aag aag atg acc acc     432
Gly Val Asn Phe Pro Ala Asp Gly Pro Val Met Lys Lys Met Thr Thr
    130                 135                 140
```

```
aac tgg gag ccc agc tgc gag aag atc acc ccc atc ctg aac gag ggc      480
Asn Trp Glu Pro Ser Cys Glu Lys Ile Thr Pro Ile Leu Asn Glu Gly
145                 150                 155                 160 atc ctg aag ggc gac gtg acc atg ttc ctg ctg aag gac ggc ggc          528
Ile Leu Lys Gly Asp Val Thr Met Phe Leu Leu Lys Asp Gly Gly
                165                 170                 175 agg tac agg tgc cag ttc gac acc gtg tac aag gcc aag gcc gac gcc      576
Arg Tyr Arg Cys Gln Phe Asp Thr Val Tyr Lys Ala Lys Ala Asp Ala
                180                 185                 190 aag aag atg ccc gag tgg cac ttc atc cag cac gag ctg acc agg gag      624
Lys Lys Met Pro Glu Trp His Phe Ile Gln His Glu Leu Thr Arg Glu
                195                 200                 205 gac agg agc gac gcc aag cac cag aag tgg agg ctg gtg gag aac gcc      672
Asp Arg Ser Asp Ala Lys His Gln Lys Trp Arg Leu Val Glu Asn Ala
210                 215                 220 atc gcc tac agg agc acc ctg ccc                                       696
Ile Ala Tyr Arg Ser Thr Leu Pro
225                 230

<210> SEQ ID NO 151
<211> LENGTH: 232
<212> TYPE: PRT
<213> ORGANISM: Artificial Sequence
<220> FEATURE:
<223> OTHER INFORMATION: Synthetic sequence COR3.01

<400> SEQUENCE: 151

Met Ala Leu Ser Lys His Gly Leu Thr Lys Asn Met Thr Thr Lys Tyr
1               5                   10                  15

Arg Met Glu Gly Cys Val Asp Gly His Lys Phe Val Ile Thr Gly Asp
                20                  25                  30

Gly Ile Gly Asp Pro Phe Glu Gly Lys Gln Thr Ser Ile Asp Leu Cys
            35                  40                  45

Val Val Glu Gly Gly Pro Leu Pro Phe Ser Glu Asp Ile Leu Ser Thr
50                  55                  60

Val Phe Asp Tyr Gly Asn Arg Val Phe Thr Lys Tyr Pro Gln Asp Leu
65                  70                  75                  80

Val Asp Tyr Phe Lys Asn Ser Cys Pro Ala Gly Tyr Thr Trp Gln Arg
                85                  90                  95

Ser Phe Leu Phe Glu Asp Gly Ala Val Cys Thr Ala Ser Ala Asp Ile
            100                 105                 110

Arg Val Ser Val Glu Glu Asn Cys Phe Tyr His Glu Ser Lys Phe His
        115                 120                 125

Gly Val Asn Phe Pro Ala Asp Gly Pro Val Met Lys Lys Met Thr Thr
    130                 135                 140

Asn Trp Glu Pro Ser Cys Glu Lys Ile Thr Pro Ile Leu Asn Glu Gly
145                 150                 155                 160

Ile Leu Lys Gly Asp Val Thr Met Phe Leu Leu Lys Asp Gly Gly
                165                 170                 175

Arg Tyr Arg Cys Gln Phe Asp Thr Val Tyr Lys Ala Lys Ala Asp Ala
                180                 185                 190

Lys Lys Met Pro Glu Trp His Phe Ile Gln His Glu Leu Thr Arg Glu
                195                 200                 205

Asp Arg Ser Asp Ala Lys His Gln Lys Trp Arg Leu Val Glu Asn Ala
210                 215                 220

Ile Ala Tyr Arg Ser Thr Leu Pro
225                 230
```

<210> SEQ ID NO 152
<211> LENGTH: 678
<212> TYPE: DNA
<213> ORGANISM: Artificial Sequence
<220> FEATURE:
<223> OTHER INFORMATION: Synthetic sequence DsRed2
<220> FEATURE:
<221> NAME/KEY: CDS
<222> LOCATION: (1)..(678)

<400> SEQUENCE: 152

```
atg gcc tcc tcc gag aac gtc atc acc gag ttc atg cgc ttc aag gtg        48
Met Ala Ser Ser Glu Asn Val Ile Thr Glu Phe Met Arg Phe Lys Val
1               5                   10                  15 cgc atg gag ggc acc gtg aac ggc cac gag ttc gag atc gag ggc gag        96
Arg Met Glu Gly Thr Val Asn Gly His Glu Phe Glu Ile Glu Gly Glu
                20                  25                  30 ggc gag ggc cgc ccc tac gag ggc cac aac acc gtg aag ctg aag gtg       144
Gly Glu Gly Arg Pro Tyr Glu Gly His Asn Thr Val Lys Leu Lys Val
            35                  40                  45 acc aag ggc ggc ccc ctg ccc ttc gcc tgg gac atc ctg tcc ccc cag       192
Thr Lys Gly Gly Pro Leu Pro Phe Ala Trp Asp Ile Leu Ser Pro Gln
        50                  55                  60 ttc cag tac ggc tcc aag gtg tac gtg aag cac ccc gcc gac atc ccc       240
Phe Gln Tyr Gly Ser Lys Val Tyr Val Lys His Pro Ala Asp Ile Pro
65                  70                  75                  80 gac tac aag aag ctg tcc ttc ccc gag ggc ttc aag tgg gag cgc gtg       288
Asp Tyr Lys Lys Leu Ser Phe Pro Glu Gly Phe Lys Trp Glu Arg Val
                85                  90                  95 atg aac ttc gag gac ggc ggc gtg gcg acc gtg acc cag gac tcc tcc       336
Met Asn Phe Glu Asp Gly Gly Val Ala Thr Val Thr Gln Asp Ser Ser
                100                 105                 110 ctg cag gac ggc tgc ttc atc tac aag gtg aag ttc atc ggc gtg aac       384
Leu Gln Asp Gly Cys Phe Ile Tyr Lys Val Lys Phe Ile Gly Val Asn
            115                 120                 125 ttc ccc tcc gac ggc ccc gtg atg cag aag aag acc atg ggc tgg gag       432
Phe Pro Ser Asp Gly Pro Val Met Gln Lys Lys Thr Met Gly Trp Glu
        130                 135                 140 gcc tcc acc gag cgc ctg tac ccc cgc gac ggc gtg ctg aag ggc gag       480
Ala Ser Thr Glu Arg Leu Tyr Pro Arg Asp Gly Val Leu Lys Gly Glu
145                 150                 155                 160 acc cac aag gcc ctg aag ctg aag gac ggc ggc cac tac ctg gtg gag       528
Thr His Lys Ala Leu Lys Leu Lys Asp Gly Gly His Tyr Leu Val Glu
                165                 170                 175 ttc aag tct atc tac atg gcc aag aag ccc gtg cag ctg ccc ggc tac       576
Phe Lys Ser Ile Tyr Met Ala Lys Lys Pro Val Gln Leu Pro Gly Tyr
                180                 185                 190 tac tac gtg gac gcc aag ctg gac atc acc tcc cac aac gag gac tac       624
Tyr Tyr Val Asp Ala Lys Leu Asp Ile Thr Ser His Asn Glu Asp Tyr
            195                 200                 205 acc atc gtg gag cag tac gag cgc acc gag ggc cgc cac cac ctg ttc       672
Thr Ile Val Glu Gln Tyr Glu Arg Thr Glu Gly Arg His His Leu Phe
        210                 215                 220 ctg tag                                                                678
Leu
225
```

<210> SEQ ID NO 153
<211> LENGTH: 225
<212> TYPE: PRT
<213> ORGANISM: Artificial Sequence
<220> FEATURE:

<223> OTHER INFORMATION: Synthetic sequence DsRed2

<400> SEQUENCE: 153

Met Ala Ser Ser Glu Asn Val Ile Thr Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Ala Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Thr His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ala Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 154
<211> LENGTH: 49
<212> TYPE: DNA
<213> ORGANISM: Artificial Sequence
<220> FEATURE:
<223> OTHER INFORMATION: Artificially synthesized primer sequence

<400> SEQUENCE: 154
gcttccaggc gcactaccgc gctgagcgcg gggacttggt tgccttttc                49

<210> SEQ ID NO 155
<211> LENGTH: 372
<212> TYPE: DNA
<213> ORGANISM: Artificial Sequence
<220> FEATURE:
<223> OTHER INFORMATION: Artificially synthesized polynucleotide
      sequence
<220> FEATURE:
<221> NAME/KEY: CDS
<222> LOCATION: (1)..(372)

<400> SEQUENCE: 155 aat gca tcc aac ttg aaa att gta aga atg gac agg aca gct gga tgt      48
Asn Ala Ser Asn Leu Lys Ile Val Arg Met Asp Arg Thr Ala Gly Cys
1               5                   10                  15

```
gtg act gga ggg gag gaa att tat ctt ctt tgt gac aaa gtt cag aaa    96
Val Thr Gly Gly Glu Glu Ile Tyr Leu Leu Cys Asp Lys Val Gln Lys
            20                  25                  30 gat gac atc cag att cga ttt tat gaa gag gaa gaa aat ggt gga gtc   144
Asp Asp Ile Gln Ile Arg Phe Tyr Glu Glu Glu Glu Asn Gly Gly Val
        35                  40                  45 tgg gaa gga ttt gga gat ttt tcc ccc aca gat gtt cat aga caa ttt   192
Trp Glu Gly Phe Gly Asp Phe Ser Pro Thr Asp Val His Arg Gln Phe
    50                  55                  60 gcc att gtc ttc aaa act cca aag tat aaa gat att aat att aca aaa   240
Ala Ile Val Phe Lys Thr Pro Lys Tyr Lys Asp Ile Asn Ile Thr Lys
65                  70                  75                  80 cca gcc tct gtg ttt gtc cag ctt cgg agg aaa tct gac ttg gaa act   288
Pro Ala Ser Val Phe Val Gln Leu Arg Arg Lys Ser Asp Leu Glu Thr
                85                  90                  95 agt gaa cca aaa cct ttc ctc tac tat cct gaa atc aaa gat aaa gaa   336
Ser Glu Pro Lys Pro Phe Leu Tyr Tyr Pro Glu Ile Lys Asp Lys Glu
            100                 105                 110 gaa gtg cag agg aaa cgt cag aag ggc tcg aga taa                   372
Glu Val Gln Arg Lys Arg Gln Lys Gly Ser Arg
        115                 120

<210> SEQ ID NO 156
<211> LENGTH: 123
<212> TYPE: PRT
<213> ORGANISM: Artificial Sequence
<220> FEATURE:
<223> OTHER INFORMATION: Artificially synthesized polypeptide sequence

<400> SEQUENCE: 156

Asn Ala Ser Asn Leu Lys Ile Val Arg Met Asp Arg Thr Ala Gly Cys
1               5                   10                  15

Val Thr Gly Gly Glu Glu Ile Tyr Leu Leu Cys Asp Lys Val Gln Lys
            20                  25                  30

Asp Asp Ile Gln Ile Arg Phe Tyr Glu Glu Glu Glu Asn Gly Gly Val
        35                  40                  45

Trp Glu Gly Phe Gly Asp Phe Ser Pro Thr Asp Val His Arg Gln Phe
    50                  55                  60

Ala Ile Val Phe Lys Thr Pro Lys Tyr Lys Asp Ile Asn Ile Thr Lys
65                  70                  75                  80

Pro Ala Ser Val Phe Val Gln Leu Arg Arg Lys Ser Asp Leu Glu Thr
                85                  90                  95

Ser Glu Pro Lys Pro Phe Leu Tyr Tyr Pro Glu Ile Lys Asp Lys Glu
            100                 105                 110

Glu Val Gln Arg Lys Arg Gln Lys Gly Ser Arg
        115                 120

<210> SEQ ID NO 157
<211> LENGTH: 393
<212> TYPE: DNA
<213> ORGANISM: Artificial Sequence
<220> FEATURE:
<223> OTHER INFORMATION: Artificially synthesized polynucleotide
      sequence
<220> FEATURE:
<221> NAME/KEY: CDS
<222> LOCATION: (1)..(393)

<400> SEQUENCE: 157 act gcc gag ctc aag atc tgc cga gtg aac cga aac tct ggc agc tgc    48
Thr Ala Glu Leu Lys Ile Cys Arg Val Asn Arg Asn Ser Gly Ser Cys
1               5                   10                  15
```

```
ctc ggt ggg gat gag atc ttc cta ctg tgt gac aag gtg cag aaa gag    96
Leu Gly Gly Asp Glu Ile Phe Leu Leu Cys Asp Lys Val Gln Lys Glu
         20                  25                  30 gac att gag gtg tat ttc acg gga cca ggc tgg gag gcc cga ggc tcc   144
Asp Ile Glu Val Tyr Phe Thr Gly Pro Gly Trp Glu Ala Arg Gly Ser
     35                  40                  45 ttt tcg caa gct gat gtg cac cga caa gtg gcc att gtg ttc cgg acc   192
Phe Ser Gln Ala Asp Val His Arg Gln Val Ala Ile Val Phe Arg Thr
 50                  55                  60 cct ccc tac gca gac ccc agc ctg cag gct cct gtg cgt gtc tcc atg   240
Pro Pro Tyr Ala Asp Pro Ser Leu Gln Ala Pro Val Arg Val Ser Met
 65                  70                  75                  80 cag ctg cgg cgg cct tcc gac cgg gag ctc agt gag ccc atg gaa ttc   288
Gln Leu Arg Arg Pro Ser Asp Arg Glu Leu Ser Glu Pro Met Glu Phe
                 85                  90                  95 cag tac ctg cca gat aca gac gat cgt cac cgg att gag gag aaa cgt   336
Gln Tyr Leu Pro Asp Thr Asp Asp Arg His Arg Ile Glu Glu Lys Arg
            100                 105                 110 aaa agg aca tat gag acc ttc aag agc atc atg aag aag agt cct ttc   384
Lys Arg Thr Tyr Glu Thr Phe Lys Ser Ile Met Lys Lys Ser Pro Phe
        115                 120                 125 agc gga taa                                                        393
Ser Gly
    130

<210> SEQ ID NO 158
<211> LENGTH: 130
<212> TYPE: PRT
<213> ORGANISM: Artificial Sequence
<220> FEATURE:
<223> OTHER INFORMATION: Artificially synthesized polypeptide sequence

<400> SEQUENCE: 158

Thr Ala Glu Leu Lys Ile Cys Arg Val Asn Arg Asn Ser Gly Ser Cys
1               5                   10                  15

Leu Gly Gly Asp Glu Ile Phe Leu Leu Cys Asp Lys Val Gln Lys Glu
            20                  25                  30

Asp Ile Glu Val Tyr Phe Thr Gly Pro Gly Trp Glu Ala Arg Gly Ser
        35                  40                  45

Phe Ser Gln Ala Asp Val His Arg Gln Val Ala Ile Val Phe Arg Thr
    50                  55                  60

Pro Pro Tyr Ala Asp Pro Ser Leu Gln Ala Pro Val Arg Val Ser Met
65                  70                  75                  80

Gln Leu Arg Arg Pro Ser Asp Arg Glu Leu Ser Glu Pro Met Glu Phe
                85                  90                  95

Gln Tyr Leu Pro Asp Thr Asp Asp Arg His Arg Ile Glu Glu Lys Arg
            100                 105                 110

Lys Arg Thr Tyr Glu Thr Phe Lys Ser Ile Met Lys Lys Ser Pro Phe
        115                 120                 125

Ser Gly
    130

<210> SEQ ID NO 159
<211> LENGTH: 41
<212> TYPE: DNA
<213> ORGANISM: Artificial Sequence
<220> FEATURE:
<223> OTHER INFORMATION: Artificially synthesized primer sequence

<400> SEQUENCE: 159
```

```
acattttcag acctattgaa actacttcct gaaaacaacg t                    41
```

<210> SEQ ID NO 160
<211> LENGTH: 42
<212> TYPE: DNA
<213> ORGANISM: Artificial Sequence
<220> FEATURE:
<223> OTHER INFORMATION: Artificially synthesized primer sequence

<400> SEQUENCE: 160

```
cttgtggtag ttggagctga cggcgtaggc aagagtgcct tg                   42
```

<210> SEQ ID NO 161
<211> LENGTH: 243
<212> TYPE: DNA
<213> ORGANISM: Artificial Sequence
<220> FEATURE:
<223> OTHER INFORMATION: Artificially synthesized polynucleotide
      sequence
<220> FEATURE:
<221> NAME/KEY: CDS
<222> LOCATION: (1)..(243)

<400> SEQUENCE: 161

```
cct tct aag aca agc aac act atc gct gtt ttc ttg ccg aac aag caa    48
Pro Ser Lys Thr Ser Asn Thr Ile Ala Val Phe Leu Pro Asn Lys Gln
1               5                   10                  15 aga aca gtg gtc aat gtg cga aat gga atg agc ttg cat gac tgc ctt    96
Arg Thr Val Val Asn Val Arg Asn Gly Met Ser Leu His Asp Cys Leu
                20                  25                  30 atg aaa gca ctc aag gtg agg ggc ctg caa cca gag tgc tgt gca gtg   144
Met Lys Ala Leu Lys Val Arg Gly Leu Gln Pro Glu Cys Cys Ala Val
            35                  40                  45 ttc aga ctt ctc cac gaa cac aaa ggt aaa aaa gca cgc tta gat tgg   192
Phe Arg Leu Leu His Glu His Lys Gly Lys Lys Ala Arg Leu Asp Trp
    50                  55                  60 aat act gat gct gcg tct ttg att gga gaa gaa ctt caa gta gat ttc   240
Asn Thr Asp Ala Ala Ser Leu Ile Gly Glu Glu Leu Gln Val Asp Phe
65                  70                  75                  80 ctg                                                               243
Leu
```

<210> SEQ ID NO 162
<211> LENGTH: 81
<212> TYPE: PRT
<213> ORGANISM: Artificial Sequence
<220> FEATURE:
<223> OTHER INFORMATION: Artificially synthesized polypeptide sequence

<400> SEQUENCE: 162

```
Pro Ser Lys Thr Ser Asn Thr Ile Ala Val Phe Leu Pro Asn Lys Gln
1               5                   10                  15

Arg Thr Val Val Asn Val Arg Asn Gly Met Ser Leu His Asp Cys Leu
                20                  25                  30

Met Lys Ala Leu Lys Val Arg Gly Leu Gln Pro Glu Cys Cys Ala Val
            35                  40                  45

Phe Arg Leu Leu His Glu His Lys Gly Lys Lys Ala Arg Leu Asp Trp
    50                  55                  60

Asn Thr Asp Ala Ala Ser Leu Ile Gly Glu Glu Leu Gln Val Asp Phe
65                  70                  75                  80

Leu
```

<210> SEQ ID NO 163
<211> LENGTH: 48
<212> TYPE: DNA
<213> ORGANISM: Artificial Sequence
<220> FEATURE:
<223> OTHER INFORMATION: Artificially synthesized polynucleotide
      sequence
<220> FEATURE:
<221> NAME/KEY: CDS
<222> LOCATION: (1)..(48)

<400> SEQUENCE: 163 ggg cag gtg gga cgg cag ctc gcc atc atc ggg gac gac atc aac cga    48
Gly Gln Val Gly Arg Gln Leu Ala Ile Ile Gly Asp Asp Ile Asn Arg
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Artificially synthesized polypeptide sequence

<400> SEQUENCE: 164

Gly Gln Val Gly Arg Gln Leu Ala Ile Ile Gly Asp Asp Ile Asn Arg
1               5                   10                  15

<210> SEQ ID NO 165
<211> LENGTH: 63
<212> TYPE: DNA
<213> ORGANISM: Artificial Sequence
<220> FEATURE:
<223> OTHER INFORMATION: Artificially synthesized polynucleotide
      sequence
<220> FEATURE:
<221> NAME/KEY: CDS
<222> LOCATION: (1)..(63)

<400> SEQUENCE: 165 cag gat gcg tcc acc aag aag ctg agc gag tgt ctc aag cgc atc ggg    48
Gln Asp Ala Ser Thr Lys Lys Leu Ser Glu Cys Leu Lys Arg Ile Gly
1               5                   10                  15 gac gaa ctg gac agt                                                63
Asp Glu Leu Asp Ser
            20

<210> SEQ ID NO 166
<211> LENGTH: 21
<212> TYPE: PRT
<213> ORGANISM: Artificial Sequence
<220> FEATURE:
<223> OTHER INFORMATION: Artificially synthesized polypeptide sequence

<400> SEQUENCE: 166

Gln Asp Ala Ser Thr Lys Lys Leu Ser Glu Cys Leu Lys Arg Ile Gly
1               5                   10                  15

Asp Glu Leu Asp Ser
            20

<210> SEQ ID NO 167
<211> LENGTH: 1449
<212> TYPE: DNA
<213> ORGANISM: Artificial Sequence
<220> FEATURE:
<223> OTHER INFORMATION: Artificially synthesized polynucleotide
      sequence
<220> FEATURE:
<221> NAME/KEY: CDS

<222> LOCATION: (1)..(1449)

<400> SEQUENCE: 167

```
atg gcg tcg ctc acc gtg aag gcc tac ctt ctg ggc aag gag gac gcg      48
Met Ala Ser Leu Thr Val Lys Ala Tyr Leu Leu Gly Lys Glu Asp Ala
1               5                   10                  15 gcg cgc gag att cgc cgc ttc agc ttc tgc tgc agc ccc gag cct gag      96
Ala Arg Glu Ile Arg Arg Phe Ser Phe Cys Cys Ser Pro Glu Pro Glu
            20                  25                  30 gcg gaa gcc gag gct gcg gcg ggt ccg gga ccc tgc gag cgg ctg ctg     144
Ala Glu Ala Glu Ala Ala Ala Gly Pro Gly Pro Cys Glu Arg Leu Leu
        35                  40                  45 agc cgg gtg gcc gcc ctg ttc ccc gcg ctg cgg cct ggc ggc ttc cag     192
Ser Arg Val Ala Ala Leu Phe Pro Ala Leu Arg Pro Gly Gly Phe Gln
    50                  55                  60 gcg cac tac cgc gat gag gac ggg gac ttg gtt gcc ttt tcc agt gac     240
Ala His Tyr Arg Asp Glu Asp Gly Asp Leu Val Ala Phe Ser Ser Asp
65                  70                  75                  80 gag gaa ttg aca atg gcc atg tcc tac gtg aag gat gac atc ttc cga     288
Glu Glu Leu Thr Met Ala Met Ser Tyr Val Lys Asp Asp Ile Phe Arg
                85                  90                  95 atc tac att aaa gag aaa acc ggt aat tcc gct gac ggc ggc gga gga     336
Ile Tyr Ile Lys Glu Lys Thr Gly Asn Ser Ala Asp Gly Gly Gly Gly
            100                 105                 110 tcg ggt ggt agt ggt ggt tca gga gga gga tcg acc caa gga gga tcc     384
Ser Gly Gly Ser Gly Gly Ser Gly Gly Gly Ser Thr Gln Gly Gly Ser
        115                 120                 125 cca gat gtc cct aga act cca gtg ggc aaa ttc cag ttc cca gga agc     432
Pro Asp Val Pro Arg Thr Pro Val Gly Lys Phe Gln Phe Pro Gly Ser
    130                 135                 140 gga gct act aac ttc agc ctg ctg aag cag gct gga gac gtg gag gag     480
Gly Ala Thr Asn Phe Ser Leu Leu Lys Gln Ala Gly Asp Val Glu Glu
145                 150                 155                 160 aac cct gga cct atg gtg agc gtg atc aag ccc gag atg aag atc aag     528
Asn Pro Gly Pro Met Val Ser Val Ile Lys Pro Glu Met Lys Ile Lys
                165                 170                 175 ctg tgc atg agg ggc acc gtg aac ggc cac aac ttc gtg atc gag ggc     576
Leu Cys Met Arg Gly Thr Val Asn Gly His Asn Phe Val Ile Glu Gly
            180                 185                 190 gag ggc aag ggc aac ccc tac gag ggc acc cag atc ctg gac ctg aac     624
Glu Gly Lys Gly Asn Pro Tyr Glu Gly Thr Gln Ile Leu Asp Leu Asn
        195                 200                 205 gtg acc gag ggc gcc ccc ctg ccc ttc gcc tac gac atc ctg acc acc     672
Val Thr Glu Gly Ala Pro Leu Pro Phe Ala Tyr Asp Ile Leu Thr Thr
    210                 215                 220 gtg ttc cag tac ggc aac agg gcc ttc acc aag tac ccc gcc gac atc     720
Val Phe Gln Tyr Gly Asn Arg Ala Phe Thr Lys Tyr Pro Ala Asp Ile
225                 230                 235                 240 cag gac tac ttc aag cag acc ttc ccc gag ggc tac cac tgg gag agg     768
Gln Asp Tyr Phe Lys Gln Thr Phe Pro Glu Gly Tyr His Trp Glu Arg
                245                 250                 255 agc atg acc tac gag gac cag ggc atc tgc acc gcc acc agc aac atc     816
Ser Met Thr Tyr Glu Asp Gln Gly Ile Cys Thr Ala Thr Ser Asn Ile
            260                 265                 270 agc atg agg ggc gac tgc ttc ttc tac gac atc agg ttc gac ggc gtg     864
Ser Met Arg Gly Asp Cys Phe Phe Tyr Asp Ile Arg Phe Asp Gly Val
        275                 280                 285 aac ttc ccc ccc aac ggc ccc gtg atg cag aag aag acc ctg aag tgg     912
Asn Phe Pro Pro Asn Gly Pro Val Met Gln Lys Lys Thr Leu Lys Trp
    290                 295                 300
```

```
gag ccc agc acc gag aag atg tac gtg agg gac ggc gtg ctg aag ggc    960
Glu Pro Ser Thr Glu Lys Met Tyr Val Arg Asp Gly Val Leu Lys Gly
305                 310                 315                 320 gac gtg aac atg gcc ctg ctg ctg gag ggc ggc cac tac agg tgc       1008
Asp Val Asn Met Ala Leu Leu Leu Glu Gly Gly His Tyr Arg Cys
            325                 330                 335 gac ttc aag acc acc tac aag gcc aag aag gac gtg agg ctg ccc gac   1056
Asp Phe Lys Thr Thr Tyr Lys Ala Lys Lys Asp Val Arg Leu Pro Asp
                340                 345                 350 tac cac ttc gtg gac cac agg atc gag atc ctg aag cac gac aag gac   1104
Tyr His Phe Val Asp His Arg Ile Glu Ile Leu Lys His Asp Lys Asp
                355                 360                 365 tac aac aag gtg aag ctg tac gag aac gcc gtg gcc agg tac agc atg   1152
Tyr Asn Lys Val Lys Leu Tyr Glu Asn Ala Val Ala Arg Tyr Ser Met
370                 375                 380 ctg ccc agc cag gcc aag acc ggt aat tcc gct gac ggc ggc gga gga   1200
Leu Pro Ser Gln Ala Lys Thr Gly Asn Ser Ala Asp Gly Gly Gly Gly
385                 390                 395                 400 tcg ggt ggt agt ggt ggt tca gga gga gga tcg acc caa gga gga tcc   1248
Ser Gly Gly Ser Gly Gly Ser Gly Gly Gly Ser Thr Gln Gly Gly Ser
                405                 410                 415 atg gcg gac gag gag aag ctg ccg ccc ggc tgg gag aag cgc atg agc   1296
Met Ala Asp Glu Glu Lys Leu Pro Pro Gly Trp Glu Lys Arg Met Ser
                420                 425                 430 cgc agc tca ggc cga gtg tac tac ttc aac cac atc act aac gcc agc   1344
Arg Ser Ser Gly Arg Val Tyr Tyr Phe Asn His Ile Thr Asn Ala Ser
            435                 440                 445 cag tgg gag cgg ccc agc ggc aac agc agc agt ggt ggc aaa aac ggg   1392
Gln Trp Glu Arg Pro Ser Gly Asn Ser Ser Ser Gly Gly Lys Asn Gly
        450                 455                 460 cag ggg gag cct gcc agg ctt cag aag aaa ctc gag gaa ctt gag ctt   1440
Gln Gly Glu Pro Ala Arg Leu Gln Lys Lys Leu Glu Glu Leu Glu Leu
465                 470                 475                 480 gat gag taa                                                       1449
Asp Glu

<210> SEQ ID NO 168
<211> LENGTH: 482
<212> TYPE: PRT
<213> ORGANISM: Artificial Sequence
<220> FEATURE:
<223> OTHER INFORMATION: Artificially synthesized polypeptide sequence

<400> SEQUENCE: 168

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Gly Pro Gly Pro Cys Glu Arg Leu Leu
        35                  40                  45

Ser Arg Val Ala Ala Leu Phe Pro Ala Leu Arg Pro Gly Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Thr Gly Asn Ser Ala Asp Gly Gly Gly Gly
            100                 105                 110
```

-continued

```
Ser Gly Gly Ser Gly Gly Gly Gly Ser Thr Gln Gly Gly Ser
            115                 120                 125

Pro Asp Val Pro Arg Thr Pro Val Gly Lys Phe Gln Phe Pro Gly Ser
130                 135                 140

Gly Ala Thr Asn Phe Ser Leu Leu Lys Gln Ala Gly Asp Val Glu Glu
145                 150                 155                 160

Asn Pro Gly Pro Met Val Ser Val Ile Lys Pro Glu Met Lys Ile Lys
                165                 170                 175

Leu Cys Met Arg Gly Thr Val Asn Gly His Asn Phe Val Ile Glu Gly
            180                 185                 190

Glu Gly Lys Gly Asn Pro Tyr Glu Gly Thr Gln Ile Leu Asp Leu Asn
        195                 200                 205

Val Thr Glu Gly Ala Pro Leu Pro Phe Ala Tyr Asp Ile Leu Thr Thr
210                 215                 220

Val Phe Gln Tyr Gly Asn Arg Ala Phe Thr Lys Tyr Pro Ala Asp Ile
225                 230                 235                 240

Gln Asp Tyr Phe Lys Gln Thr Phe Pro Glu Gly Tyr His Trp Glu Arg
                245                 250                 255

Ser Met Thr Tyr Glu Asp Gln Gly Ile Cys Thr Ala Thr Ser Asn Ile
            260                 265                 270

Ser Met Arg Gly Asp Cys Phe Phe Tyr Asp Ile Arg Phe Asp Gly Val
        275                 280                 285

Asn Phe Pro Pro Asn Gly Pro Val Met Gln Lys Lys Thr Leu Lys Trp
290                 295                 300

Glu Pro Ser Thr Glu Lys Met Tyr Val Arg Asp Gly Val Leu Lys Gly
305                 310                 315                 320

Asp Val Asn Met Ala Leu Leu Leu Glu Gly Gly Gly His Tyr Arg Cys
                325                 330                 335

Asp Phe Lys Thr Thr Tyr Lys Ala Lys Lys Asp Val Arg Leu Pro Asp
            340                 345                 350

Tyr His Phe Val Asp His Arg Ile Glu Ile Leu Lys His Asp Lys Asp
        355                 360                 365

Tyr Asn Lys Val Lys Leu Tyr Glu Asn Ala Val Ala Arg Tyr Ser Met
370                 375                 380

Leu Pro Ser Gln Ala Lys Thr Gly Asn Ser Ala Asp Gly Gly Gly Gly
385                 390                 395                 400

Ser Gly Gly Ser Gly Gly Ser Gly Gly Gly Ser Thr Gln Gly Gly Ser
                405                 410                 415

Met Ala Asp Glu Glu Lys Leu Pro Pro Gly Trp Glu Lys Arg Met Ser
            420                 425                 430

Arg Ser Ser Gly Arg Val Tyr Tyr Phe Asn His Ile Thr Asn Ala Ser
        435                 440                 445

Gln Trp Glu Arg Pro Ser Gly Asn Ser Ser Ser Gly Gly Lys Asn Gly
450                 455                 460

Gln Gly Glu Pro Ala Arg Leu Gln Lys Lys Leu Glu Glu Leu Glu Leu
465                 470                 475                 480

Asp Glu
```

<210> SEQ ID NO 169
<211> LENGTH: 684
<212> TYPE: DNA
<213> ORGANISM: Artificial Sequence
<220> FEATURE:
<223> OTHER INFORMATION: Artificially synthesized polynucleotide sequence

```
<220> FEATURE:
<221> NAME/KEY: CDS
<222> LOCATION: (1)..(684)

<400> SEQUENCE: 169 atg ctc gaa cca tac tgg ctt cca aat ttc atg gat gtt ttt act tgg      48
Met Leu Glu Pro Tyr Trp Leu Pro Asn Phe Met Asp Val Phe Thr Trp
1               5                   10                  15 tcc ctt cca ttt gtt ggg gaa aaa gtg act gag atg ctg gta aat gtc      96
Ser Leu Pro Phe Val Gly Glu Lys Val Thr Glu Met Leu Val Asn Val
            20                  25                  30 ctc aac atc tgc tca gat gat gaa cta ggg tca gaa gaa gat gga ttt     144
Leu Asn Ile Cys Ser Asp Asp Glu Leu Gly Ser Glu Glu Asp Gly Phe
        35                  40                  45 gat ggt gca aca gct gca gcc cgg aaa gag gtc gag gag gca agt tat     192
Asp Gly Ala Thr Ala Ala Ala Arg Lys Glu Val Glu Glu Ala Ser Tyr
50                  55                  60 cct ttg gaa atg tgc tca cac ttt gat gcg gat gaa att aaa agg cta     240
Pro Leu Glu Met Cys Ser His Phe Asp Ala Asp Glu Ile Lys Arg Leu
65                  70                  75                  80 gga aag aga ttt aag aag ctt gat ttg gac aat tct ggt tct ttg agt     288
Gly Lys Arg Phe Lys Lys Leu Asp Leu Asp Asn Ser Gly Ser Leu Ser
                85                  90                  95 gtg gaa gag ttc atg tct ctg cct gag tta caa cag aat cct tta gta     336
Val Glu Glu Phe Met Ser Leu Pro Glu Leu Gln Gln Asn Pro Leu Val
            100                 105                 110 cag cga gta ata gat ata ttc gac aca gat ggg aat gga gaa gta gac     384
Gln Arg Val Ile Asp Ile Phe Asp Thr Asp Gly Asn Gly Glu Val Asp
        115                 120                 125 ttt aaa gaa ttc att gag ggc gtc tct cag ttc agt gtc aaa gga gat     432
Phe Lys Glu Phe Ile Glu Gly Val Ser Gln Phe Ser Val Lys Gly Asp
130                 135                 140 aag gag cag aaa ttg agg ttt gct ttc cgt atc tat gac atg gat aaa     480
Lys Glu Gln Lys Leu Arg Phe Ala Phe Arg Ile Tyr Asp Met Asp Lys
145                 150                 155                 160 gat ggc tat att tcc aat ggg gaa ctc ttc cag gta ttg aag atg atg     528
Asp Gly Tyr Ile Ser Asn Gly Glu Leu Phe Gln Val Leu Lys Met Met
                165                 170                 175 gtg ggg aac aat ctg aaa gat aca cag tta cag caa att gta gac aaa     576
Val Gly Asn Asn Leu Lys Asp Thr Gln Leu Gln Gln Ile Val Asp Lys
            180                 185                 190 acc ata ata aat gca gat aag gat gga gat gga aga ata tcc ttt gaa     624
Thr Ile Ile Asn Ala Asp Lys Asp Gly Asp Gly Arg Ile Ser Phe Glu
        195                 200                 205 gaa ttc tgt gct gtt gta ggt ggc cta gat atc cac aaa aag atg gtg     672
Glu Phe Cys Ala Val Val Gly Gly Leu Asp Ile His Lys Lys Met Val
210                 215                 220 gta gat gtg tga                                                     684
Val Asp Val
225

<210> SEQ ID NO 170
<211> LENGTH: 227
<212> TYPE: PRT
<213> ORGANISM: Artificial Sequence
<220> FEATURE:
<223> OTHER INFORMATION: Artificially synthesized polypeptide sequence

<400> SEQUENCE: 170

Met Leu Glu Pro Tyr Trp Leu Pro Asn Phe Met Asp Val Phe Thr Trp
1               5                   10                  15
```

```
Ser Leu Pro Phe Val Gly Glu Lys Val Thr Glu Met Leu Val Asn Val
            20                  25                  30

Leu Asn Ile Cys Ser Asp Asp Glu Leu Gly Ser Glu Gly Asp Gly Phe
        35                  40                  45

Asp Gly Ala Thr Ala Ala Arg Lys Glu Val Glu Glu Ala Ser Tyr
    50                  55                  60

Pro Leu Glu Met Cys Ser His Phe Asp Ala Asp Glu Ile Lys Arg Leu
65                   70                  75                  80

Gly Lys Arg Phe Lys Lys Leu Asp Leu Asp Asn Ser Gly Ser Leu Ser
                85                  90                  95

Val Glu Glu Phe Met Ser Leu Pro Glu Leu Gln Gln Asn Pro Leu Val
            100                 105                 110

Gln Arg Val Ile Asp Ile Phe Asp Thr Asp Gly Asn Gly Glu Val Asp
        115                 120                 125

Phe Lys Glu Phe Ile Glu Gly Val Ser Gln Phe Ser Val Lys Gly Asp
    130                 135                 140

Lys Glu Gln Lys Leu Arg Phe Ala Phe Arg Ile Tyr Asp Met Asp Lys
145                 150                 155                 160

Asp Gly Tyr Ile Ser Asn Gly Glu Leu Phe Gln Val Leu Lys Met Met
                165                 170                 175

Val Gly Asn Asn Leu Lys Asp Thr Gln Leu Gln Gln Ile Val Asp Lys
            180                 185                 190

Thr Ile Ile Asn Ala Asp Lys Asp Gly Asp Gly Arg Ile Ser Phe Glu
        195                 200                 205

Glu Phe Cys Ala Val Val Gly Gly Leu Asp Ile His Lys Lys Met Val
    210                 215                 220

Val Asp Val
225

<210> SEQ ID NO 171
<211> LENGTH: 696
<212> TYPE: DNA
<213> ORGANISM: Artificial Sequence
<220> FEATURE:
<223> OTHER INFORMATION: Synthetic sequence COR5
<220> FEATURE:
<221> NAME/KEY: CDS
<222> LOCATION: (1)..(696)

<400> SEQUENCE: 171 atg gcc ctg agc aag cac ggc ctg acc aag aac atg acc acc aag tac      48
Met Ala Leu Ser Lys His Gly Leu Thr Lys Asn Met Thr Thr Lys Tyr
1               5                   10                  15 agg atg gag ggc tgc gtg gac ggc cac aag ttc gtg atc acc ggc gac      96
Arg Met Glu Gly Cys Val Asp Gly His Lys Phe Val Ile Thr Gly Asp
                20                  25                  30 ggc atc ggc gac ccc ttc gag ggc aag cag acc agc atc gac ctg tgc     144
Gly Ile Gly Asp Pro Phe Glu Gly Lys Gln Thr Ser Ile Asp Leu Cys
            35                  40                  45 gtg gtg gag ggc ggc ccc ctg ccc ttc agc gag gac atc ctg agc acc     192
Val Val Glu Gly Gly Pro Leu Pro Phe Ser Glu Asp Ile Leu Ser Thr
        50                  55                  60 gtg ttc gac tac ggc aac agg gtg ttc acc aag tac ccc cag gac ctg     240
Val Phe Asp Tyr Gly Asn Arg Val Phe Thr Lys Tyr Pro Gln Asp Leu
65                  70                  75                  80 gtg gac tac ttc aag aac agc tgc ccc gcc ggc tac acc tgg cag agg     288
Val Asp Tyr Phe Lys Asn Ser Cys Pro Ala Gly Tyr Thr Trp Gln Arg
                85                  90                  95
```

```
agc ttc ctg ttc gag gac ggc gcc gtg tgc acc gcc agc gcc gac atc      336
Ser Phe Leu Phe Glu Asp Gly Ala Val Cys Thr Ala Ser Ala Asp Ile
            100                 105                 110 agg gtg agc gtg gag gag aac tgc ttc tac cac gag agc aag ttc cac      384
Arg Val Ser Val Glu Glu Asn Cys Phe Tyr His Glu Ser Lys Phe His
        115                 120                 125 ggc gtg aac ttc ccc gcc gac ggc cca gtg atg aag aag atg acc acc      432
Gly Val Asn Phe Pro Ala Asp Gly Pro Val Met Lys Lys Met Thr Thr
    130                 135                 140 aac tgg gag ccc agc tgc gag aag atc acc ccc atc ctg aac gag ggc      480
Asn Trp Glu Pro Ser Cys Glu Lys Ile Thr Pro Ile Leu Asn Glu Gly
145                 150                 155                 160 atc ctg aag ggc gac gtg acc atg ttc ctg ctg aag gac ggc ggc          528
Ile Leu Lys Gly Asp Val Thr Met Phe Leu Leu Lys Asp Gly Gly
                165                 170                 175 agg tac agg tgc cag ttc gac acc gtg tac aag gcc aag gcc gac gcc      576
Arg Tyr Arg Cys Gln Phe Asp Thr Val Tyr Lys Ala Lys Ala Asp Ala
            180                 185                 190 aag gat atg ccc gag atg cac ttc atc cag cac gag ctg acc agg gag      624
Lys Asp Met Pro Glu Met His Phe Ile Gln His Glu Leu Thr Arg Glu
        195                 200                 205 gac agg agc gac gcc aag cac cag aag tgg agg ctg gtg gag agc gcc      672
Asp Arg Ser Asp Ala Lys His Gln Lys Trp Arg Leu Val Glu Ser Ala
    210                 215                 220 atc gcc tac agg agc acc ccg ccc                                      696
Ile Ala Tyr Arg Ser Thr Pro Pro
225                 230

<210> SEQ ID NO 172
<211> LENGTH: 232
<212> TYPE: PRT
<213> ORGANISM: Artificial Sequence
<220> FEATURE:
<223> OTHER INFORMATION: Synthetic sequence COR5

<400> SEQUENCE: 172

Met Ala Leu Ser Lys His Gly Leu Thr Lys Asn Met Thr Thr Lys Tyr
1               5                   10                  15

Arg Met Glu Gly Cys Val Asp Gly His Lys Phe Val Ile Thr Gly Asp
            20                  25                  30

Gly Ile Gly Asp Pro Phe Glu Gly Lys Gln Thr Ser Ile Asp Leu Cys
        35                  40                  45

Val Val Glu Gly Gly Pro Leu Pro Phe Ser Glu Asp Ile Leu Ser Thr
    50                  55                  60

Val Phe Asp Tyr Gly Asn Arg Val Phe Thr Lys Tyr Pro Gln Asp Leu
65                  70                  75                  80

Val Asp Tyr Phe Lys Asn Ser Cys Pro Ala Gly Tyr Thr Trp Gln Arg
                85                  90                  95

Ser Phe Leu Phe Glu Asp Gly Ala Val Cys Thr Ala Ser Ala Asp Ile
            100                 105                 110

Arg Val Ser Val Glu Glu Asn Cys Phe Tyr His Glu Ser Lys Phe His
        115                 120                 125

Gly Val Asn Phe Pro Ala Asp Gly Pro Val Met Lys Lys Met Thr Thr
    130                 135                 140

Asn Trp Glu Pro Ser Cys Glu Lys Ile Thr Pro Ile Leu Asn Glu Gly
145                 150                 155                 160

Ile Leu Lys Gly Asp Val Thr Met Phe Leu Leu Lys Asp Gly Gly
                165                 170                 175
```

```
Arg Tyr Arg Cys Gln Phe Asp Thr Val Tyr Lys Ala Lys Ala Asp Ala
            180             185             190

Lys Asp Met Pro Glu Met His Phe Ile Gln His Glu Leu Thr Arg Glu
        195             200             205

Asp Arg Ser Asp Ala Lys His Gln Lys Trp Arg Leu Val Glu Ser Ala
        210             215             220

Ile Ala Tyr Arg Ser Thr Pro Pro
225             230
```

METHOD FOR DETECTING PROTEIN-PROTEIN INTERACTION

CROSS REFERENCE TO RELATED APPLICATIONS

This application Divisional of U.S. application Ser. No. 14/363,201, filed Jun. 5, 2014 (now allowed); which is a National Stage of International Application No. PCT/JP2012/081539, filed on Dec. 5, 2012, which claims priority from Japanese Patent Application No. 2011-266103, filed on Dec. 5, 2011, the contents of all of which are incorporated herein by reference in their entirety.

TECHNICAL FIELD

The present invention relates to a method for detecting a protein-protein interaction, applications thereof, and a kit for use in the method.

BACKGROUND ART

Methods for detecting a protein-protein interaction can be roughly categorized into two groups. One is a method characterized by using a protein having been separated from living cells. Examples of such a method include surface plasmon resonance, protein mass spectroscopy, and anisotropy measurements. However, these methods have difficulty detecting an interaction in an environment similar to an actual intracellular environment.

Then, as the second method, a method has s been developed, in which a protein-protein interaction is detected using living cells. Typical methods thereof are a yeast two hybrid system which detects a transcriptional activity of a reporter, and modified methods thereof. Besides, another method has been also developed, which utilizes reconstitution of enzymes such as β-galactosidase and dihydrofolate reductase (DHFR).

Nevertheless, these methods have problems that they are incapable of detecting a position where a protein-protein interaction has taken place (positional information on the protein-protein interaction), as well as a period until a protein-protein interaction takes place, a period until the interaction ends, a duration of the interaction, and the like (temporal information on the protein-protein interaction).

Meanwhile, the method for detecting a protein-protein interaction using living cells also includes a method utilizing reconstitution of a fluorescent protein. Nevertheless, once reconstituted, the fluorescent protein does not dissociate. Accordingly, this method has a problem that it is incapable of detecting a period until a protein-protein interaction ends, a duration of the interaction, and the like. Further, there is another problem that a period until a protein-protein interaction takes place and the like cannot be detected because emission of fluorescence requires a certain time after a protein-protein interaction takes place.

Furthermore, there is also a method utilizing a luciferase reconstitution technique. In such a method, a luciferase is reversibly reconstituted and dissociated. However, since the luminescent signal emitted by a reconstituted luciferase is weak, the exposure time has to be a long in order to obtain intracellular positional information, and positional information and temporal information on a protein-protein interaction with high turnover rate cannot be obtained.

Additionally, in the methods utilizing the reconstitution of a fluorescent protein, a luciferase, or the like, a signal can be detected only after such a reconstitution. This also brings about such a problem that it is difficult to trace, for example, both before and after a protein-protein interaction takes place, proteins which are located at different positions by the interaction.

On the other hand, as a method for detecting a protein-protein interaction in living cells, fluorescence resonance energy transfer (FRET) has been developed, which detects energy transfer dependent on a distance between molecules. This method has an advantage of obtaining positional information and temporal information on where and when a protein-protein interaction takes place. Nevertheless, since a positional relation between a donor fluorescent protein and an acceptor fluorescent protein used in the method is important to detect the protein-protein interaction, the method involves a complicated step of investigating the optimization of a linker (spacer) connecting these fluorescent proteins to a detection-target protein, so that such a system has been difficult to construct. Further, it has also been difficult to analyze the result due to cross excitation by which an acceptor fluorescent protein is excited, and to bleed-through in which fluorescence of a donor fluorescent protein bleeds through a filter (absorption filter) set for detecting fluorescence of an acceptor fluorescent protein. Moreover, use of fluorescent proteins of two colors (donor fluorescent protein and acceptor fluorescent protein) also brings about a problem that only limited fluorescent proteins are usable in order to detect information other than a detection-target protein.

Recently, Tobias Meyer et al. have reported a method for detecting a protein-protein interaction by utilizing intracellular localization (translocation) (PTL 1). In this method, one of proteins subjected to interaction detection is fused to a protein that specifically binds to a particular site in a cell, while the other of the proteins subjected to interaction detection is fused to a fluorescent protein or the like. Then, these fusion proteins were expressed in a cell, and the protein-protein interaction is detected on the basis of a signal of the fluorescent protein or the like at the particular site in the cell.

In addition, Nibert et al. have reported a method for detecting a protein-protein interaction, using a fusion protein in which one of proteins subjected to interaction detection is fused to a protein for forming a viral inclusion body, and using, as an indicator, accumulation of the other of the proteins subjected to interaction detection in the viral inclusion body (PTL 2).

However, in these methods for detecting a protein-protein interaction by utilizing intracellular localization, one of proteins subjected to interaction detection is forcibly (artificially) translocated and confined at a particular site in a cell. Accordingly, the detection is impossible at a site where a protein-protein interaction naturally takes place, that is, in an intracellular environment unique to the protein-protein interaction, which brings about a problem that positional information on the protein-protein interaction cannot be obtained, and other similar problems. Moreover, it is also impossible to detect the interaction between proteins localized in a natural state at the same site as the site of the intracellular localization.

Against this problem, Sara Peterson Bjorn et al. have reported a method for detecting a protein-protein interaction (redistribution-trap method), in which proteins are allowed to interact with each other in an intracellular environment where the proteins naturally function, and then the cells are stimulated with a drug or the like to thereby induce aggregate formation from the interacting proteins, the aggregate formation being indicative of the interaction (PTL 3).

However, this method needs to stimulate cells at certain time so that the aggregate formation can be induced, and also needs to remove the drug or the like used for the stimulation to detect the presence or absence of an interaction subsequently after the stimulation. Hence, the method has problems such as being incapable of obtaining temporal information on when the protein-protein interaction takes place, and incapable of detecting a protein-protein interaction that changes (takes place, ends, takes place again, and so forth) for a certain period and at a certain position.

CITATION LIST

Patent Literature

[PTL 1] International Publication No. WO2000/017221
[PTL 2] International Publication No. WO2006/099486
[PTL 3] U.S. Pat. No. 7,282,347

SUMMARY OF INVENTION

Technical Problem

The present invention has been made in consideration of the above-described problems in the conventional techniques. An object of the present invention is to provide a method capable of detecting a protein-protein interaction in a cell in an intracellular environment unique to the protein-protein interaction, and also capable of detecting positional information and temporal information on the protein-protein interaction.

Solution to Problem

The present inventors have come up with an idea of utilizing, in detecting an interaction between two proteins (a first protein and a second protein), a first fusion protein comprising the first protein and an association-inducing protein, and a second fusion protein comprising the second protein and a fluorescent protein having a multimerization ability. Specifically, the inventors have come up with a construction of a system as follows. When the two fusion proteins are expressed in a cell, an interaction if any between the first protein and the second protein induces an association action between the association-inducing protein and another association-inducing protein. Thereby, the fusion proteins autonomously form an assembly, and the fluorescent protein contained in the fusion protein is detected as a fluorescent focus (see FIGS. 1 and 2). Further, the inventors have come up with the utilization, as the association-inducing protein, of a protein having such natures of: being present in a dispersed manner in a cell when fused to monomeric Azami Green 1 (mAG1), one of monomeric fluorescent proteins; and forming a fluorescent focus (assembly) in a cell when fused to a fluorescent protein having a multimerization ability.

Hence, the present inventors, first, expressed in cells candidate proteins fused to mAG1 or fluorescent proteins having a multimerization ability, and screened for association-inducing proteins on the basis of fluorescent focus formation (see FIGS. 3 and 4).

The screening result has revealed that a PB1 domain of p62, a PB1 domain of TFG, a PB1 domain of PKCiota, a SAM domain of TEL, a SAM domain of DGK delta, and a SAM domain of Tankyrase-1 are usable as the association-inducing protein.

Then, the present inventors have revealed that the use of these identified proteins as association-inducing proteins in combination with fluorescent proteins having a multimerization ability indeed enables detection of certain protein-protein interactions on the basis of fluorescent foci.

This method is capable of detecting a protein-protein interaction in an intracellular environment unique to the protein interaction, and also capable of detecting positional information and temporal information on the protein-protein interaction. Moreover, it is also possible to identify an amino acid residue involved in the protein-protein interaction, and to screen for a substance modulating the protein-protein interaction.

Thus, the present invention relates to a method for detecting a protein-protein interaction, applications thereof, and a kit for use in the method. More specifically, the present invention provides the following inventions.

(1) A method for detecting an interaction between a first protein and a second protein, the method comprising the steps of:
    expressing in a cell a first fusion protein comprising the first protein and an association-inducing protein, and a second fusion protein comprising the second protein and a fluorescent protein having a multimerization ability;
    detecting a fluorescent focus formed by an association between the first fusion protein and the second fusion protein in the cell; and
    determining an interaction between the first protein and the second protein according to the detection of the fluorescent focus.

(2) The method according to (1), wherein the fluorescent focus is detected to detect the interaction taking place or ending, a period until the interaction takes place or ends, or a duration of the interaction.

(3) The method according to (1), wherein the fluorescent focus is detected to detect the interaction taking place or ending in response to a particular stimulus, a period until the interaction takes place or ends, or a duration of the interaction.

(4) The method according to any one of (1) to (3) for screening for a protein interacting with a particular protein, wherein
    one of the first protein and the second protein is the particular protein, while the other is a test protein, and
    a protein interacting with the particular protein is selected according to the detection of the fluorescent focus.

(5) The method according to any one of (1) to (3) for identifying any one of an amino acid residue in the first protein and an amino acid residue in the second protein, which are involved in the interaction, wherein
    in a case where a protein in which a mutation is introduced is used as any one of the first protein and the second protein, if a fluorescence intensity of the fluorescent focus is reduced in comparison with a protein in which no mutation is introduced, the amino acid residue in which the mutation is introduced is determined to be involved in the interaction.

(6) A method for screening for a substance modulating an interaction between a first protein and a second protein, the method comprising the steps of:
    expressing in a cell a first fusion protein comprising the first protein and an association-inducing protein, and a second fusion protein comprising the second protein and a fluorescent protein having a multimerization ability, in presence of a test compound;

detecting a fluorescent focus formed by an association between the first fusion protein and the second fusion protein in the cell; and selecting the test compound as a substance inducing the interaction if a fluorescence intensity of the fluorescent focus is higher than a fluorescence intensity of a fluorescent focus formed in absence of the test compound, and selecting the test compound as a substance suppressing the interaction if the fluorescence intensity of the fluorescent focus is lower than the fluorescence intensity of the fluorescent focus formed in the absence of the test compound.

(7) The method according to any one of (1) to (6), wherein the association-inducing protein is at least one protein selected from the group consisting of a PB1 domain of p62, a PB1 domain of TFG, a PB1 domain of PKCiota, a SAM domain of TEL, a SAM domain of DGK delta, and a SAM domain of Tankyrase-1.

(8) A method for screening for an association-inducing protein, the method comprising the steps of:
  (a) expressing in a cell a fusion protein comprising a test protein and mAG1;
  (b) expressing in a cell a fusion protein comprising the test protein and a fluorescent protein having a multimerization ability; and
  (c) selecting the test protein as an association-inducing protein if a fluorescent focus is not detected in step (a) but a fluorescent focus is detected in step (b).

(9) The method according to any one of (1) to (8), wherein the fluorescent protein having a multimerization ability is at least one fluorescent protein selected from the group consisting of monomeric Kusabira-Orange 2, Azami-Green, Kusabira-Orange 1, dimeric Keima-Red, Kikume Green-Red, monomeric Keima-Red, monomeric Midoriishi-Cyan1, monomeric Kusabira-Orange 1, monomeric Kikume Green-Red1, Midoriishi-Cyan1, Kusabira-Cyan1, dimeric Azami-Green (AB), dimericAzami-Green (AC), TGuv, Momiji, COR3.01, COR5, and DsRed2.

(10) A kit for use in the method according to any one of (1) to (9), the kit comprising an instruction and at least one substance selected from the group consisting of the following (a) to (j):
  (a) a vector comprising a DNA encoding the association-inducing protein and a cloning site allowing an insertion of a DNA encoding a certain protein in such a manner that the certain protein is fused to the association-inducing protein when expressed;
  (b) a vector comprising a DNA encoding the fluorescent protein having a multimerization ability and a cloning site allowing an insertion of a DNA encoding a certain protein in such a manner that the certain protein is fused to the fluorescent protein when expressed;
  (c) a vector comprising a DNA encoding mAG1 and a cloning site allowing an insertion of a DNA encoding a certain protein in such a manner that the certain protein is fused to the mAG1 when expressed;
  (d) a vector encoding the first fusion protein;
  (e) a vector encoding the second fusion protein;
  (f) a vector set comprising the vector according to any one of (a) and (d) and the vector according to any one of (b) and (e);
  (g) a vector set comprising the vector according to (b) and the vector according to (c);
  (h) a transformed cell comprising a vector encoding the first fusion protein;
  (i) a transformed cell comprising a vector encoding the second fusion protein; and
  (j) a transformed cell comprising a vector encoding the first fusion protein and a vector encoding the second fusion protein.

Advantageous Effects of Invention

The present invention makes it possible to detect a protein-protein interaction in an intracellular environment unique thereto, and to detect positional information and temporal information on the protein-protein interaction.

BRIEF DESCRIPTION OF DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

<Method for Detecting Protein-Protein Interaction>

Figure 1:
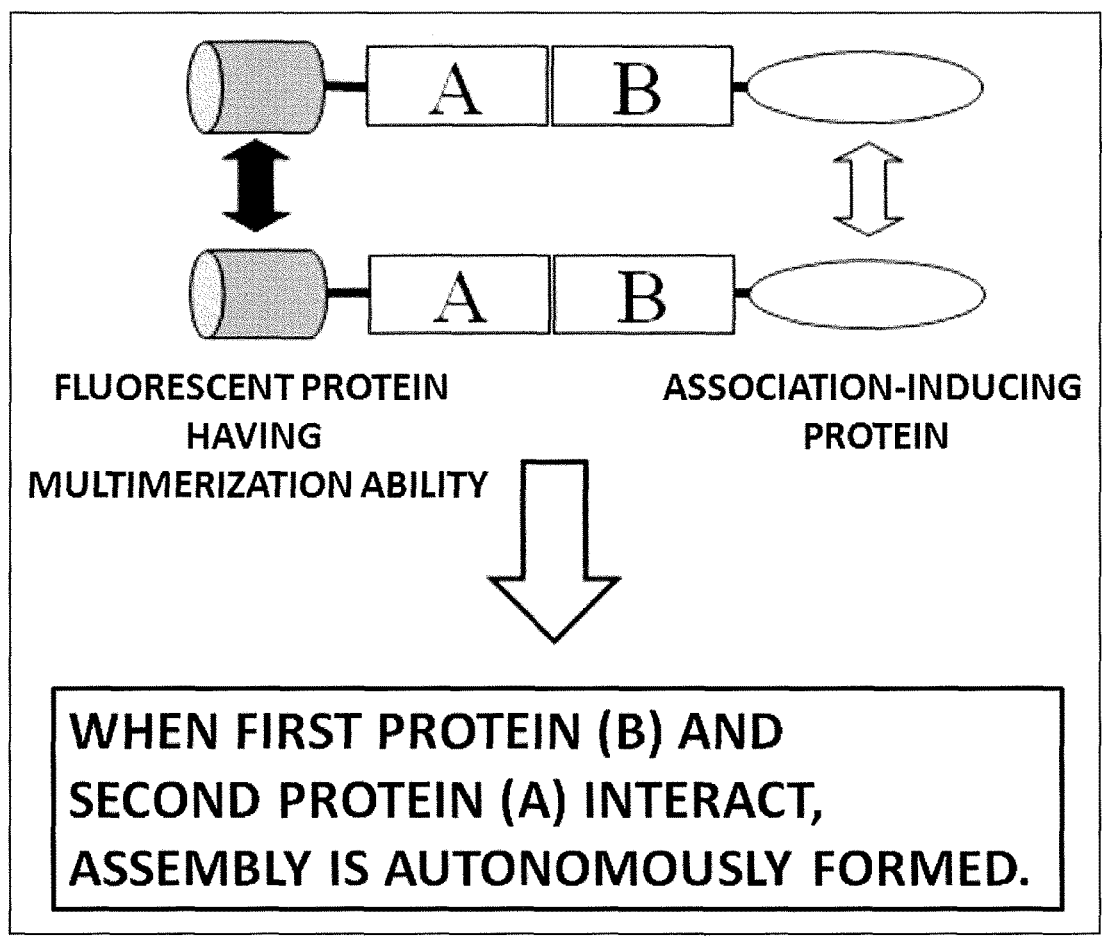
FIG. 1 is a diagram for illustrating a concept of a method for detecting a protein-protein interaction of the present invention. Specifically, the diagram illustrates that when a first fusion protein comprising a first protein (B) and an association-inducing protein and a second fusion protein comprising a second protein (A) and a fluorescent protein having a multimerization ability are expressed in a cell, an interaction between the first protein (B) and the second protein (A) can be determined according to the detection of a fluorescent focus formed by assembly formation between the first fusion protein and the second fusion protein in the cell.

A method for detecting a protein-protein interaction of the present invention is a method for detecting an interaction between a first protein and a second protein, the method comprising the steps of:

expressing in a cell a first fusion protein comprising the first protein and an association-inducing protein, and a second fusion protein comprising the second protein and a fluorescent protein having a multimerization ability;

detecting a fluorescent focus formed by an association between the first fusion protein and the second fusion protein in the cell; and determining an interaction between the first protein and the second protein according to the detection of the fluorescent focus.

In the present invention, the term "protein" means a molecule in which 2 or more amino acids are linked by a peptide bond(s), and modified products thereof. Thus, the term is a concept including not only full-length proteins, but also so-called oligopeptides and polypeptides. Examples of the modification of the protein include phosphorylation, glycosylation, palmitoylation, prenylation (for example, geranylgeranylation), methylation, acetylation, ubiquitination, SUMOylation, hydroxylation, and amidation.

As the "first protein" and the "second protein" according to the present invention, it is possible to use desired proteins intended for detection of interaction.

The "interaction between the first protein and the second protein" according to the present invention includes not only direct interactions, but also indirect interactions such as an interaction for forming a complex in which another molecule (protein, nucleic acid, sugar, lipid, low-molecular-weight compound, or the like) is interposed between the first protein and the second protein.

The "fluorescent protein having a multimerization ability" according to the present invention is a fluorescent protein capable of forming a fluorescent focus, when fused to a PB1 domain of p62 (p62(PB1)) and expressed in a cell, as a result that the fusion proteins with the p62(PB1) are associated with each other. Thus, the "fluorescent protein having a multimerization ability" includes not only fluorescent proteins capable of forming a homomultimer in a cell without fusing with p62(PB1), but also fluorescent proteins such as mKO2 generally believed to be monomeric fluorescent proteins, as described in Examples later. Examples of such a "fluorescent protein having a multimerization ability" include Midoriishi-Cyan1 (MiCy1), Kusabira-Orange 1 (KO1), dKeima570 (dimeric Keima570), dimeric Keima-Red (dKeima, dKeima-Red), Azami-Green (AG), Kaede, Kikume Green-Red (KikGR, KikGR1), monomeric Kusabira-Orange 1 (mKO1), monomeric Kusabira-Orange 2 (mKO2), TurboGFP, TurboYFP, ZsGreen, DsRed, HcRed, eqFP578, eqFP611, EosFP, FP484, Renilla GFP, Dendra, IFP1.4, iRFP, monomeric Keima-Red (mKeima, mKeima-Red), monomericMidoriishi-Cyan1 (mMiCy1), monomeric Kikume Green-Red1 (mKikGR1), Kusabira-Cyan1 (KCy1), dimeric Azami-Green (AB) (dAG (AB)), dimeric Azami-Green (AC) (dAG (AC)), TGuv, Momiji, COR3.01, COR5, and DsRed2. Preferable are mKO2, mKeima, mMiCy1, mKO1, mKikGR1, MiCy1, KCy1, KO1, dKeima, dAG (AB), dAG(AC), TGuv, Momiji, KikGR, AG, COR3.01, COR5, and DsRed2. Moreover, from the viewpoint of facilitating detection of a clear fluorescent focus in the method of the present invention, more preferable are fluorescent proteins capable of forming a homotetramer, such as TGuv, Momiji, AG, KikGR, COR3.01, COR5, and DsRed2, and particularly preferable is AG.

Note that, typically, mKO2, AG, KO1, dKeima, KikGR, mKeima, mMiCy1, mKO1, mKikGR1, MiCy1, KCy1, dAG (AB), dAG (AC), TGuv, Momiji, COR3.01, DsRed2, and COR5 are respectively a protein having the amino acid sequence of SEQ ID NO: 133, a protein having the amino acid sequence specified under Genbank ACCESSION No: AB107915, a protein having the amino acid sequence specified under Genbank ACCESSION No: AB128820, a protein having the amino acid sequence specified under Genbank ACCESSION No: AB209968, a protein having the amino acid sequence specified under Genbank ACCESSION No: AB193293, a protein having the amino acid sequence specified under Genbank ACCESSION No: AB209969, a protein having the amino acid sequence of SEQ ID NO: 137, a protein having the amino acid sequence specified under Genbank ACCESSION No: AB128821, a protein having the amino acid sequence of SEQ ID NO: 139, a protein having the amino acid sequence specified under Genbank ACCESSION No: AB128822, a protein having the amino acid sequence of SEQ ID NO: 141, a protein having the amino acid sequence of SEQ ID NO: 143, a protein having the amino acid sequence of SEQ ID NO: 145, a protein having the amino acid sequence of SEQ ID NO: 147, a protein having the amino acid sequence of SEQ ID NO: 149, a protein having the amino acid sequence of SEQ ID NO: 151, a protein having the amino acid sequence of SEQ ID NO: 153, and a protein having the amino acid sequence of SEQ ID NO: 172.

The amino acid sequences of these fluorescent proteins may be mutated naturally (i.e., non-artificially). Moreover, a mutation can also be introduced artificially. Such a mutant can also be used in the present invention, as long as it can emit fluorescence and form a homomultimer in a cell.

The "association-inducing protein" according to the present invention is a protein allowing a fluorescent focus to be detected when fused to a fluorescent protein having a multimerization ability and expressed in a cell, as a result that such fusion proteins are associated with each other, and being present in a dispersed state in a cell when fused to monomeric Azami Green 1 (mAG1) and expressed, as illustrated in Examples and FIGS. 3 and 4 later.

The "association-inducing protein" according to the present invention is preferably a PB1 domain of p62, a PB1 domain of TFG, a PB1 domain of PKCiota, a SAM domain of TEL, a SAM domain of DGK delta, and a SAM domain of Tankyrase-1. From the viewpoint of facilitating detection of a fluorescent focus in the method of the present invention, more preferable are a PB1 domain of p62, a PB1 domain of TFG, a SAM domain of TEL, a SAM domain of DGK delta, and a SAM domain of Tankyrase-1.

In addition, typically, a PB1 domain of p62, a PB1 domain of TFG, a PB1 domain of PKCiota, a SAM domain of TEL, a SAM domain of DGK delta, and a SAM domain of Tankyrase-1 are respectively a protein having the amino acid sequence specified under SEQ ID NO: 4, a protein having the amino acid sequence specified under SEQ ID NO: 12, a protein having the amino acid sequence specified under SEQ ID NO: 10, a protein having the amino acid sequence specified under SEQ ID NO: 14, a protein having the amino acid sequence specified under SEQ ID NO: 18, and a protein having the amino acid sequence specified under SEQ ID NO: 20.

The amino acid sequences of these "association-inducing proteins" may be mutated naturally (i.e., non-artificially). Moreover, a mutation can also be introduced artificially. Such a mutant having no association ability by itself can also be used in the present invention, as long as it has such a nature of forming an assembly (fluorescent focus) when fused to a fluorescent protein having a multimerization ability.

In the "first fusion protein" according to the present invention, the association-inducing protein may be fused on either the N-terminus side or the C-terminus side of the first protein. Further, the association-inducing protein may be fused to the first protein directly, or may be fused indirectly via a spacer protein. Furthermore, the "first fusion protein" according to the present invention may be fused to another functional protein. In this case, the other functional protein may be fused on one or both of the N-terminus side and the C-terminus side of the fusion protein, or may be fused directly or indirectly between the association-inducing protein and the first protein. The other functional protein is not particularly limited, and selected as appropriate depending on a function desirably provided to the fusion protein according to the present invention. Examples of a functional protein used to facilitate purification of the fusion protein include a Myc-tag protein, a His-tag protein, a hemagglutin (HA)-tag protein, a FLAG-tag protein (registered trademark, Sigma-Aldrich Co.), a glutathione S-transferase (GST) protein, and also a fluorescent protein that exhibits wavelength characteristics different from those of the fluorescent protein having a multimerization ability in the second fusion protein.

In the "second fusion protein" according to the present invention, the fluorescent protein having a multimerization ability may be fused on either the N-terminus side or the C-terminus side of the second protein, as in the case of the "first fusion protein." Moreover, the fluorescent protein having a multimerization ability may be fused to the second protein directly, or may be fused indirectly via the spacer protein. Furthermore, the "second fusion protein" according to the present invention may be fused to the above-described other functional protein. In this case, the other functional protein may be fused on one or both of the N-terminus side and the C-terminus side of the fusion protein, or may be fused directly or indirectly between the fluorescent protein having a multimerization ability and the second protein, as in the case of the "first fusion protein."

The "cell" according to the present invention are not particularly limited, and may be an eukaryotic cell, or may be a prokaryotic cell. Examples of the "cell" include an animal cell (HeLaS3 cell, U2OS cell, and the like), an insect cell (Sf9 cell, and the like), a plant cell, yeast, and *Escherichia coli*. Moreover, such cells may be in a state of being cultured in vitro (for example, cells grown in a medium or on a medium), or in a state of being present in vivo (for example, cells in a transgenic animal in which a DNA encoding the first fusion protein and a DNA encoding the second fusion protein are introduced).

The expression of the fusion proteins in the cell according to the present invention may be a transient expression or a constitutive expression, depending on the purpose. The fusion proteins in the cell can be expressed by introducing into the cell a vector according to the present invention, which will be described later. Examples of known techniques for introducing the vector into the cell include, in the case of an animal cell, a lipofection method, an electroporation method, a phosphate calcium method, a DEAE-dextran method, and methods utilizing a virus (adenovirus, lentivirus, adeno-associated virus, or the like). Moreover, in the case of an insect cell, the examples include methods utilizing a baculovirus. Further, in the case of a plant cell, the examples include an *Agrobacterium* method, an electroporation method, a lithium acetate method, and the like. In addition, in the case of yeasts, the examples include a lithium acetate method, an electroporation method, and a spheroplast method. Furthermore, in the case of *Escherichia coli*, the examples include a heat shock method (for example, a calcium chloride method, a rubidium chloride method), an electroporation method, and the like.

A "fluorescent focus" to be detected in the present invention is formed by an association between the first fusion protein and the second protein. Typically, the "fluorescent focus" has a fluorescence intensity in a region of 0.2 to 5 µm, the fluorescence intensity being higher than a fluorescence intensity of a fluorescent protein having a multimerization ability, which is present in a dispersed state (see Examples described later and FIGS. 1 and 2).

The "detection of the fluorescent focus" can be carried out, for example, through observation using a fluorescence microscope including an excitation filter and an absorption filter corresponding to a fluorescent protein having a multimerization ability, and analysis using an imaging cytometer such as IN Cell Analyzer (manufactured by GE Healthcare).

In the method of the present invention, if the fluorescent focus is detected in the cell, it can be determined that the first protein and the second protein interact with each other; meanwhile, if the fluorescent focus is not detected, it can be determined that the first protein and the second protein do not interact with each other.

<Screening Method for Association-Inducing Protein>

The association-inducing protein according to the present invention can be selected, as described in Examples later, by a screening method comprising the following steps (a) to (c):
(a) expressing in a cell a fusion protein comprising a test protein and mAG1;
(b) expressing in a cell a fusion protein comprising the test protein and a fluorescent protein having a multimerization ability; and
(c) selecting the test protein as an association-inducing protein if a fluorescent focus is not detected in step (a) but a fluorescent focus is detected in step (b).

The "test protein" according to the present invention is not particularly limited, and it is possible to use desired proteins intended for detection of association-inducing ability.

Note that the "mAG1" (monomeric Azami Green 1) is typically a protein having the amino acid sequence of SEQ ID NO: 135. Moreover, the amino acid sequence of a protein may be mutated naturally (i.e., non-artificially). Further, a mutation can also be introduced artificially. Such a mutant can also be used in the present invention, as long as it can emit fluorescence and can be present in a monomeric form in the cell.

The fluorescent protein having a multimerization ability used in the screening method for an association-inducing protein of the present invention is as described above.

In the "fusion protein comprising the test protein and mAG1" or the "fusion protein comprising the test protein and the fluorescent protein having a multimerization ability" according to the present invention, the mAG1 or the fluorescent protein having a multimerization ability may be fused on either the N-terminus side or the C-terminus side of the test protein. Moreover, the mAG1 or the fluorescent protein having a multimerization ability may be fused to the test protein directly, or may be fused on indirectly via the spacer protein. The "test protein" according to the present invention may be fused to the above-described other functional protein. In this case, the other functional protein may be fused on one or both of the N-terminus side and the C-terminus side of the fusion protein, or may be fused directly or indirectly between the mAG1 or the fluorescent protein having a multimerization ability and the test protein.

In the screening of the present invention, the test protein is selected as an association-inducing protein if a fluorescent focus is not detected when fused to the mAG1 and expressed in the cell but a fluorescent focus is detected when fused to the fluorescent protein having a multimerization ability and expressed in the cell.

<Method for Obtaining Temporal Information and the Like on Protein-Protein Interaction>

As described in Examples, particularly Example 12, later, the method of the present invention is capable of detecting not only a protein-protein interaction taking place, but also a protein-protein interaction ending, on the basis of the presence or absence of the fluorescent focus according to the present invention. Moreover, as described in Examples such as Examples 19, 24 to 28, it is also possible to trace occurrence or the like of such a protein-protein interaction over time. Further, as described in Examples such as Examples 20 to 22, the present invention is also capable of detecting a protein-protein interaction in any region in a cell without being influenced by localization of an association-inducing protein and a fluorescent protein having a multimerization ability, and so forth.

Thus, the present invention can provide a method, wherein the fluorescent focus according to the present invention is detected to detect an interaction taking place or ending, a period until the interaction takes place or ends, or a duration of the interaction.

In detecting the "interaction taking place or ending" in the manner described above, the present invention is also capable of specifying an intracellular region where the protein-protein interaction takes place as described particularly in Example 21 later.

Additionally, as described in Examples such as Examples 19, 23, 27 to 29 later, according to the present invention, detecting the "interaction taking place or ending" makes it possible to detect a signal transduction occurring and ending, in which the protein-protein interaction is involved, a period until the signal transduction occurs or ends, and a duration of the signal transduction, and also to specify an intracellular region where the signal transduction occurs.

Moreover, as described in Examples later, the present invention is capable of detecting the interaction between the first protein and the second protein, even if the interaction takes place or ends in response to a particular stimulus. Thus, the present invention can also provide a method for detecting the fluorescent focus according to the present invention, wherein the fluorescent focus is detected to detect the interaction taking place or ending in response to a particular stimulus, a period until the interaction takes place or ends, or a duration of the interaction.

It is only necessary that the "particular stimulus" according to the present invention be a stimulus capable of directly or indirectly inducing or inhibiting a protein-protein interaction. Moreover, the "particular stimulus" may be a stimulus attributable to an endogenous factor produced in a cell (for example, increase or decrease in intracellular calcium ion concentration, activation or inactivation of an enzyme), or may be a stimulus applied to a cell from the outside (for example, administration of a ligand (agonist or antagonist) to a receptor in a cell).

Further, as particularly described in Examples 19, 24 to 28 later, such a method of the present invention is also capable of detecting a particular stimulation starting or ending, a period until the stimulation starts or ends, or a duration of the stimulation, by detecting the fluorescent focus according to the present invention.

Furthermore, as described in Examples such as Examples 11 and 13 later, the method of the present invention is also capable of detecting an increase or decrease of a protein-protein interaction in accordance with a degree of the particular stimulus (for example, in a case where the particular stimulus is a drug, its concentration). Thus, in the case where the particular stimulus is a drug, the 50% effective concentration (EC50) and the 50% inhibitory concentration (IC50) of the drug against a protein-protein interaction can be determined by the present invention.

In addition, as described in Example 29 later, the method of the present invention is capable of distinguishing and detecting, in a single cell, multiple types of protein-protein interactions, multiple types of protein-protein interactions dependent respectively on particular stimuli, and eventually a signal transduction in which these protein-protein interactions are involved.

<Screening Method for Protein Interacting with Particular Protein>

As described in Examples, particularly Example 30, later, the present invention makes it possible to detect any protein-protein interaction. Thus, the present invention can provide a method for screening for a protein interacting with a particular protein, wherein one of the first protein and the second protein is the particular protein, while the other is a test protein, and a protein interacting with the particular protein is selected according to the detection of the fluorescent focus according to the present invention.

The "test protein" according to the present invention is not particularly limited. Protein groups encoded by cDNA libraries can be suitably used from the viewpoint that it is possible to comprehensively and efficiently select proteins interacting with particular proteins.

<Method for Identifying Amino Acid Residue Involved in Protein-Protein Interaction>

As described in Examples later, the fluorescence intensity of a fluorescent focus and a strength of a protein-protein interaction correlate with each other in the present invention. Thus, the present invention can provide a method for identifying any one of an amino acid residue in the first protein and an amino acid residue in the second protein, which are involved in the protein interaction, wherein in a case where a protein in which a mutation is introduced is used as any one of the first protein and the second protein, if an intensity of the fluorescent focus is reduced in comparison with a case of using a protein in which no mutation is introduced, the amino acid residue in which the mutation is introduced is determined to be involved in the interaction.

The "fluorescence intensity of the fluorescent focus" according to the present invention includes not only a fluorescence intensity of a single fluorescent focus, but also a total fluorescence intensity of fluorescent foci present in a certain region (for example, in one cell, in one field of view and in one fluorescence image observed with a fluorescence microscope).

Those skilled in the art can prepare the "protein obtained by introducing a mutation into the first protein and the like" by selecting known techniques as appropriate. An example of such known techniques includes site-directed mutagenesis.

<Screening Method for Substance Capable of Modulating Protein-Protein Interaction>

As described above, in the method of the present invention, a strength of a protein-protein interaction can be grasped on the basis of the fluorescence intensity of the fluorescent focus. Thus, the present invention can provide a method comprising the steps of:

expressing in a cell a first fusion protein comprising a first protein and an association-inducing protein, and a second fusion protein comprising a second protein and a fluorescent protein having a multimerization ability, in presence of a test compound;

detecting a fluorescent focus formed by an association between the first fusion protein and the second fusion protein in the cell; and selecting the test compound as a substance inducing the interaction if an intensity of the fluorescent focus is higher than an intensity of a fluorescent focus formed in absence of the test compound, or selecting the test compound as a substance suppressing the interaction if the intensity of the fluorescent focus is lower than the intensity of the fluorescent focus formed in the absence of the test compound.

The test compound used in the screening method of the present invention is not particularly limited. Examples thereof include an expression product from a gene library, a synthetic low-molecular-weight compound library, a peptide library, an antibody, a substance released by a bacterium, a liquid extract and a culture supernatant of cells (microorganisms, plant cells, animal cells), a purified or partially purified polypeptide, an extract derived from a marine organism, plant, or animal, soil, and a random phage peptide display library.

Moreover, examples of a state of being in the presence of the test compound include a state where the cell according to the present invention are in contact with the test compound by addition or the like of the test compound to a medium, and a state where the test compound is introduced in the cell according to the present invention.

<Kit for Use in Methods of the Present Invention>

The present invention can provide a kit for use in the above-described methods. The kit of the present invention is a kit comprising an instruction and at least one substance selected from the group consisting of the following (a) to (j):

(a) a vector comprising a DNA encoding the association-inducing protein and a cloning site allowing an insertion of a DNA encoding a certain protein in such a manner that the certain protein is fused to the association-inducing protein when expressed;

(b) a vector comprising a DNA encoding the fluorescent protein having a multimerization ability and a cloning site allowing an insertion of a DNA encoding a certain protein in such a manner that the certain protein is fused to the fluorescent protein when expressed;

(c) a vector comprising a DNA encoding mAG1 and a cloning site allowing an insertion of a DNA encoding a certain protein in such a manner that the certain protein is fused to the fluorescent protein when expressed;

(d) a vector encoding the first fusion protein;

(e) a vector encoding the second fusion protein;

(f) a vector set comprising the vector according to any one of (a) and (d) and the vector according to any one of (b) and (e);

(g) a vector set comprising the vector according to (b) and the vector according to (c);

(h) a transformed cell comprising a vector encoding the first fusion protein;

(i) a transformed cell comprising a vector encoding the second fusion protein; and (j) a transformed cell comprising a vector encoding the first fusion protein and a vector encoding the second fusion protein.

It is only necessary that the vectors according to the present invention comprise a regulatory sequence necessary for an expression (transcription and translation) of the inserted DNA in the cell according to the present invention. Examples of such a regulatory sequence include a promoter, an enhancer, a silencer, a terminator, a poly(A) tail, and a ribosomal binding site (Shine-Dalgarno (SD) sequence). Further, the vectors according to the present invention may comprise a selection marker (such as a drug resistance gene), and a reporter gene (such as a luciferase gene, a β-galactosidase gene, a chloramphenicol acetyltransferase (CAT) gene). Moreover, examples of a type of such vectors according to the present invention include a plasmid vector, an episomal vector, and a viral vector.

The proteins encoded by the vectors according to the present invention are, as described above, a protein having an association-inducing ability, a fluorescent protein having a multimerization ability, mAG1, and fusion proteins with these proteins. From the viewpoint of further improving the efficiency of expressing a DNA encoding such a protein, a DNA having codons optimized in accordance with the species of a cell expressing the protein (for example, humanized-codon DNA) may be inserted in the vectors according to the present invention.

Examples of the "cloning site allowing an insertion of a DNA encoding a certain protein" in (a), (b), and (c) above include a multiple cloning site containing one or more restriction-enzyme recognition sites, a TA cloning site, and a GATEWAY (registered trademark) cloning site.

To a preparation of the vectors according to the present invention, other components such as a buffer, a stabilizer, a preservative, and an antiseptic may be added.

The transformed cell according to the present invention can be prepared, as described above, by introducing the vectors according to the present invention into a cell. Moreover, to a preparation of the transformed cell according to the present invention, a medium necessary for storage and culturing of the cell and other components such as a stabilizer, a preservative, and an antiseptic may be added or attached.

The "instruction" according to the present invention is an instruction for utilizing the vectors or the transformed cell in the methods of the present invention. The instruction may comprise, for example, experimental techniques and experimental conditions for the methods of the present invention, and information on the preparation of the present invention (for example, information such as a vector map indicating the base sequence, cloning site, and the like of the vectors, information on the origin and nature of the transformed cell, culture conditions of the cell, and so forth).

EXAMPLES

Hereinafter, the present invention will be described more specifically based on Examples. However, the present invention is not limited to the following Examples.

Example 1

<Screening 1 for Association-Inducing Protein>

Figure 2:
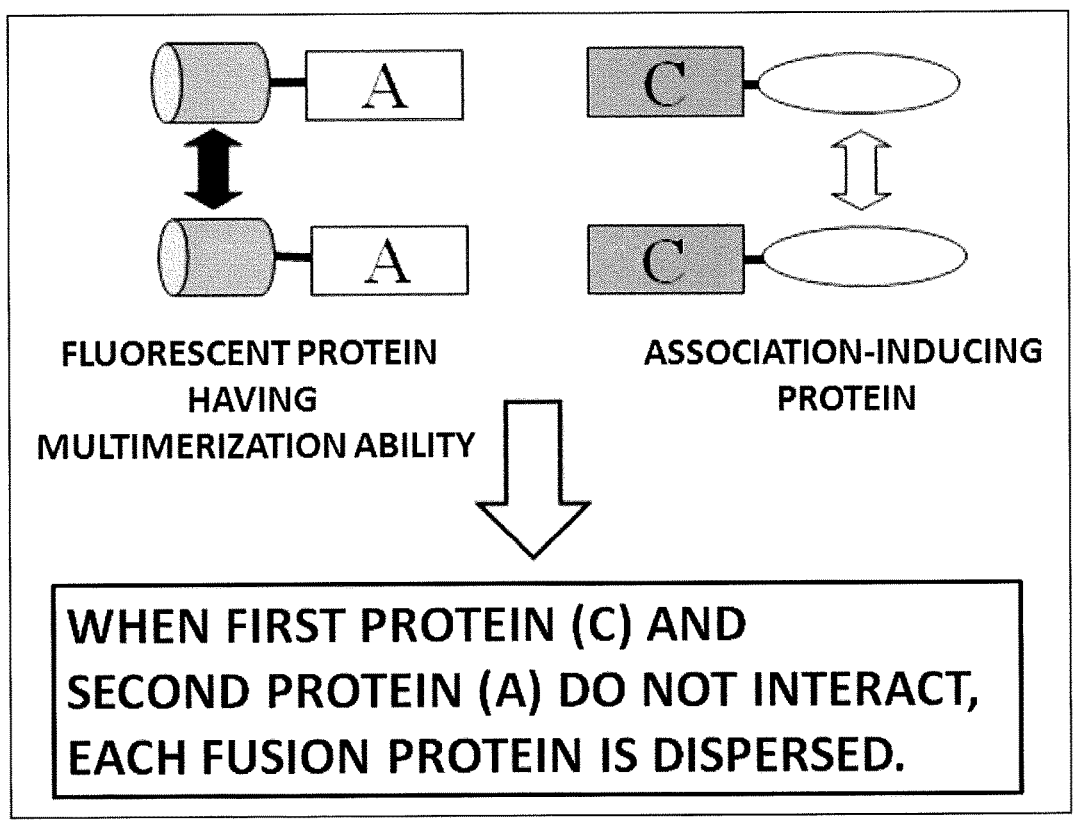
FIG. 2 is a diagram for illustrating the concept of the method for detecting a protein-protein interaction of the present invention. Specifically, the diagram illustrates that in a case where a first protein (C) does not interact with a second protein (A), even if a first fusion protein comprising the first protein (C) and an association-inducing protein and a second fusion protein comprising the second protein (A) and a fluorescent protein having a multimerization ability are expressed in a cell, the first fusion protein and the second fusion protein are not associated with each other, and are present in a dispersed manner in the cell, so that no fluorescent focus is detected.
Figure 3:
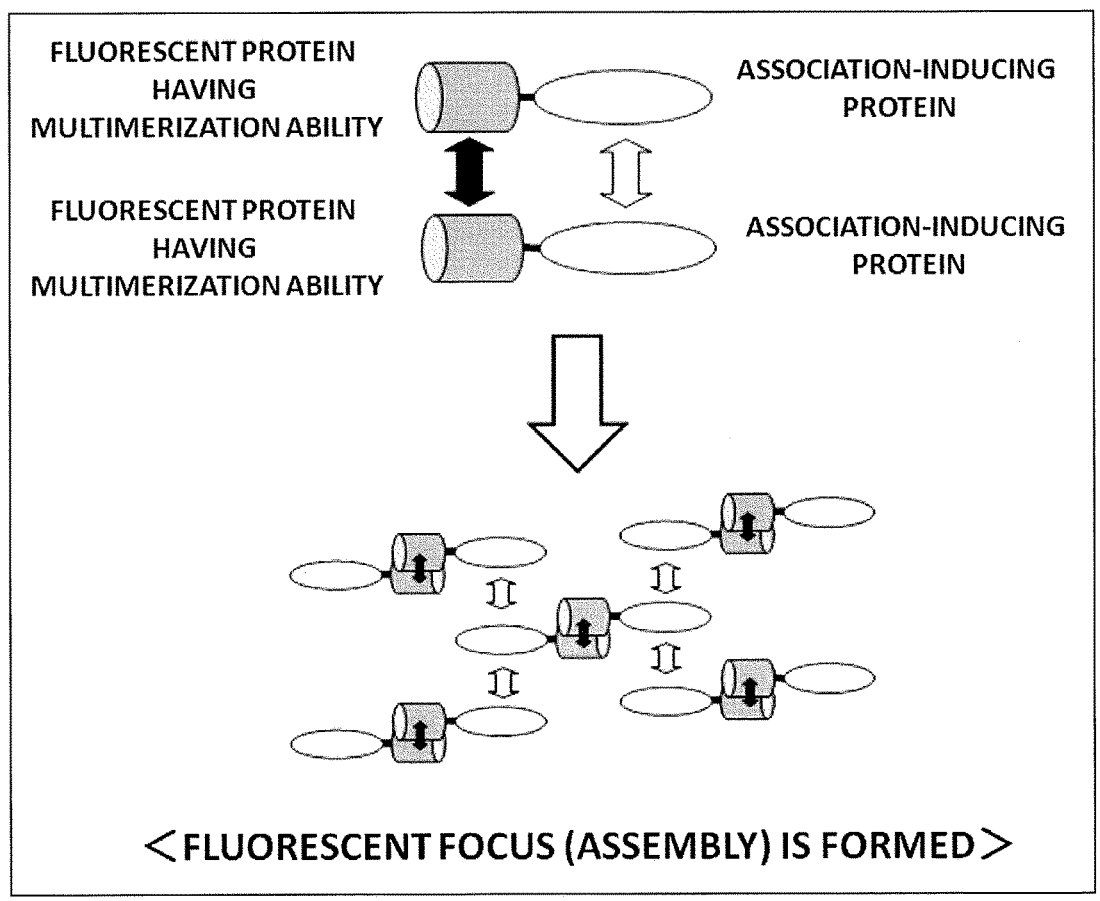
FIG. 3 is a diagram for illustrating a concept of a screening method for an association-inducing protein according to the present invention. Specifically, the diagram illustrates that an association-inducing protein according to the present invention is capable of forming an assembly (fluorescent focus) in a cell, when fused to a fluorescent protein having a multimerization ability.
Figure 4:
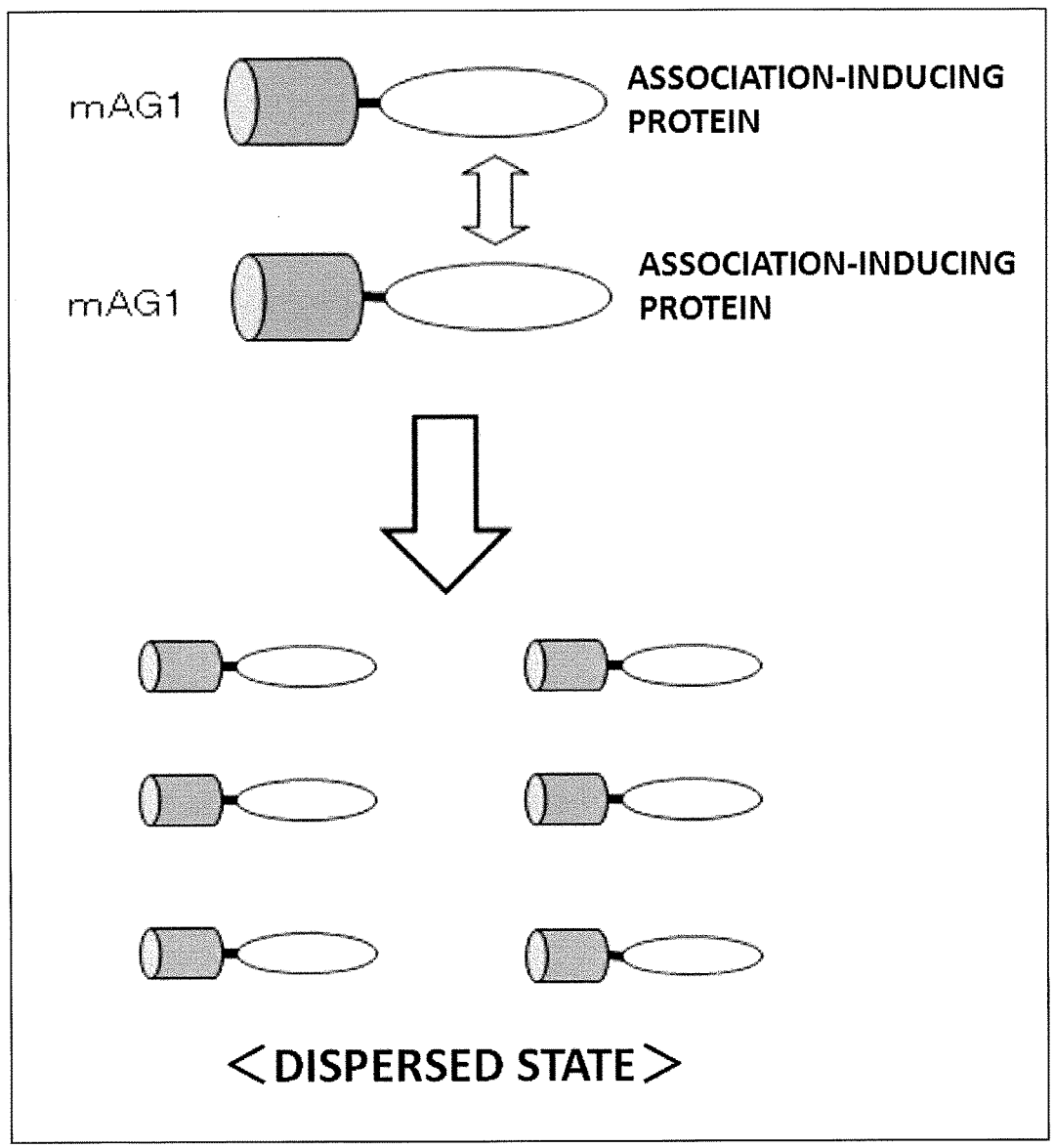
FIG. 4 is a diagram for illustrating the concept of the screening method for an association-inducing protein according to the present invention. Specifically, the diagram illustrates that the association-inducing protein according to the present invention is present in a dispersed manner in a cell, when fused to monomeric Azami Green 1 (mAG1).

For constructing a system for detecting a protein-protein interaction, proteins were searched for, which functioned as the "association-inducing protein" according to the present invention, on the basis of the concept illustrated in FIGS. 1 and 2 and by the method illustrated in FIGS. 3 and 4. Specifically, screened for were proteins, which were present in a dispersed manner in a cell when fused to monomeric Azami Green 1 (mAG1) (see FIG. 4), while being capable of forming a fluorescent focus (assembly) in a cell when fused to a fluorescent protein having a multimerization ability (see FIG. 3).

Figure 5:
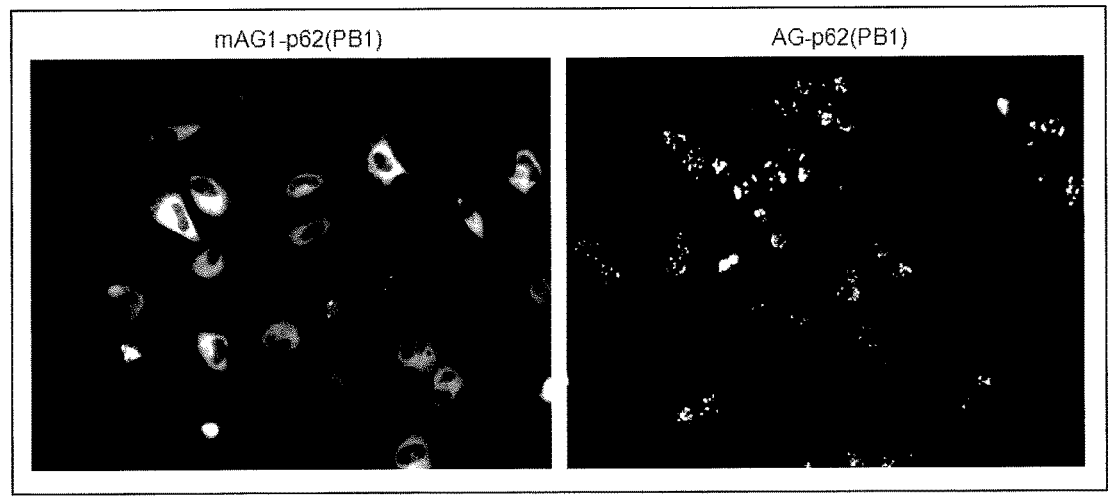
FIG. 5 shows micrographs for illustrating the result of analyzing the presence or absence of fluorescent focus formation by expressing in cultured cells a protein (mAG1-p62(PB1)) composed of mAG1 fused to a PB1 domain of p62 (p62(PB1)), and a protein (AG-p62(PB1)) composed of p62(PB1) fused to Azami Green (AG) serving as the fluorescent protein having a multimerization ability.

As such screening targets, first of all, attention was focused on a PB1 (Phox and Bem1p) domain. A protein composed of mAG1 fused to a PB1 domain of p62 (hereinafter, also referred to as "p62(PB1)"), and a protein composed of p62(PB1) fused to Azami Green (AG) serving as the fluorescent protein having a multimerization ability were expressed in cultured cells. Then, an association between the fusion proteins and eventually the presence or absence of formation of a fluorescent focus formed by the assembly formation were examined by a method described below. Note that AG has been known to form a homotetramer. FIG. 5 shows the obtained result.

(Preparation of Plasmid DNAs)

As a plasmid DNA for fusing mAG1, phmAG1-MCLinker (manufactured by limited company Amalgaam Co., Ltd.) was used.

Meanwhile, in preparing a plasmid for fusing AG (phAG-MCLinker), first, a humanized-codon Azami Green (AG) gene (DNA encoding a region having the amino acid sequence of SEQ ID NO: 2 (the DNA had the base sequence of SEQ ID NO: 1) was artificially synthesized. PCR amplification was carried out using the artificially synthesized humanized-codon AG (hAG) gene as a template, and the following primer set:

```
hAG forward primer 1;
                                         (SEQ ID NO: 57)
5'-CTAGCTAGCATTGCCACCATGGTGAGCGTGATCAAGCCCGAG-3',
and hAG reverse primer 1;
                                         (SEQ ID NO: 58)
5'-ACTACCGGTCTTGGCCTGGCTGGGCAGCATGCTGTACC-3'.
```

Then, the amplification product thus obtained was cleaved with NheI and AgeI, and inserted into phmAG1-MCLinker having been treated with the same restriction enzymes. Thus, phAG-MCLinker was prepared.

Further, in preparing phmAG1-p62(PB1) and phAG-p62(PB1), first, a DNA encoding a PB1 domain of p62 (region having the amino acid sequence of SEQ ID NO: 4) (the DNA had the base sequence of SEQ ID NO: 3) was amplified from a cDNA library of HeLaS3 cells by PCR using the following primer set:

```
p62(PB1) forward primer 1;
                                         (SEQ ID NO: 59)
5'-AAGAATTCGATGGCGTCGCTCACCGTGAAGGCCTACCTTCTGGGC-
3',
and p62(PB1) reverse primer 1;
                                         (SEQ ID NO: 60)
5'-AATTGGCGGCCGCTTATTTCTCTTTAATGTAGATTCGGAAGATGTC-
3'.
```

Then, the amplification product thus obtained was cleaved with EcoRI and NotI, and inserted into phAG-MCLinker and phmAG1-MCLinker having been treated with the same restriction enzymes; thus, phAG-p62(PB1) and phmAG1-p62(PB1) were prepared, respectively.

(Transfection into Cultured Cells)

HeLaS3 cells were used as cultured cells into which the phAG-p62(PB1) and the phmAG1-p62(PB1) were introduced. Note that HeLaS3 cells were cultured in DMEM Low glucose (manufactured by SIGMA ALDRICH CO.) containing 10% FBS (manufactured by Equitech-Bio Inc.). Moreover, on the day before the transfection, the HeLaS3 cells were seeded onto a 35-mm glass base dish (manufactured by Asahi Glass Co., Ltd.). Further, at the time of the transfection, 1 μg of the phAG-p62(PB1) or phmAG1-p62(PB1) was diluted with OptiMEM (manufactured by Life Technologies Corporation), and 10 μl of PolyFect® Transfection Reagent (manufactured by QIAGEN N.V.) was added thereto and stirred. Then, the resultant was further mixed with 600 μl of the culture solution, subsequently added to the HeLaS3 cells, and observed 22 hours thereafter.

(Observation of Transfected Cells)

After the transfection treatment, the HeLaS3 cells were observed in a buffer at pH 7.4 containing Hanks' Balanced Salt Solutions (manufactured by Life Technologies Corporation) and 20 mM HEPES (manufactured by Dojindo Laboratories), using an IX-71 inverted fluorescence microscope (manufactured by Olympus Corporation), a U-MGF-PHQ filter (manufactured by Olympus Corporation), and an ORCA-ER digital camera (manufactured by Hamamatsu Photonics K. K.).

As apparent from the result shown in FIG. 5, p62(PB1) was present in a dispersed state in the cells when fused to mAG1. On the other hand, when p62(PB1) was fused to AG, a fluorescent protein having a multimerization ability, fluorescent foci were detected in the cells, revealing that fusion proteins composed of p62(PB1) and AG were associated with each other, forming the fluorescent foci. Thus, it was revealed that the PB1 domain of p62 itself did not have an association ability, but had a nature of forming an assembly (fluorescent focus) when fused to the fluorescent protein having a multimerization ability, suggesting that the PB1 domain of p62 was suitably usable as the association-inducing protein according to the present invention.

Example 2

<Detection 1 of Protein-Protein Interaction>

Figure 6:
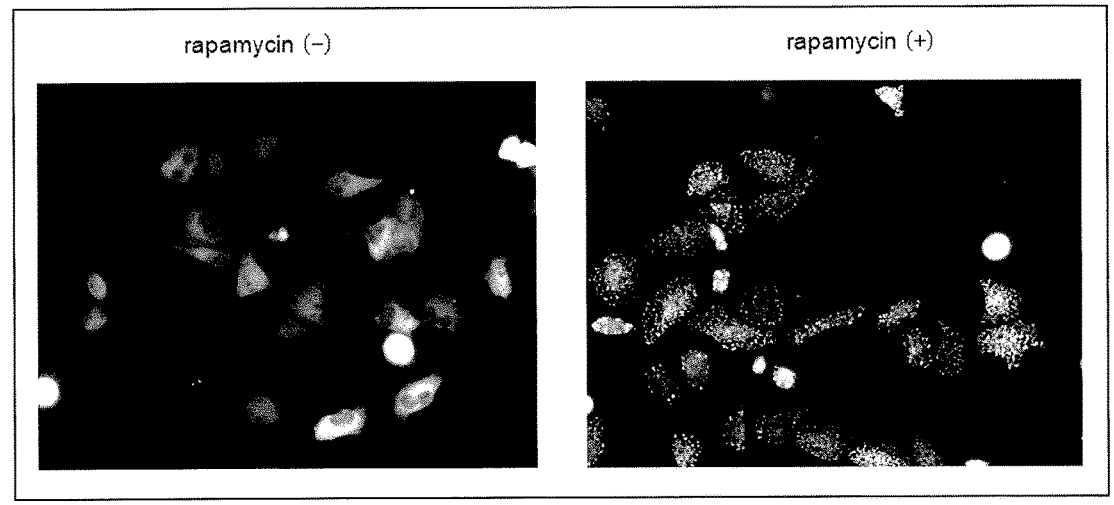
FIG. 6 shows micrographs for illustrating the result of analyzing the presence or absence of fluorescent focus formation by expressing in cultured cells a fusion protein composed of a FRB domain of a mTOR protein and an AG protein, and a fusion protein composed of p62(PB1) and FKBP12. Note that a FRB domain of a mTOR protein (mTOR(FRB)) and a FKBP12 protein are known to interact with each other in the presence of rapamycin.
Figure 7:
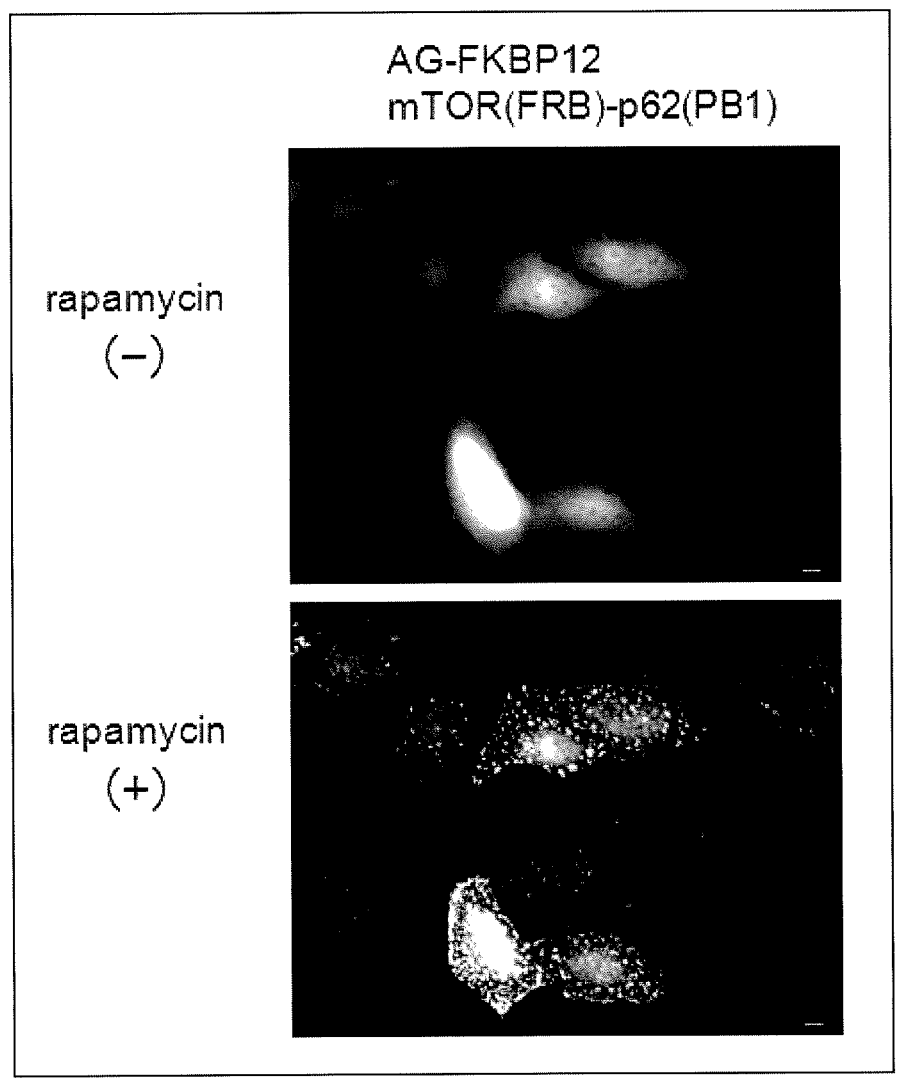
FIG. 7 shows micrographs for illustrating the result of analyzing the presence or absence of fluorescent focus formation by expressing in cultured cells a fusion protein composed of a FRB domain of a mTOR protein and p62 (PB1), and a fusion protein composed of an AG protein and FKBP12. Note that, in the figure, the scale bars at the lower right portions represent 5 μm.
Figure 8:
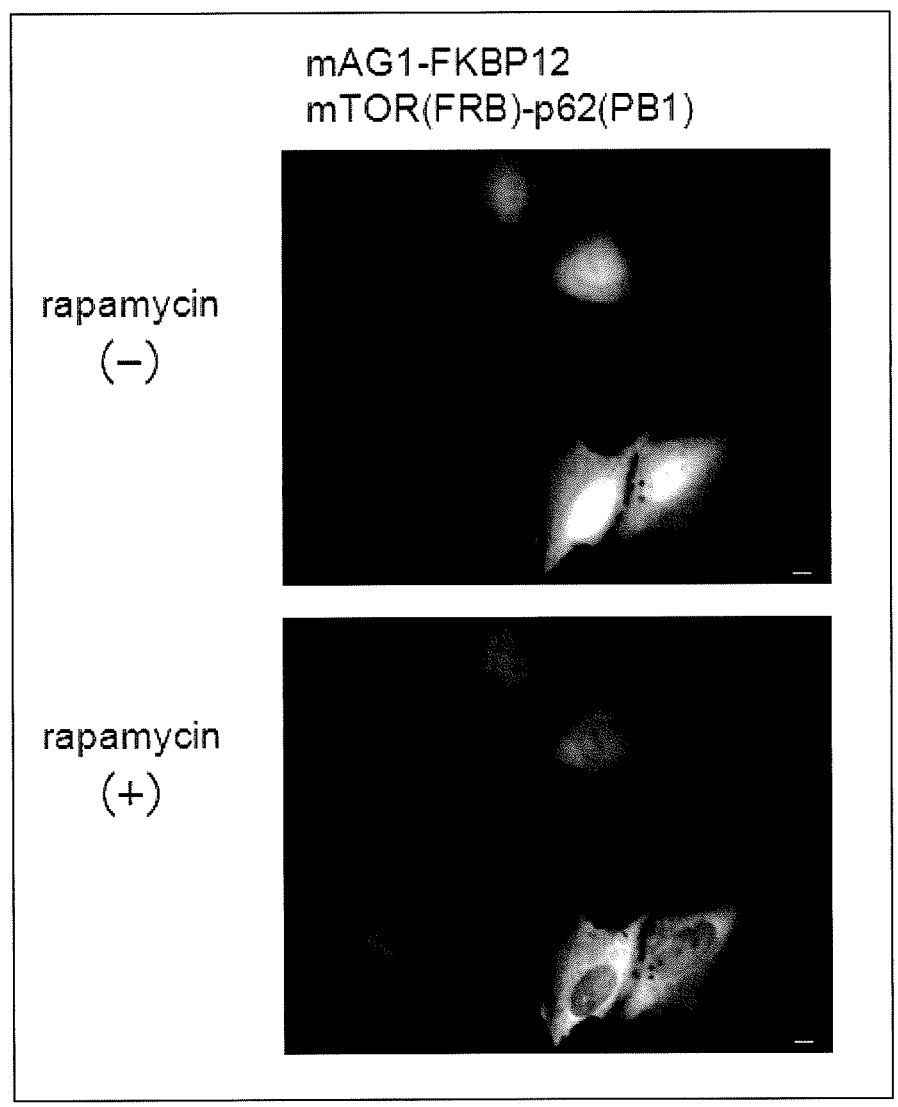
FIG. 8 shows micrographs for illustrating the result of analyzing the presence or absence of fluorescent focus formation by expressing in cultured cells the fusion protein composed of a FRB domain of a mTOR protein and p62 (PB1), and a fusion protein composed of a mAG1 protein and FKBP12. Note that, in the figure, the scale bars at the lower right portions represent 5 μm.

In order to verify that the PB1 domain of p62 was suitably usable as the association-inducing protein according to the present invention, in other words, to verify that the PB1 domain of p62 was applicable to the model illustrated in FIGS. 1 and 2, a test was conducted by a method described below using proteins whose interaction was inducible by adding a drug. FIGS. 6 to 8 show the obtained results.

Note that a FRB domain of a mTOR protein (also referred to as "mTOR(FRB)" or "mTOR(FRB domain)") and a FKBP12 protein used in Example 2 have been known to interact with each other in the presence of rapamycin (see Chen J et al., Proc Natl Acad Sci USA., May 23, 1995, vol. 92, no. 11, pp. 4947 to 4951).

(Preparation of Plasmid DNAs)

In preparing a plasmid for fusing AG (phAG-MNLinker), first, a humanized-codon Azami Green (AG) gene was amplified by PCR using phAG-MCLinker as a template and the following primer set:

```
hAG forward primer 2;
                                         (SEQ ID NO: 61)
5'-GGACCGGTATGGTGAGCGTGATCAAGCCCGAG-3',
and hAG reverse primer 2;
                                         (SEQ ID NO: 62)
5'-TTTCTAGATCACTTGGCCTGGCTGGGCAGCATGC-3'.
```

Then, the amplification product thus obtained was cleaved with AgeI and XbaI, and inserted into phmAG1-MNLinker (manufactured by limited company Amalgaam Co., Ltd.) having been treated with the same restriction enzymes. Thus, phAG-MNLinker was prepared.

Meanwhile, in preparing a plasmid for fusing p62(PB1) (pp62(PB1)-MNLinker), first, the DNA encoding a PB1 domain of p62 (region having the amino acid sequence of SEQ ID NO: 4) (the DNA had the base sequence of SEQ ID NO: 3) was amplified from the cDNA library of HeLaS3 cells by PCR using the following primer set:

```
p62(PB1) forward primer 2;
                                         (SEQ ID NO: 63)
5'-GGGACCGGTATGGCGTCGCTCACCGTGAAGGCCTACCTTC-3',
and p62(PB1) reverse primer 2;
                                         (SEQ ID NO: 64)
5'-ACCTCTAGATTATTTCTCTTTAATGTAGATTCGGAAGATG-3'.
```

Then, the amplification product thus obtained was cleaved with AgeI and XbaI, and inserted into phmAG1-MNLinker having been treated with the same restriction enzymes. Thus, pp62(PB1)-MNLinker was prepared.

Further, in preparing the plasmid for fusing p62(PB1) (pp62(PB1)-MCLinker), first, the DNA encoding a PB1 domain of p62 (region having the amino acid sequence of SEQ ID NO: 4) (the DNA had the base sequence of SEQ ID NO: 3) was amplified by PCR using the pp62(PB1)-MN-Linker as a template and the following primer set:

```
p62(PB1) forward primer 3;
                                (SEQ ID NO: 65)
5'-TAGCGCTAGCATTGCCACCATGGCGTCGCTCACCGTGAAGG
CCTACCTTC-3',
and p62(PB1) reverse primer 3;
                                (SEQ ID NO: 66)
5'-AAAACCGGTTTTCTCTTTAATGTAGATTCGGAAGATG-3'.
```

Then, the amplification product thus obtained was cleaved with NheI and AgeI, and inserted into phmAG1-MCLinker having been treated with the same restriction enzymes. Thus, pp62(PB1)-MCLinker was prepared.

Moreover, in preparing pmTOR(FRB domain)-hAG, first, a DNA encoding a FRB domain of mTOR (region having the 2025th to 2114th amino acids of the mTOR protein, the region had the amino acid sequence of SEQ ID NO: 22) (the DNA had the base sequence of SEQ ID NO: 21) was amplified from the cDNA library of HeLaS3 cells by PCR using the following primer set:

```
mTOR(FRB) forward primer;
                                (SEQ ID NO: 67)
5'-GCCGAATTCGGCCACCATGGAGATGTGGCATGAAGGCCTGG
AAGAGGCATCTCG-3',
and mTOR(FRB) reverse primer;
                                (SEQ ID NO: 68)
5'-GGGCTCGAGCCCTGCTTTGAGATTCGTCGGAACACATGATA
ATAGAGGTCCC-3'.
```

Then, the amplification product thus obtained was cleaved with EcoRI and XhoI, and inserted into phAG-MNLinker having been treated with the same restriction enzymes. Thus, pmTOR(FRB domain)-hAG was prepared. Note that the pmTOR(FRB domain)-hAG encodes a fusion protein composed of mTOR(FRB) and an AG protein (the fusion protein may also be referred to as "mTOR(FRB)-AG").

Further, in preparing pp62(PB1)-FKBP12, first, a DNA encoding FKBP12 (full length, region having the amino acid sequence of SEQ ID NO: 24) (the DNA had the base sequence of SEQ ID NO: 23) was amplified from the cDNA library of HeLaS3 cells by PCR using the following primer set:

```
FKBP12 forward primer;
                                (SEQ ID NO: 69)
5'-GCCGAATTCGATGGGAGTGCAGGTGGAAACC-3',
and FKBP12 reverse primer;
                                (SEQ ID NO: 70)
5'-GGGCTCGAGTTATTCCAGTTTTAGAAGCTCCA-3'.
```

Then, the amplification product thus obtained was cleaved with EcoRI and XhoI, and inserted into pp62(PB1)-MCLinker having been treated with the same restrictionenzymes. Thus, pp62(PB1)-FKBP12 was prepared. Note that the pp62(PB1)-FKBP12 encodes a fusion protein composed of p62(PB1) and a FKBP12 protein (the fusion protein may also be referred to as "p62(PB1)-FKBP12").

Meanwhile, in preparing phAG-FKBP12, first, phAG-MCLinker was cleaved with NheI and AgeI to prepare a hAG1 gene. Then, the hAG1 gene was inserted into pp62(PB1)-FKBP12 having been treated with the same restriction enzymes to cut out a p62(PB1) region therefrom. Thus, phAG-FKBP12 was prepared.

Further, in preparing phmAG1-FKBP12, first, phmAG1-MCLinker was cleaved with NheI and AgeI to prepare a hmAG1 gene. Then, the hmAG1 gene was inserted into pp62(PB1)-FKBP12 having been treated with the same restriction enzymes to cut out a p62(PB1) region therefrom. Thus, phmAG1-FKBP12 was prepared. Note that the phmAG1-FKBP12 encodes a fusion protein composed of a mAG1 protein and a FKBP12 protein (the fusion protein may also be referred to as "mAG1-FKBP12").

Furthermore, in preparing pmTOR(FRB domain)-p62 (PB1), first, pp62(PB1)-MNLinker was cleaved with AgeI and XbaI to prepare a p62(PB1) gene. Then, the gene was inserted into pmTOR(FRB domain)-hAG having been treated with the same restriction enzymes to cut out a hAG region therefrom. Thus, pmTOR(FRB domain)-p62(PB1) was prepared. Note that the pmTOR(FRB domain)-p62 (PB1) encodes a fusion protein composed of mTOR(FRB) and p62(PB1) (the fusion protein may also be referred to as "mTOR(FRB)-p62(PB1)").

(Transfection into Cultured Cells, and Observation of Transfected Cells)

Each of the following combinations of the plasmid DNAs was mixed in equal amounts and introduced into HeLaS3 cells by the same method as that described in Example 1:

a combination of pmTOR(FRB domain)-hAG with pp62(PB1)-FKBP12;

a combination of phAG-FKBP12 with pmTOR(FRB domain)-p62(PB1); and a combination of phmAG1-FKBP12 with pmTOR(FRB domain)-p62(PB1).

Moreover, the transfected cells were observed also by the same method as that described in Example 1. Then, fluorescence images were captured before 100 nM rapamycin (manufactured by Merck KGaA) was added and 300 seconds after the addition.

As apparent from the result shown in FIG. 6, mTOR (FRB)-AG was present in a dispersed manner before rapamycin was added (seethe left panel in FIG. 6); meanwhile, fluorescent foci were detected in the cells after the addition (see the right panel in FIG. 6). Moreover, as apparent from the result shown in FIG. 7, AG-FKBP12 was present in a dispersed manner before rapamycin was added (see the upper panel in FIG. 7); meanwhile, fluorescent foci were detected in the cells after the addition (see the lower panel in FIG. 7). Thus, it was revealed that by the rapamycin-dependent interaction between mTOR(FRB) and the FKBP12 protein, mTOR(FRB)-AG was autonomously associated with p62(PB1)-FKBP12, and AG-FKBP12 was autonomously associated with mTOR(FRB)-p62(PB1), thereby both forming fluorescent foci.

On the other hand, as apparent from the result shown in FIG. 8, in the case where mAG1 was used as the fluorescent protein, no fluorescent focus was detected in the cells after rapamycin was added, and no rapamycin-dependent assembly formation was observed. Thus, it was revealed that if the fluorescent protein having a multimerization ability and the association-inducing protein were not used in combination, no assembly was formed by the protein-protein interaction and no fluorescent focus was detected, verifying that the model illustrated in FIGS. 1 and 2 was practicable.

Example 3

<Detection 2 of Protein-Protein Interaction>

Figure 9:
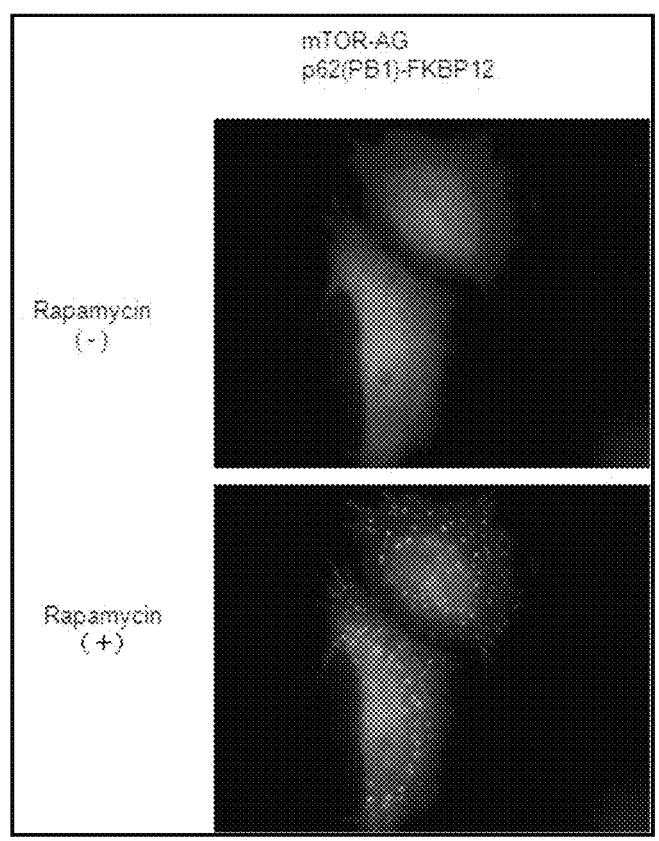
FIG. 9 shows micrographs for illustrating the result of analyzing the presence or absence of fluorescent focus formation by expressing in cultured cells a fusion protein (mTOR-AG) composed of a FRB domain of a mTOR protein and an AG protein, and a fusion protein (p62(PB1)-FKBP12) composed of a p62(PB1) protein and FKBP12, in the absence (−) or presence (+) of rapamycin.
Figure 10:
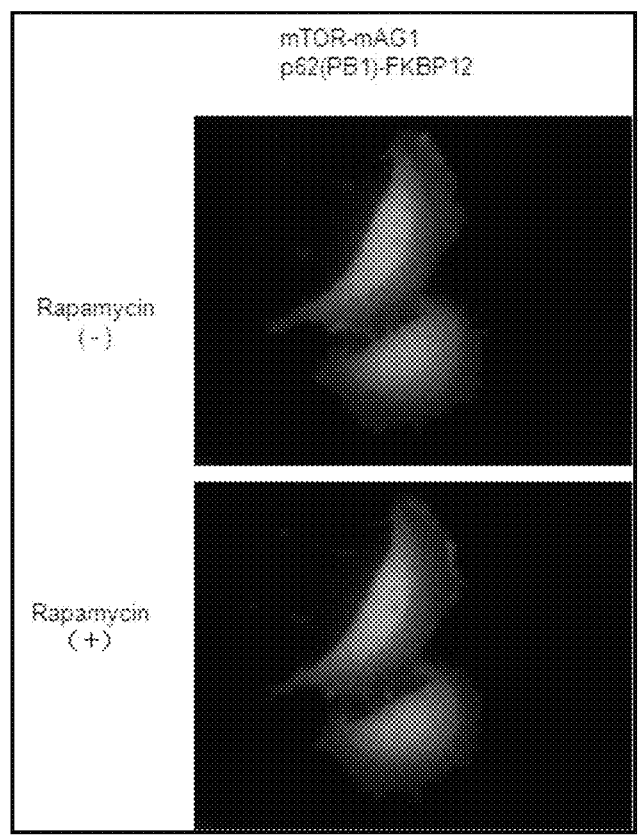
FIG. 10 shows micrographs for illustrating the result of analyzing the presence or absence of fluorescent focus formation by expressing in cultured cells a fusion protein (mTOR-mAG1) composed of a FRB domain of a mTOR protein and a mAG1 protein, and the fusion protein (p62(PB1)-FKBP12) composed of a p62(PB1) protein and FKBP12, in the absence (−) or presence (+) of rapamycin.
Figure 11:
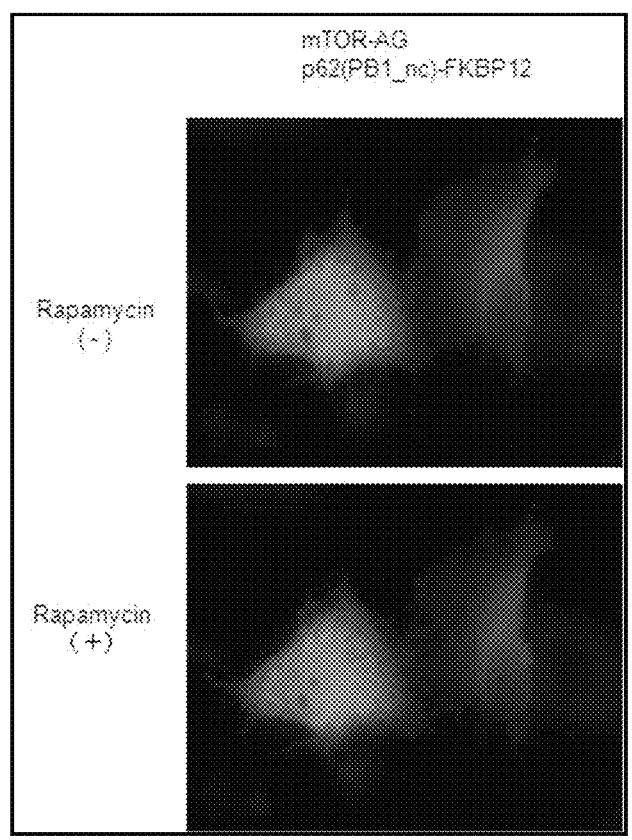
FIG. 11 shows micrographs for illustrating the result of analyzing the presence or absence of fluorescent focus formation by expressing in cultured cells the fusion protein (mTOR-AG) composed of a FRB domain of a mTOR protein and an AG protein, and a fusion protein (p62 (PB1_nc)-FKBP12) composed of a p62(PB1) protein mutant having lost no homomultimerization ability and FKBP12, in the absence (−) or presence (+) of rapamycin.

In order to verify that the PB1 domain of p62 was applicable to the model illustrated in FIGS. 1 and 2, a test was conducted by a method described below using the FRB domain of mTOR and FKBP12 described above. FIGS. 9 to 11 show the obtained results.

(Transfection into Cultured Cells, and Observation of Transfected Cells)

Each of the following combinations of the plasmid DNAs was mixed in equal amounts and introduced into HeLaS3 cells by the same method as that described in Example 2. Then, fluorescence images were captured before 100 nM rapamycin (manufactured by Merck KGaA) was added and 300 seconds after the addition.

A combination of pmTOR(FRB domain)-hAG with pp62 (PB1)-FKBP12;
a combination of pmTOR(FRB domain)-hmAG1 with pp62(PB1)-FKBP12; and
a combination of pmTOR(FRB domain)-hAG with pp62 (PB1_nc)-FKBP12.

(Preparation of Plasmid DNAs)

By the same method as that described in Example 2, pmTOR(FRB domain)-hmAG1 was prepared by cutting out a DNA encoding hAG from pmTOR(FRB domain)-hAG, and inserted a DNA encoding hmAG1 into that position instead.

Moreover, pp62(PB1_nc)-FKBP12 was prepared by introducing a mutation using pp62(PB1)-FKBP12 as a template, and AMAP™ Multi Site-directed Mutagenesis Kit (manufactured by limited company Amalgaam Co., Ltd.) according to the attached instruction, with the following primer:

a primer having the DNA sequence of SEQ ID NO: 154: 5'-GCTTCCAGGCGCACTACCGCGCT-GAGCGCGGGGACTTGGTTGCCTTTTC-3'. Note that p62(PB1_nc) is a mutant obtained by introducing a 2-amino acid mutation to an interface where p62 (PB1) interacts with another p62(PB1), so that the mutant has no association-inducing ability.

As apparent from the result shown in FIG. 9, similarly to the result described in Example 2, mTOR(FRB)-AG was present in a dispersed manner before rapamycin was added (see the upper panel in the figure); meanwhile, fluorescent foci were detected in the cells after the addition (see the lower panel in the figure).

On the other hand, as apparent from the result shown in FIG. 10, similarly to the result described in Example 2, in the case where mAG1 was used as the fluorescent protein, no fluorescent focus was detected in the cells even after rapamycin was added, and no rapamycin-dependent assembly formation was observed.

Further, as apparent from the result shown in FIG. 11, in the case where the mutant p62(PB1_nc) no longer capable of forming a homomultimer was used in place of p62(PB1) also, no fluorescent focus was detected in the cells even after rapamycin was added, and no rapamycin-dependent assembly formation was observed.

Thus, it was revealed that if the fluorescent protein having a multimerization ability and the association-inducing protein were not used in combination, no assembly was formed by the protein-protein interaction and no fluorescent focus was detected, verifying that the model illustrated in FIGS. 1 and 2 was practicable.

It should be noted that the method for detecting a protein-protein interaction of the present invention is a method totally different from conventional methods for detecting a protein-protein interaction in that fluorescent foci are autonomously formed only when a protein-protein interaction takes place.

Example 4

<Screening 2 for Association-Inducing Protein>

In order to find out association-inducing proteins having natures similar to those of p62(PB1), screening was carried out by the same method as that described in Example 1.

As such screening targets other than the PB1 domain, attention was focused on a SAM domain. A protein composed of mAG1 fused to a PB1 domain or a SAM domain derived from proteins, or a protein composed of AG serving as the fluorescent protein having a multimerization ability fused to a PB1 domain or a SAM domain derived from proteins was expressed in cultured cells. Then, an association between the fusion proteins and eventually the presence or absence of formation of a fluorescent focus formed by the association were examined by a method described below. FIGS. 12 to 15 show the obtained results.

(Preparation of Plasmid DNAs)

To fuse the PB1 domain or the SAM domain derived from the proteins on the C-terminus side of a fluorescent protein via a flexible linker for the expression, phmAG1-MCLinker was used as a plasmid for fusing mAG1, and phAG-MCLinker was used as a plasmid for fusing AG.

Specifically, in preparing phmAG1-MEK5(PB1) and phAG-MEK5(PB1), first, a DNA encoding a PB1 domain of MEK5 (region having the 16th to 109th amino acids of the MEK5 protein, the region had the amino acid sequence of SEQ ID NO: 6, also referred to as "MEK5(PB1)") (the DNA had the base sequence of SEQ ID NO: 5) was amplified from the cDNA library of HeLaS3 cells by PCR using the following primer set:

```
MEK5(PB1) forward primer;
                                    (SEQ ID NO: 71)
5'-CCGAATTCGGTGCTGGTAATTCGCATCAAGATCCCAAA-3',
and MEK5(PB1) reverse primer;
                                    (SEQ ID NO: 72)
5'-TTCTCGAGTTAGCAGGCTCTTGGAAATATCTGCAG-3'.
```

Then, the amplification product thus obtained was cleaved with EcoRI and XhoI, and inserted into phmAG1-MCLinker and phAG-MCLinker having been treated with the same restriction enzymes; thus, phmAG1-MEK5(PB1) and phAG-MEK5(PB1) were prepared, respectively. Note that these plasmid DNAs encode a fusion protein composed of a mAG1 protein and MEK5(PB1) (the fusion protein may also be referred to as "mAG1-MEK5(PB1)"), and a fusion protein composed of an AG protein and MEK5(PB1) (the fusion protein may also be referred to as "AG-MEK5(PB1)"), respectively.

Meanwhile, in preparing phmAG1-Nbr1(PB1) and phAG-Nbr1(PB1), first, a DNA encoding a PB1 domain of Nbr1 (region having the 4th to 85th amino acids of the Nbr1 protein, the region had the amino acid sequence of SEQ ID NO: 8, also referred to as "Nbr1(PB1)") (the DNA had the base sequence of SEQ ID NO: 7) was amplified from the cDNA library of HeLaS3 cells by PCR using the following primer set:

```
Nbr1(PB1) forward primer;
                                      (SEQ ID NO: 73)
5'-AAGAATTCGGCAGGTTACTCTAAATGTGACTTTTAAA-3',
and Nbr1(PB1) reverse primer;
                                      (SEQ ID NO: 74)
5'-TTCTCGAGTTACCCTTCGTGGACTTGCATCTGCAGTT-3'.
```

Then, the amplification product thus obtained was cleaved with EcoRI and XhoI, and inserted into phmAG1-MCLinker and phAG-MCLinker having been treated with the same restriction enzymes; thus, phmAG1-Nbr1(PB1) and phAG-Nbr1(PB1) were prepared, respectively. Note that these plasmid DNAs encode a fusion protein composed of a mAG1 protein and Nbr1(PB1) (the fusion protein may also be referred to as "mAG1-Nbr1(PB1)"), and a fusion protein composed of an AG protein and Nbr1(PB1) (the fusion protein may also be referred to as "AG-Nbr1(PB1)"), respectively.

Further, in preparing phmAG1-PKCiota(PB1) and phAG-PKCiota(PB1), first, a DNA encoding a PB1 domain of PKCiota (region having the 16th to 99th amino acids of the PKCiota protein, the region had the amino acid sequence of SEQ ID NO: 10, also referred to as "PKCiota(PB1)") (the DNA had the base sequence of SEQ ID NO: 9) was amplified from the cDNA library of HeLaS3 cells by PCR using the following primer set:

```
PKCiota(PB1) forward primer;
                                      (SEQ ID NO: 75)
5'-AAGAATTCGCAGGTCCGGGTGAAAGCCTACTACCGCG-3',
and PKCiota(PB1) reverse primer 18;
                                      (SEQ ID NO: 76)
5'-TTCTCGAGTTAACAAGGGAACACATGAATCAAGAGTTCAG-3'.
```

Then, the amplification product thus obtained was cleaved with EcoRI and XhoI, and inserted into phmAG1-MCLinker and phAG-MCLinker having been treated with the same restriction enzymes; thus, phmAG1-PKCiota(PB1) and phAG-PKCiota(PB1) were prepared, respectively. Note that these plasmid DNAs encode a fusion protein composed of a mAG1 protein and PKCiota(PB1) (the fusion protein may also be referred to as "mAG1-PKCiota(PB1)"), and a fusion protein composed of an AG protein and PKCiota(PB1) (the fusion protein may also be referred to as "AG-PKCiota (PB1)"), respectively.

Moreover, in preparing phmAG1-TFG(PB1) and phAG-TFG(PB1), first, a DNA encoding a PB1 domain of TFG (region having the 10th to 91st amino acids of the TFG protein, the region had the amino acid sequence of SEQ ID NO: 12, also referred to as "TFG(PB1)") (the DNA had the base sequence of SEQ ID NO: 11) was amplified from the cDNA library of HeLaS3 cells by PCR using the following primer set:

```
TFG(PB1) forward primer 1;
                                      (SEQ ID NO: 77)
5'-AACTGCAGCAAAGCTAATCATCAAAGCTCAACTTGGGGA-3',
and TFG(PB1) reverse primer 1;
                                      (SEQ ID NO: 78)
5'-TTAAGCTTTTAATTAACAAATAATGTCAGTTTCAGTAT-3'.
```

Then, the amplification product thus obtained was cleaved with PstI and HindIII, and inserted into phmAG1-MCLinker and phAG-MCLinker having been treated with the same restriction enzymes; thus, phmAG1-TFG(PB1) and phAG-TFG(PB1) were prepared, respectively. Note that these plasmid DNAs encode a fusion protein composed of a mAG1 protein and TFG(PB1) (the fusion protein may also be referred to as "mAG1-TFG(PB1)"), and a fusion protein composed of an AG protein and TFG(PB1) (the fusion protein may also be referred to as "AG-TFG(PB1)"), respectively.

Further, in preparing phmAG1-TEL(SAM) and phAG-TEL(SAM), first, a DNA encoding a SAM domain of TEL (region having the 38th to 124th amino acids of the TFG protein, the region had the amino acid sequence of SEQ ID NO: 14, also referred to as "TEL(SAM)") (the DNA had the base sequence of SEQ ID NO: 13) was amplified from the cDNA library of HeLaS3 cells by PCR using the following primer set:

```
TEL(SAM) forward primer;
                                      (SEQ ID NO: 79)
5'-AAAAGGATCCGCCACCATGCCTCGAGCGCTCAGGATGGAGGAA-3',
and TEL(SAM) reverse primer;
                                      (SEQ ID NO: 80)
5'-AAAAAAGCTTTTACCTCTGCTTCAGAATATGCTGAAGGAGTT-3'.
```

Then, the amplification product thus obtained was cleaved with BamHI and HindIII, and inserted into phmAG1-MCLinker and phAG-MCLinker having been treated with the same restriction enzymes; thus, phmAG1-TEL(SAM) and phAG-TEL(SAM) were prepared, respectively. Note that these plasmid DNAs encode a fusion protein composed of a mAG1 protein and TEL(SAM) (the fusion protein may also be referred to as "mAG1-TEL(SAM)"), and a fusion protein composed of an AG protein and TEL(SAM) (the fusion protein may also be referred to as "AG-TEL(SAM)"), respectively.

Additionally, in preparing phmAG1-EphB2(SAM) and phAG-EphB2(SAM), first, a DNA encoding a SAM domain of EphB2 (region having the 905th to 981st amino acids of the EphB2 protein, the region had the amino acid sequence of SEQ ID NO: 16, also referred to as "EphB2(SAM)") (the DNA had the base sequence of SEQ ID NO: 15) was amplified from the cDNA library of HeLaS3 cells by PCR using the following primer set:

```
EphB2(SAM) forward primer;
                                      (SEQ ID NO: 81)
5'-AAAAGGATCCGCCACCATGCTGGACCGCACGATCCCCGA-3',
and EphB2(SAM) reverse primer;
                                      (SEQ ID NO: 82)
5'-AAAAAAGCTTTTAAATCTGGTTCATCTGCGCCCG-3'.
```

Then, the amplification product thus obtained was cleaved with BamHI and HindIII, and inserted into phmAG1-MCLinker and phAG-MCLinker having been treated with the same restriction enzymes; thus, phmAG1-EphB2(SAM) and phAG-EphB2(SAM) were prepared, respectively. Note that these plasmid DNAs encode a fusion protein composed of a mAG1 protein and EphB2(SAM) (the fusion protein may also be referred to as "mAG1-EphB2(SAM)"), and a fusion protein composed of an AG protein and EphB2 (SAM) (the fusion protein may also be referred to as "AG-EphB2(SAM)"), respectively.

Furthermore, in preparing phmAG1-DGK delta(SAM) and phAG-DGK delta(SAM), first, a DNA encoding a SAM domain of DGK delta (region having the 1097th to 1164th amino acids of the DGK delta protein, the region had the amino acid sequence of SEQ ID NO: 18, also referred to as "DGK delta(SAM)") (the DNA had the base sequence of SEQ ID NO: 17) was amplified from the cDNA library of HeLaS3 cells by PCR using the following primer set:

```
DGK delta(SAM) forward primer;
                                    (SEQ ID NO: 83)
5'-AAAAGGTACCGCCACCATGCCGGTTCACCTCTGGGGGACA-3',
and DGK delta(SAM) reverse primer;
                                    (SEQ ID NO: 84)
5'-AAAAAAGCTTTTAGCTGCGGCTCAGCTCCTTGAT-3'.
```

Then, the amplification product thus obtained was cleaved with KpnI and HindIII, and inserted into phmAG1-MCLinker and phAG-MCLinker having been treated with the same restriction enzymes; thus, phmAG1-DGK delta(SAM) and phAG-DGK delta(SAM) were prepared, respectively. Note that these plasmid DNAs encode a fusion protein composed of a mAG1 protein and DGK delta(SAM) (the fusion protein may also be referred to as "mAG1-DGK delta(SAM)"), and a fusion protein composed of an AG protein and DGK delta(SAM) (the fusion protein may also be referred to as "AG-DGK delta(SAM)"), respectively.

In addition, in preparing phmAG1-Tankyrase(SAM) and phAG-Tankyrase(SAM), first, a DNA encoding a SAM domain of Tankyrase (region having the 952nd to 1078th amino acids of the Tankyrase protein, the region had the amino acid sequence of SEQ ID NO: 20, also referred to as "Tankyrase(SAM)") (the DNA had the base sequence of SEQ ID NO: 19) was amplified from the cDNA library of HeLaS3 cells by PCR using the following primer set:

```
Tankyrase(SAM) forward primer;
                                    (SEQ ID NO: 85)
5'-AAAAGGATCCGCCACCATGCTGATAGATGCCATGCCCCCAGA-3',
and Tankyrase(SAM) reverse primer;
                                    (SEQ ID NO: 86)
5'-AAAAAAGCTTTTAAATTCGAATGACATTGTATCTGTTGAAGA-3'.
```

Then, the amplification product thus obtained was cleaved with BamHI and HindIII, and inserted into phmAG1-MCLinker and phAG-MCLinker having been treated with the same restriction enzymes; thus, phmAG1-Tankyrase(SAM) and phAG-Tankyrase(SAM) were prepared, respectively. Note that these plasmid DNAs encode a fusion protein composed of a mAG1 protein and Tankyrase(SAM) (the fusion protein may also be referred to as "mAG1-Tankyrase(SAM)"), and a fusion protein composed of an AG protein and Tankyrase(SAM) (the fusion protein may also be referred to as "AG-Tankyrase(SAM)"), respectively.

(Transfection into Cultured Cells, and Observation of Transfected Cells)

Each of the plasmid DNAs was introduced into HeLaS3 cells by the same method as that described in Example 1. Moreover, the transfected cells were observed also by the same method as that described in Example 1.

Figure 13:
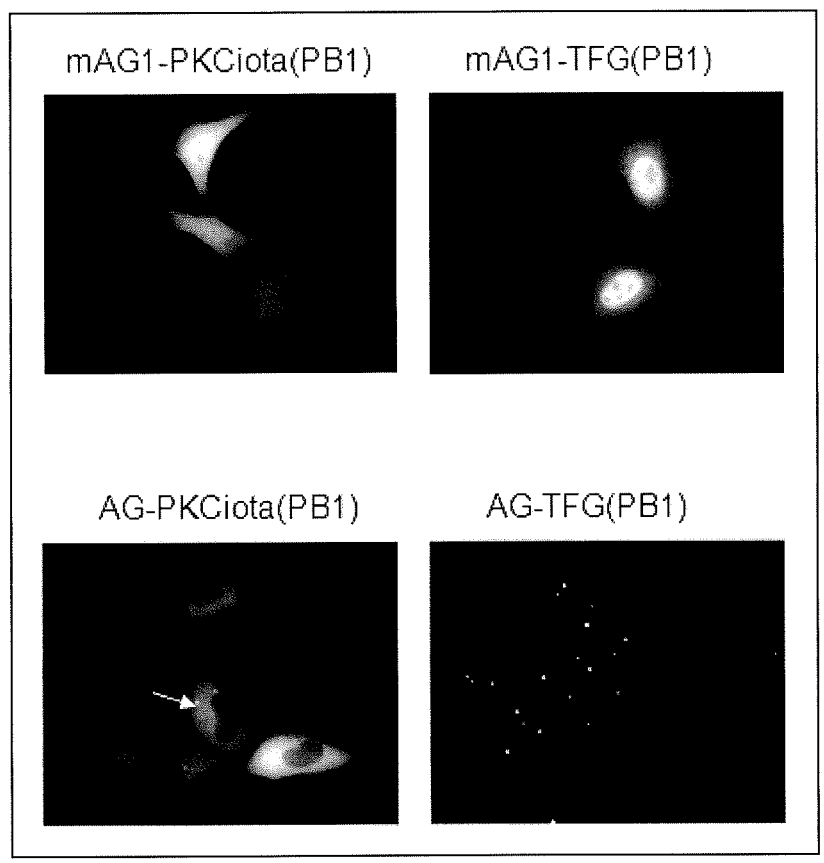
FIG. 13 shows micrographs for illustrating the result of analyzing the presence or absence of fluorescent focus formation by expressing in cultured cells a protein composed of a mAG1 protein or an AG protein fused to a PB1 domain of PKCiota (PKCiota(PB1)) or a PB1 domain of TFG (TFG(PB1)).
Figure 14:
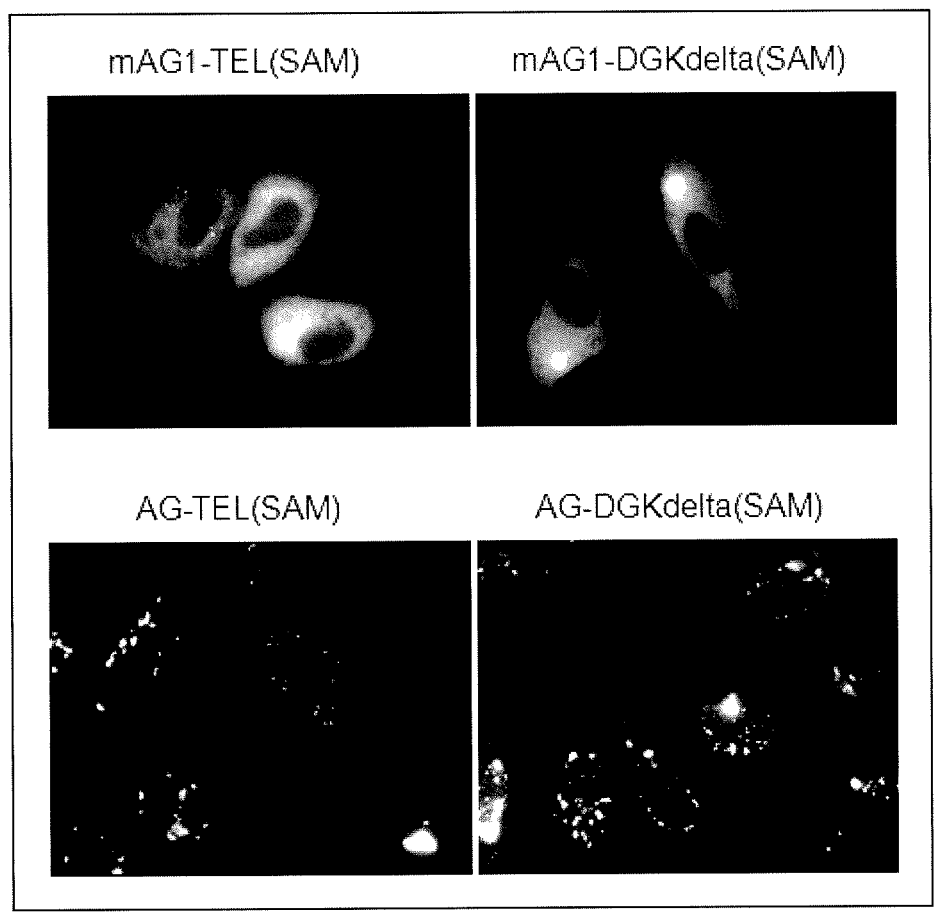
FIG. 14 shows micrographs for illustrating the result of analyzing the presence or absence of fluorescent focus formation by expressing in cultured cells a protein composed of a mAG1 protein or an AG protein fused to a SAM domain of TEL (TEL(SAM)) or a SAM domain of DGK delta (DGKd) (DGK delta(SAM)).
Figure 15:
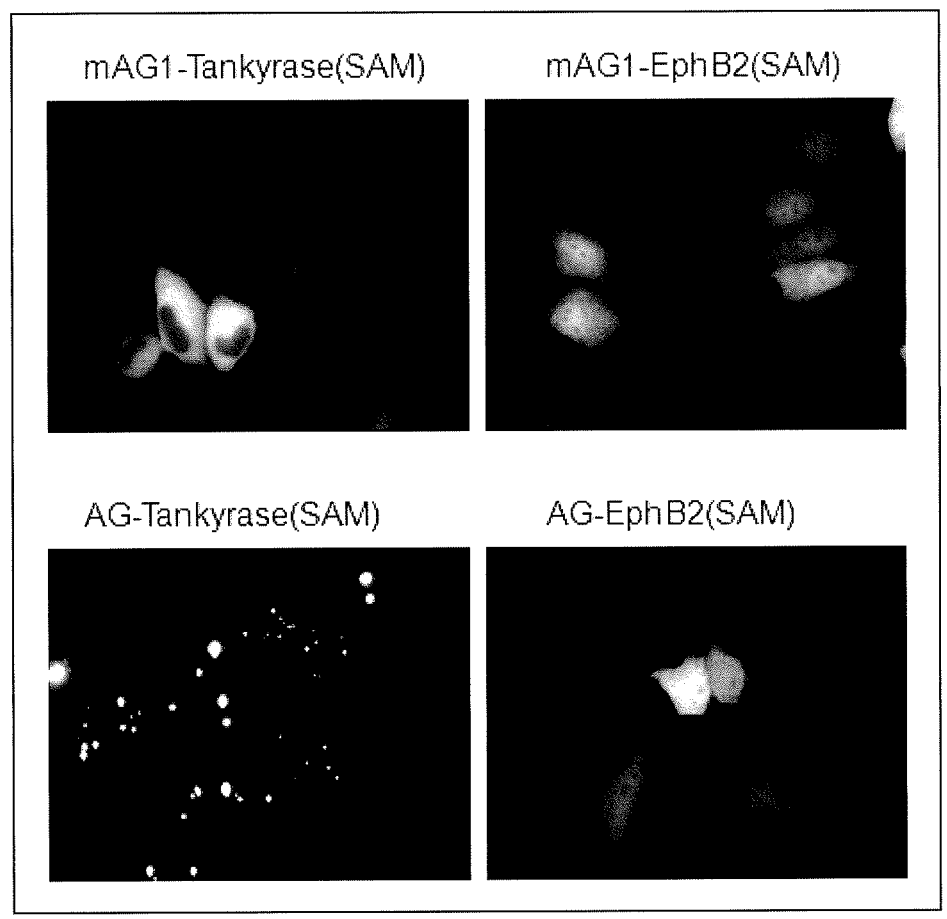
FIG. 15 shows micrographs for illustrating the result of analyzing the presence or absence of fluorescent focus formation by expressing in cultured cells a protein composed of a mAG1 protein or an AG protein fused to a SAM domain of Tankyrase (Tankyrase(SAM)) or a SAM domain of EphB2 (EphB2(SAM)).

As apparent from the results shown in FIGS. 13, 14, and 15, PKCiota(PB1), TFG(PB1), TEL(SAM), DGK delta (SAM), and Tankyrase(SAM) were dispersed when fused to mAG1, and formed fluorescent foci (assemblies) when fused to AG. Note that the cells expressing AG-PKCiota(PB1) included both of cells forming fluorescent foci and cells not forming fluorescent foci. In contrast, in all the cells expressing the other fusion proteins comprising the AG protein, fluorescent foci were detected.

Figure 12:
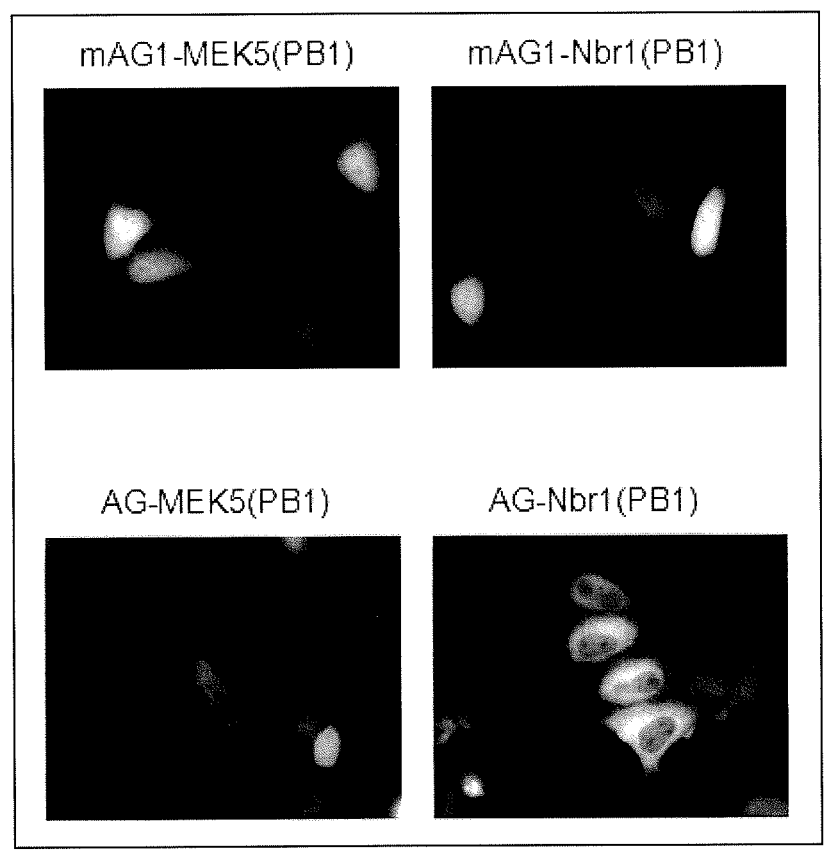
FIG. 12 shows micrographs for illustrating the result of analyzing the presence or absence of fluorescent focus formation by expressing in cultured cells a protein composed of a mAG1 protein or an AG protein (fluorescent protein having a multimerization ability) fused to a PB1 domain of MEK5 (MEK5(PB1)) or a PB1 domain of Nbr1 (Nbr1(PB1)).

On the other hand, as apparent from the results shown in FIGS. 12 and 15, when MEK5(PB1), Nbr1(PB1), and EphB2(SAM) were fused to mAG1 or when fused to AG, no fluorescent focus formation was observed.

Thus, it was revealed that TFG(PB1), TEL(SAM), DGK delta(SAM), and Tankyrase(SAM) were usable as the association-inducing protein according to the present invention.

Example 5

<Detection 3 of Protein-Protein Interaction>

Figure 16:
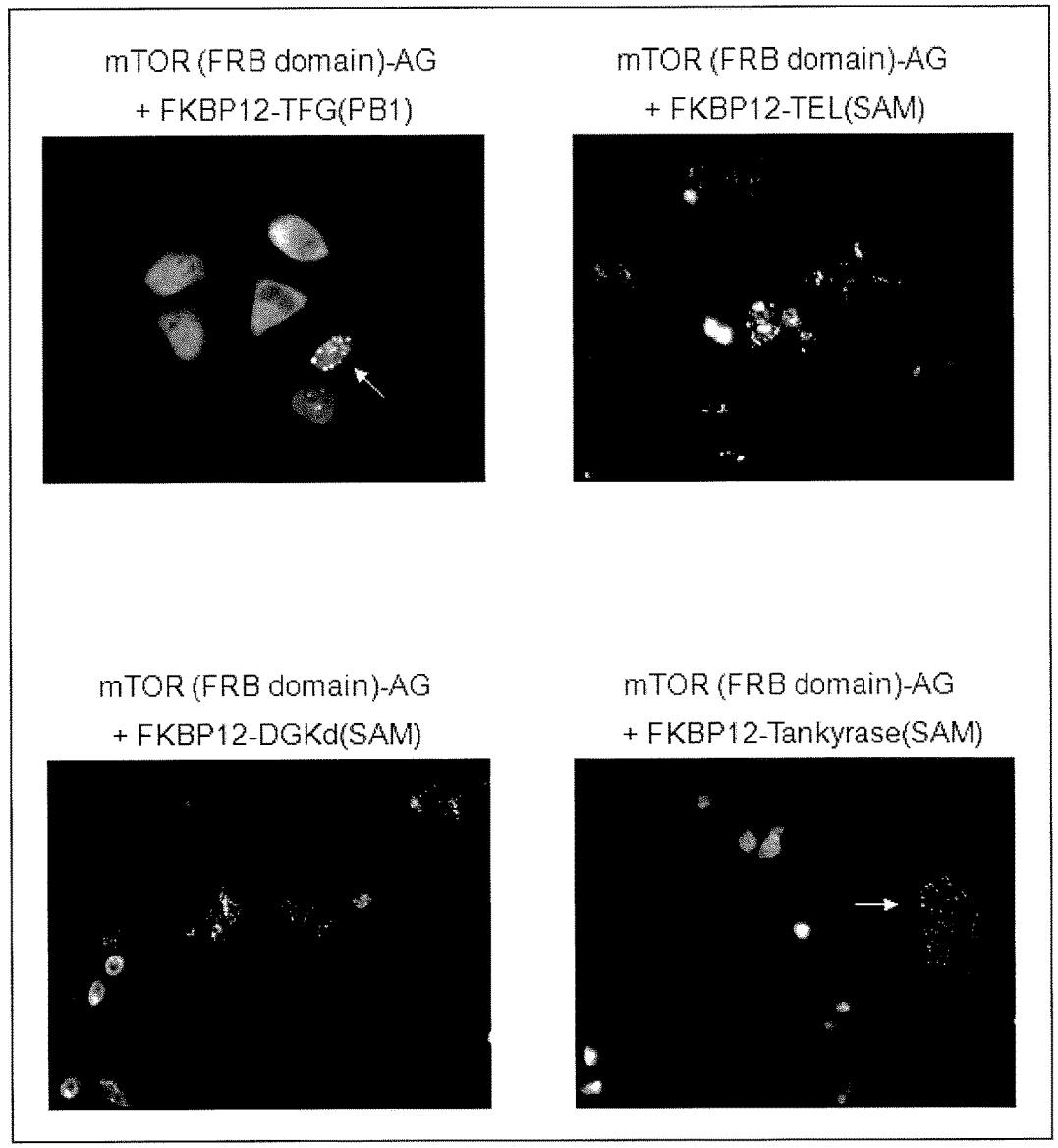
FIG. 16 shows micrographs for illustrating the result of analyzing the presence or absence of fluorescent focus formation by expressing in cultured cells the following fusion-protein combinations, in the presence of rapamycin: a combination of a fusion protein (mTOR(FRB domain)-AG) composed of a FRB domain of a mTOR protein and an AG protein with a fusion protein (FKBP12-TFG(PB1)) composed of a FKBP12 protein and TFG(PB1); a combination of mTOR(FRB domain)-AG with a fusion protein (FKBP12-TEL(SAM)) composed of a FKBP12 protein and TEL(SAM); a combination of mTOR(FRB domain)-AG with a fusion protein (FKBP12-DGKd(SAM)) composed of a FKBP12 protein and DGK delta(SAM); and a combination of mTOR(FRB domain)-AG with a fusion protein (FKBP12-Tankyrase(SAM)) composed of a FKBP12 protein and Tankyrase(SAM).

In order to verify that the association-inducing proteins selected in Example 4 were suitably usable in the method for detecting a protein-protein interaction of the present invention, a test described below was conducted by the same method as that described in Example 2. FIG. 16 shows the obtained result.

(Preparation of Plasmid DNAs)

In preparing pFKBP12-TFG(PB1), first, a TFG(PB1) gene was amplified from phAG-TFG(PB1) by PCR using the following primer set:

```
TFG(PB1) forward primer 2;
                                    (SEQ ID NO: 87)
5'-AAACCGGTAAGCTAATCATCAAAGCTCAACTT-3',
and TFG(PB1) reverse primer 2;
                                    (SEQ ID NO: 88)
5'-TTTCTAGATTAATTAACAAATAATGTCAGTTTCAGTAT-3'.
```

Then, the amplification product thus obtained was cleaved with AgeI and XbaI, and inserted into pFKBP12-p62(PB1) having been treated with the same restriction enzymes to cut out a p62(PB1) region therefrom. Thus, pFKBP12-TFG (PB1) was prepared. Note that the pFKBP12-TFG(PB1) encodes a fusion protein composed of a FKBP12 protein and TFG(PB1) (the fusion protein may also be referred to as "FKBP12-TFG(PB1)").

Meanwhile, in preparing pFKBP12-TEL(SAM), first, a TEL(SAM) gene was amplified from phAG-TEL(SAM) by PCR using the following primer set:

```
TEL(SAM) forward primer 2;
                                    (SEQ ID NO: 89)
5'-AAAAACCGGTCCTCGAGCGCTCAGGATGGAGGAA-3',
and TEL(SAM) reverse primer 2;
                                    (SEQ ID NO: 90)
5'-AAAATCTAGATTACCTCTGCTTCAGAATATGCTGAAGGAGTT-3'.
```

Then, the amplification product thus obtained was cleaved with AgeI and XbaI, and inserted into pFKBP12-p62(PB1) having been treated with the same restriction enzymes to cut out a p62(PB1) region therefrom. Thus, pFKBP12-TEL (SAM) was prepared. Note that the pFKBP12-TEL(SAM) encodes a fusion protein composed of a FKBP12 protein and TEL(SAM) (the fusion protein may also be referred to as "FKBP12-TEL(SAM)").

Further, in preparing pFKBP12-DGK delta(SAM), first, a DGK delta(SAM) gene was amplified from phAG-DGK delta(SAM) by PCR using the following primer set:

```
DGK delta(SAM) forward primer 2;
                                 (SEQ ID NO: 91)
5'-AAAAACCGGTCCGGTTCACCTCTGGGGGACAGA-3',
and DGK delta(SAM) reverse primer 2;
                                 (SEQ ID NO: 92)
5'-AAAATCTAGATTAGCTGCGGCTCAGCTCCTTGAT-3'.
```

Then, the amplification product thus obtained was cleaved with AgeI and XbaI, and inserted into pFKBP12-p62(PB1) having been treated with the same restriction enzymes to cut out a p62(PB1) region therefrom. Thus, pFKBP12-DGK delta(SAM) was prepared. Note that the pFKBP12-DGK delta(SAM) encodes a fusion protein composed of a FKBP12 protein and DGK delta(SAM) (the fusion protein may also be referred to as "FKBP12-DGKd(PB1)").

Moreover, in preparing pFKBP12-Tankyrase(SAM), first, a Tankyrase(SAM) gene was amplified from phAG-Tankyrase(SAM) by PCR using the following primer set:

```
Tankyrase(SAM) forward primer 2;
                                 (SEQ ID NO: 93)
5'-AAAAACCGGTCTGATAGATGCCATGCCCCCAGA-3',
and Tankyrase(SAM) reverse primer 2;
                                 (SEQ ID NO: 94)
5'-AAAATCTAGATTAAATTCGAATGACATTGTATCTGTTGAAGA-3'.
```

Then, the amplification product thus obtained was cleaved with AgeI and XbaI, and inserted into pFKBP12-p62(PB1) having been treated with the same restriction enzymes to cut out a p62(PB1) region therefrom. Thus, pFKBP12-Tankyrase(SAM) was prepared. Note that pFKBP12-Tankyrase(SAM) encodes a fusion protein composed of a FKBP12 protein and Tankyrase(SAM) (the fusion protein may also be referred to as "FKBP12-Tankyrase(SAM)").

(Transfection into Cultured Cells, and Observation of Transfected Cells)

Each of the following combinations of the plasmid DNAs was mixed in equal amounts and introduced into HeLaS3 cells by the same method as that described in Example 1:
 a combination of pmTOR(FRB domain)-hAG with pFKBP12-TFG(PB1);
 a combination of pmTOR(FRB domain)-hAG with pFKBP12-TEL(SAM);
 a combination of pmTOR(FRB domain)-hAG with pFKBP12-DGK delta(SAM); and
 a combination of pmTOR(FRB domain)-hAG with pFKBP12-Tankyrase(SAM).

Moreover, the transfected cells were observed also by the same method as that described in Example 1. Then, it was confirmed that no fluorescent focus was detected in each of the cultured cells before 100 nM rapamycin (manufactured by Merck KGaA) was added, and fluorescence images were captured 300 seconds after the addition.

As apparent from the result shown in FIG. 16, even when any of the fusion proteins were expressed, mTOR(FRB domain)-AG was present in a dispersed manner before rapamycin was added (unillustrated); meanwhile, fluorescent foci were detected in all the cells after the addition. In other words, it was revealed that by the rapamycin-dependent interaction between mTOR(FRB domain) and the FKBP12 protein, mTOR(FRB domain)-AG was autonomously associated with FKBP12-TEL(SAM) and so forth, thereby forming fluorescent foci.

Thus, it was revealed that the use of not only p62(PB1) but also the other types of domains derived from the other proteins, such as TEL(SAM), as the association-inducing protein enabled detection of a protein-protein interaction. Moreover, this result verified that the model illustrated in FIGS. 3 and 4 was practicable as the screening method for an association-inducing protein according to the present invention.

Example 6

<Detection 3 of Protein-Protein Interaction>

Figure 17:
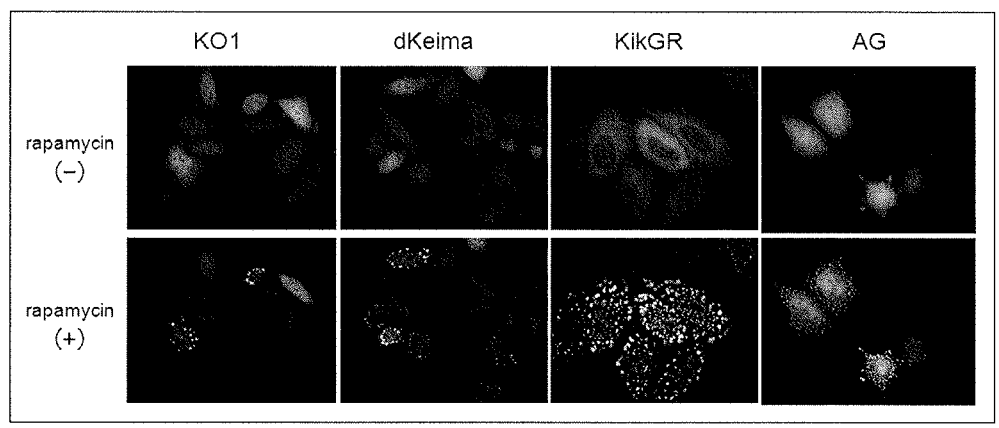
FIG. 17 shows micrographs for illustrating the result of analyzing whether or not it is possible to detect a rapamycin-dependent interaction between mTOR(FRB) and a FKBP12 protein according to fluorescent focus formation by using KO1, dKeima, KikGR, or AG as the fluorescent protein having a multimerization ability according to the present invention.

Whether or not fluorescent proteins other than the AG protein were applicable as the fluorescent protein having a multimerization ability in the method for detecting a protein interaction of the present invention was examined by a method described below. FIG. 17 shows the obtained result.

Note that the fluorescent proteins thus examined were Kusabira-Orange 1 (KO1), dimeric Keima-Red (dKeima), and Kikume Green-Red (KikGR), which have been known to form a homodimer, a homodimer, and a homotetramer, respectively.

(Preparation of Plasmid DNAs)

In preparing pmTOR(FRB domain)-hKO1, first, a hKO1 gene was amplified from phKO1-MN1 (manufactured by limited company Amalgaam Co., Ltd.) by PCR using the following primer set:

```
hKO1 forward primer;
                                 (SEQ ID NO: 95)
5'-AAAAACCGGTATGGTGAGCGTGATCAAGCCCGAG-3',
and hKO1 reverse primer;
                                 (SEQ ID NO: 96)
5'-AAAATCTAGATTAGCAGTGGGCCACGGCGTCCTCC-3'.
```

Then, the amplification product thus obtained was cleaved with AgeI and XbaI, and inserted into pmTOR(FRB domain)-hAG having been treated with the same restriction enzymes to cut out a hAG region therefrom. Thus, pmTOR (FRB domain)-hKO1 was prepared.

Meanwhile, in preparing pmTOR(FRB domain)-hdKeima-Red, first, a hdKeima gene was prepared by cleaving phdKeima-Red-MNLinker (manufactured by limited company Amalgaam Co., Ltd.) with AgeI and XbaI. Then, the obtained hdKeima gene was inserted into pmTOR(FRB domain)-hAG having been treated with the same restriction enzymes to cut out a hAG region therefrom. Thus, pmTOR (FRB domain)-hdKeima-Red was prepared.

Further, in preparing pmTOR(FRB domain)-hKikGR1, first, a hKikGR1 gene was prepared by cleaving phKikGR1-MNLinker (manufactured by limited company Amalgaam Co., Ltd.) with AgeI and XbaI. Then, the obtained hKikGR1 gene was inserted into pmTOR(FRB domain)-hAG having been treated with the same restriction enzymes to cut out a hAG region therefrom. Thus, pmTOR(FRB domain)-phKikGR1 was prepared.

(Transfection into Cultured Cells, and Observation of Transfected Cells)

Each of the following combinations of the plasmid DNAs was mixed in equal amounts and introduced into HeLaS3 cells by the same method as that described in Example 1:
 a combination of pmTOR(FRB domain)-hKO1 with pp62 (PB1)-FKBP12;

a combination of pmTOR(FRB domain)-hdKeima-Red with pp62(PB1)-FKBP12;

a combination of pmTOR(FRB domain)-hKikGR1 with pp62(PB1)-FKBP12; and a combination of pmTOR(FRB domain)-hAG with pp62 (PB1)-FKBP12.

Moreover, the transfected cells were observed also by the same method as that described in Example 1. Note that the KO1 was observed using an excitation filter (BP520-540HQ, Olympus Corporation), a dichroic mirror (DM545HQ, manufactured by Olympus Corporation), and an absorption filter (BA555-600HQ, manufactured by Olympus Corporation). The dKeima was observed using an excitation filter (440AF21, manufactured by OMEGA OPTICAL, INC.), a dichroic mirror (455DRLP, manufactured by OMEGA OPTICAL, INC.), and an absorption filter (610ALP, manufactured by OMEGA OPTICAL, INC.). Then, fluorescence images were captured before 100 nM rapamycin (manufactured by Merck KGaA) was added and 300 seconds after the addition.

As apparent from the result shown in FIG. 17, as in the case of using the AG protein, all of the examined fluorescent proteins demonstrated that mTOR(FRB) fused to the fluorescent proteins was present in a dispersed manner before rapamycin was added; meanwhile, fluorescent foci (assemblies) were formed after the addition. Thus, it was verified that, in the present invention, the use of not only the AG protein but also the other fluorescent proteins having a multimerization ability, such as the KO1 protein, enabled detection of a protein-protein interaction.

Example 7

<Screening 1 of Fluorescent Protein Having Multimerization Ability>

Figure 18:
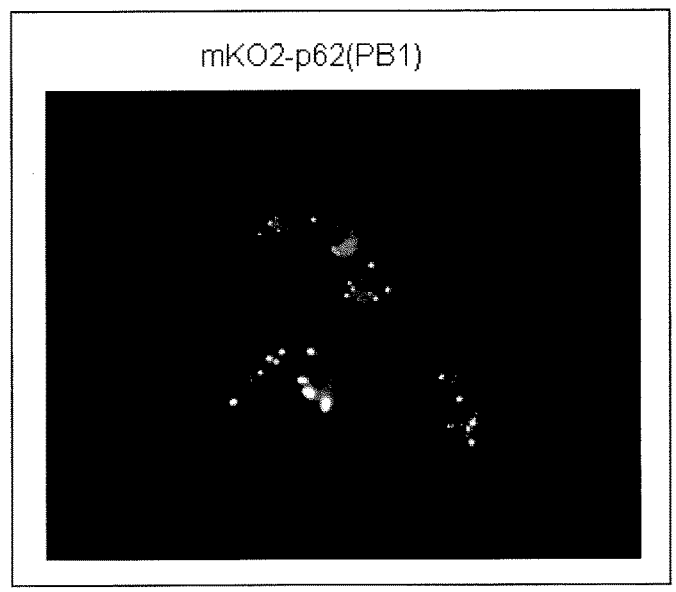
FIG. 18 shows a micrograph for illustrating the result of analyzing the presence or absence of fluorescent focus formation by expressing in cultured cells a protein composed of monomeric Kusabira-Orange 2 (mKO2) fused to p62(PB1).

Whether or not a fluorescent protein other than AG, KO1, dKeima, and KikGR was applicable as the fluorescent protein having a multimerization ability in the method for detecting a protein interaction of the present invention was examined by a method described below. Specifically, examined was whether or not an assembly (fluorescent focus) as shown in FIG. 3 was formed when monomeric Kusabira-Orange (mKO2) was fused with p62(PB1) serving as the association-inducing protein and expressed in cells. FIG. 18 shows the obtained result.

First, as in the case of "phmAG1-p62(PB1) and phAG-p62(PB1)" described in Example 1, the DNA encoding p62(PB1) was amplified by PCR. The amplification product thus obtained was cleaved with EcoRI and NotI, and inserted into phmKO2-MCLinker (manufactured by limited company Amalgaam Co., Ltd.) having been treated with the same restriction enzymes. Thus, phmKO2-p62(PB1) was prepared. Then, the phmKO2-p62(PB1) was introduced into HeLaS3 cells by the same method as that described in Example 1. Moreover, the transfected cells were observed also by the same method as that described in Example 6. FIG. 18 shows the obtained result.

As apparent from the result shown in FIG. 18, mKO2-p62(PB1) proteins encoded by phmKO2-p62(PB1) were associated with each other, thereby forming fluorescent foci. Thus, it was revealed that not only the above-described fluorescent proteins capable of forming a homomultimer in cells, such as AG, KO1, dKeima, and KikGR, but also mKO2 generally believed to be a monomeric fluorescent protein were usable as the fluorescent protein having a multimerization ability in the method of the present invention.

Example 8

<Screening 2 of Fluorescent Proteins Having Multimerization Ability>

It was confirmed by the following method that other than AG, KO1, dKeima, and KikGR described above, MiCy1, KCy1, dAG (AB), and dAG (AC) (fluorescent protein capable of homodimerization) as well as TGuv, Momiji, COR3.01, COR5, and DsRed2 (fluorescent protein capable of homotetramerization), which had been known as fluorescent proteins capable of forming a homomultimer in cells, were also usable in the method for detecting a protein interaction of the present invention.

Moreover, in order to find out fluorescent proteins generally believed to be monomeric fluorescent proteins such as mKO2 but usable in the method of the present invention, screening was carried out by the following method.

(Method for Detecting Protein-Protein Interaction)

By the same method as that described in Examples 5 and 6, p62(PB1)-FKBP12, FKBP12-DGKd(SAM), FKBP12-TEL(SAM), or FKBP12-Tankyrase(SAM), and mTOR (FRB) fused to corresponding one of fluorescent proteins shown in Table 1 were expressed in HeLaS3 cells to evaluate a degree of fluorescent focus (assembly) formation after rapamycin was added. Note that plasmid DNAs encoding fusion proteins composed of mTOR(FRB) and the corresponding fluorescent proteins were prepared as appropriate by the same method as that described in Example 2. Moreover, regarding the combinations of FKBP12-Tankyrase (SAM) with mKO2, mKeima, mMiCy1, mKO1, MiCy1, and TGuv, the test was conducted by introducing the genes into 293T cells. Specifically, the 293T cells were cultured in DMEM High glucose (manufactured by SIGMA ALDRICH CO.) containing 10% FBS (manufactured by Equitech-Bio Inc.). Moreover, the 293T cells were seeded onto an 8-well chamber (manufactured by Nunc A/S) 6 hours before the plasmid DNAs were introduced. Further, at the time of the transfection, 200 ng of the plasmid DNA encoding FKBP12-Tankyrase(SAM) and 200 ng of one of the plasmid DNAs encoding fusion proteins composed of the fluorescent proteins and mTOR(FRB) were diluted with 30 µl of OptiMEM (manufactured by Life Technologies Corporation), and 1.2 µl of TurboFect Transfection Reagent (manufactured by Thermo Fisher Scientific Inc.) was added thereto and stirred. Then, the resultant was further mixed with 300 µl of the culture solution, subsequently added to the 293T cells, and observed 48 hours later. Table 1 shows the obtained result. In Table 1, "+++" indicates a combination from which fluorescent foci were observed in 50% or more of the HeLaS3 cells; "++" indicates a combination from which fluorescent foci were observed in 50% or less of the HeLaS3 cells; and "+" indicates a combination from which fluorescent foci were observed in 293T cells expressing a larger amount of proteins than that in the HeLaS3 cells.

TABLE 1

|  |  | P62 (PB1) | DGKd (SAM) | TEL (SAM) | Tankyrase (SAM) |
| --- | --- | --- | --- | --- | --- |
| mKO2 | monomer | +++ | +++ | ++ | + |
| mKeima | monomer | +++ | +++ | ++ | + |
| mMiCy1 | monomer | +++ | +++ | +++ | + |

TABLE 1-continued

|  |  | P62 (PB1) | DGKd (SAM) | TEL (SAM) | Tankyrase (SAM) |
|---|---|---|---|---|---|
| mKO1 | monomer | +++ | +++ | +++ | + |
| mKikGR1 | monomer | +++ | +++ | +++ | +++ |
| MiCy1 | dimer | +++ | +++ | +++ | + |
| KCy1 | dimer | +++ | +++ | +++ | ++ |
| KO1 | dimer | +++ | +++ | +++ | ++ |
| dKeima | dimer | +++ | +++ | +++ | ++ |
| dAG(AB) | dimer | +++ | +++ | +++ | ++ |
| dAG(AC) | dimer | +++ | +++ | +++ | ++ |
| TGuv | tetramer | +++ | +++ | +++ | + |
| Momiji | tetramer | +++ | +++ | +++ | +++ |
| KikGR | tetramer | +++ | +++ | +++ | +++ |
| AG | tetramer | +++ | +++ | +++ | +++ |
| COR3.01 | tetramer | +++ | +++ | +++ | +++ |
| COR5 | tetramer | +++ | +++ | +++ | +++ |
| DsRed2 | tetramer | +++ | +++ | +++ | +++ |

As apparent from the result shown in Table 1, it was confirmed that all of the fluorescent proteins capable of forming a homomultimer in cells were usable in the method of the present invention. Moreover, the results of TEL (SAM) and Tankyrase(SAM) seem to suggest a tendency that the higher the multimerization ability of a fluorescent protein, the more likely that fluorescent foci (assemblies) are formed by the protein-protein interaction. Further, as shown in Table 1, it was revealed that mKeima, mMiCy1, mKO1, and mKikGR1 generally believed to be monomeric fluorescent proteins, other than mKO2, were also usable in the method of the present invention.

Example 9

<Detection 5 of Protein-Protein Interaction>
It was confirmed by a method described below that, even in combination with TFG(PB1) serving as the association-inducing protein, the use of the fluorescent proteins having a multimerization ability and confirmed in Examples 6 to 8 to be usable in the method of the present invention enabled detection of a protein-protein interaction. Table 2 shows the obtained result.
(Method for Detecting Protein-Protein Interaction)
By the same method as that described in Examples 5 and 6, TFG(PB1) and mTOR(FRB) fused to mKikGR1, dAG (AC), Momiji, KikGR, AG, COR3.01, COR5, or DsRed2 were expressed in HeLaS3 cells to evaluate a degree of fluorescent focus (assembly) formation after rapamycin was added. Moreover, by the same method as that described in Example 8, TFG(PB1) and mTOR(FRB) fused to KO1 or dAG (AB) were expressed in 293T cells to evaluate a degree of fluorescent focus (assembly) formation after rapamycin was added. Table 2 shows the obtained result. In Table 2, "++" indicates a combination from which fluorescent foci were observed in 50% or less of the HeLaS3 cells, and "+" indicates a combination from which fluorescent foci were observed in the 293T cells expressing a larger amount of proteins than that in the HeLaS3 cells.

TABLE 2

|  |  | TFG (PB1) |
|---|---|---|
| mKikGR1 | monomer | ++ |
| KO1 | dimer | + |
| dAG(AB) | dimer | + |
| dAG(AC) | dimer | ++ |
| Momiji | tetramer | ++ |
| KikGR | tetramer | ++ |

TABLE 2-continued

|  |  | TFG (PB1) |
|---|---|---|
| AG | tetramer | ++ |
| COR3.01 | tetramer | ++ |
| COR5 | tetramer | ++ |
| DsRed2 | tetramer | ++ |

As apparent from the result shown in Table 2, it was confirmed that the use of the fluorescent proteins having a multimerization ability in combination with the other association-inducing protein than the proteins described in Example 8 also enabled detection of a protein-protein interaction.

Example 10

<Detection 6 of Protein-Protein Interaction>
The fluorescent focus (assembly) according to the present invention is, as described above, attributable to a protein-protein interaction. Hence, a fluorescence intensity of a fluorescent focus presumably reflects a strength of the protein-protein interaction. Moreover, in the method for detecting a protein-protein interaction, quantification and comparison, if possible, of the strength of the interaction are useful in evaluating a substance (inhibitor) suppressing a protein-protein interaction, and evaluating a factor modulating a protein-protein interaction.

For this reason, the concentration of a compound inducing a protein-protein interaction was changed to test whether or not the fluorescence intensity of fluorescent foci (assemblies) was changed in a manner dependent on the concentration of the compound by a method described below.

Figure 19:
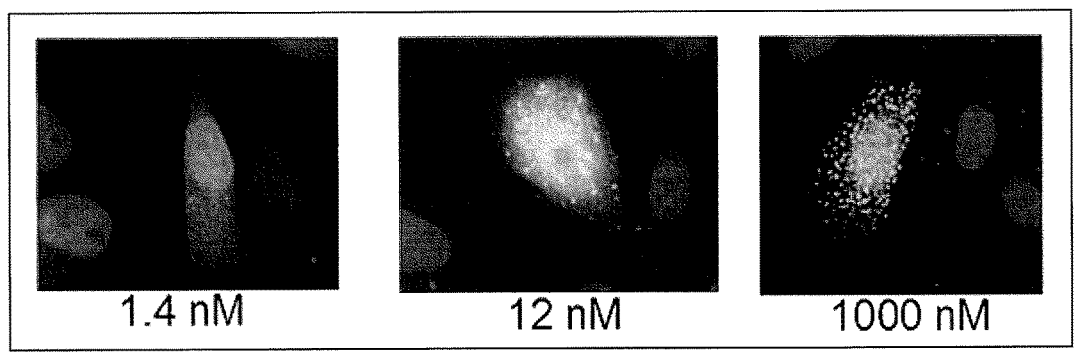
FIG. 19 shows micrographs for illustrating that the result of analyzing whether or not a fluorescence intensity of a fluorescent focus formed by an association between mTOR (FRB domain)-AG and FKBP12-p62(PB1) is dependent on the rapamycin concentration.

(Transfection into Cells, and Observation and Analysis of Transfected Cells)
pmTOR(FRB domain)-hAG and pFKBP12-p62(PB1) were mixed in equal amounts and introduced into HeLaS3 cells by the same method as that described in Example 1. The cells were collected 24 hours after the introduction, and seeded onto 96 MicroWell Optical Bottom Plate (manufactured by Nunc A/S) at 20000 cells/well. Then, 24 hours after the seeding, a solution of Hoechst 33342 (manufactured by Dojindo Laboratories) diluted with an observation buffer to 5.6 μg/ml was added to the plate, and allowed for further culturing for 30 minutes. Thereafter, the plate was washed twice with D-PBS(-) (manufactured by Wako Pure Chemical Industries, Ltd.). Then, the medium was replaced with rapamycin having been diluted with an observation buffer to predetermined concentrations, and 15 minutes later the resultant was fixed with 4% Paraformaldehyde Phosphate Buffer Solution (manufactured by Wako Pure Chemical Industries, Ltd.). Note that the concentrations of rapamycin used were 0.1 nM, 0.2 nM, 0.5 nM, 1.4 nM, 4.1 nM, 12.3 nM, 37.0 nM, 111.1 nM, 333.3 nM, and 1000 nM. Then, the prepared samples were observed using IN Cell Analyzer 1000 (manufactured by GE Healthcare). FIG. 19 shows part of the obtained result.

Figure 20:
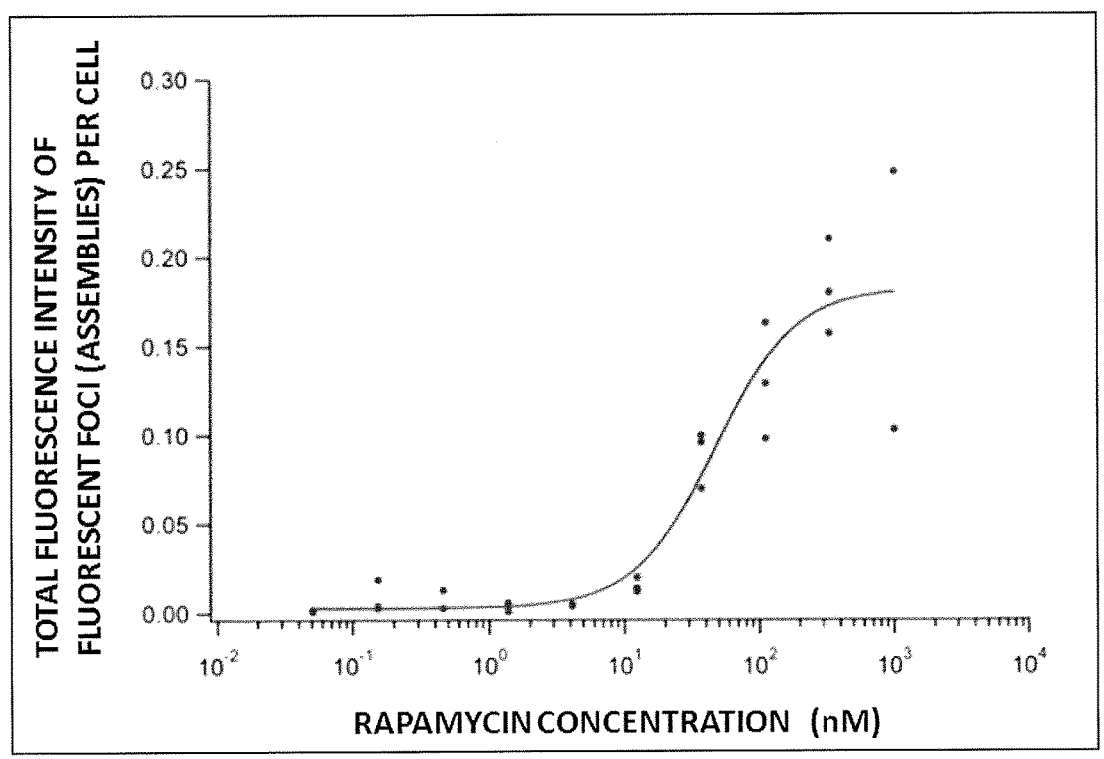
FIG. 20 is a graph for illustrating that the result of analyzing whether or not the fluorescence intensity of the fluorescent focus formed by the association between mTOR (FRB domain)-AG and FKBP12-p62(PB1) is dependent on the rapamycin concentration.

Further, fluorescence images were analyzed in multiple fields of view. A total luminance (total fluorescence intensity) of fluorescent foci (assemblies) per cell in an image of wells to which rapamycin was added at predetermined concentrations was calculated to analyze a correlation with the rapamycin concentration. FIG. 20 shows part of the obtained result. Note that, in FIG. 20, the X axis represents the concentration of rapamycin added to each well; the Y axis represents the total luminance (total fluorescence intensity) of fluorescent foci (assemblies) per cell; and dots represent the measurement values. Moreover, using Igor® (manufactured by WaveMetrics, Inc.), a fitting curve was drawn through the dots, which represents a function fitted to an equation:

$y$=base+(max−base)/[1+(xhalf/$x$)^rate], where [Dot Intensity/Cells]=$y$, and [Canc. (nM)]=$x$. (base=0.0028731, max=0.1823, rate=1.4516, xhalf=46.99).

As apparent from the results shown in FIGS. 19 and 20, it was revealed that when the compound rapamycin inducing an interaction between mTOR(FRB domain) and a FKBP12 protein was added to the cells expressing mTOR(FRB domain)-AG and FKBP12-p62(PB1), the fluorescence intensity of fluorescent foci was increased in a manner dependent on the concentration of rapamycin added. It was also demonstrated that the assemblies between mTOR(FRB domain)-AG and FKBP12-p62(PB1) were formed in a manner dependent on the concentration.

Example 11

<Detection 7 of Protein-Protein Interaction>

Whether or not the method of the present invention was utilizable in determining the 50% effective concentration (EC50) and the 50% inhibitory concentration (IC50) of a drug against a protein-protein interaction was evaluated by a method described below.

(Preparation of Plasmid DNA)

Using pmTOR(FRB domain)-hAG described in Example 2 and pFucci-S/G2/M Green-Hyg (manufactured by limited company Amalgaam Co., Ltd.), pmTOR(FRB domain)-hAG_Hyg was prepared according to a conventional method, so that the drug resistance gene was converted to a hygromycin B resistance gene.

(Preparation of Stably-Expressing Cell Line)

By the same method as that described in Example 1, the pmTOR(FRB domain)-hAG_Hyg and pp62(PB1)-FKBP12 described in Example 2 were introduced in a HeLaS3 cell line, and cultured.

Moreover, 24 hours after the plasmid DNAs were introduced in the HeLaS3 cell line, the medium was replaced with a medium containing 600 µg/mL of G418 (manufactured by Wako Pure Chemical Industries, Ltd.) and 150 µg/mL of hygromycin (manufactured by Nacalai Tesque, Inc.). Then, cells survived after culturing for one week with this medium were cloned by a colony pick-up method.

(Observation and Analysis of Transfected Cells)

The cloned cell lines were seeded onto 96-well plates. Then, after washing twice with PBS on the next day, an observation buffer containing Hoechst 33342 (manufactured by Dojindo Laboratories) was added to the cell line seeded onto each well, followed by incubation at 37° C. for 15 minutes for nuclear staining.

Further, these cell lines were washed twice with an observation buffer. Then, an observation buffer containing rapamycin, or rapamycin and FK506 at certain concentrations was added to each well, and incubated for 20 minutes.

Note that the concentration of rapamycin added was 0.39 nM, 0.78 nM, 1.56 nM, 3.13 nM, 6.25 nM, 12.50 nM, 25.00 nM, 50.00 nM, 100.00 nM, 200.00 nM, 400.00 nM, or 800.00 nM. Moreover, FK506 is known as a substance competitively inhibiting an interaction between FKBP12 and rapamycin. In this Example, FK506 was added to each well after diluted with a buffer containing 20 nM rapamycin in such a manner that the FK506 concentration was 0.008 µM, 0.016 µM, 0.031 µM, 0.063 µM, 0.125 µM, 0.250 µM, 0.500 µM, 1.000 µM, 2.000 µM, 4.000 µM, 8.000 µM, or 16.000 µM.

Figure 21:
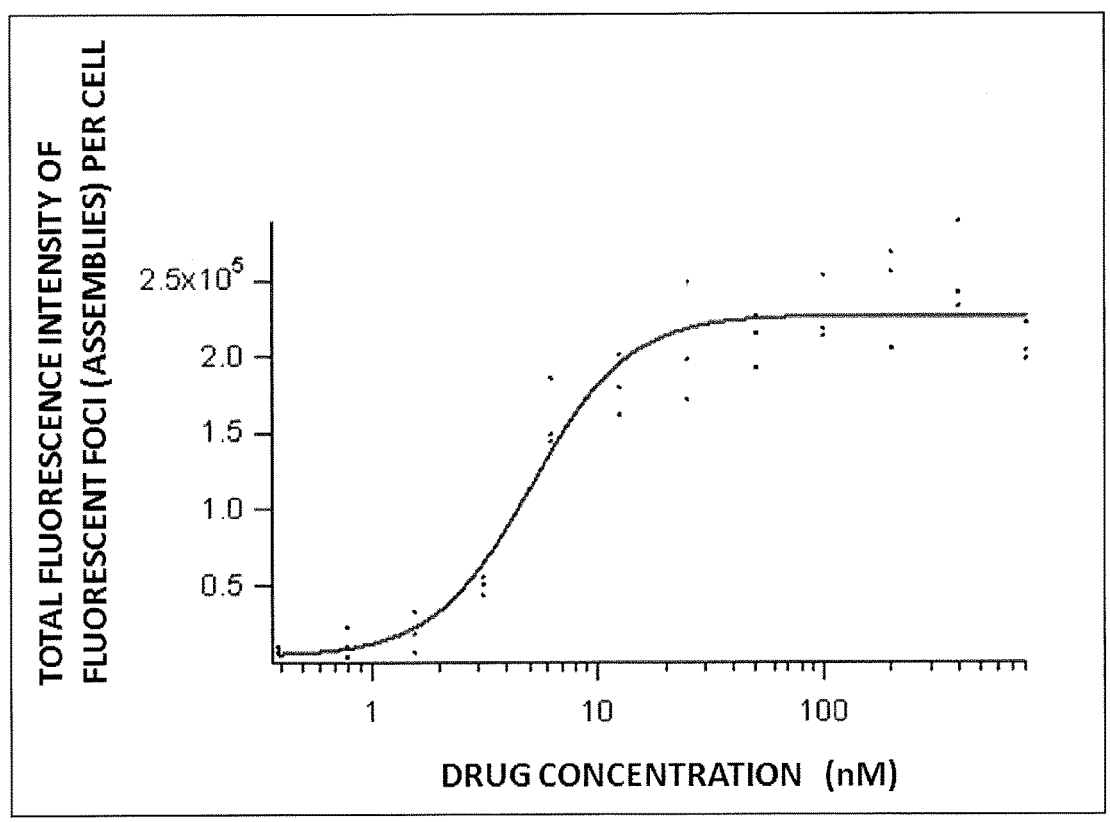
FIG. 21 is a graph for illustrating that the result of analyzing whether or not a fluorescence intensity of a fluorescent focus formed by an association between mTOR (FRB domain)-AG and p62(PB1)-FKBP12 is dependent on the rapamycin concentration.

After each drug was added and incubated, 4% Paraformaldehyde Phosphate Buffer Solution (manufactured by Wako Pure Chemical Industries, Ltd.) was added to each well, followed by incubation at room temperature for 15 minutes. Thereby, these cell lines were fixed. Then, these cell lines were washed three times with an observation buffer. Subsequently, an image of three fields of view was obtained for each well using a fluorescence microscope. Thereafter, each fluorescence image was analyzed using iCY (see de Chaumont F et al., Nature Methods, June 28, vol. 9, no. 7, pp. 690 to 696), and a total luminance (total fluorescence intensity) of fluorescent foci (assemblies) per cell was calculated to analyze a correlation with the concentration of the drugs added. FIG. 21 shows the result obtained by adding only rapamycin, and FIG. 22 shows the result obtained by adding rapamycin and FK506.

Figure 22:
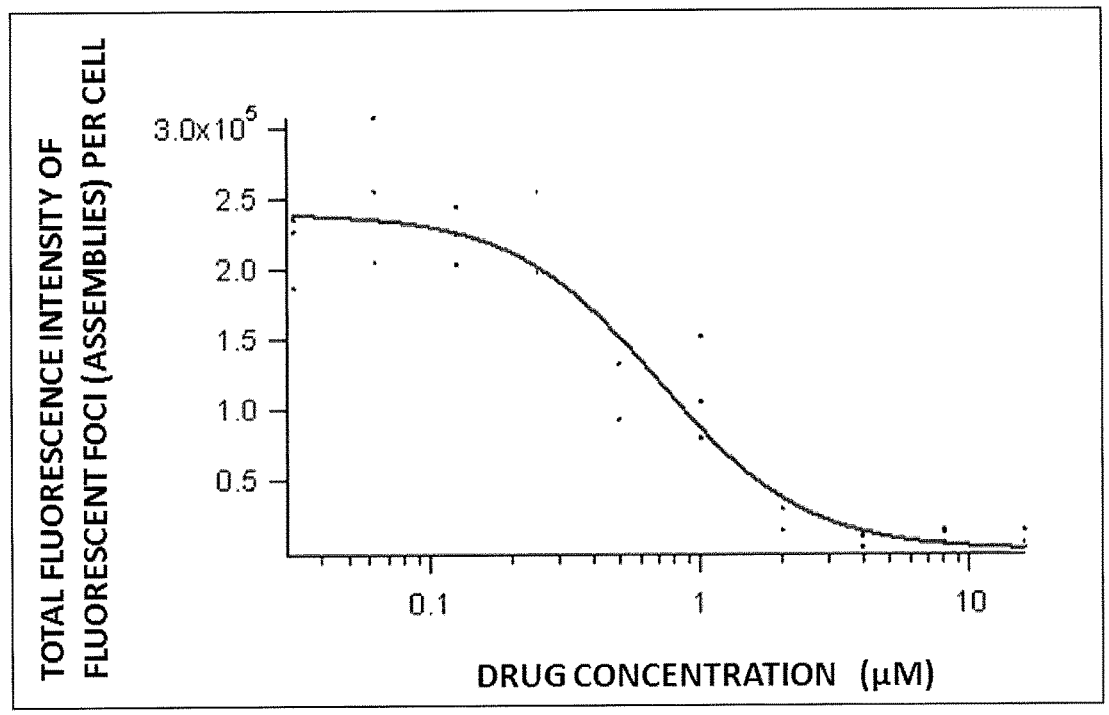
FIG. 22 is a graph for illustrating the result of analyzing whether or not the fluorescence intensity of the fluorescent focus formed by the association between mTOR(FRB domain)-AG and p62(PB1)-FKBP12 in the presence of rapamycin is suppressed in a manner dependent on the concentration FK506. Note that FK506 competitively inhibits between an interaction between a FKBP12 protein and rapamycin, thereby inhibiting an interaction between the FKBP12 protein and a FRB domain of a mTOR protein (mTOR(FRB)).

Note that, in FIGS. 21 and 22, the X axis represents the concentration of the drug added to the cell line; the Y axis represents the total luminance (total fluorescence intensity) of fluorescent foci (assemblies) per cell; and dots represent measurement values. Moreover, a fitting curve drawn through the dots shows the analysis result using Igor® (manufactured by WaveMetrics, Inc.).

As apparent from the result shown in FIG. 21, it was revealed that when the compound rapamycin inducing an interaction between mTOR(FRB domain) and a FKBP12 protein was added to the cells stably expressing mTOR(FRB domain)-AG and p62(PB1)-FKBP12, the fluorescence intensity of fluorescent foci was increased in a manner dependent on the concentration of rapamycin added. It was demonstrated that assemblies between mTOR(FRB domain)-AG and p62(PB1)-FKBP12 were formed in a manner dependent on the concentration. Further, the EC50 of rapamycin for the protein-protein interaction between mTOR(FRB domain) and FKBP12 was 3.36 nM by the calculation according to f(x)=max+(min−max)/(1+(x/EC50)^hill) based on the fitting curve shown in FIG. 21.

On the other hand, as apparent from the result shown in FIG. 22, it was revealed that when FK506 was added in the presence of rapamycin, the fluorescence intensity of fluorescent foci was decreased in a manner dependent on the concentration of FK506 added. It was demonstrated that the assembly formation between mTOR(FRB domain)-AG and p62(PB1)-FKBP12 was inhibited in a manner dependent on the concentration. Further, the IC50 of FK506 for the interaction between rapamycin and FKBP12 and eventually for the protein-protein interaction between mTOR(FRB domain) and FKBP12 was 0.68 µM by the calculation according to f(x)=min+(max−min)/(1+(x/IC50)^hill) based on the fitting curve shown in FIG. 22.

Example 12

<Detection 8 of Protein-Protein Interaction>

For the same purposes as those in Examples 10 and 11, whether or not fusion proteins constituting assemblies (fluorescent foci) were dispersed by an inhibitor specific to a protein-protein interaction in the method of the present invention, and whether or not the fluorescence intensity of fluorescent foci was changed in a manner dependent on the inhibitor concentration by changing the inhibitor concentration were tested by a method described below.

Note that the detection target in this test was an interaction between a p53 protein and an MDM2 protein, and that Nutlin-3 known as an inhibitor against the interaction was used in Example 12 (see Vassilev L T et al., Science, Feb. 6, 2004, vol. 303, no. 5659, pp. 844 to 848).

(Preparation of Plasmid DNAs)

In preparing pp62(PB1)-p53, first, a DNA encoding a portion of p53 (region having the 1st to 70th amino acids of the p53 protein, the region had the amino acid sequence of SEQ ID NO: 26) (the DNA had the base sequence of SEQ ID NO: 25) was amplified from a cDNA library of U2OS cells by PCR using the following primer set:

```
p53 forward primer;
                                      (SEQ ID NO: 97)
5'-AAGGATCCATGGAGGAGCCGCAGTCAGATCCTAGCGTCG-3',
and p53 reverse primer48;
                                      (SEQ ID NO: 98)
5'-TTGCGGCCGCTTAAGCAGCCTCTGGCATTCTGGGAGCTTCATC-3'
```

Then, the amplification product thus obtained was cleaved with BamHI and NotI, and inserted into pp62(PB1)-MCLinker having been treated with the same restriction enzymes. Thus, pp62(PB1)-p53 was prepared.

Moreover, in preparing phAG-MDM2, first, a DNA encoding a portion of MDM2 (region having the 7th to 125th amino acids of the MDM2 protein, the region had the amino acid sequence of SEQ ID NO: 28) (the DNA had the base sequence of SEQ ID NO: 27) was amplified from the cDNA library of U2OS cells by PCR using the following primer set:

```
MDM2 forward primer;
                                      (SEQ ID NO: 99)
5'-AAGGATCCATGTGCAATACCAACATGTCTGTACCTACTGATGGT
GC-3',
and MDM2 reverse primer;
                                      (SEQ ID NO: 100)
5'-TTCTCGAGTTAACCTGAGTCCGATGATTCCTGCTGATTG-3'.
```

Then, the amplification product thus obtained was cleaved with BamHI and XhoI, and inserted into phAG-MCLinker having been treated with the same restriction enzymes. Thus, phAG-MDM2 was prepared.

Figure 23:
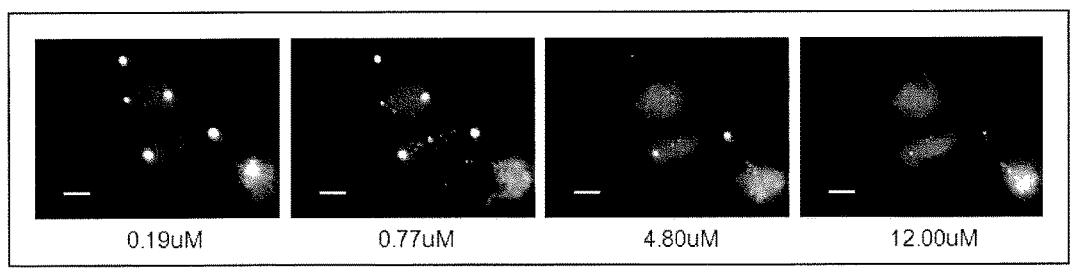
FIG. 23 shows micrographs for illustrating the result of analyzing a fluorescence intensity of a fluorescent focus in the presence of Nutlin-3 by expressing in cultured cells a fusion protein (p62(PB1)-p53) composed of p62(PB1) and a portion of p53, and a fusion protein (AG-MDM2) composed of an AG protein and MDM2. Note that Nutlin-3 is known as an inhibitor against an interaction between a p53 protein and an MDM2 protein. Moreover, in the figure, the scale bars at the lower left portions represent 10 μm.
Figure 24:
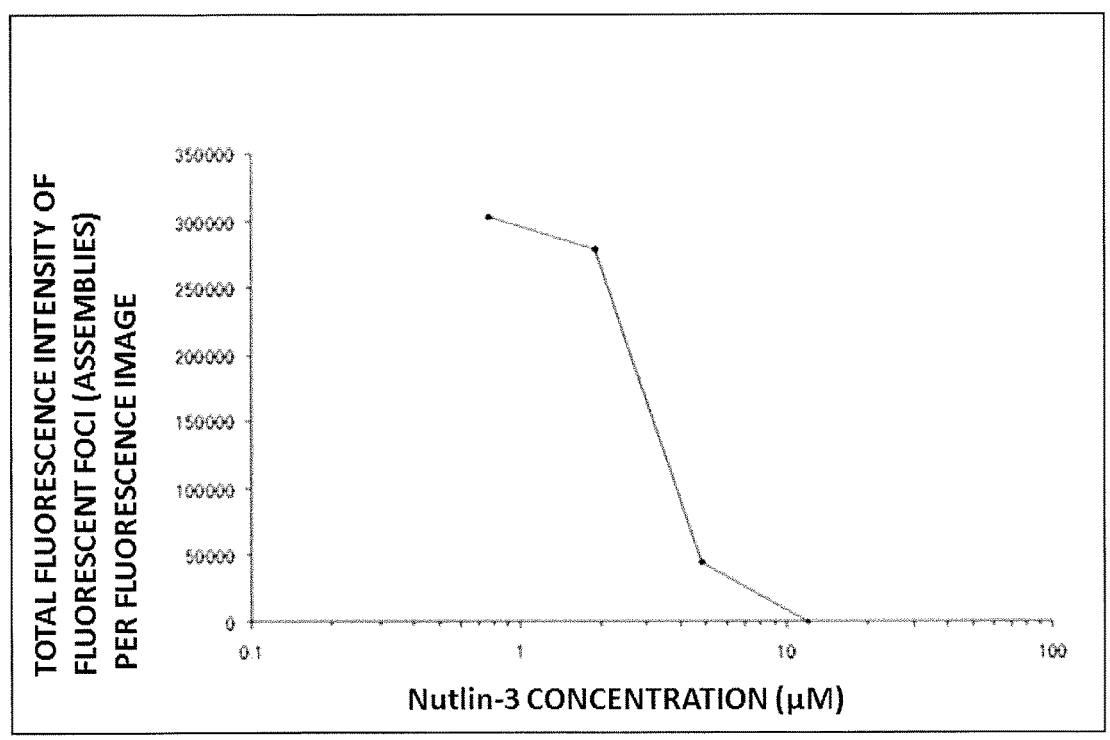
FIG. 24 is a graph for illustrating the result of analyzing whether or not the fluorescence intensity of the fluorescent focus formed by the association between p62(PB1)-p53 and AG-MDM2 is suppressed in a manner dependent on the Nutlin-3 concentration.

(Transfection into Cells, and Observation and Analysis of Transfected Cells)

pp62(PB1)-p53 and phAG-MDM2 were mixed in equal amounts and introduced into HeLaS3 cells by the same method as that described in Example 1. The culture solution was discarded 24 hours after the introduction, and 1.5 ml of an observation buffer containing 0.19 µM Nutlin-3 was added to the resultant. Fluorescence images were captured 15 minutes thereafter. Subsequently, the observation buffer was discarded, and 1.5 ml of an observation buffer containing 0.77 µM Nutlin-3 was added to the resultant. Fluorescence images were again captured 15 minutes thereafter. The same procedure was carried out using 4.8 µM and 12 µM Nutlin-3, as well. FIG. 23 shows the obtained result. Moreover, a total luminance of fluorescent foci (assemblies) in a fluorescence image of cells to which Nutlin-3 was added at predetermined concentrations was calculated to create a graph for illustrating a correlation with the Nutlin-3 concentration. FIG. 24 shows the obtained result. Note that, in FIG. 24, the X axis represents the concentration of Nutlin-3 added to the cells, and the Y axis represents the total luminance (total fluorescence intensity) of fluorescent foci per fluorescence image (one field of view).

As apparent from the result shown in FIG. 23, when p62(PB1)-p53 and AG-MDM2 were expressed in the cells, fluorescent foci were detected. Moreover, as a result of the stepwise increase in the concentration of the inhibitor (Nutlin-3) added against the interaction between p53 and MDM2, fluorescent foci (assemblies) were observed to be gradually extinguished within the same field of view, confirming that the fusion proteins constituting the assemblies were being dispersed. Further, as apparent from the result shown in FIG. 24, the fluorescence luminance of the fluorescent foci in the field of view was decreased in a manner dependent on the inhibitor concentration.

Example 13

<Detection 9 of Protein-Protein Interaction>

As in Example 11, whether or not the method of the present invention was utilizable in determining the IC50 of an inhibitor specific to a protein-protein interaction was evaluated by a method described below.

(Preparation of Plasmid DNA)

First, using phAG-MDM2 described in Example 12 and pFucci-S/G2/M Green-Hyg (manufactured by limited company Amalgaam Co., Ltd.), phAG-MDM2 Hyg was prepared according to a conventional method, so that the drug resistance gene was converted from a G418 resistance gene to a hygromycin B resistance gene.

(Preparation of Stably-Expressing Cell Line)

Next, the phAG-MDM2_Hyg and pp62(PB1)-p53 described in Example 12 were introduced into a CHO-K1 cell line. Note that CHO-K1 cells were cultured in NUTRIENT MIXTURE F-12 HAM (manufactured by SIGMA ALDRICH CO.) containing 10% FBS (manufactured by Equitech-Bio Inc.).

Then, 24 hours after the plasmid DNAs were introduced in the CHO-K1 cell line, the medium was replaced with one containing 100 µg/ml of G418 (manufactured by Wako Pure Chemical Industries, Ltd.) and 200 µg/ml of hygromycin (manufactured by Nacalai Tesque, Inc.). Further, cells survived after culturing for one week with this medium were monocloned by limiting dilution.

(Observation and Analysis of Transfected Cells)

After the nuclear staining on the monocloned cell line by the same method as that described in Example 11, an observation buffer containing Nutlin-3 (manufactured by CALBIOCHEM) at certain concentrations was added to each well, and incubated for 20 minutes. Note that Nutlin-3 was prepared and added in such a manner that the final concentration was 0.2 µM, 0.3 µM, 0.6 µM, 0.9 µM, 1.6 µM, 2.6 µM, 4.3 µM, 7.2 µM, 12.0 µM, or 20.0 µM.

Figure 25:
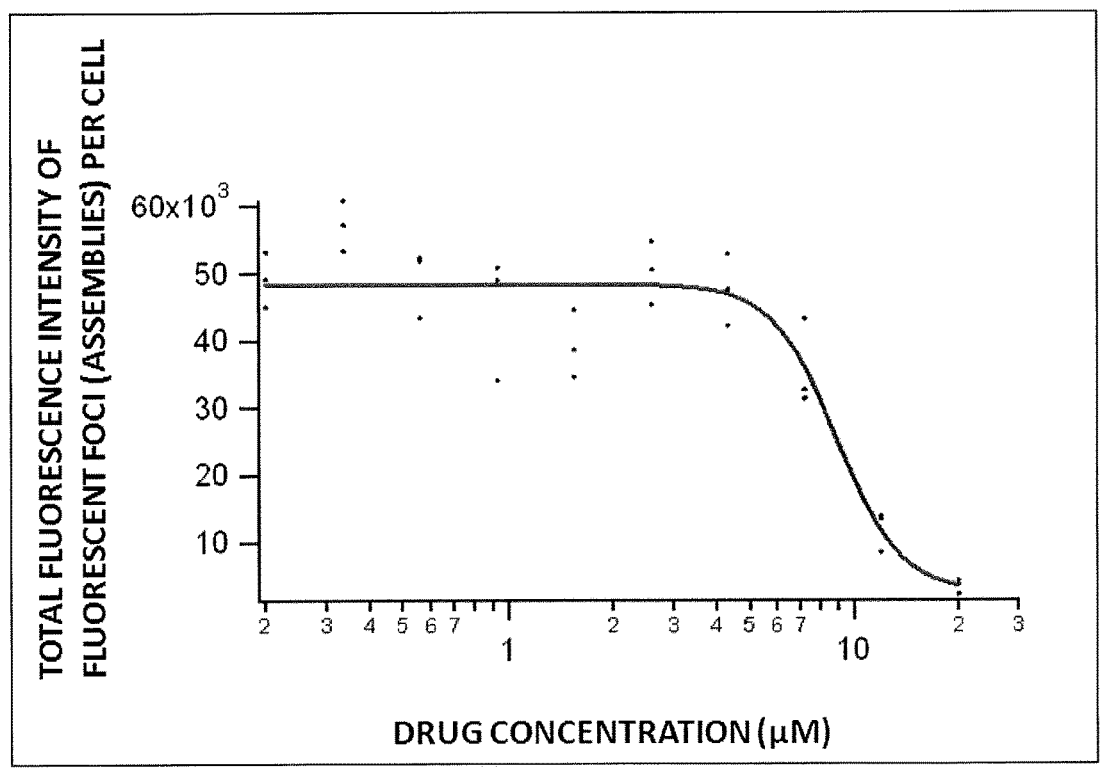
FIG. 25 is a graph for illustrating the result of analyzing whether or not the fluorescence intensity of the fluorescent focus formed by the association between p62(PB1)-p53 and AG-MDM2 is suppressed in a manner dependent on the Nutlin-3 concentration.

Subsequently, the cell line was fixed by the same method as that described in Example 11. An image of each well was obtained with a fluorescence microscope, and each fluorescence image was analyzed using iCY. A total luminance of fluorescent foci per cell was calculated to analyze a correlation with the concentration of Nutlin-3 added. FIG. 25 shows the obtained result. Note that, in FIG. 25, the X axis represents the concentration of the drug added to the cell line; the Y axis represents the total luminance (total fluorescence intensity) of fluorescent foci (assemblies) per cell; and dots represent measurement values. Moreover, a fitting curve drawn through the dots shows the analysis result using Igor®.

Although unillustrated, in CHO-K1 cells also stably expressing p62(PB1)-p53 and AG-MDM2, fluorescent foci (assemblies) attributable to a protein-protein interaction between p53 and MDM2 were observed as in Example 12.

Moreover, as shown in FIG. 25, the fluorescence luminance of these assemblies was decreased in a manner dependent on the concentration of the inhibitor Nutlin-3. Further, the IC50 of Nutlin-3 for the protein-protein interaction between p53 and MDM2 was 8.9 µM by the calculation according to f(x)=min+(max−min)/(1+(x/IC50)^hill) based on the fitting curve shown in FIG. 25.

The results described in Examples 10 to 13 above verified that the fluorescence luminance of the fluorescent focus according to the present invention reflected the strength of the protein-protein interaction, making quantification of the protein-protein interaction possible. Furthermore, it was also revealed that the assembly formation was reversible. It was demonstrated that the quantification was practicable by using fixed cells (see FIG. 20), and also using a live imaging technique with living cells (see FIG. 24). In addition, it was revealed as described in Examples 11 and 13 that the present invention enabled detection of a promoting reaction and an inhibiting reaction both dependent on the concentration of a drug for a protein-protein interaction, and further enabled calculations of the EC50 and the IC50 of the drug. Thus, it was demonstrated that the method for detecting a protein-protein interaction of the present invention was applicable to evaluation of and screening for a substance modulating a protein-protein interaction.

Example 14

<Detection 10 of Protein-Protein Interaction>

It has been known that p50 and p65 form a heterodimer, constituting NFκB. Further, NFκB functions in the nucleus as a transcription factor playing a role in modulating inflammatory cytokine expression. However, it has been known that the interaction with IκBα retains NFκB in the cytoplasm, suppressing the transcription function (see Marc D. Jacobs et al., Cell, Dec. 11, 1998, vol. 95, pp. 749 to 758). Thus, an overexpression of p50 and p65 disturbs the stoichiometric balance with endogenous IκBα, so that the heterodimer is localized mainly in the nucleus. On the other hand, if IκBα is overexpressed, the heterotrimer further including IκBα is retained in the cytoplasm.

For this reason, in this Example, whether or not the method of the present invention enabled detection of a change in intracellular localization of a complex containing p50 and p65 in accordance with the presence or absence of IκBα was tested by a method described below.

First, each of pp62(PB1)-p50 and phAG-p65 was prepared by the same method as that described in Example 2. DNAs (SEQ ID NOs: 155 and 157, respectively) encoding regions having the amino acid sequences of SEQ ID NOs: 156 and 158 had been inserted in the pp62(PB1)-p50 and the phAG-p65, respectively.

Meanwhile, pIκBα was prepared by the same method as that described in Example 1 using a DNA sequence encoding the amino acid sequence specified under Genbank ACCESSION No: NP 065390.1.

Figure 26:
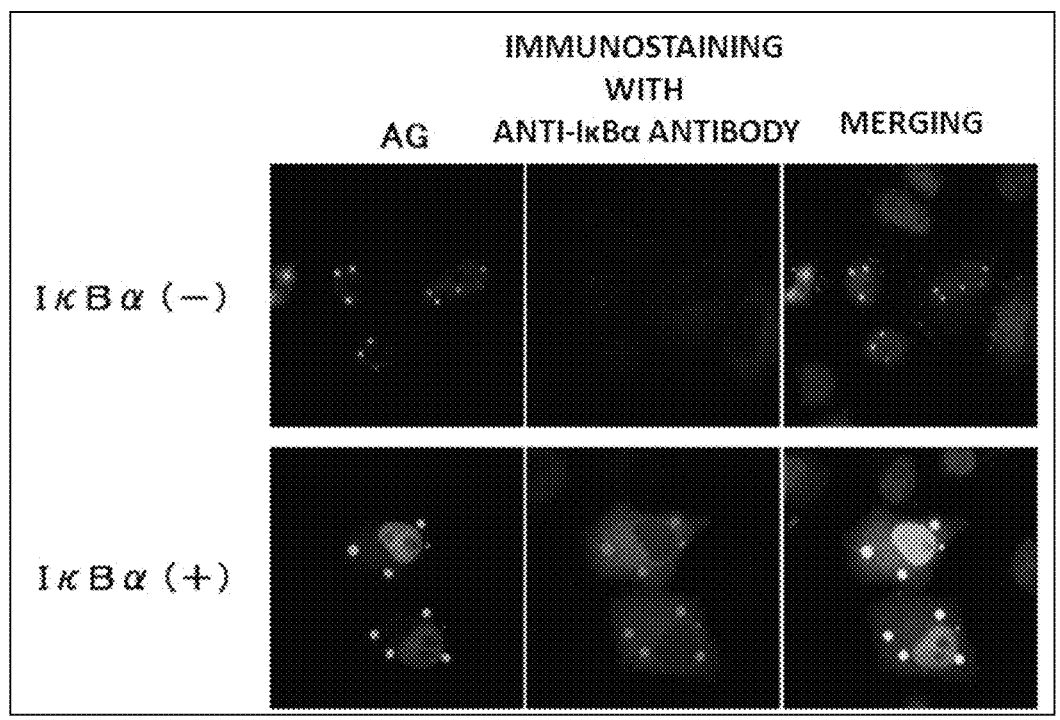
FIG. 26 shows micrographs for illustrating the result of observing cells expressing p62(PB1)-p50 and AG-p65 (IκBα (−)), and cells expressing p62(PB1)-p50, AG-p65, and IκBα (IκBα (+)). Note that p50 and p65 form a heterodimer, which is localized in the nucleus, and also localized in the cytoplasm by the interaction with IκBα. Moreover, in the figure, "AG" shows the result of detecting AG-derived fluorescence. "Immunostaining with anti-IκBα antibody" shows the result of observing cells subjected to this immunostaining. "Merging" shows the result of merging the "AG", the "immunostaining with anti-IκBα antibody," and the result of observing cells whose nuclei were stained with Hoechst 33342.

Then, HeLaS3 cells were seeded onto 4 wells in an 8-well chamber (manufactured by Nunc A/S). On the next day, the plasmid DNAs were introduced into these cells. In the transfection, 100 ng of each of pp62(PB1)-p50 and phAG-p65 was added to OptiMEM (manufactured by Life Technologies Corporation), and pIκBα was further added thereto in different amounts for the use. Note that the amounts of the pIκBα added were 0 ng (not added) or 100 ng. Further, to make total amounts of the plasmid DNAs added all equal, 300 ng or 0 ng of pmKeima-Red-S1 (manufactured by limited company Amalgaam Co., Ltd.) was added. Then, 1.5 µl of PolyFect® Transfection Reagent was added to each OptiMEM and stirred. Furthermore, after mixed with 200 µl of the culture solution, the resultant was added to the HeLaS3 cells. Subsequently, 22 hours after this transfection, the cells were fixed with 4% Paraformaldehyde Phosphate Buffer Solution (manufactured by Wako Pure Chemical Industries, Ltd.) at room temperature for 15 minutes. After the cell membranes were solubilized with 0.2% TritonX-100/PBS for 5 minutes, immunostaining was carried out using an anti-IκBα antibody (manufactured by Cell Signaling Technology, Inc.). Furthermore, the nuclei were stained using Hoechst 33342. Then, the immunostained cells were observed by the same method as that described in Example 1. FIG. 26 shows the obtained result. Note that, in the figure, "merging" shows the result of merging images of AG-derived fluorescence (two panels on the left in the figure), images showing the result of the immunostaining with the anti-IκBα antibody (two panels in the middles of the figure), and images showing the result of the nuclear staining with Hoechst 33342.

As apparent from the result shown in FIG. 26, it was confirmed that, in the cells into which IκBα was not introduced, heterodimers formed from p50 and p65 were formed in the nuclei. On the other hand, when IκBα was introduced, IκBα-derived signals were detected (see the lower panel in the middle of the figure) at the same locations as the fluorescent foci detected in the image of the AG-derived fluorescence (see the lower left panel in the figure), confirming that the complex containing p50 and p65 included IκBα. Further, the method of the present invention also confirmed that in the presence of IκBα, the localization of the complex containing p50 and p65 was changed from the inside of the nuclei to the inside of the cytoplasms.

Example 15

<Detection 11 of Protein-Protein Interaction>

In this Example, utilizing the complex containing p50 and p65 detected also in Example 14, whether or not the method of the present invention enabled quantitative detection of a change in intracellular localization of the complex in accordance with the quantitative balance with IκBα was tested by a method described below.

First, HeLaS3 cells were seeded onto 4 wells in an 8-well chamber (manufactured by Nunc A/S). Then, on the next day, pp62(PB1)-p50, phAG-p65, and pIκBα, which were described in Example 13, were introduced into these cells. In the transfection, 100 ng of each of pp62(PB1)-p50 and phAG-p65 added to OptiMEM (manufactured by Life Technologies Corporation), and the pIκBα was further added thereto in different amounts for the use. Note that the amounts of the pIκBα added were (0) not added, (1) 33 ng, (2) 100 ng, and (3) 300 ng. Further, to make total amounts of the plasmid DNAs added all equal, pmKeima-Red-S1 (manufactured by limited company Amalgaam Co., Ltd.) was added in amounts of: 300 ng in the case of (0); 267 ng, (1); 200 ng, (2); and 0 ng, (3). Then, 1.5 µl of PolyFect® Transfection Reagent was added to each OptiMEM and stirred. Furthermore, after mixed with 200 µl of the culture solution, the resultant was added to the HeLaS3 cells, and observed 22 hours thereafter by the same method as that described in Example 1.

Figure 27:
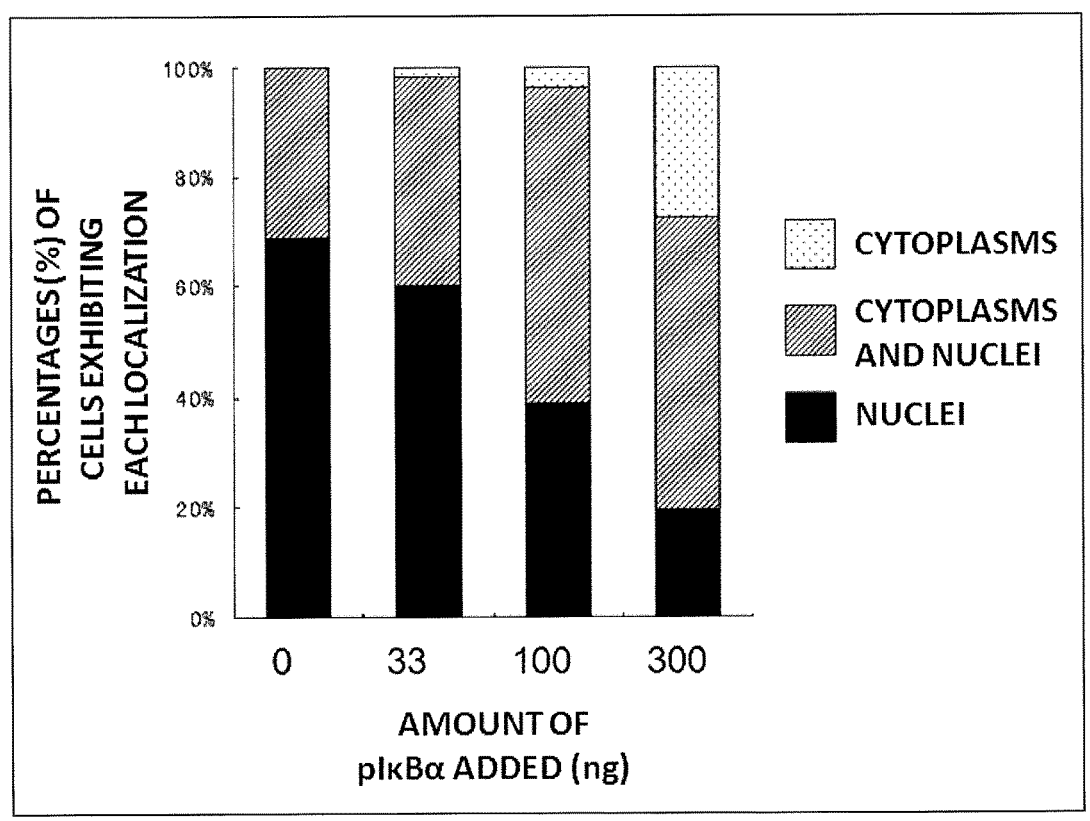
FIG. 27 is a graph for illustrating the result of analyzing whether or not intracellular localization of a fluorescent focus formed by an association between p62(PB1)-p50 and AG-p65 is changed in accordance with the amount of IκBα introduced to the cells (the amount of pIκBα added).

After 150 or more cells in which the plasmid DNAs were introduced under the (0) to (3) conditions were photographed, the cells were classified into three groups (A) to (C) according to the fluorescent focus localization. Specifically, cells are classified as (A) if fluorescent foci were detected only in the cytoplasms; (B), if detected in the cytoplasms and the nuclei; and (C), if detected only in the nuclei. Then, a percentage of the cell count in each group was calculated, and a graph was created. FIG. 27 shows the obtained result.

As apparent from the result shown in FIG. 27, the percentage of fluorescent foci detected in the cytoplasms was increased in a manner dependent on the IκBα amount. Thus, the present invention can provide a method for grouping cells according to fluorescent focus localization, and comparing the number of cells in each group. Further, it was revealed as described in Example 14 also that by utilizing localization of an interaction between direct detection targets, a first protein and a second protein (for example, p50 and p65), the method of the present invention enabled quantification of an influence of a third protein (for example, IκBα) on the interaction as well as the amount of the third protein expressed.

Example 16

<Detection 12 of Protein-Protein Interaction>

It has been known that, in the nucleus of a cell, p21 recognizes and interacts with a complex composed of CDK4 and Cyclin D1 (see LaBaer J et al., Genes Dev., Apr. 1, 1997, vol. 11, no. 7, pp. 847 to 862). Moreover, it has also been revealed that such heterotrimer formation inhibits cell-cycle progression (transition from a G1 phase to an S phase) otherwise promoted by a complex composed of CDK4 and Cyclin D1.

For this reason, in this Example, as in Examples 14 and 15, whether or not the present invention enabled detection of formation of a complex composed of three types of different proteins was tested by a method described below.

(Preparation of Plasmid DNA)

pp62(PB1)-CDK4, phAG-p21, and pCyclin D1 were prepared by the same method as that described in Example 1 on the basis of DNA sequences encoding the amino acid sequences specified under Genbank ACCESSION Nos: NP_000066.1, NP_000380.1, and NP_444284.1, respectively.

(Transfection into Cultured Cells, Cell Immunostaining, and Observation of Cells)

HeLaS3 cells were used as cultured cells into which the plasmid DNAs were introduced. Moreover, the HeLaS3 cells were cultured by the same method as that described in Example 1. Further, in the transfection, the HeLaS3 cells were seeded onto 2 wells of an 8-well chamber (manufactured by Nunc A/S). On the next day, by the same method as that described in Example 1, 130 ng of each plasmid DNA in the following combinations was introduced into the HeLaS3 cells using 1 μl of Transfection Reagent:

a combination of pp62(PB1)-CDK4 and phAG-p21 with pCyclin D1; and a combination of pp62(PB1)-CDK4 and phAG-p21 with phmKGC-MN (manufactured by limited company Amalgaam Co., Ltd.) (note that the phmKGC-MN was added to makes total amounts of the plasmids all equal).

Figure 28:
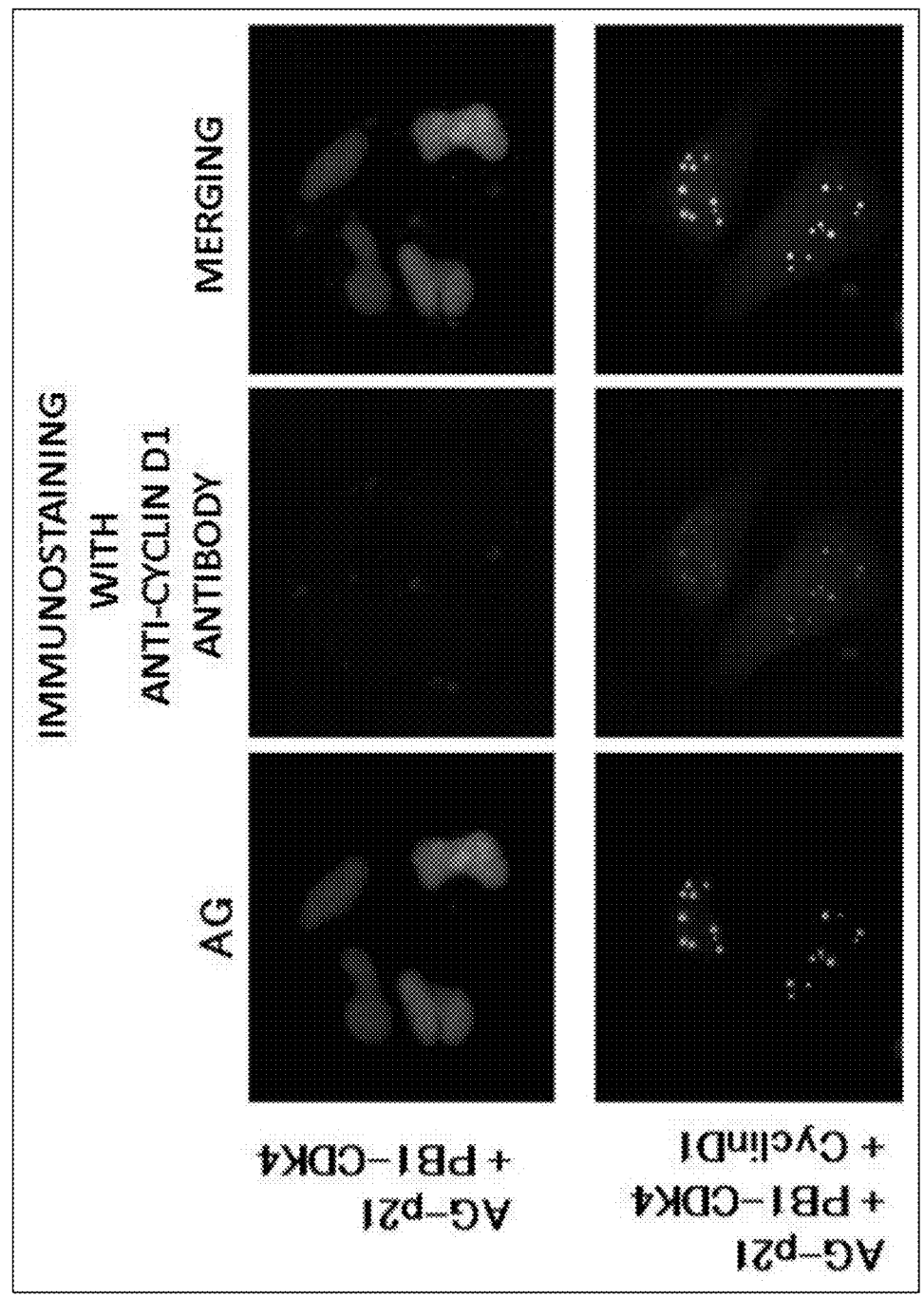
FIG. 28 shows micrographs for illustrating the result of observing cells co-expressing p62(PB1)-CDK4 and AG-p21 (AG-p21+PB1-CDK4), and cells expressing p62(PB1)-CDK4, AG-p21, and Cyclin D1 (AG-p21+PB1-CDK4+Cyclin D1). Note that p21 interacts with a complex composed of CDK4 and Cyclin D1. Moreover, in the figure, "AG" shows the result of detecting AG-derived fluorescence. "Immunostaining with anti-Cyclin D1 antibody" shows the result of observing cells subjected to this immunostaining. "Merging" shows the result of merging the "AG" and the "immunostaining with anti-Cyclin D1 antibody."

Then, 24 hours after the transfection, the cells were fixed with 4% Paraformaldehyde Phosphate Buffer Solution (manufactured by Wako Pure Chemical Industries, Ltd.) at room temperature for 15 minutes. After the cell membranes were solubilized with 0.2% TritonX-100/PBS for 5 minutes, immunostaining was carried out using 4 μg/ml of an anti-Cyclin D1 antibody (manufactured by MEDICAL & BIOLOGICAL LABORATORIES CO., LTD.). The immunostained cells were observed by the same method as that described in Example 1. FIG. 28 shows the obtained result.

As apparent from the result shown in FIG. 28, no clear assembly (fluorescent focus) was observed in many cells only by expressing p62(PB1)-CDK4 and AG-p21. Nevertheless, when Cyclin D1 was forcibly expressed together with p62(PB1)-CDK4 and AG-p21, this made possible stoichiometrically uniform expression of the elements necessary for the heterotrimer formation, and clear fluorescent foci were observed in almost all the cells. Further, the immunostaining images of Cyclin D1 confirmed that Cyclin D1 was localized in the observed fluorescent foci.

Thus, similarly to the results described in Examples 14 and 15, it was confirmed that the present invention enabled detection of a protein-protein interaction in formation of a complex of a trimer or a higher multimer.

Moreover, suppose a case where two types of proteins (p50 and p65 in Examples 14 and 15, CDK4 and p21 in Example 16) are expected to form a complex including a "certain molecule" (IκBα in Examples 14 and 15, Cyclin D1 in Example 16) as described above. In this case, if the two types of proteins are expressed in cells as a "first fusion protein comprising an association-inducing protein" and a "second fusion protein comprising a fluorescent protein having a multimerization ability" respectively, and a protein encoded by a cDNA expression library is further expressed in the cells, the present invention makes it possible to search for the "certain molecule" (constitutional factor of the complex) on the basis of a fluorescent focus (for example, formation or extinction a fluorescent focus, a change in fluorescent focus localization).

Further, as described in Examples 14 to 16, the present invention makes it possible to analyze an expressed amount of a constitutional factor (IκBα in Examples 14 and 15, Cyclin D1 in Example 16) of a complex on the basis of a fluorescent focus, and eventually, by utilizing the expressed amount, to analyze states of cells, such as a cell cycle controlled by the complex and a stress to which the complex is to respond.

Example 17

<Detection 13 of Protein Interaction>

As described in Examples 10 to 13, it was revealed that the fluorescence intensity of the fluorescent focus according to the present invention reflected a strength of a protein-protein interaction. Thus, the method for detecting a protein-protein interaction of the present invention presumably is capable of identifying an amino acid important for the interaction on the basis of the fluorescence intensity of the fluorescent focus according to the present invention. For this reason, a test was conducted by a method described below, utilizing an amino acid mutation known to be involved in reduction or enhancement of a protein-protein interaction.

Note that the detection target in this test was an interaction between a Sec5 protein and a RalB protein. A Sec5 protein has been known to interact with a RalB protein in a GTP-activated form (see Moskalenko S et al., Nat Cell Biol., January 2002, vol. 4, no. 1, pp. 66 to 72). It has been known that the interaction is reduced with an inactive mutant RalB(S28N) of RalB, but enhanced with an active mutant RalB(Q72L) of RalB(see Shipitsin M et al., Mol Cell Biol., July 2004, vol. 24, iss. 13, pp. 5746 to 5756). Further, a RalB protein, which is a membrane-anchored protein, has been revealed to be localized at the cell membranes by palmitoylation of the C-terminus thereof.

(Preparation of Plasmid DNA)

In preparing pp62(PB1)-Sec5, first, a DNA encoding a portion of Sec5 (region having the 1st to 99th amino acids of the Sec5 protein, the region had the amino acid sequence of SEQ ID NO: 30) (the DNA had the base sequence of SEQ ID NO: 29) was amplified from the cDNA library of HeLaS3 cells by PCR using the following primer set:

```
Sec5 forward primer;
                                        (SEQ ID NO: 101)
5'-CCCGGATCCATGTCTCGATCACGACAACCC-3',
and Sec5 reverse primer;
                                        (SEQ ID NO: 102)
5'-GGGAAGCTTTTATTAGCCTATTTTCTCAGGTTTGAGTA-3'.
```

Then, the amplification product thus obtained was cleaved with BamHI and HindIII, and inserted into pp62(PB1)-MCLinker having been treated with the same restriction enzymes. Thus, pp62(PB1)-Sec5 was prepared. Note that the pp62(PB1)-Sec5 encodes a fusion protein composed of p62(PB1) and a partial Sec5 protein (the fusion protein may also be referred to as "p62(PB1)-Sec5").

Meanwhile, in preparing phAG-RalB(WT), first, a DNA encoding RalB(protein having the amino acid sequence of SEQ ID NO: 32) (the DNA had the base sequence of SEQ ID NO: 31) was amplified from the cDNA library of HeLaS3 cells by PCR using the following primer set:

```
RalB forward primer;
                                        (SEQ ID NO: 103)
5'-CCCGGATCCATGGCTGCCAACAAGAGTAAG-3',
and RalB reverse primer;
                                        (SEQ ID NO: 104)
5'-GGGAAGCTTTTATCATAGTAAGCAACATCTTTC-3'.
```

Then, the amplification product thus obtained was cleaved with BamHI and HindIII, and inserted into phAG-MCLinker having been treated with the same restriction enzymes. Thus, phAG-RalB(WT) was prepared. Note that the phAG-RalB(WT) encodes a fusion protein composed of an AG protein and a RalB protein (the fusion protein may also be referred to as "AG-RalB(WT)").

Further, phAG-RalB(Q72L) was prepared using phAG-RalB(WT) as a template, and AMAP™ Multi Site-directed Mutagenesis Kit (manufactured by limited company Amalgaam Co., Ltd.), and according to the attached instruction, a mutation was introduced using the following primer:

```
RalB(Q72L) primer;
                                        (SEQ ID NO: 105)
5'-CTGGACACCGCTGGGCTAGAGGACTACGCAGCCA-3'.
```

Note that the amino acid sequence of a RalB(Q72L) protein is shown in SEQ ID NO: 34. Moreover, the base sequence of a DNA encoding the protein is shown in SEQ ID NO:33. Further, phAG-RalB(Q72L) encodes a fusion protein composed of an AG protein and a RalB(Q72L) protein (the fusion protein may also be referred to as "AG-RalB(Q72L)").

In addition, phAG-RalB(S28N) was prepared using phAG-RalB(WT) as a template, and AMAP™ Multi Site-directed Mutagenesis Kit, and according to the attached instruction, a mutation was introduced using the following primer:

```
RalB(S28N) primer;
                                        (SEQ ID NO: 106)
5'-CAGCGGAGGCGTTGGCAAGAACGCCCTGACGCTTCAGTTCA-3'.
```

Note that the amino acid sequence of a RalB(S28N) protein is shown in SEQ ID NO: 36. Moreover, the base sequence of a DNA encoding the protein is shown in SEQ ID NO: 35. phAG-RalB(S28N) encodes a fusion protein composed of an AG protein and a RalB(S28N) protein (the fusion protein may also be referred to as "AG-RalB(S28N)").

(Transfection into Cultured Cells, and Observation of Transfected Cells)

Each of the following combinations of the plasmid DNAs was mixed in equal amounts and introduced into HeLaS3 cells by the same method as that described in Example 1:

a combination of pp62(PB1)-Sec5 with phAG-RalB (WT);

a combination of pp62(PB1)-Sec5 with phAG-RalB (Q72L);

a combination of pp62(PB1)-Sec5 with phAG-RalB (S28N); and a combination of pp62(PB1) with phAG-RalB(WT).

Figure 29:
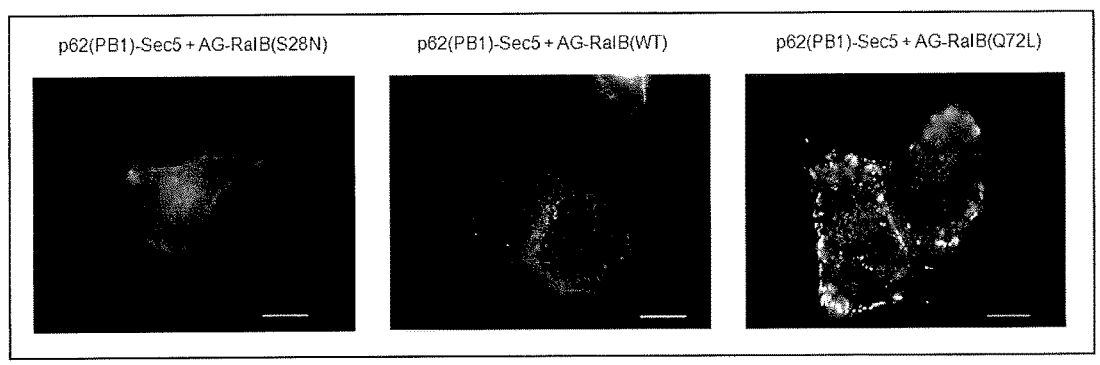
FIG. 29 shows micrographs for illustrating the result of analyzing a fluorescence intensity and localization of a fluorescent focus by expressing in cultured cells the following fusion-protein combinations. Note that, in the figure, the scale bars at the lower right portions represent 20 μm: a combination of a fusion protein (p62(PB1)-Sec5) composed of p62(PB1) and a portion of a Sec5 protein with a fusion protein (AG-RalB(WT)) composed of an AG protein and a RalB protein (wildtype); a combination of p62(PB1)-Sec5 with a fusion protein (AG-RalB(S28N)) composed of an AG protein and a RalB protein (inactive mutant); and a combination of p62(PB1)-Sec5 with a fusion protein (AG-RalB(Q72L)) composed of an AG protein and a RalB protein (active mutant). Note that a Sec5 protein is known to interact with a RalB protein in a GTP-activated form. Moreover, it is known that the interaction is reduced with an inactive mutant RalB(S28N) of RalB, but enhanced with an active mutant RalB(Q72L) of RalB. Further, it has also been revealed that a RalB protein is localized at the cell membrane by palmitoylation of the C-terminus thereof.
Figure 30:
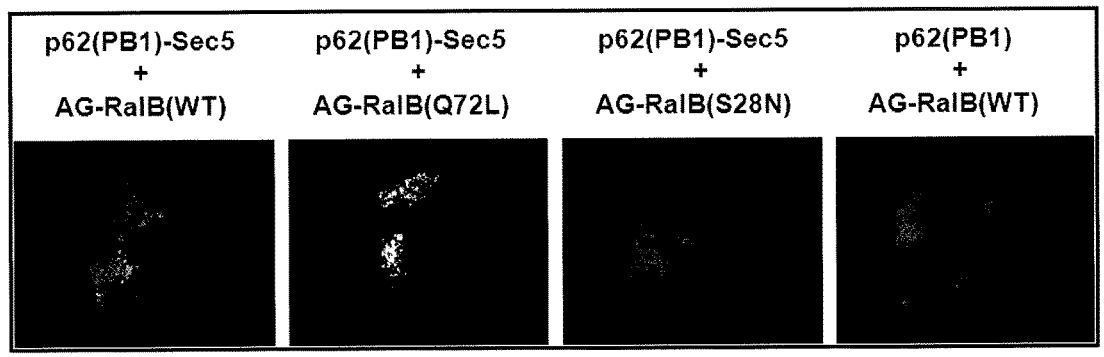
FIG. 30 shows micrographs for illustrating the result of detecting fluorescence only in the vicinity of the cell membrane by expressing in cultured cells the following fusion-protein combinations: a combination of p62(PB1)-Sec5 with AG-RalB(WT); a combination of p62(PB1)-Sec5 with AG-RalB(Q72L); a combination of p62(PB1)-Sec5 with AG-RalB(S28N); and a combination of p62(PB1) with AG-RalB(WT).

Moreover, the transfected cells were observed also by the same method as that described in Example 1. FIG. 29 shows the obtained result. Further, images were obtained using a total internal reflection fluorescence microscopy system with arc lamp source (manufactured by Olympus Corporation, IX71-ARCEVA) capable of exciting only the vicinity of the cell membrane. FIG. 30 shows the obtained result.

As apparent from the result shown in FIG. 29, since the RalB protein having the C-terminus palmitoylated was localized at the cell membranes, when the wildtype RalB protein (RalB(WT)) was expressed, fluorescent foci derived from the interaction with the Sec5 protein were detected in the vicinity of the cell membranes. On the other hand, no fluorescent focus was detected in the cells co-expressing p62(PB1)-Sec5 and AG-RalB(S28N). It was confirmed as described above that the inactive mutant RalB(S28N) of RalB reduced the interaction with the Sec5 protein. Moreover, in the cells co-expressing p62(PB1)-Sec5 and AG-RalB(Q72L), fluorescent foci were detected, which had a higher fluorescence intensity (luminance) than that in the cells co-expressing p62(PB1)-Sec5 and AG-RalB(WT). It was also confirmed as described above that the active mutant RalB(Q72L) of RalB enhanced the interaction with the Sec5 protein.

Further, as apparent from the result shown in FIG. 30, in the cells co-expressing p62(PB1)-Sec5 and AG-RalB(WT), assemblies were observed. The result shown in FIG. 30 was a result of using the observation system capable of exciting only the vicinity of the cell membrane. Thus, similarly to the result shown in FIG. 29, it was verified that the method of the present invention enabled detection of the interaction between the wildtype RalB protein and the Sec5 protein in the vicinity of the cell membranes.

Furthermore, as apparent from the result shown in FIG. 30, in the cells co-expressing p62(PB1)-Sec5 and AG-RalB (Q72L), more significant assembly formation was observed. On the other hand, in the cells co-expressing p62(PB1)-Sec5 and AG-RalB(S28N), no assembly was observed. Thus, similarly to the result shown in FIG. 29, it was verified that the method of the present invention enabled detection of reduction of the interaction with the Sec5 protein by RalB (S28N), and enhancement of the interaction by RalB(Q72L).

Example 18

<Detection 14 of Protein Interaction>

As in Example 17, a test was conducted by a method described below, using an amino acid mutation known to be involved in reduction of a protein-protein interaction.

(Preparation of Plasmid DNA)

pp62(PB1)-p53_W23L was prepared by introducing a mutation into pp62(PB1)-p53 described in Example 12 by the same method as that described in Example 17 using a primer having the base sequence of SEQ ID NO: 159 (5'-ACATTTTCAGACCTATTGAAACTACTTCCT-GAAAACAACGT-3').

Note that the amino acid at position 23 of p53 is located at an interaction interface site between p53 and MDM2. Further, a "W23L" mutation of p53 has been known as a mutation resulting in reduction of the interaction (see literature Zondlo S C, Biochemistry., Oct. 3, 2006, vol. 45, no. 39, pp. 11945 to 11957).

(Transfection into Cultured Cells, and Observation of Transfected Cells)

Figure 31:
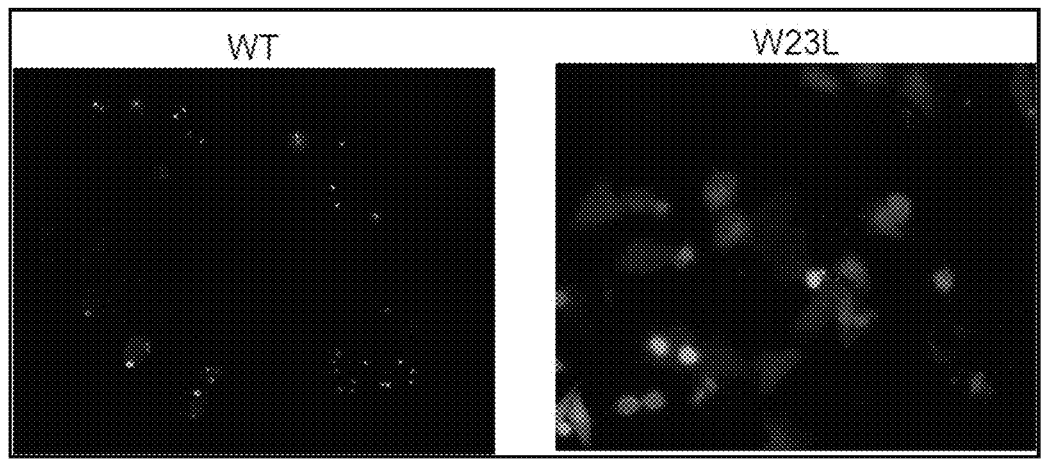
FIG. 31 shows micrographs for illustrating the result of observing cells (WT) co-expressing p62(PB1)-p53 and AG-MDM2, and cells (W23L) co-expressing p62(PB1)-p53_W23L and AG-MDM2. Note that the amino acid at position 23 of p53 is located at an interaction interface site between p53 and MDM2, and a W23L mutation of p53 reduces the interaction.

Each of the following combinations of the plasmid DNAs was mixed in equal amounts and introduced into cells by the same method as that described in Example 1, and the cells were observed. FIG. 31 shows the obtained result. A combination of pp62(PB1)-p53 with phAG-MDM2. A combination of pp62(PB1)-p53_W23L with phAG-MDM2.

As apparent from the result shown in FIG. 31, in the cells co-expressing p62(PB1)-p53 and AG-MDM2, fluorescent foci (assembly formation) were significantly observed (the left panel in the figure). On the other hand, in the cells co-expressing p62(PB1)-p53_W23L and AG-MDM2, no assembly was observed (the right panel in the figure).

Thus, as described in Examples 17 and 18, it was revealed that the method for detecting a protein-protein interaction of the present invention was also capable of identifying the amino acid important for the interaction on the basis of the fluorescence intensity of the fluorescent focus according to the present invention. Particularly, the method of the present invention is capable of very easily specifying an amino acid involved in a protein-protein interaction by introducing a mutation into an interface of the interaction and detecting the presence or absence of the interaction. In other words, combining a method for introducing a mutation into a protein such as alanine scanning with the method of the present invention makes it possible to search for a site (hot spot) important for a protein interaction very easily.

Example 19

<Detection 15 of Protein-Protein Interaction>

As described above, it was demonstrated that the method for detecting a protein-protein interaction of the present invention enabled quantitative measurement of when a protein-protein interaction took place and ended in real time. Hence, a test was conducted regarding whether or not the use of the method of the present invention enabled detection of how an endogenous signal transduction in cells changed over time, according to a protein-protein interaction that took place in response to the signal.

Figure 32:
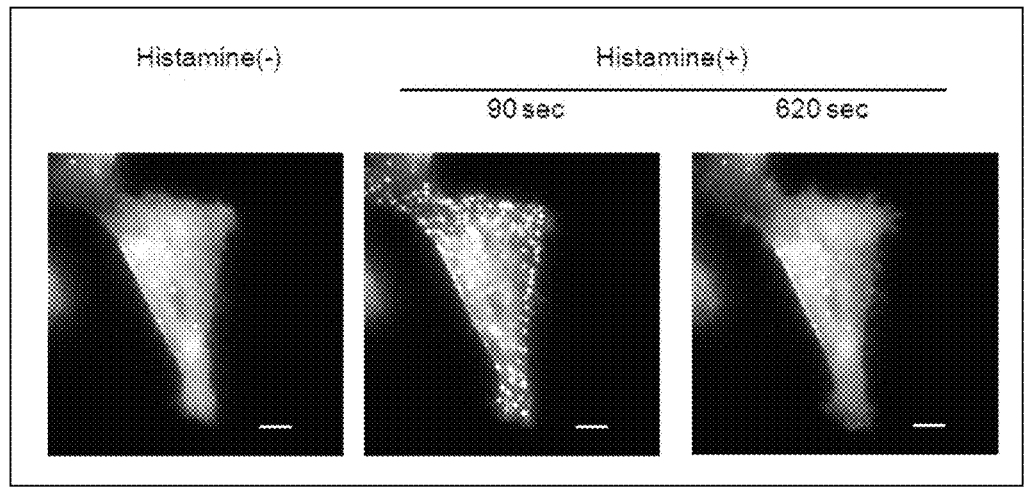
FIG. 32 shows micrographs for illustrating the result of observing formation and extinction of a fluorescent focus formed by an association between a fusion protein (Calmodulin-AG) composed of a calmodulin protein and an AG protein, and a fusion protein composed (M13peptide-p62(PB1)) of a partial sequence (M13 peptide) of myosin light chain kinase 2 and p62(PB1), before histamine addition, 90 seconds after the addition, and 620 seconds after the addition. Note that, in the figure, the scale bars at the lower right portions represent 5 μm. Moreover, it has been revealed that an interaction between calmodulin and an M13 peptide takes place in response to a transient increase in intracellular calcium ion concentration that occurs when a G protein-coupled receptor (GPCR) receives a ligand (for example, histamine).

Specifically, the protein-protein interaction as the detection target in this test was an interaction between calmodulin and a partial sequence (M13 peptide) of myosin light chain kinase 2. It has been revealed that the interaction takes place in response to a transient increase in intracellular calcium ion concentration (second messenger) that occurs when a G protein-coupled receptor (GPCR) receives a ligand (see Miyawaki A et al., Nature, Aug. 28, 1997, vol. 388, no. 6645, pp. 882 to 887). Hence, whether or not it was possible to detect a change in intracellular calcium ion concentration over time according to the interaction was tested by a method described below. FIG. 32 shows the obtained result.

(Preparation of Plasmid DNAs)

In preparing pCalmodulin-hAG, first, a DNA encoding calmodulin (protein having the amino acid sequence of SEQ ID NO: 38) (the DNA had the base sequence of SEQ ID NO: 37) was amplified from the cDNA library of HeLaS3 cells by PCR using the following primer set:

```
calmodulin forward primer;
                                    (SEQ ID NO: 107)
5'-TTGGATCCGCCACCATGGACCAACTGACAGAAGAGCAGATTGC-3',
and calmodulin reverse primer;
                                    (SEQ ID NO: 108)
5'-AAGAATTCCCCTTTGCTGTCATCATTTGTACAAACTCTTC-3'
```

Then, the amplification product thus obtained was cleaved with BamHI and EcoRI, and inserted into phAG-MNLinker having been treated with the same restriction enzymes. Thus, pCalmodulin-hAG was prepared. Note that the pCalmodulin-hAG encodes a fusion protein composed of a calmodulin protein and an AG protein (the fusion protein may also be referred to as "Calmodulin-AG").

Meanwhile, in preparing pM13peptide-p62(PB1), first, a DNA encoding a portion of myosin light chain kinase 2 (region having the 566th to 591st amino acids of the myosin light chain kinase 2 protein, the region had the amino acid sequence of SEQ ID NO: 40) (the DNA had the base sequence of SEQ ID NO: 39) was amplified from the cDNA library of HeLaS3 cells by PCR using the following primer set:

```
M13 peptide forward primer;
                                    (SEQ ID NO: 109)
5'-TTGGATCCGCCACCATGAAGAGGCGCTGGAAGAAAAACTTCA
TTGC-3',
and M13 peptide reverse primer;
                                    (SEQ ID NO: 110)
5'-CCGAATTCCCCAGTGCCCCGGAGCTGGAGATCTTCTTG-3'.
```

Then, the amplification product thus obtained was cleaved with BamHI and EcoRI, and inserted into pp62(PB1)-MNLinker having been treated with the same restriction enzymes. Thus, pM13peptide-p62(PB1) was prepared. Note that the pM13peptide-p62(PB1) encodes a fusion protein composed of an M13 peptide and p62(PB1) (the fusion protein may also be referred to as "M13peptide-p62(PB1)").

(Transfection into Cultured Cells, and Observation of Transfected Cells)

pCalmodulin-hAG and pM13peptide-p62(PB1) were mixed in equal amounts and introduced into HeLaS3 cells by the same method as that described in Example 1. Then, 200 µM histamine (manufactured by Wako Pure Chemical Industries, Ltd.) was added thereto, and fluorescence images were captured over time. Note that it has been revealed that histamine functions as a ligand of an H1 receptor, one of GPCRs, which is expressed also in HeLaS3 cells.

As apparent from the result shown in FIG. 32, before the ligand (histamine) was added, Calmodulin-AG was present in a dispersed manner in the cells. Meanwhile, 90 seconds after the ligand was added, fluorescent focus formation was detected, confirming the assembly formation with M13peptide-p62(PB1). Nevertheless, 490 seconds after the cytoplasm calcium ion concentration was decreased, the fluorescent foci (assemblies) were extinguished.

Thus, it was revealed that the use of the method for detecting a protein-protein interaction of the present invention enabled real-time measurement of the calcium ion concentration transiently increased by the signal transduction from the H1 receptor.

Moreover, the result of this Example 19 also demonstrated that the present invention enabled detection of the transient protein-protein interaction, further that the present invention was applicable to detection of and screening for: an endogenous factor such as a second messenger causing a protein-protein interaction; a signal transduction to which the second messenger or the like contributed; and a stimulus from the outside such as an extracellular ligand eliciting the signal transduction.

Example 20

<Detection 16 of Protein-Protein Interaction>

In conventional methods for detecting a protein-protein interaction represented by WO2000/017221 A and WO2006/099486 A, one of proteins constituting a complex formed by a protein-protein interaction is forcibly (artificially) confined in a particular region in a cell. Accordingly, the detection was impossible in an intracellular environment unique to the interaction. In contrast, in the method for detecting a protein-protein interaction of the present invention, fluorescent foci (assemblies) are autonomously formed only when an interaction takes place. Hence, it is expected that the problems in the conventional method can be solved. For this reason, whether or not the present invention enabled detection of an interaction in any region in a cell was tested by a method described below.

(Preparation of Plasmid DNA)

In preparing pmTOR(FRB domain)-AGNLS, first, an AGNLS gene was amplified from pNP-AG (manufactured by limited company Amalgaam Co., Ltd.) by PCR using the following primer set:

```
AGNLS forward primer;
                                (SEQ ID NO: 111)
5'-AAACCGGTATGGTGAGTGTGATTAAACCAGAG-3',
and AGNLS reverse primer;
                                (SEQ ID NO: 112)
5'-AATCTAGATTATTTATCCTTTTCCTTTTTACTCTTCTTCTTAG
CTACTTC-3'.
```

Then, the amplification product thus obtained was cleaved with AgeI and XbaI, and inserted into pmTOR(FRB domain)-hAG having been treated with the same restriction enzymes to cut out a hAG region therefrom. Thus, pmTOR (FRB domain)-AGNLS was prepared. Note that the pmTOR (FRB domain)-AGNLS encodes a fusion protein composed of mTOR(FRB domain), an AG protein, and a nuclear localization signal (NLS) (the fusion protein may also be referred to as "mTOR(FRB domain)-AGNLS"). Moreover, mTOR(FRB domain)-AGNLS is to be localized in the nucleus of a cell because the nuclear localization signal is fused to the C-terminus of the mTOR(FRB domain)-AG.

Meanwhile, in preparing pp62(PB1)-HRas, first, a DNA encoding an HRas protein was amplified from the cDNA library of HeLaS3 cells by PCR using the following primer set. The amplification product thus obtained was cleaved with EcoRI and XhoI.

```
HRas forward primer;
                                (SEQ ID NO: 113)
5'-AAGAATTCGATGACGGAATATAAGCTGGTGGTGGTGGGCGCCGT
CGGTGTGGGCAAGAGTGC-3',
and HRas reverse primer;
                                (SEQ ID NO: 114)
5'-TTCTCGAGACCTCCGGAGACGTTCAGCTTCCGCAGCTTGTGCTG
CCGGATCTCACGCACCAAC-3'.
```

Further, a prenylated sequence derived from a KRas protein was amplified by PCR using the following primer set. The amplification product thus obtained was cleaved with XhoI and NotI.

```
KRas forward primer;
                                (SEQ ID NO: 115)
5'-AACTCGAGAAGATGAGCAAAGATGGTAAAAAGAAGAAAAAGAAG
TCAAAGACAAAGTGTG-3',
and KRas reverse primer;
                                (SEQ ID NO: 116)
5'-TTGCGGCCGCTTACATAATTACACACTTTGTCTTTGACTTCTTT
TTCTTCTTTTTACCAT-3'.
```

Then, the two DNA fragments prepared in this manner were inserted into pp62(PB1)-MCLinker having been treated with EcoRI and NotI. Thus, pp62(PB1)-HRas(WT) was prepared.

Furthermore, pp62(PB1)-HRas encoding a fusion protein composed of a constitutively-active mutant HRas and p62 (PB1) was prepared by introducing a mutation using pp62 (PB1)-HRas(WT) as a template, and AMAP™ Multi Site-directed Mutagenesis Kit (manufactured by limited company Amalgaam Co., Ltd.) according to the attached instruction, with the following primer:

```
HRas mutant primer;
                                (SEQ ID NO: 117)
5'-GCTGGTGGTGGTGGGCGCCGTCGGTGTGGGCAAGAGTGCGC-3'.
```

Note that the pp62(PB1)-HRas encodes a protein obtained by fusing p62(PB1) with a DNA encoding HRas having the C-terminus to which the KRas protein-derived prenylated sequence is added (the protein had the amino acid sequence of SEQ ID NO: 42) (the DNA had the base sequence of SEQ ID NO: 41). Moreover, since having the prenylated sequence, this fusion protein is subjected to post-translation lipid modification in cells, and localized at the cell membranes.

In preparing phAG-cRaf, first, a DNA encoding a portion of cRaf (region having the 51st to 131st amino acids of the cRaf protein, the region had the amino acid sequence of SEQ ID NO: 44) (the DNA had the base sequence of SEQ ID NO: 43) was amplified by PCR using the cDNA library of HeLaS3 cells as a template and the following primer set:

```
cRaf forward primer;
                                (SEQ ID NO: 118)
5'-AAGGTACCCCTTCTAAGACAAGCAACACTATCCGTGTTTTCTT
GCCGAACAAGCAAAGAA-3',
and
```

-continued

```
cRaf reverse primer 71;
                                         (SEQ ID NO: 119)
5'-TTAAGCTTTTACAGGAAATCTACTTGAAGTTCTTCTCCAATCA
AAGACGCAG-3'.
```

Then, the amplification product thus obtained was cleaved with KpnI and HindIII, and inserted into phAG-MCLinker having been treated with the same restriction enzymes. Thus, phAG-cRaf was prepared. Note that the phAG-cRaf is a fusion protein composed of an AG protein and a portion of a cRaf protein (the fusion protein may also be referred to as "AG-cRaf"). Moreover, the portion of a cRaf protein has been known to interact with an HRas protein (see Mochizuki N et al., Nature, Jun. 28, 2001, vol. 411, no. 6841, pp. 1065 to 1068).

Further, in preparing pSmac-p62(PB1), first, a DNA encoding a fusion protein composed of a portion of Smac (region having the 1st to 10th amino acids of the Smac protein, the region had the amino acid sequence of SEQ ID NO: 46) and p62(PB1) was amplified from pp62(PB1)-MNL by PCR using the following primer set:

```
Smac forward primer;
                                         (SEQ ID NO: 120)
5'-AGGATCCGCCACCATGGCCGTGCCCATCGCCCAGAAATCAGAG
AATTCGG-3',
and p62(PB1) reverse primer 2;
                                         (SEQ ID NO: 64)
5'-ACCTCTAGATTATTTCTCTTTAATGTAGATTCGGAAGATG-3'
```

Then, the amplification product thus obtained was cleaved with BamHI and XbaI, and inserted into pp62(PB1)-MNL having been treated with the same restriction enzymes to cut out the linker and p62(PB1) therefrom. Thus, pSmac-p62(PB1) was prepared. Note that the pSmac-p62(PB1) encodes a fusion protein composed of a portion of Smac and p62(PB1) (the fusion protein may also be referred to as "Smac-p62(PB1)").

In addition, in preparing pXIAP-hAG, first, a DNA encoding a portion of XIAP (region having the 243rd to 356th amino acids of the XIAP protein, the region had the amino acid sequence of SEQ ID NO: 48) (the DNA had the base sequence of SEQ ID NO: 47) was amplified from the cDNA library of HeLaS3 cells by PCR using the following primer set:

```
XIAP forward primer;
                                         (SEQ ID NO: 121)
5'-TTGGATCCGCCACCATGGCTGTGAGTTCTGATAGGAATTTCCC
AAATTC-3',
and XIAP reverse primer;
                                         (SEQ ID NO: 122)
5'-TTGAATTCTCAGTAGTTCTTACCAGACACTCCTCAAGTGAATG
AG-3'.
```

Then, the amplification product thus obtained was cleaved with BamHI and EcoRI, and inserted into phAG-MNLinker having been treated with the same restriction enzymes. Thus, pXIAP-hAG was prepared. Note that the pXIAP-hAG encodes a fusion protein composed of a portion of XIAP and an AG protein (the fusion protein may also be referred to as "XIAP-AG"). Moreover, it has been known that the portion of Smac and the portion of XIAP interact with each other in the cytoplasm (see Liu Z et al., Nature, Dec. 21-28, 2000, vol. 408, no. 6815, pp. 1004 to 1008).

Further, in preparing pp62(PB1)-BclX(L), first, a DNA encoding a portion of BclX(L) (region having the 1st to 209th amino acids of the BclX(L) protein, the region had the amino acid sequence of SEQ ID NO: 50) (the DNA had the base sequence of SEQ ID NO: 49) was amplified from the cDNA library of HeLaS3 cells by PCR using the following primer set:

```
BclX(L) forward primer;
                                         (SEQ ID NO: 123)
5'-TTCTCGAGGATGTCTCAGAGCAACCGGGAGCTGGTGGTTGAC-3',
and BclX(L) reverse primer;
                                         (SEQ ID NO: 124)
5'-CTAAGCGGCCGCTTAGCGTTCCTGGCCCTTTCGGCTCTCGGCTG-3'.
```

Then, the amplification product thus obtained was cleaved with XhoI and NotI, and inserted into pp62(PB1)-MCLinker having been treated with the same restriction enzymes. Thus, pp62(PB1)-BclX(L) was prepared. Note that the pp62(PB1)-BclX(L) encodes a fusion protein composed of p62(PB1) and a portion of BclX(L) (the fusion protein may also be referred to as "p62(PB1)-BclX(L)").

In addition, in preparing phAG-BAD, first, a DNA encoding a portion of BAD (region having the 103rd to 127th amino acids of the BAD protein, the region had the amino acid sequence of SEQ ID NO: 52) (the DNA had the base sequence of SEQ ID NO: 51) was amplified by PCR using the following primer set:

```
BAD forward primer 1;
                                         (SEQ ID NO: 125)
5'-GCAGCACAGCGCTATGGCCGCGAGCTCCGGAGGATGAGTGACGAG
TTTGT-3', BAD forward primer 2;
                                         (SEQ ID NO: 126)
5'-TTGGATCCAACCTCTGGGCAGCACAGCGCTATGGCCGCGAGCTCC
GGAGG-3',
and BAD reverse primer;
                                         (SEQ ID NO: 127)
5'-TTGAATTCTTACTTCTTAAAGGAGTCCACAAACTCGTCACTCATC
CTCCG-3'.
```

Then, the amplification product thus obtained was cleaved with BamHI and EcoRI, and inserted into phAG-MCLinker having been treated with the same restriction enzymes. Thus, phAG-BAD was prepared. Note that the phAG-BAD encodes a fusion protein composed of an AG protein and a portion of BAD (the fusion protein may also be referred to as "AG-BAD"). Moreover, it has been known that the portion of BclX(L) and the portion of BAD interact with each other in the cytoplasm (see Sattler M et al., Science, Feb. 14, 1997, vol. 275, no. 5302, pp. 983 to 986).

(Transfection into Cultured Cells, and Observation of Transfected Cells)

Each of the following combinations of the plasmid DNAs was mixed in equal amounts and introduced into HeLaS3 cells by the same method as that described in Example 1:

a combination of pFKBP12-p62(PB1) with pmTOR(FRB domain)-AGNLS;

a combination of pp62(PB1)-HRas with phAG-cRaf;

a combination of pSmac-p62(PB1) with pXIAP-hAG; and a combination of pp62(PB1)-BclX(L) with phAG-BAD.

Moreover, the transfected cells were observed also by the same method as that described in Example 1. Nevertheless, regarding the cells in which the pFKBP12-p62(PB1) and the pmTOR(FRB domain)-AGNLS were introduced, fluorescence images and phase contrast images were captured 300 seconds after 100 nM rapamycin was added. FIGS. 33 to 36 show the obtained results.

Figure 33:
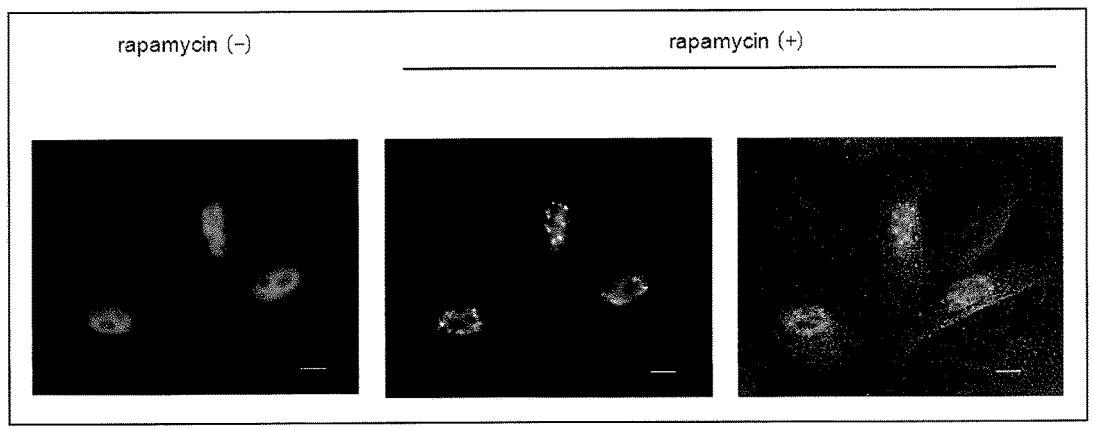
FIG. 33 shows micrographs for illustrating the result of observing localization of a fluorescent focus formed by an association between FKBP12-p62(PB1) and a fusion protein (mTOR(FRB domain)-AGNLS) composed of mTOR(FRB domain), an AG protein, and a nuclear localization signal (NLS). Note that, from the left, the first panel shows a fluorescence image of cells before rapamycin addition, the second panel shows a fluorescence image of the cells after the rapamycin addition, and the third panel shows the result of merging superimposing the fluorescence image and bright-field image of the cells after the rapamycin addition. Moreover, in the figure, the scale bars at the lower right portions represent 5 μm.

As apparent from the result shown in FIG. 33, when mTOR(FRB domain)-AGNLS and FKBP12-p62(PB1) were expressed in the cells, mTOR(FRB domain)-AGNLS was localized in a dispersed state because the mTOR(FRB domain)-AGNLS had the nuclear localization signal sequence at the C-terminus thereof (see the left panel in FIG. 33). Moreover, by the addition of rapamycin, fluorescent foci formed by an association between FKBP12-p62(PB1) and mTOR(FRB domain)-AGNLS were detected only in the nuclei (see two panels on the right in FIG. 33).

Figure 34:
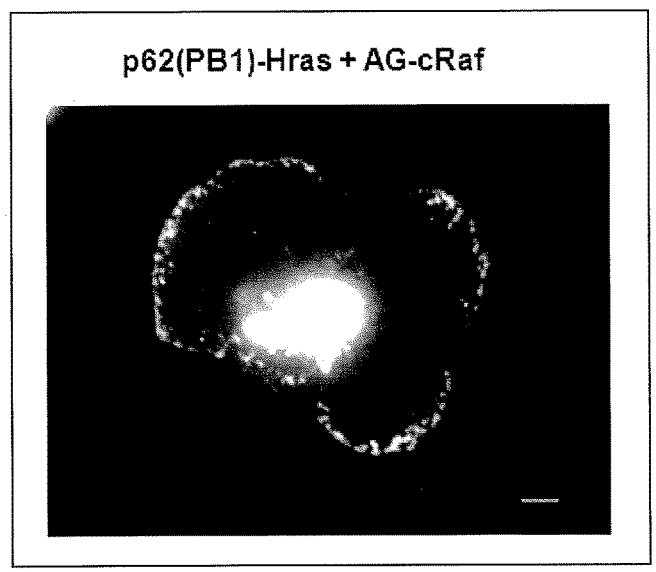
FIG. 34 shows a micrograph for illustrating the result of observing localization of a fluorescent focus formed by an association between a fusion protein (AG-cRaf) composed of an AG protein and a cRaf protein, and a fusion protein (p62(PB1)-HRas) composed of p62(PB1) and an HRas protein, the p62(PB1)-HRas having a prenylated sequence at the C-terminus. Note that, in the figure, the scale bar at the lower right portion represents 5 μm.

Further, as apparent from the result shown in FIG. 34, when p62(PB1)-HRas having the prenylated sequence at the C-terminus thereof and AG-cRaf were expressed in the cells, by the prenylated sequence, fluorescent foci formed by an association between the p62(PB1)-HRas and the AG-cRaf were detected from the cell membranes.

Figure 35:
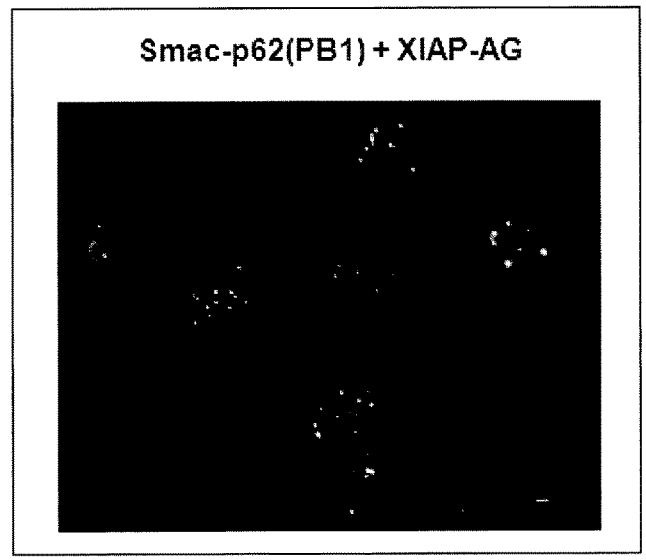
FIG. 35 shows a micrograph for illustrating the result of observing localization of a fluorescent focus formed by an association between a fusion protein (Smac-p62(PB1)) composed of a portion of a Smac protein and p62(PB1), and a fusion protein (XIAP-AG) composed of a portion of a XIAP protein and an AG protein. Note that, in the figure, the scale bar at the lower right portion represents 5 μm.

Furthermore, as apparent from the result shown in FIG. 35, when Smac-p62(PB1) and XIAP-AG were expressed in the cells, fluorescent foci formed by an association between Smac-p62(PB1) and XIAP-AG were also detected in the cytoplasms, reflecting the interaction between the Smac protein and the XIAP protein, which had been known to take place in the cytoplasm.

Figure 36:
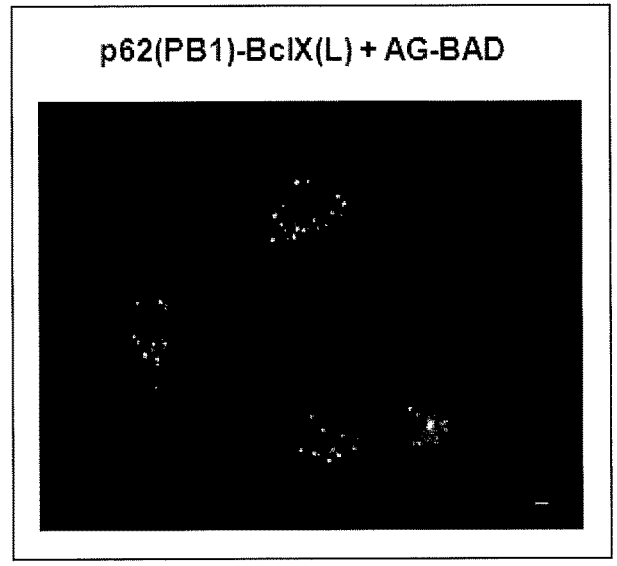
FIG. 36 shows a micrograph for illustrating the result of observing localization of a fluorescent focus formed by an association between a fusion protein (p62(PB1)-BclX(L)) composed of p62(PB1) and a portion of a BclX(L) protein, and a fusion protein (AG-BAD) composed of an AG protein and a portion of a BAD protein. Note that, in the figure, the scale bar at the lower right portion represents 5 μm.

Additionally, as apparent from the result shown in FIG. 36, when p62(PB1)-BclX(L) and AG-BAD were expressed in the cells, fluorescent foci formed by an association between p62(PB1)-BclX(L) and AG-BAD were detected also in the cytoplasms, reflecting the interaction between the BclX(L) protein and the BAD protein, which had been known to take place in the cytoplasm.

Example 21

<Detection 17 of Protein-Protein Interaction>

As in the case of Example 20, whether or not the use of the method of the present invention enabled detection of a protein-protein interaction in an intracellular environment unique to a target protein was tested by a method described below.

Note that, in this Example 21, the detection target was a protein-protein interaction between a Rac1 protein and PBD (p21 binding domain). The Rac1 protein is a low-molecular-weight G protein, and guanine nucleotide exchange factors (GEFs) such as Tiam1, Trio, and VAV1 convert the Rac1 protein from an inactive GDP-bound form to an active GTP-bound form. Moreover, it has been known that an active Rac1 protein and PBD of a Cdc42/Rac effector protein (p21-activated kinase 1: PAK1) interact with each other. Further, GEFs are localized differently depending on the type, and are localized inside the nucleus, at the border (near the cell membrane), and so on, of a cell. For this reason, while a Rac1 protein is present everywhere in the cell, an activation of the Rac1 protein and an interaction between an active Rac1 protein and PBD take place in intracellular regions in accordance with GEFs localized differently depending on the type (see Benard V et al., J Biol Chem., May 7, 1999, vol. 274, no. 19, pp. 13198 to 13204).

(Preparation of Plasmid DNA)

In preparing phAG-Rac1, first, a DNA encoding a Rac1 protein (protein having the amino acid sequence of SEQ ID NO: 54) (the DNA had the base sequence of SEQ ID NO: 53) was amplified from the cDNA library of HeLaS3 cells by PCR using the following primer set:

```
Rac1 forward primer;
                                    (SEQ ID NO: 128)
5'-GAGAATTCGATGCAGGCCATCAAGTGTGTGGTGG-3',
and Rac1 reverse primer;
                                    (SEQ ID NO: 129)
5'-GGCTCGAGTTACAACAGCAGGCATTTTCTCTTCC-3'.
```

Then, the amplification product thus obtained was cleaved with EcoRI and XhoI, and inserted into phAG-MNLinker having been treated with the same restriction enzymes. Thus, phAG-Rac1 was prepared.

Meanwhile, in preparing pp62(PB1)-PBD, first, a DNA encoding PBD (region having the 67th to 150th amino acids of the PAK1 protein, the region had the amino acid sequence of SEQ ID NO: 56) (the DNA had the base sequence of SEQ ID NO: 55) was amplified from the cDNA library of HeLaS3 cells by PCR using the following primer set:

```
PBD forward primer;
                                    (SEQ ID NO: 130)
5'-TTGGATCCAAGAAAGAGAAAGAGCGGCCAGAGATTTCTCT
CCC-3',
and PBD reverse primer;
                                    (SEQ ID NO: 131)
5'-CCGAATTCTTACGCTGACTTATCTGTAAAGCTCATGTATT
TCTGGC-3'.
```

Then, the amplification product thus obtained was cleaved with BamHI and EcoRI, and inserted into pp62(PB1)-MCLinker having been treated with the same restriction enzymes. Thus, pp62(PB1)-PBD was prepared.

(Transfection into Cultured Cells, and Observation of Transfected Cells)

Each of the following combinations of the plasmid DNAs was mixed in equal amounts and introduced into U2OS cells by the same method as that described in Example 1:

a combination of phAG-Rac1 with pp62(PB1)-PBD; and a combination of phAG-Rac1 with pp62(PB1)-MN-Linker.

Figure 37:
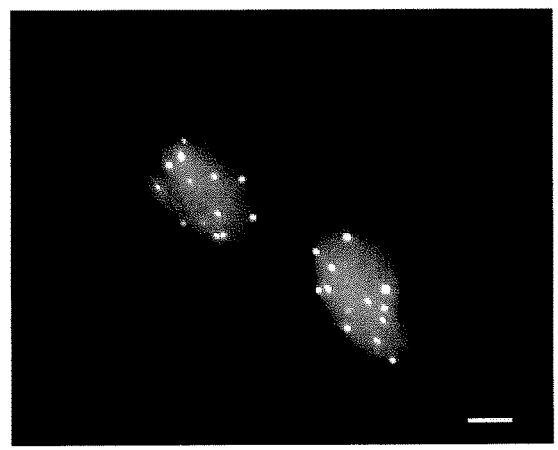
FIG. 37 shows a micrograph for illustrating that a fluorescent focus formed by an association between a fusion protein (AG-Rac1) composed of an AG protein and a Rac1 protein, and a fusion protein (p62(PB1)-PBD) composed of p62(PB1) and a p21 binding domain is localized in the nucleus. Note that, in the figure, the scale bar at the lower right portion represents 5 μm. Moreover, guanine nucleotide exchange factors (GEFs) convert a Rac1 protein to an active form. Further, it is known that an active Rac1 protein and PBD interact with each other. Furthermore, GEFs are localized differently depending on the type. For this reason, an interaction between a Rac1 protein and PBD takes place in intracellular regions in accordance with the GEFs localized differently depending on the type.
Figure 38:
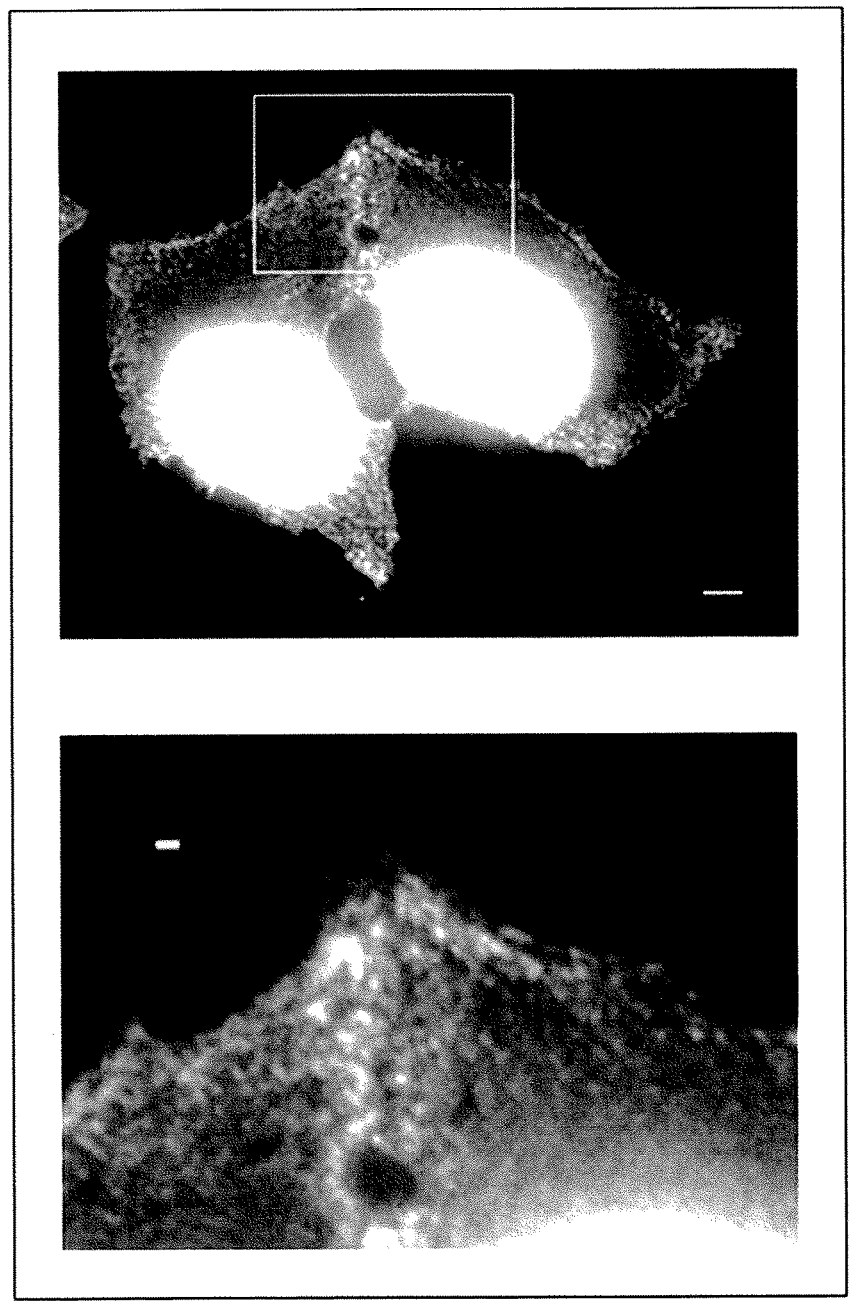
FIG. 38 shows micrographs for illustrating that a fluorescent focus formed by an association between AG-Rac1 and p62(PB1)-PBD is localized at the border of cells. Note that, in the figure, the lower panel is obtained by enlarging a region surrounded by the white line in the upper panel. Moreover, the scale bar at the lower right portion of the upper panel represent 5 µm, and the scale bar at the upper left portion of the lower panel represents 1 µm.
Figure 39:
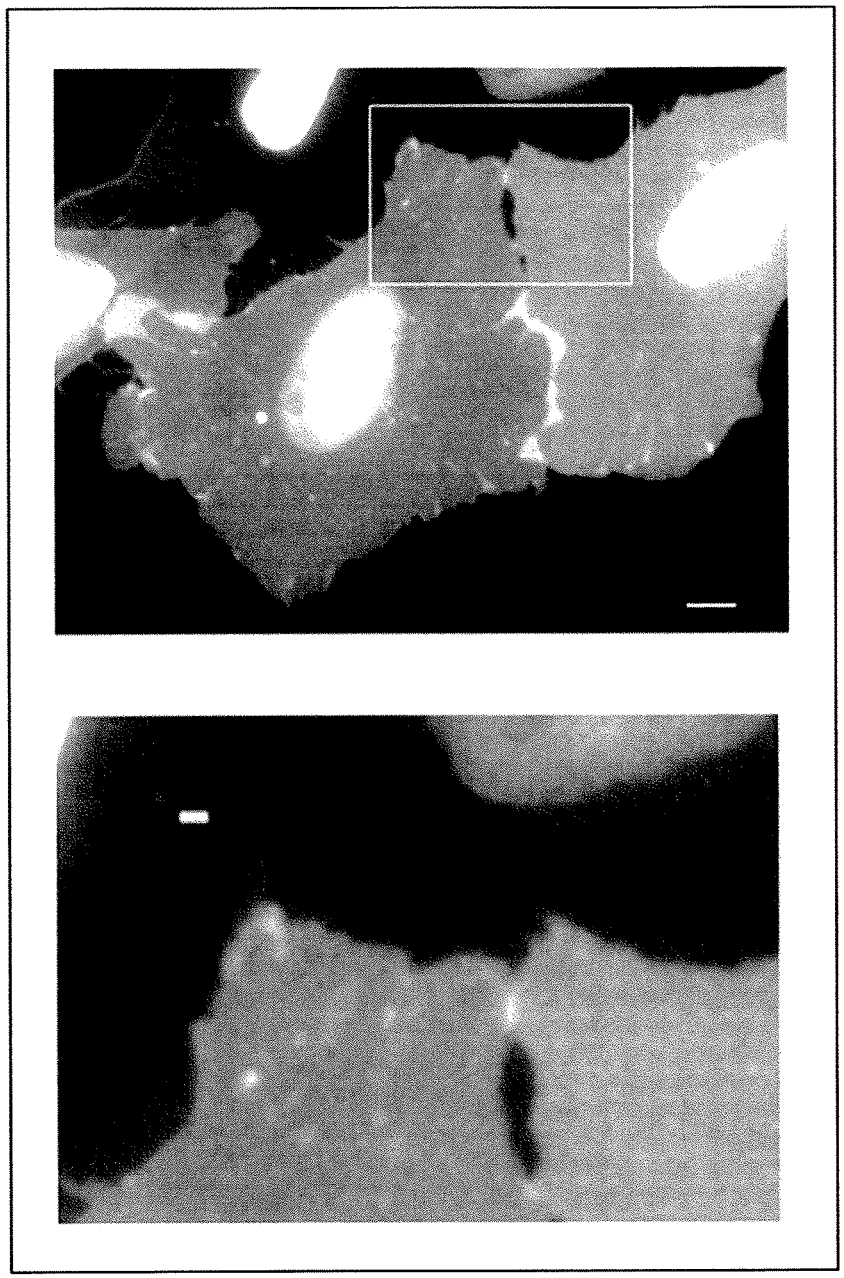
FIG. 39 shows micrographs for illustrating that when AG-Rac1 and p62(PB1) are expressed in cells, these proteins do not interact with each other, so that no fluorescent focus is detected at the border and so on of a cell. Note that, in the figure, the lower panel is obtained by enlarging a region surrounded by the white line in the upper panel. Moreover, the scale bar at the lower right portion of the upper panel represents 5 µm, and the scale bar at the upper left portion of the lower panel represents 1 µm.

FIGS. 37 to 39 show the obtained results.

As apparent from the results shown in FIGS. 37 and 38, when AG-Rac1 and p62(PB1)-PBD were expressed in the cells, fluorescent foci formed by an association between AG-Rac1 and p62(PB1)-PBD were detected in the nuclei (FIG. 37) and at the borders of the cells (FIG. 38).

On the other hand, as apparent from the result shown in FIG. 39, when AG-Rac1 and p62(PB1) not fused to PBD were expressed in the cells, no fluorescent focus was detected.

The above results demonstrated that it was possible to detect the same protein-protein interaction in multiple regions in the cell. Thus, it was revealed that without forcibly (artificially) confining in a particular region in a cell a protein constituting a complex formed by a protein-protein interaction, the present invention enabled detection of the protein-protein interaction in a unique intracellular environment in accordance with the localization of the protein.

Moreover, it was also demonstrated that by detecting the protein-protein interaction, the present invention enabled detection of the active (GTP-bound form) Rac1 protein. Further, it was verified that it was also possible to detect the localization and activity of the intracellular enzyme GEF by detecting the conversion to the active GTP-bound form, thus revealing that the method of the present invention enabled detection of an activity of an endogenous factor according to a protein-protein interaction.

Example 22

<Detection 18 of Protein-Protein Interaction>

As described in Example 21, it has been revealed that an active Rac1 protein and PBD of a Cdc42/Rac effector protein (p21-activated kinase 1: PAK1) interact with each other.

Moreover, it has also been known that the localization of a Rac1 protein is changed by geranylgeranyl group modification (prenylation) on the C-terminus of the Rac1 protein. Further, it has also been known that a Rac1 protein interacts with RhoGDI via a geranylgeranyl group of the Rac1 protein.

Hence, it was confirmed by a method described below that the method of the present invention enabled detection of a change in localization of these protein-protein interactions.

First, pRhoGDI-p62(PB1) was prepared by the same method as that described in Example 2 on the basis of a DNA sequence encoding the amino acid sequence specified under Genbank ACCESSION No: NP_004300. Moreover, phAG-Rac1 and pp62(PB1)-PBD were as described in Example 21.

Then, each of the following combinations of the plasmid DNAs was mixed in equal amounts and introduced into cells by the same method as in Example 2:
    a combination of phAG-Rac1 with pp62(PB1)-PBD; and
    a combination of phAG-Rac1 with pRhoGDI-p62(PB1).

Figure 40:
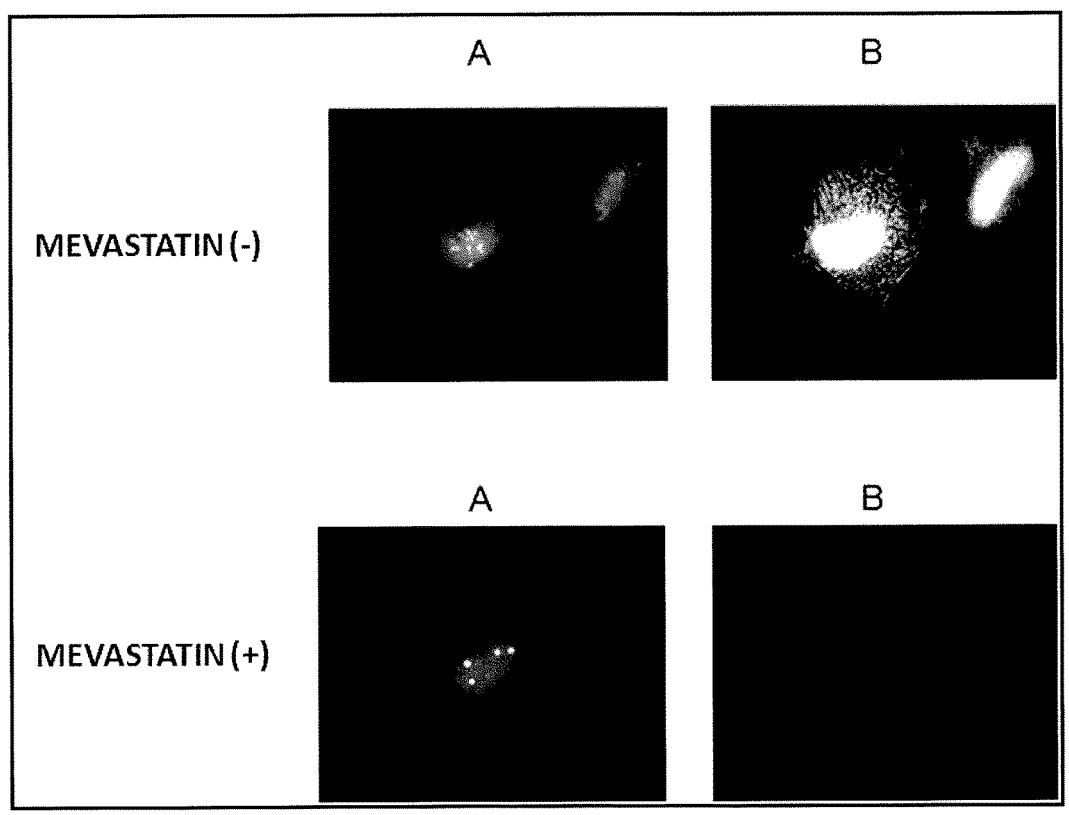
FIG. 40 shows micrographs for illustrating the result of observing cells expressing AG-Rac1 and p62(PB1)-PBD in the absence (−) or presence (+) of an inhibitor mevastatin against geranylgeranyl group modification. Note that if geranylgeranyl group modification is inhibited, Rac1 is localized in the nucleus. Moreover, the figure shows the results of observing the same cells; "A" is observed using a normal inverted epifluorescence microscope; and "B" is observed using a total internal reflection fluorescence microscopy system with arc lamp source capable of exciting only the vicinity of the cell membrane.
Figure 41:
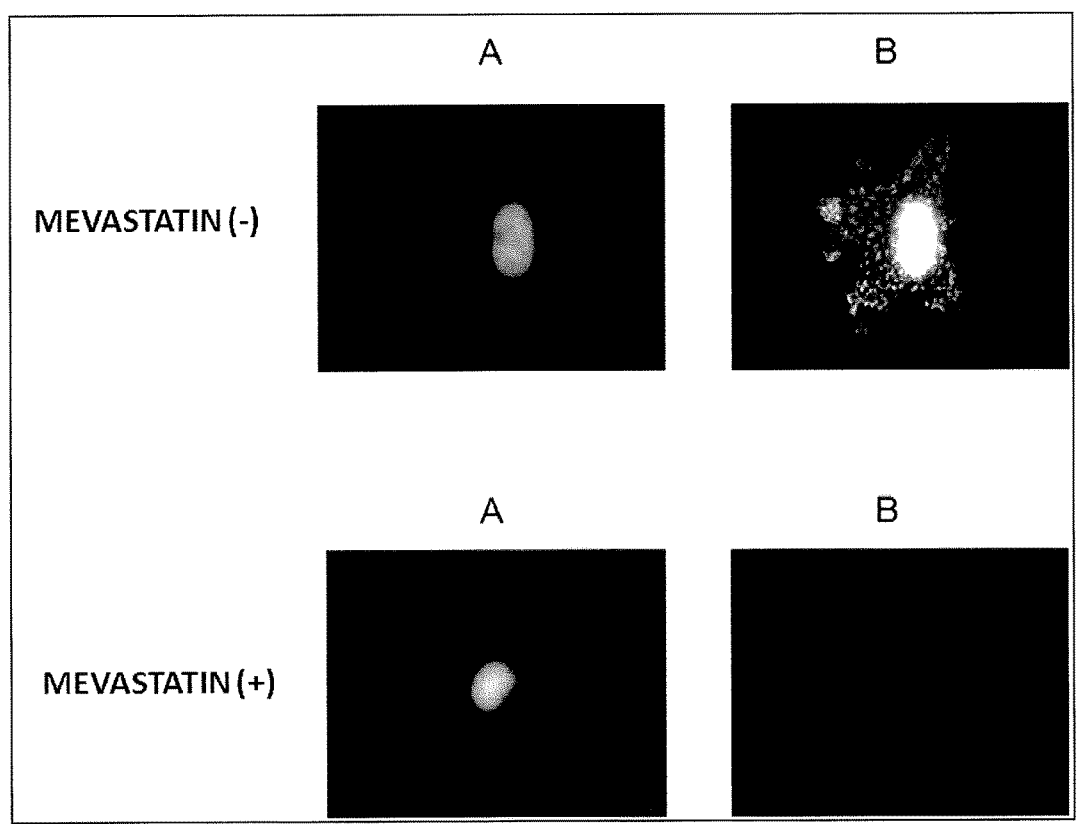
FIG. 41 shows micrographs for illustrating the result of observing cells expressing AG-Rac1 and RhoGDI-p62(PB1) in the absence (−) or presence (+) of an inhibitor mevastatin against geranylgeranyl group modification. Note that a Rac1 protein interacts with RhoGDI via a geranylgeranyl group of the Rac1 protein. Moreover, the figure shows the results of observing the same cells; "A" is observed using a normal inverted epifluorescence microscope; and "B" is observed using a total internal reflection fluorescence microscopy system with arc lamp source capable of exciting only the vicinity of the cell membrane.

Then, after culturing for 6 hours after the transfection, an inhibitor mevastatin (Enzo Life Sciences, Inc.) against geranylgeranyl group modification was added to the final concentration of 10 μM, allowed for further culturing for 15 hours, and observed. FIG. 40 shows the result of the cells co-expressing AG-Rac1 and p62(PB1)-PBD. FIG. 41 shows the result of the cells co-expressing AG-Rac1 and RhoGDI-p62(PB1). Note that the same cells are shown in each of FIGS. 40 and 41: (A) is photographed by the same method as that described in Example 1 using a normal inverted epifluorescence microscope; and (B) is photographed by the same method as that described in Example 17 using a total internal reflection fluorescence microscopy system with arc lamp source.

As apparent from the result shown in the two upper panels of FIG. 40, the method of the present invention confirmed that, in a normal state, the protein-protein interaction between Rac1 and PBD took place both inside and outside the nuclei; in other words, Rac1 was present in an activated state.

It has been known that if geranylgeranyl group modification is inhibited with a drug such as mevastatin, Rac1 is localized in the nucleus. Regarding this knowledge, the method of the present invention also confirmed as apparent from the result shown in the two lower panels of FIG. 40 that the interaction between Rac1 and PBD was changed by the mevastatin treatment, so that the interaction took place only in the nuclei. Further, by detecting the interaction, the method of the present invention also confirmed that Rac1 was present in an activated state even without the geranylgeranyl group modification.

Meanwhile, regarding the interaction between Rac1 and RhoGDI, the method of the present invention confirmed as apparent from the result shown in the two upper panels of FIG. 41 that, in a normal state, the protein-protein interaction between Rac1 and RhoGDI took place outside the nuclei.

On the other hand, as apparent from the result shown in the two lower panels of FIG. 41, the method of the present invention confirmed that Rac1 was localized only in the nuclei by the mevastatin treatment as described above, and further that since the geranylgeranyl group modification of Rac1 was suppressed, the interaction between Rac1 and RhoGDI was reduced.

Thus, the present invention confirmed that it was possible to detect how the protein-protein interaction in multiple regions in the cell was changed by a stimulus from the outside. Furthermore, it was confirmed that it was also possible to detect the presence or absence of a modification of a protein influencing a protein-protein interaction (for example, geranylgeranyl group modification of Rac1 in relation to a Rac1-RhoGDI interaction).

Example 23

An interaction between KRas and cRaf is one of important signal transductions for cell proliferation, differentiation, and so forth. Moreover, it has been revealed that this protein-protein interaction takes place by an activation of KRas as a result of signaling via Grb2-SOS from an EGF receptor activated by an epidermal growth factor (EGF). Further, it has also been known that this protein-protein interaction changes the localization of cRaf from the cytoplasm to the cell membrane.

As described above, since the interaction between KRas and cRaf is dependent on EGF, the interaction does not take place in the absence of EGF. However, among KRas mutants, there are also constitutively-active mutants (for example, KRasG12D) capable of interacting with cRaf in the absence of EGF. Furthermore, such mutants have been detected in various cancers. Thus, in the development of effective cancer treatments, and so forth, it is important to detect positional information and temporal information on a protein-protein interaction such as assembly formation between KRas or mutants thereof and cRaf, and localization of the assembly.

For this reason, whether or not the present invention enabled detection of a difference in protein-protein interaction between a protein having a disease-associated mutation and a wildtype protein thereof was tested by a method described below.

(Preparation of Plasmid DNAs)

pp62(PB1)-KRas(WT) was prepared by the same method as that described in Example 2 on the basis of a DNA sequence encoding the amino acid sequence specified under Genbank ACCESSION No: NP_004976.

Regarding pp62(PB1)-KRas(G12D), a mutation was introduced into pp62(PB1)-KRas (WT) by the same method as that described in Example 17 using a primer having the DNA sequence of SEQ ID NO: 160 (5'-CTTGTGGTAGT-TGGAGCTGACGGCGTAGGCAAGAGTGCCTTG-3').

phAG-cRaf(R59A) was prepared by the same method as that described in Example 2 on the basis of a DNA sequence (SEQ ID NO: 161) encoding a protein having the amino acid sequence of SEQ ID NO: 162. Note that, as cRaf, a mutant of the protein (cRaf(R59A)) was used in this Example with reference to the method described in Harvey C D et al., Science., Jul. 4, 2008, vol. 321, no. 5885, pp. 136-140.

(Transfection into Cultured Cells, and Observation of Transfected Cells)

The plasmid DNAs were mixed in equal amounts in the following combinations, and were introduced into Cos-7 cells by the same method as that described in Example 2:

a combination of pp62(PB1)-KRas(WT) with phAG-cRaf (R59A); and a combination of pp62(PB1)-KRas(G12D) with phAG-cRaf(R59A).

Figure 42:
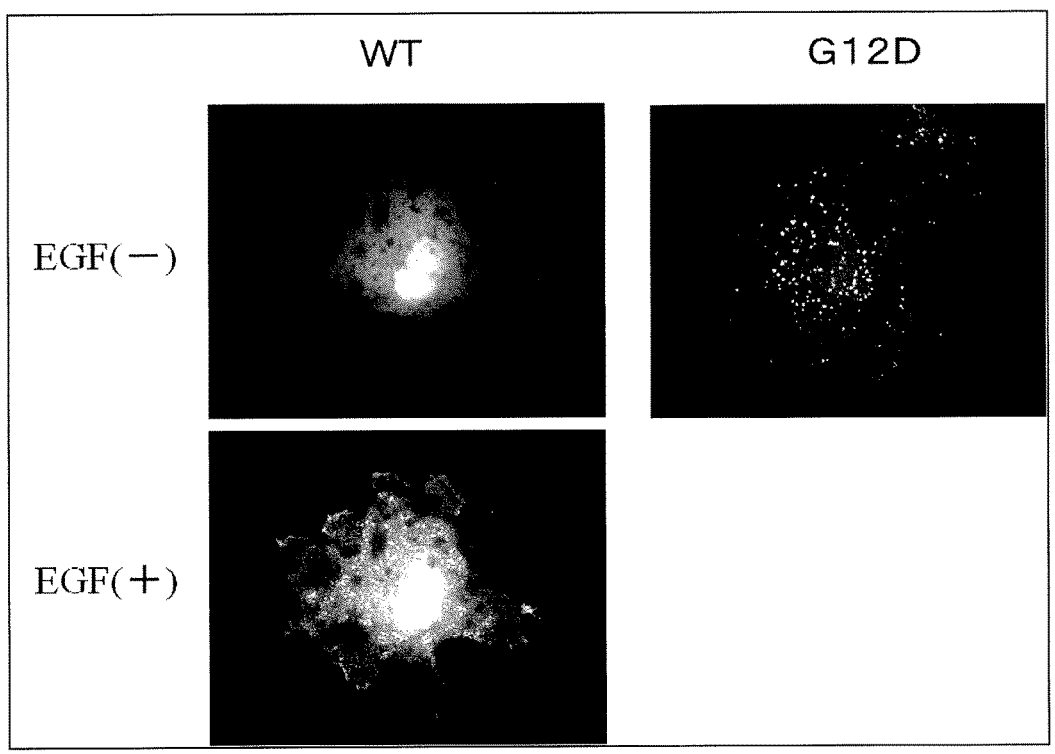
FIG. 42 shows micrographs for illustrating the result of detecting only fluorescence in the vicinity of the cell membranes of cells(WT) expressing p62(PB1)-KRas(WT) and AG-cRaf(R59A), and cells (G12D) expressing p62(PB1)-KRas(G12D) and AG-cRaf(R59A), after EGF addition (+) or no addition (−). Note that KRas activated in a manner dependent on EGF interacts with cRaf. Moreover, this protein-protein interaction changes the localization of cRaf from the cytoplasm to the cell membrane.

The cells were observed using a total internal reflection fluorescence microscopy system with arc lamp source (manufactured by Olympus Corporation, IX71-ARCEVA) capable of exciting only the vicinity of the cell membrane. Additionally, regarding the combination of pp62(PB1)-KRas (WT) with the phAG-cRaf (R59A), an image was obtained when no EGF was added. After that, EGF (manufactured by SIGMA CO.) was added to the cells to the final concentration of 50 ng/ml and left standing at 37° C. for 30 minutes. Then, the resultant was observed again. FIG. 42 shows the obtained result.

As apparent from the result shown in FIG. 42, in the cells co-expressing p62(PB1)-KRas(WT) and AG-cRaf(R59A), no fluorescent focus (assembly formation) was observed when no stimulus was applied from the outside (no EGF addition). Meanwhile, as EGF was added, the assembly formation was observed at the cell membranes. On the other hand, in the combination of pp62(PB1)-KRas(G12D) with phAG-cRaf(R59A), the assembly formation was observed at the cell membranes even without a stimulus from the outside.

Thus, the present invention makes it possible to clearly understand a difference (such as dependency on external stimulus) of a protein-protein interaction caused by a mutation associated with a disease. Therefore, the method of the present invention is effective in analyzing the intracellular dynamics and the function of a protein and the like associated with the disease.

Example 24

<Detection 20 of Protein-Protein Interaction>

As described in Example 19 also, it was confirmed by a method described below that the present invention enabled detection of a change in protein-protein interaction over time.

Note that, in Example 24, the targeted protein-protein interactions were: an interaction between BclX(L) and Bak, and an interaction between BclX(L) and Bax. It has been revealed that both Bak and Bax interact with BclX(L) via BH3 domains thereof. It has been revealed that the dissociation constant between BclX(L) and Bak BH3 domain is 340 nM, and the dissociation constant between BclX(L) and Bax BH3 domain is 13 µM (see Sattler M et al., Science., Feb. 14, 1997, vol. 275, no. 5302, pp. 983 to 986). Additionally, it has also been known that these protein-protein interactions are competitively inhibited by ABT-737 (BH3 mimetic).

(Preparation of Plasmid DNAs)

pBak-hAG was prepared by the same method as that described in Example 2 using a DNA (SEQ ID NO: 163) encoding a region having the amino acid sequence of SEQ ID NO: 164. phAG-Bax was prepared by the same method as that described in Example 2 using a DNA (SEQ ID NO: 165) encoding a region having the amino acid sequence of SEQ ID NO: 166. Moreover, pp62(PB1)-BclX(L) was as described in Example 20.

(Transfection into Cultured Cells, and Observation of Transfected Cells)

The plasmid DNAs were mixed in equal amounts in the following combinations, and the genes were introduced into 293 cells by the same method as that described in Example 2:

a combination of pp62(PB1)-BclX(L) with pBak-hAG; and a combination of pp62(PB1)-BclX(L) with phAG-Bax.

Figure 43:
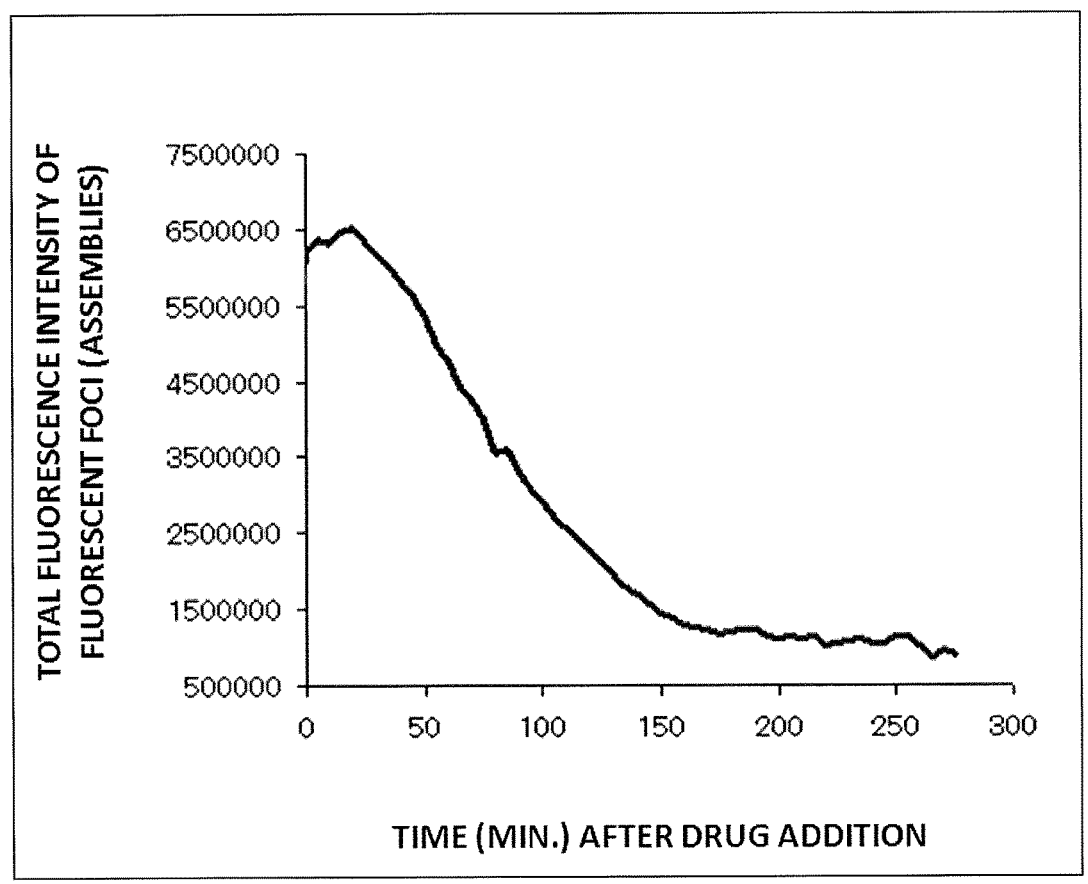
FIG. 43 is a graph for illustrating a change over time in a total fluorescence intensity of fluorescent foci in cells co-expressing p62(PB1)-BclX(L) and Bak-AG after ABT-737 addition. Note that although BclX(L) and Bak interact with each other via a BH3 domain, this protein-protein interaction is competitively inhibited by ABT-737 (BH3 mimetic).
Figure 44:
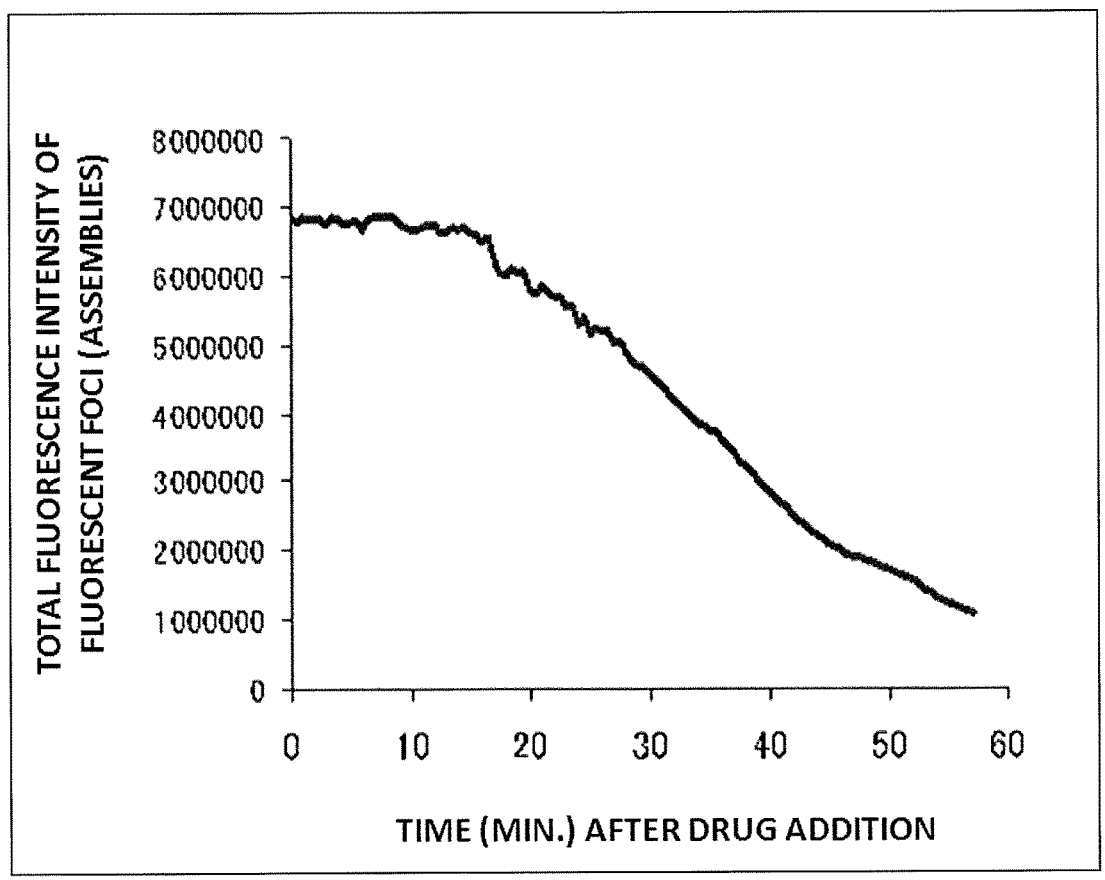
FIG. 44 is a graph for illustrating a change over time in a total fluorescence intensity of fluorescent foci in cells co-expressing p62(PB1)-BclX(L) and AG-Bax, after ABT-737 addition. Note that although BclX(L) and Bax interact with each other via a BH3 domain, this protein-protein interaction is competitively inhibited by ABT-737.

Then, to the 293 cells into these plasmid DNAs were introduced, ABT-737 (manufactured by Santa Cruz Biotechnology, Inc.) was added to the final concentration of 15 µM, and images were obtained by the same method as that described in Example 2 every 30 minutes for the cells co-expressing p62(PB1)-BclX(L) and Bak-AG, and every 5 minutes for the cells co-expressing p62(PB1)-BclX(L) and AG-Bax. On the basis of the obtained images, analysis was performed by the same method as that described in Example 11, and a graph was prepared by plotting a total fluorescence intensity of fluorescent foci (assemblies) against time. Note that, in the graph, the x axis represents time (minutes), provided that time when the drug was added is 0, and the y axis represents the total fluorescence intensity of fluorescent foci (assemblies). FIG. 43 shows the result of the cells co-expressing p62(PB1)-BclX(L) and Bak-AG. FIG. 44 shows the result of the cells co-expressing p62(PB1)-BclX(L) and AG-Bax.

As apparent from the results shown in FIGS. 43 and 44, in both of the interaction between BclX(L) and Bak and the interaction between BclX(L) and Bax, the total fluorescence luminances of assemblies formed in a manner dependent on these protein-protein interactions were decreased over time by the addition of ABT-737. Thus, the present invention verified that by detecting the fluorescent foci, it was possible to detect a period until the protein-protein interactions ended.

Moreover, the time when the total fluorescence luminance reached a half value was approximately 80 minutes in the case of BclX(L) and Bak, and approximately 35 minutes in the case of BclX(L) and Bax. Since the rate of decreasing assemblies was slower in BclX(L) and Bak with a smaller dissociation constant (dissociation constant: 340 nM) than in BclX(L) and Bax (dissociation constant: 13 µM), it was confirmed as described above that the present invention enabled evaluation of a strength of the protein-protein interaction.

Example 25

<Detection 21 of Protein-Protein Interaction>

As described in Example 24 also, it was confirmed by a method described below that the present invention enabled detection of a change over time in when a protein-protein interaction took place.

Figure 45:
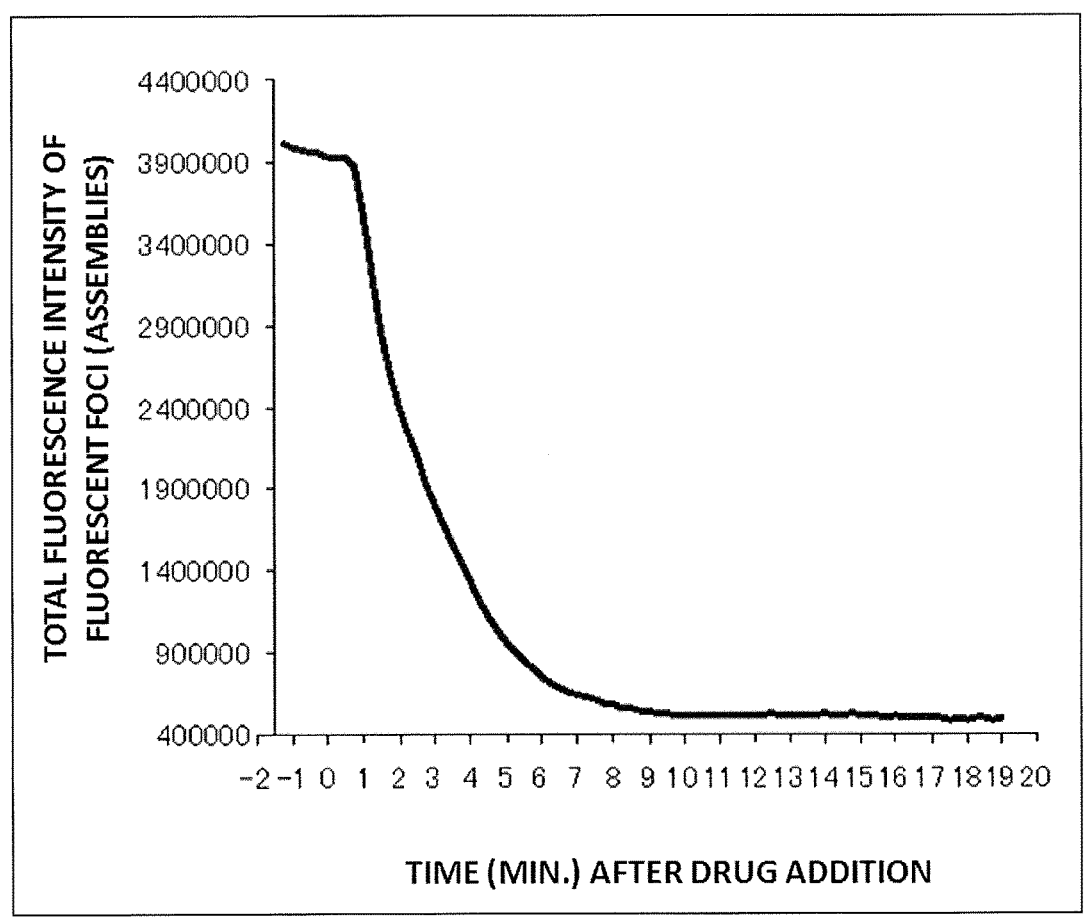
FIG. 45 is a graph for illustrating a change over time in a total fluorescence intensity of fluorescent foci in cells stably expressing p62(PB1)-p53 and AG-MDM2, before and after Nutlin-3 addition. Note that, in the graph, the x axis represents time (minutes), provided that time when Nutlin-3 was added is 0.

First, CHO-K1 cells stably expressing p62(PB1)-p53 and AG-MDM2 described in Example 13 were seeded onto a 35-mm glass base dish (manufactured by Asahi Glass Co., Ltd.). Then, on the next day, Nutlin-3 (manufactured by CALBIOCHEM) was added thereto to the final concentration of 10 µM, and observed by the same method as that described in Example 1. Images were obtained 2 minutes before the addition and thereafter every 15 seconds. The obtained images were used to analyze a total fluorescence luminance of assemblies by employing the same method as that described in Example 11, and a graph was prepared by plotting the total fluorescence luminance against time. FIG. 45 shows the obtained result.

As apparent from the result shown in FIG. 45, the total fluorescence luminance of assemblies was decreased as soon as Nutlin-3 (manufactured by CALBIOCHEM) was added. The time when the half value was reached was approximately 3 minutes. Thus, the present invention confirmed that, by detecting the fluorescent foci, it was possible to detect a period until the protein-protein interaction ended and the process.

Example 26

<Detection 22 of Protein-Protein Interaction>

As described above, it was confirmed by a method described below that the present invention enabled detection of a change over time in when a protein-protein interaction took place.

Figure 46:
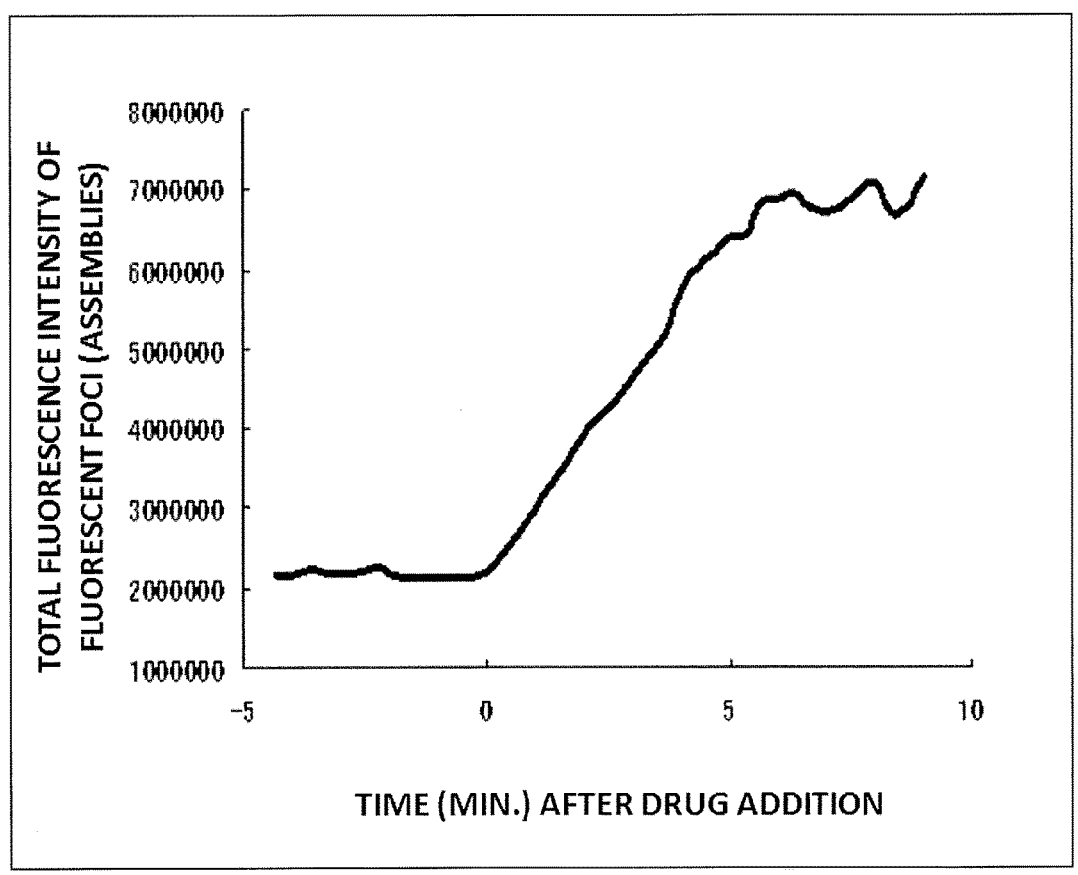
FIG. 46 is a graph for illustrating a change over time in a total fluorescence intensity of fluorescent foci in cells stably expressing mTOR(FRB domain)-AG and p62(PB1)-FKBP12, before and after rapamycin addition. Note that, in the graph, the x axis represents time (minutes), provided that time when rapamycin was added is 0.

First, to HeLaS3 cells stably expressing mTOR(FRB domain)-AG and p62(PB1)-FKBP12 described in Example 11, rapamycin was added to the final concentration of 20 nM, and analyzed by the same method as that described in Example 11. FIG. 46 shows the obtained result.

As apparent from the result shown in FIG. 46, after rapamycin was added, assembly formation was induced as time elapsed. The time when the half value was reached was approximately 3 minutes. Thus, it was confirmed that the present invention enabled detection of time when the protein-protein interaction took place and the process, by detecting the fluorescent foci.

Example 27

<Detection 23 of Protein-Protein Interaction>

It has been revealed that when ERK in cells is activated by an EGF stimulus, the ERK substrate (ERK_substrate) is phosphorylated; as a result, the ERK_substrate and a ww domain of a Pin1 protein (Pin1(ww)) interact with each other. Further, it has also been known that if a MEK inhibitor U0126 is added, the ERK activity is decreased; as a result, the ERK substrate is dephosphorylated, terminating the interaction between the ERK substrate and Pin1(ww).

In this Example, it was confirmed by a method described below that: the present invention enabled detection of an interaction between an ERK substrate and Pin1(ww) induced indirectly by EGF through ERK activation; the present invention enabled detection of an interaction between an ERK substrate and Pin1(ww) suppressed indirectly by U0126 through ERK inactivation; and the present invention enabled detection of an EGF stimulus-dependent signal transduction over time.

(Preparation of Plasmid DNA)

In this Example, in order to detect an EGF stimulus-dependent interaction between an ERK substrate and Pin1 (ww), pp62(PB1)-ERK_substrate-P2A-hAG-Pin1(ww)-NES was prepared with reference to a system for detecting the interaction by utilizing FRET (see Christopher D. Harvey et al., Proc Natl Acad Sci USA., Dec. 9, 2008, vol. 105, nol. 49, pp. 19264 to 19269). Specifically, pp62(PB1)-ERK_substrate-P2A-hAG-Pin1(ww)-NES was prepared by the same method as that described in Example 2 using a chemically synthesized DNA (SEQ ID NO: 167) encoding a region having the amino acid sequence of SEQ ID NO: 168.

Note that, in the amino acid sequence of SEQ ID NO: 168, the amino acid sequence from positions 1 to 102 shows the amino acid sequence of p62(PB1). The amino acid sequence from positions 103 to 128 shows a linker sequence. The amino acid sequence from positions 129 to 138 shows the amino acid sequence from positions 43 to 52 of human Cdc25C that is the ERK substrate, and the amino acid sequence from positions 139 to 142 shows the amino acid sequence of an ERK docking site. The amino acid sequence from positions 146 to 164 shows the amino acid sequence of a P2A peptide. The amino acid sequence from positions 165 to 390 shows the amino acid sequence of AG. The amino acid sequence from positions 391 to 416 shows a linker sequence. The amino acid sequence from positions 417 to 470 shows the amino acid sequence of Pin1(ww). The amino acid sequence from positions 471 to 482 shows the amino acid sequence of a nuclear export signal (NES) of MEK.

Moreover, the P2A peptide inserted between p62(PB1)-ERK_substrate and AG-Pin1(ww)-NES is a CHYSEL (cis-acting hydrolase element) sequence derived from porcine teschovirus. It has been known that when the protein is translated, ribosome skipping occurs, generating cleavage in front of proline at the end of the amino acid sequence (ATNFSLLKQAGDVEENPGP) (see Donnelly M L et al., J Gen Virol., may 2001, vol. 82, no. 5, pp. 1013 to 1025). Thus, if the pp62(PB1)-ERK_substrate-P2A-hAG-Pin1 (ww)-NES is introduced into cells, this is consequently cleaved into:

a product having a portion of the P2A peptide fused to the C-terminus of p62(PB1)-ERK_substrate; and a product having a portion of the P2A peptide fused to the N-terminus of AG-Pin1(ww)-NES. The two are expressed in the cells.

Figure 47:
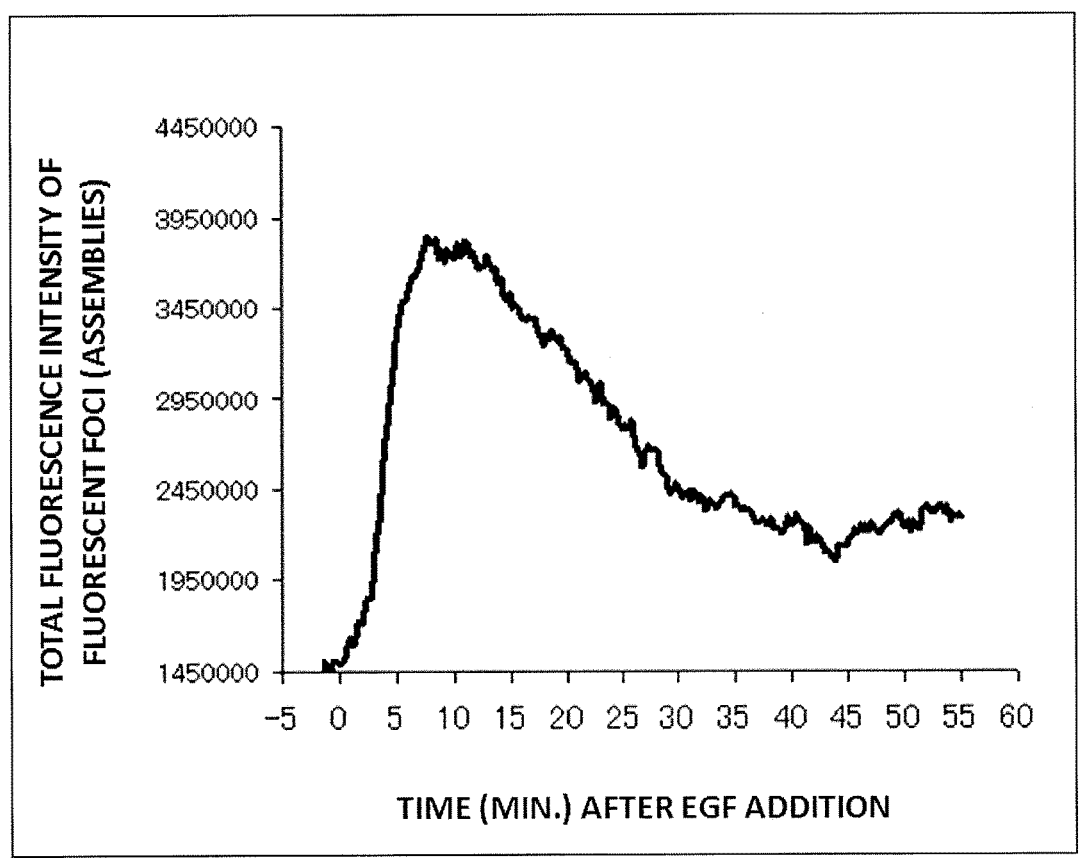
FIG. 47 is a graph for illustrating a change over time in a total fluorescence intensity of fluorescent foci in cells expressing p62(PB1)-ERK_substrate and AG-Pin1(ww)-NES, before and after EGF and U0126 addition. Note that when ERK in cells is activated by an EGF stimulus, the ERK substrate (ERK_substrate) is phosphorylated; as a result, the ERK_substrate and a ww domain of a Pin1 protein (Pin1(ww)) interact with each other. Further, if a MEK inhibitor U0126 is added, the ERK activity is decreased; as a result, the ERK substrate is dephosphorylated, terminating the interaction between the ERK substrate and Pin1(ww). In the graph, the x axis represents time (minutes), provided that time when EGF was added is 0. Additionally, U0126 was added to the cells, 14 minutes after the EGF addition.

(Transfection into Cultured Cells, and Observation of Transfected Cells)

pp62(PB1)-ERK_substrate-P2A-hAG-Pin1(ww)-NES was transfected into 293 cells by the same method as that described in Example 1. On the next day, EGF (manufactured by SIGMA CO.) was added to the cells to the final concentration of 50 ng/ml. Further, 14 minutes thereafter, U0126 was added to the cells to the final concentration of 10 μM. Meanwhile, the cell observation was started 2 minutes before the EGF addition, and the observed images were obtained every 15 seconds. The obtained images were used to analyze a total fluorescence luminance of fluorescent foci (assemblies) by the same method as that described in Example 11, and a graph was prepared by plotting the total fluorescence luminance against time. FIG. 47 shows the obtained result.

As apparent from the result shown in FIG. 47, in the cells expressing p62(PB1)-ERK_substrate and AG-Pin1(ww)-NES, after EGF was added, fluorescent foci (assemblies) were significantly observed as time elapsed. However, after U0126 was added, the fluorescent foci were slowly decreased, reflecting the promotion of ERK substrate dephosphorylation in response to endogenous ERK inactivation due to the addition.

The change over time in the total fluorescence luminance of fluorescent foci (assemblies) representing the interaction between the ERK substrate and Pin1(ww) was substantially the same as the result obtained by measuring an ERK substrate-Pin1(ww) interaction using FRET described in Christopher D. Harvey et al., Proc Natl Acad Sci USA., Dec. 9, 2008, vol. 105, no. 49, pp. 19264 to 19269.

In this manner, the present invention makes it possible to detect a protein-protein interaction induced or inhibited indirectly by a particular stimulus, by detecting fluorescent foci. Moreover, the present invention also makes it possible to detect a signal transduction over time.

Example 28

<Detection 24 of Protein-Protein Interaction>

As described above, based on the interaction between HRas and cRaf described in Example 20, it was confirmed that the present invention enabled detection of a change over time in when a protein-protein interaction took place.

Figure 48:
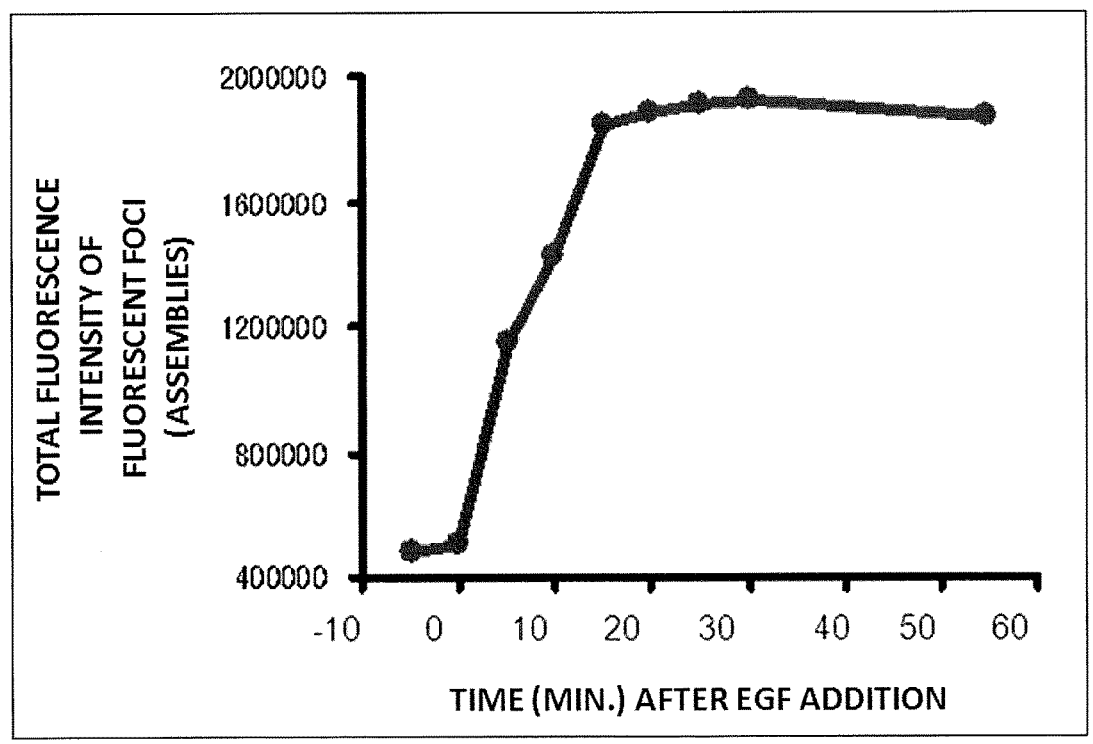
FIG. 48 is a graph for illustrating a change over time in a total fluorescence intensity of fluorescent foci in cells expressing p62(PB1)-HRas(WT) and AG-cRaf(R59A), before and after EGF addition. Note that, in the graph, the x axis represents time (minutes), provided that time when EGF was added is 0.

Specifically, pp62(PB1)-HRas(WT) described in Example 20 and phAG-cRaf (R59A) described in Example 23 were introduced into cells by the same method as that described in Example 23. EGF (manufactured by SIGMA CO.) was added thereto to the final concentration of 50 ng/ml. A measurement apparatus capable of detecting a fluorescent signal only in the vicinity of the cell membrane was used for the observation. Note that the observation was started 5 minutes before the EGF addition, and continued at 5-minute intervals for 30 minutes after the addition. The observation was made another 30 minutes thereafter. On the basis of the obtained image data, analysis was performed by the same method as that described in Example 11, and a graph was prepared by plotting a total fluorescence intensity of fluorescent foci (assemblies) against time. Note that, in the graph, the x axis represents time (minutes), provided that time when EGF was added is 0, and the y axis represents the total fluorescence intensity of fluorescent foci (assemblies). FIG. 48 shows the obtained result.

As apparent from the result shown in FIG. 48, the interaction between HRas and cRaf that took place by adding EGF was successfully detected over time.

Moreover, as described above, it has been known that cRaf interacts with HRas activated as a result of signaling via a Grb2-SOS complex from an EGF receptor of cells to which EGF has been added. Thus, the result shown in FIG. 48 confirmed that the present invention enabled tracing over time of a process in which an intracellular signal transduction pathway (such as a signal transduction pathway via a Grb2-SOS complex) was activated in response to a stimulus (such as EGF) applied to cells from the outside.

Example 29

<Detection 25 of Protein-Protein Interaction>

As described above, it has been revealed that rapamycin binds to a FKBP12 protein, and this complex further binds to a FRB domain of a mTOR protein (mTOR(FRB)). A mTOR protein is a serine/threonine kinase having a function of activating signal transductions involved in protein synthesis and cell proliferation. It has also been revealed that the function is inhibited by such complex formation between a FKBP12 protein and rapamycin.

Furthermore, a FKBP12 protein has been known to interact with a protein phosphatase (calcineurin) composed of a catalytic subunit A (calcineurin A) and a regulatory subunit B (calcineurin B) via FK506. Calcineurin is an enzyme having a very important function in signal transductions in T cells and the like. It has also been revealed that the function is inhibited by such complex formation between a FKBP12 protein and FK506.

Hence, in this Example, a test was conducted by a method described below regarding whether or not the present invention enabled detection and distinguishment of: a complex of FKBP12 and mTOR(FRB) formed in a manner dependent on rapamycin in a single cell in which FKBP12, mTOR (FRB), calcineurin A and calcineurin B were co-expressed; a complex of FKBP12 with calcineurin A and calcineurin B formed in a manner dependent on FK506; and eventually an inhibition of signal transductions in which these complexes were involved.

Note that as the "calcineurin A and calcineurin B" expressed in the cell, a mCAB protein was used, which was composed of a portion of calcineurin A fused to a portion of calcineurin B (see Clemons P A et al., Chem Biol., January 2002, vol. 9, iss. 1, pp. 49 to 61).

First, phAG-mCAB, pp62(PB1)-FKBP12, and pmTOR (FRB)-hKO1 were introduced into HeLaS3 cells. The phAG-mCAB was prepared by the same method as that described in Example 2 using an artificially synthesized DNA (SEQ ID NO: 169) encoding a region having the amino acid sequence of SEQ ID NO; 170. The pp62(PB1)-FKBP12 was as described in Example 2. The pmTOR (FRB)-hKO1 (pmTOR(FRB domain)-hKO1) was as described in Example 6.

Moreover, the HeLaS3 cells were cultured by the same method as that described in Example 1. Further, in the transfection, the HeLaS3 cells were seeded onto 2 wells of an 8-well chamber (manufactured by Nunc A/S). On the next day, by the same method as that described in Example 1, 130 ng of each of the plasmid DNAs was introduced into the HeLaS3 cells using 1 µl of Transfection Reagent.

Figure 49:
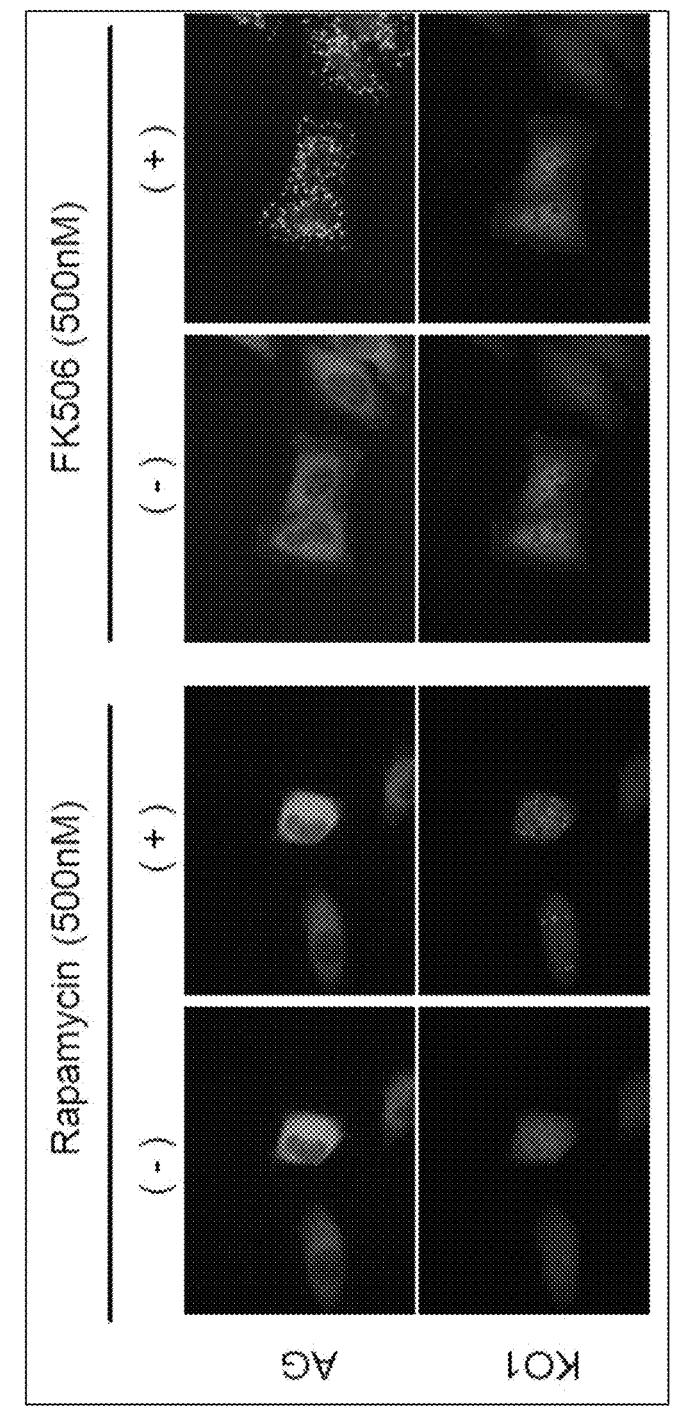
FIG. 49 shows micrographs for illustrating the result of observing cells expressing AG-mCAB, p62(PB1)-FKBP12, and mTOR(FRB)-KO1, in the absence (−) or presence (+) of rapamycin, or in the absence (−) or presence (+) of FK506. Note that rapamycin binds to a FKBP12 protein, forming a complex, and further that this complex binds to a FRB domain of a mTOR protein (mTOR(FRB)). Moreover, mCAB (protein composed of a portion of calcineurin A fused to a portion of calcineurin B) interacts with a FKBP12 protein via FK506. In the figure, "AG" and "KO1" show the results of detecting fluorescences derived from AG and KO1, respectively.

Then, 24 hours thereafter, the transfected cells were observed by the same method as that described in Example 1. To the cells, rapamycin or FK506 was added to the final concentration of 500 nM, and observed another 15 minutes thereafter. FIG. 49 shows the obtained result.

As apparent from the result shown in FIG. 49, by adding rapamycin to the cells expressing AG-mCAB, p62(PB1)-FKBP12, and mTOR(FRB)-KO1, the interaction between mTOR(FRB) and FKBP12 was observed in the form of fluorescent foci emitting a KO1-derived fluorescent signal. On the other hand, by adding FK506, the interaction between mCAB and FKBP12 was observed in the form of fluorescent foci emitting an AG-derived fluorescent signal.

Thus, it was confirmed that the present invention enabled detection of multiple types of protein-protein interactions in a single cell, particularly, various protein-protein interactions dependent on different stimuli in a single cell.

Moreover, the present invention can provide a method for detecting and distinguishing multiple types of signal transductions in a single cell by detecting various protein-protein interactions involved in signal transductions in a single cell.

Furthermore, as described in this Example also, unlike FRET that is another method for detecting a protein-protein interaction in living cells, it is not necessary to select a fluorescent protein meeting the conditions of an acceptor and a donor; in addition, it is not necessary to take into consideration cross excitation by which an acceptor fluorescent protein is excited, and bleed-through in which fluorescence of a donor fluorescent protein bleeds through a filter (absorption filter) set for detecting fluorescence of an acceptor fluorescent protein. Thus, in the present invention, combinations of various fluorescent proteins having different wavelength characteristics can be easily selected and utilized.

Example 30

<Detection 26 of Protein-Protein Interaction>

Whether or not the method of the present invention enabled detection of known protein-protein interactions shown in Table 3 by using p62(PB1) as the association-inducing protein and an AG protein as the fluorescent protein having a multimerization ability was tested by the method described in Example 2.

TABLE 3

| Protein-protein interaction | |
|---|---|
| Cdk5 | P25 |
| Plk | Wee1 |
| calcineurin Aα | VIVIT peptide |
| JNK | JIP |
| CREB | CBP |
| ERK2 | MEK |
| MEK | cRaf |
| β-catenin | TCF |

As a result, although unillustrated, it was verified that it was possible to detect the protein-protein interactions in all the combinations in the form of fluorescent foci. It was demonstrated that the present invention was a generally-adoptable method for detecting a protein-protein interaction.

INDUSTRIAL APPLICABILITY

As has been described above, the present invention makes it possible to detect a protein-protein interaction in an intracellular environment unique thereto, and to detect positional information and temporal information on the protein-protein interaction. Moreover, in the present invention, a strength of a protein-protein interaction correlates with the fluorescence intensity of a fluorescent focus. Accordingly, the method is utilizable in identifying an amino acid residue involved in a protein-protein interaction, and also in screening for a substance modulating a protein-protein interaction, on the basis of the fluorescence intensity.

Thus, the method for detecting a protein-protein interaction and so forth of the present invention and a kit for use in these methods are useful in the development of pharmaceutical products and so on through elucidations of various signal transductions in vivo, various biological reaction controls, and the like, and eventually through elucidations of disease mechanisms.

SEQUENCE LISTING FREE TEXT

SEQ ID NOs: 1 and 2
<223> humanized-codon Azami Green (AG)
SEQ ID NOs: 3 and 4
<223> PB1 domain of p62
SEQ ID NOs: 5 and 6
<223> PB1 domain of MEK5
SEQ ID NOs: 7 and 8
<223> PB1 domain of Nbr1
SEQ ID NOs: 9 and 10
<223> PB1 domain of PKCiota
SEQ ID NOs: 11 and 12
<223> PB1 domain of TFG
SEQ ID NOs: 13 and 14
<223> SAM domain of TEL
SEQ ID NOs: 15 and 16
<223> SAM domain of EphB2
SEQ ID NOs: 17 and 18
<223> SAM domain of DGK delta
SEQ ID NOs: 19 and 20
<223> SAM domain of Tankyrase-1
SEQ ID NOs: 21 and 22
<223> FRB domain of mTOR
SEQ ID NOs: 23 and 24
<223> FKBP12
SEQ ID NOs: 25 and 26
<223> p53
SEQ ID NOs: 27 and 28
<223> MDM2
SEQ ID NOs: 29 and 30
<223> Sec5
SEQ ID NOs: 31 and 32
<223> RalB
SEQ ID NOs: 33 and 34
<223> RalB protein Q72L mutant
SEQ ID NOs: 35 and 36
<223> RalB protein S28N mutant
SEQ ID NOs: 37 and 38
<223> calmodulin
SEQ ID NOs: 39 and 40
<223> M13 peptide
SEQ ID NOs: 41 and 42
<223> HRas
SEQ ID NOs: 43 and 44
<223> cRaf
SEQ ID NOs: 45 and 46
<223> Smac
SEQ ID NOs: 47 and 48
<223> XIAP
SEQ ID NOs: 49 and 50
<223> BclX(L)
SEQ ID NOs: 51 and 52
<223> BAD
SEQ ID NOs: 53 and 54
<223> Rac1
SEQ ID NOs: 55 and 56
<223> PBD
SEQ ID NO: 57
<223> artificially synthesized hAG forward primer 1 sequence
SEQ ID NO: 58
<223> artificially synthesized hAG reverse primer 1 sequence
SEQ ID NO: 59
<223> artificially synthesized p62(PB1) forward primer 1 sequence
SEQ ID NO: 60
<223> artificially synthesized p62(PB1) reverse primer 1 sequence
SEQ ID NO: 61
<223> artificially synthesized hAG forward primer 2 sequence
SEQ ID NO: 62
<223> artificially synthesized hAG reverse primer 2 sequence
SEQ ID NO: 63
<223> artificially synthesized p62(PB1) forward primer 2 sequence
SEQ ID NO: 64
<223> artificially synthesized p62(PB1) reverse primer 2 sequence
SEQ ID NO: 65
<223> artificially synthesized p62(PB1) forward primer 3 sequence
SEQ ID NO: 66
<223> artificially synthesized p62(PB1) reverse primer 3 sequence
SEQ ID NO: 67
<223> artificially synthesized mTOR(FRB) forward primer sequence SEQ ID NO: 68
<223> artificially synthesized mTOR(FRB) reverse primer sequence
SEQ ID NO: 69
<223> artificially synthesized FKBP12 forward primer sequence
SEQ ID NO: 70
<223> artificially synthesized FKBP12 reverse primer sequence
SEQ ID NO: 71
<223> artificially synthesized MEK(PB1) forward primer sequence
SEQ ID NO: 72
<223> artificially synthesized MEK(PB1) reverse primer sequence
SEQ ID NO: 73
<223> artificially synthesized Nbr1(PB1) forward primer sequence
SEQ ID NO: 74
<223> artificially synthesized Nbr1(PB1) reverse primer sequence
SEQ ID NO: 75
<223> artificially synthesized PKCiota(PB1) forward primer sequence
SEQ ID NO: 76
<223> artificially synthesized PKCiota(PB1) reverse primer sequence
SEQ ID NO: 77
<223> artificially synthesized TFG(PB1) forward primer sequence
SEQ ID NO: 78
<223> artificially synthesized TFG(PB1) reverse primer sequence
SEQ ID NO: 79
<223> artificially synthesized TEL(SAM) forward primer sequence
SEQ ID NO: 80
<223> artificially synthesized TEL(SAM) reverse primer sequence
SEQ ID NO: 81
<223> artificially synthesized EphB2(SAM) forward primer sequence
SEQ ID NO: 82
<223> artificially synthesized EphB2(SAM) reverse primer sequence
SEQ ID NO: 83
<223> artificially synthesized DGK delta(SAM) forward primer sequence
SEQ ID NO: 84
<223> artificially synthesized DGK delta(SAM) reverse primer sequence
SEQ ID NO: 85
<223> artificially synthesized Tankyrase(SAM) forward primer sequence
SEQ ID NO: 86
<223> artificially synthesized Tankyrase(SAM) reverse primer sequence
SEQ ID NO: 87
<223> artificially synthesized TFG(PB1) forward primer 2 sequence
SEQ ID NO: 88
<223> artificially synthesized TFG(PB1) reverse primer 2 sequence
SEQ ID NO: 89
<223> artificially synthesized TEL(SAM) forward primer 2 sequence
SEQ ID NO: 90
<223> artificially synthesized TEL(SAM) reverse primer 2 sequence
SEQ ID NO: 91
<223> artificially synthesized DGK delta(SAM) forward primer 2 sequence
SEQ ID NO: 92
<223> artificially synthesized DGK delta(SAM) reverse primer 2 sequence
SEQ ID NO: 93
<223> artificially synthesized Tankyrase(SAM) forward primer 2 sequence
SEQ ID NO: 94
<223> artificially synthesized Tankyrase(SAM) reverse primer 2 sequence
SEQ ID NO: 95
<223> artificially synthesized hKO1 forward primer sequence
SEQ ID NO: 96
<223> artificially synthesized hKO1 reverse primer sequence
SEQ ID NO: 97
<223> artificially synthesized p53 forward primer sequence
SEQ ID NO: 98
<223> artificially synthesized p53 reverse primer sequence
SEQ ID NO: 99
<223> artificially synthesized MDM2 forward primer sequence
SEQ ID NO: 100
<223> artificially synthesized MDM2 reverse primer sequence
SEQ ID NO: 101
<223> artificially synthesized Sec5 forward primer sequence
SEQ ID NO: 102
<223> artificially synthesized Sec5 reverse primer sequence
SEQ ID NO: 103
<223> artificially synthesized RalB forward primer sequence
SEQ ID NO: 104
<223> artificially synthesized RalB reverse primer sequence
SEQ ID NO: 105
<223> artificially synthesized RalB(Q72L) mutation primer sequence
SEQ ID NO: 106
<223> artificially synthesized RalB(S28N) mutation primer sequence
SEQ ID NO: 107
<223> artificially synthesized calmodulin forward primer sequence
SEQ ID NO: 108
<223> artificially synthesized calmodulin reverse primer sequence
SEQ ID NO: 109
<223> artificially synthesized M13 peptide forward primer sequence
SEQ ID NO: 110
<223> artificially synthesized M13 peptide reverse primer sequence
SEQ ID NO: 111
<223> artificially synthesized AGNLS forward primer sequence
SEQ ID NO: 112
<223> artificially synthesized AGNLS reverse primer sequence
SEQ ID NO: 113
<223> artificially synthesized HRas forward primer sequence SEQ ID NO: 114
<223> artificially synthesized HRas reverse primer sequence
SEQ ID NO: 115
<223> artificially synthesized KRas forward primer sequence
SEQ ID NO: 116
<223> artificially synthesized KRas reverse primer sequence
SEQ ID NO: 117
<223> artificially synthesized HRas mutant primer sequence
SEQ ID NO: 118
<223> artificially synthesized cRaf forward primer sequence
SEQ ID NO: 119
<223> artificially synthesized cRaf reverse primer sequence
SEQ ID NO: 120
<223> artificially synthesized Smac forward primer sequence
SEQ ID NO: 121
<223> artificially synthesized XIAP forward primer sequence
SEQ ID NO: 122
<223> artificially synthesized XIAP reverse primer sequence
SEQ ID NO: 123
<223> artificially synthesized BclX(L) forward primer sequence
SEQ ID NO: 124
<223> artificially synthesized BclX(L) reverse primer sequence
SEQ ID NO: 125
<223> artificially synthesized BAD forward primer 1 sequence
SEQ ID NO: 126
<223> artificially synthesized BAD forward primer 2 sequence
SEQ ID NO: 127
<223> artificially synthesized BAD reverse primer sequence
SEQ ID NO: 128
<223> artificially synthesized Rac1 forward primer sequence
SEQ ID NO: 129
<223> artificially synthesized Rac1 reverse primer sequence
SEQ ID NO: 130
<223> artificially synthesized PBD forward primer sequence
SEQ ID NO: 131
<223> artificially synthesized PBD reverse primer sequence
SEQ ID NO: 132
<223> base sequence of monomeric KO (Kusabira-Orange)
SEQ ID NO: 133
<223> amino acid sequence of monomeric KO (Kusabira-Orange)
SEQ ID NOs: 134 and 135
<223> humanized-codon mAG1
SEQ ID NOs: 136 and 137
<223> mMiCy1
SEQ ID NOs: 138 and 139
<223> mKikGR1
SEQ ID NOs: 140 and 141
<223> KCy1
SEQ ID NOs: 142 and 143
<223> dAG (AB)
SEQ ID NOs: 144 and 145
<223> dAG (AC)
SEQ ID NOs: 146 and 147
<223> TGuv
SEQ ID NOs: 148 and 149
<223> Momiji
SEQ ID NOs: 150 and 151
<223> COR3.01
SEQ ID NOs: 152 and 153
<223> DsRed2
SEQ ID NOs: 154, 159, and 160
<223> artificially synthesized primer sequences
SEQ ID NOs: 155, 157, 161, 163, 165, 167, and 169
<223> artificially synthesized polynucleotide sequences
SEQ ID NOs: 156, 158, 162, 164, 166, 168, and 170
<223> artificially synthesized polypeptide sequences
SEQ ID NOs: 171 and 172
<223> COR5

The invention claimed is:

1. A method for screening for a substance modulating an interaction between a first protein and a second protein, the method comprising the steps of:
   expressing in a cell a first fusion protein comprising the first protein and an association-inducing protein, and a second fusion protein comprising the second protein and a fluorescent protein having a multimerization ability and emitting fluorescence, in presence of a test compound;
   detecting a fluorescent focus formed by an association between the first fusion protein and the second fusion protein in the cell; and
   selecting the test compound as a substance inducing the interaction if a fluorescence intensity of the fluorescent focus is higher than a fluorescence intensity of a fluorescent focus formed in absence of the test compound, or selecting the test compound as a substance suppressing the interaction if the fluorescence intensity of the fluorescent focus is lower than the fluorescence intensity of the fluorescent focus formed in the absence of the test compound, wherein
   the association-inducing protein is at least one protein selected from the group consisting of a PB1 domain of p62, a PB1 domain of TFG, a PB1 domain of PKCiota, a SAM domain of TEL, a SAM domain of DGK delta, and a SAM domain of Tankyrase-1;
   the fluorescent protein having a multimerization ability is at least one fluorescent protein selected from the group consisting of a florescent protein capable of forming a homomultimer, monomeric Kusabira-Orange 2, monomeric Keima-Red, monomeric Midoriishi-Cyan1, monomeric Kusabira-Orange 1, and monomeric Kikume Green-Red1;
   the fluorescent focus has a fluorescence intensity in a region of 0.2 to 5 μm, the fluorescence intensity being higher than a fluorescence intensity of the fluorescent protein having a multimerization ability, which is present in a dispersed state in the cell, and
   the association inducing protein is able to form a fluorescent focus when fused to the fluorescent protein having a multimerization ability.

* * * * *